US012655421B2

(12) United States Patent
Chong et al.

(10) Patent No.: US 12,655,421 B2
(45) Date of Patent: Jun. 16, 2026

(54) CRISPR DNA TARGETING ENZYMES AND SYSTEMS

(71) Applicant: ARBOR BIOTECHNOLOGIES, INC., Cambridge, MA (US)

(72) Inventors: Shaorong Chong, Cambridge, MA (US); Winston X. Yan, Boston, MA (US); David A. Scott, Cambridge, MA (US); David R. Cheng, Boston, MA (US); Pratyusha Hunnewell, Needham, MA (US)

(73) Assignee: ARBOR BIOTECHNOLOGIES, INC., Cambridge, MA (US)

( * ) Notice: Subject to any disclaimer, the term of this patent is extended or adjusted under 35 U.S.C. 154(b) by 1676 days.

(21) Appl. No.: 17/020,414

(22) Filed: Sep. 14, 2020

(65) Prior Publication Data

US 2020/0407716 A1    Dec. 31, 2020

Related U.S. Application Data

(60) Division of application No. 16/680,104, filed on Nov. 11, 2019, now Pat. No. 10,808,245, which is a continuation of application No. PCT/US2019/022375, filed on Mar. 14, 2019.

(60) Provisional application No. 62/775,885, filed on Dec. 5, 2018, provisional application No. 62/772,038, filed on Nov. 27, 2018, provisional application No. 62/746,528, filed on Oct. 16, 2018, provisional application No. 62/740,856, filed on Oct. 3, 2018, provisional application No. 62/703,857, filed on Jul. 26, 2018, provisional application No. 62/679,628, filed on Jun. 1, 2018, provisional application No. 62/672,489, filed on May 16, 2018, provisional application No. 62/666,397, filed on May 3, 2018, provisional application No. 62/642,919, filed on Mar. 14, 2018.

(51) Int. Cl.
*C12N 15/11* (2006.01)
*C12N 9/22* (2006.01)
*C12N 15/90* (2006.01)

(52) U.S. Cl.
CPC ............... *C12N 15/11* (2013.01); *C12N 9/22* (2013.01); *C12N 15/902* (2013.01); *C12N 2310/20* (2017.05); *C12N 2310/531* (2013.01); *C12N 2800/80* (2013.01)

(58) Field of Classification Search
CPC ........ C12N 15/11; C12N 9/22; C12N 15/902; C12N 2310/20; C12N 2310/531; C12N 2800/80; C12N 15/102; C12N 15/113; C12N 15/90
See application file for complete search history.

(56) References Cited

U.S. PATENT DOCUMENTS

| | | | |
|---|---|---|---|
| 10,808,245 | B2 | 10/2020 | Chong et al. |
| 2017/0211142 | A1 | 7/2017 | Smargon et al. |
| 2018/0371487 | A1 | 12/2018 | Yang et al. |

FOREIGN PATENT DOCUMENTS

| | | |
|---|---|---|
| CN | 106852157 | 6/2017 |
| CN | 107250363 A | 10/2017 |
| CN | 111690720 A | 9/2020 |
| CN | 112195164 A | 1/2021 |
| WO | 2012164565 A1 | 12/2012 |
| WO | 2016106236 A1 | 6/2016 |
| WO | 2017091630 A1 | 6/2017 |
| WO | 2017127807 A1 | 7/2017 |
| WO | 2017219027 A1 | 12/2017 |
| WO | 2018035250 A1 | 2/2018 |
| WO | 2018035388 A1 | 2/2018 |
| WO | 2019178427 A1 | 9/2019 |
| WO | 2019178428 A1 | 9/2019 |
| WO | 2019201331 A1 | 10/2019 |
| WO | 2019/217944 A1 | 11/2019 |
| WO | 2020028823 A1 | 2/2020 |
| WO | 2020088450 A1 | 5/2020 |
| WO | 2020/168051 A1 | 8/2020 |
| WO | 2020/168075 A1 | 8/2020 |
| WO | 2020/168088 A1 | 8/2020 |
| WO | 2020/168122 A1 | 8/2020 |
| WO | 2020/168132 A1 | 8/2020 |
| WO | 2020181101 A1 | 9/2020 |
| WO | 2020/236936 A1 | 11/2020 |

OTHER PUBLICATIONS

Shmakov, S. et al. "Diversity and evolution of class 2 CRISPR-Cas system". Nature Review Microbiology, vol. 15(3) (2017), pp. 169-182. (Year: 2017).*
Hillary, V.E. et al. "A review on the mechanism and applications of CRISPR/Cas9/Cas12/Cas13/Cas14 proteins utilized for genome engineering". Molecular Biotechnology, vol. 65 (2023), pp. 311-325. (Year: 2023).*

(Continued)

*Primary Examiner* — Nancy J Leith
*Assistant Examiner* — Alexandra Geraldine Dace Denito
(74) *Attorney, Agent, or Firm* — K&L Gates LLP

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of nucleic acids such as DNA. Each system includes one or more protein components and one or more nucleic acid components that together target nucleic acids.

29 Claims, 68 Drawing Sheets

Specification includes a Sequence Listing.

(56) References Cited

OTHER PUBLICATIONS

Yan, W.X. et al. "Functionally diverse type V CRISPR-Cas systems." Science, vol. 363 (2018), pp. 88-91. (Year: 2018).*

Chen et al., "CRISPR-Cas12a target binding unleashes indiscriminate single-stranded DNase activity," Science 360(6387) 436-9 (Feb. 2018).

Dong et al., "The crystal structure of Cpf1 in complex with CRISPR RNA," Nature 532(7600): 522-6 (Apr. 2016).

Gaudelli et al., "Programmable base editing of A.T to G.C in genomic DNA without DNA cleavage," Nature 551(7681): 464-71 (Oct. 2017).

International Search Report for International Application No. PCT/US2019/022375, mailed Jun. 13, 2019 (6 pages).

Kim et al., "Efficient Transcriptional Gene Repression by Type V-A CRISPR-Cpf1 from Eubacterium eligens," ACS Synthetic Biology 6(7): 1273-82 (Apr. 2017).

Koonin et al., "Diversity, classification and evolution of CRISPR-Cas systems," Current Opinion in Microbiology 37:67-78 (Jun. 2017).

Liu et al., "C2c1-sgRNA Complex Structure Reveals RNA-Guided DNA Cleavage Mechanism," Mol Cell. 65(2):310-22 (Dec. 2016).

Makarova et al., "An updated evolutionary classification of CRISPR-Cas systems," Nat. Rev. Microbiol. 13 (11):722-36 (Sep. 2015).

Makarova et al., "Classification and Nomenclature of CRISPR-Cas Systems: Where from Here?" CRISPR J. 1(5):325-36 (Oct. 2018).

Murugan et al., "The Revolution Continues: Newly Discovered Systems Expand the CRISPR-Cas Toolkit," Molecular Cell 68(1): 15-25 (Oct. 2017).

Ran et al., "Double nicking by RNA-guided CRISPR Cas9 for enhanced genome editing specificity," Cell 154(6):1380-9 (Aug. 2013).

Shmakov et al., "Discovery and Functional Characterization of Diverse Class 2 CRISPR-Cas Systems," Molecular Cell 60(3): 385-97 (Oct. 2015).

Stella et al., "Class 2 CRISPR-Cas RNA-guided endonucleases: Swiss Army knives of genome editing," Nature Structural Molecular Biology 24(11): 882-92 (Oct. 2017).

Written Opinion of the International Searching Authority for International Application No. PCT/US2019/022375 (7 pages).

Wu et al., "Structural basis of stringent PAM recognition by CRISPR-C2c1 in complex with sgRNA," Cell Res. 27(5):705-8 (Apr. 2017).

Yamano et al., "Crystal Structure of Cpf1 in Complex with Guide RNA and Target DNA," Cell 165(4):949-62 (Apr. 2016).

Yan et al., "Cas13d is a Compact RNA-Targeting Type VI CRISPR Effector Positively Modulated by a WYL-Domain-Containing Accessory Protein," Mol. Cell 70(2)327-39.e5 (Mar. 2018).

Yan et al., "Functionally diverse type V CRISPR-Cas systems," Science 363(6422):88-91 (Dec. 2018).

Yang et al., "PAM-Dependent Target DNA Recognition and Cleavage by C2c1 CRISPR-Cas Endonuclease," Cell 167(7):1814-28 (Dec. 2016).

Zetsche et al., "Cpf1 is a single RNA-guided endonuclease of a class 2 CRISPR-Cas system," Cell 163(3), 759-71 (Sep. 2015).

Sequence Alignment of SEQ ID No. 5 with BGX25975, Search conducted on Jun. 5, 2020, 4 pages. (Year: 2020).

Sequence Alignment of SEQ ID No. 5 with BGX25978, Search conducted on Jun. 11, 2020, 7 pages. (Year: 2020).

Sequence Alignment of SEQ ID No. 5 with BGX25997, Search conducted on Jun. 11, 2020, 7 pages. (Year: 2020).

Al-Shayeb et al., "Clades of huge phages from across Earth's ecosystems," Nature (2020) vol. 578, pp. 425-431 and Methods pages.

Databse EMBL Online—Speth D.R. et al. "Candidatus Scalindua brodae CHAT domain protein," retrieved from UNIPARC accession No. UPI0005442945, database Accession No. KHE91663, dated Dec. 14, 2014.

Garrett et al., "CRISPR-based immune systems of the Sulfolobales: complexity and diversity," Biochem Soc Trans (2011) vol. 39, pp. 51-57.

International Search Report for PCT/US2019/032750, mailed Sep. 25, 2019.

Makarova et al., "Annotation and Classification of CRISPR-Cas Systems," Methods Mol Biol (2015) vol. 1311, pp. 47-75.

Makarova et al., "Unification of Cas protein families and a simple scenario for the origin and evolution of CRISPR-Cas systems," Biology Direct (2011) vol. 6, Article 38, 27 pages.

Pausch et al., "CRISPR-Cas-Phi from huge phages is a hypercompact genome editor," Science (2020) vol. 369, pp. 333-337.

Tamulaitis et al., "Type III CRISPR-Cas Immunity: Major Differences Brushed Aside," Trends Microbiol (2017) vol. 25, No. 1, pp. 49-61.

International Search Report and Written Opinion for International Application No. PCT/US2019/022376 dated Jun. 17, 2019.

Strutt et al. "RNA-dependent RNA targeting by CRISPR-Cas9" eLIFE (2018) vol. 7, e 32724, pp. 1-17.

Smargon et al. "Cas13b is a Type VI-B CRISPR-Associated RNA-Guided RNase Differentially Regulated by Accessory Proteins Csx27 and Csx28" Molecular Cell (2017) vol. 65, No. 4, pp. 618-630.

O'Connell et al. "Programmable RNA recognition and cleavage by CRISPR/Cas9" Nature (2014) vol. 516, No. 7530, pp. 263-266.

Abudayyeh et al. "C2c2 is a single-component programmable RNA-guided RNA-targeting CRISPR effector" Science (2016) vol. 353, No. 6299, pp. aaf5573-1-aaf5573-9.

Bisaria et al., "Lessons from Enzyme Kinetics Reveal Specificity Principles for RNA-Guided Nucleases in RNA Interference and CRISPR-Based Genome Editing," Cell Systems 4(1): 21-9 (Jan. 2017).

Boyle et al., "Quantification of Cas9 binding and cleavage across diverse guide sequences maps landscapes of target engagement," Science Advances 7(8): eabe5496 (Feb. 2021).

Chen et al., "Enhanced proofreading governs CRISPR-Cas9 targeting accuracy," Nature 550(7676)407-10 (Sep. 2017).

Huang et al., "Structural basis for two metal-ion catalysis of DNA cleavage by Cas12i2," Nature Communications 11(1): 5241 (Oct. 2020).

Jones et al., "Massively parallel kinetic profiling of natural and engineered CRISPR nucleases," Nature Biotechnology 39(1): 84-93 (Jan. 2021).

Klein et al., "Hybridization Kinetics Explains CRISPR-Cas Off-Targeting Rules," Cell Reports 22(6): 1413-23 (Feb. 2018).

Kleinstiver et al., "Engineered CRISPR-Cas 12a variants with increased activities and improved targeting ranges for gene, epigenetic and base editing," Nature Biotechnology 37(3): 276-82 (Feb. 2019).

Kleinstiver et al., "High-fidelity CRISPR-Cas9 nucleases with no detectable genome-wide off-target effects," Nature 529(7587): 490-5 (Jan. 2016).

Slaymaker et al., "Rationally engineered Cas9 nucleases with improved specificity," Science 351(6268): 84-8 (Jan. 2016).

Strecker et al., "Engineering of CRISPR-Cas12b for human genome editing," Nature Communications 10(1): 212 (Jan. 2019).

Strohkendl et al., "Kinetic basis for DNA target specificity of CRISPR-Cas12a," Molecular Cell 71(5): 816-24 (Sep. 2018).

Zhang et al., "Mechanisms for target recognition and cleavage by the Cas12i RNA-guided endonuclease," Nature Structural & Molecular Biology 27:1069-76 (Sep. 2020).

Sequence Alignment of SEQ ID No. 5 with BHT45754, Search conducted on Apr. 26, 2021, 4 pages. (Year: 2021).

Sequence Alignment of SEQ ID No. 5 with BIV42102, Search conducted on Apr. 26, 2021, 3 pages. (Year: 2021).

He et al., "Genome-editing: focus on the off-target effects" Chinese Journal of Biotechnology (2017) No. 10, pp. 104-122.

* cited by examiner

Type V-I    Cas12i - Functional Domains

Cas12i (1055 aa)

RuvC domain architecture:

Type V-I    Direct Repeat - Secondary Structures

3300020193
-7.5 kcal/mol
(SEQ ID NO: 162)

3300020214
-6.5 kcal/mol
(SEQ ID NO: 163)

3300002408
-6.2 kcal/mol
(SEQ ID NO: 157)

3300009183
-5.2 kcal/mol
(SEQ ID NO: 160)

3300002294
-5.1 kcal/mol
(SEQ ID NO: 158)

Type V-I Cas12i1 – *in vivo* Target Depletion pACYC184 Targets

RNA expression (count)

Forward DR
orientation fold depletion

Type V-I   Cas12i1 – *in vivo* Target Depletion

*E. coli* Essentil Gene Targets

Type V-I Cas12i2 - *in vivo* Target Depletion

*E. coli* Essential Gene Targets

Type V-I    dCas12i2 D599A

Type V-I    Cas12i1 Components - Activity Summary

Type V-I    Cas12i2 Components – Activity Summary

Type V-I   Cas12i1 Target PAM

Type V-I   Cas12i2 Target PAM

Type V-I    Cas12i1 Target Flank Dependency - Combinatorial Violin Plots

Type V-I    Cas12i2 Target Flank Dependency - Combinatorial Violin Plots

Type V-I    Cas12i2 – Mature crRNA

Cas12i2 min. CRISPR array

Position along minimal CRISPR array

Reads Mapped

5'-AGAAAUCCGUCUUUCAUUGACGGNNNNNNNNNNNNNNNNNNNN-3'

Type V-I  Cas12i1 autonomous crRNA biogenesis

15% TBE-Urea 24-28 pre-crRNA [100nM]

EDTA [50mM]

Cas12i1 [15 - 500nM]

pre-crRNA (131 nt)

Mature-crRNA

150

80

50

Type V-I  Cas12i1 activity on target ssDNA

Type V-I Cas12i1 activity on collateral ssDNA

Type V-I Cas12i1 activity on target dsDNA

Type V-I   Cas12i1 cleavage efficiency of target dsDNA strands

GFP Fluorescence depletion assay - experimental design

GFP Fluorescence depletion assay - substrate and target design pET plasmid (6 kb)

*In vitro* RNA/DNA manipulation screen

Type V-I

*In vitro* PAM screen substrate

5' Fiducial    5' PAM    target    3' PAM    3' Fiducial ssDNA substrate    NNNNNN    OR    NNNNNN dsDNA substrate    NNNNNN    NNNNNN second strand synthesis (DNA PolI)

Type V-I

*In vitro* RNA/DNA manipulation screen ssDNA cleavage: unidirectional seugencing of cut and uncut products ssDNA 5' crRNA (1) second strand synthesis +
(2) adapter ligation

I5/P5

(3) selective amplification

P7/I7

Type V-I Cas12i1 – *In vitro* screen

**Type V-I  Cas12i1 – *In vitro* screen**

I5/P5

P7/I7

['pool_71_S71-Bin-TS_dsDNA-TS_f5p7']

['pool_69_S69-Apo_dsDNA-TS_f5p7']

Target length (from 3' side)

Type V-I   Cas12i1 – *In vitro* screen

Type V-I  Cas12i1 – *In vitro* screen spacer

Type V-I  Cas12i1 – *In vitro screen*

Non-target strand +24/-4
Target strand +19/-9

Type V-I  Cas12i1 – *In vitro* screen

Type V-I  Cas12i2 – *In vitro* screen

Type V-I Cas12i2 - *In vitro* screen spacer

Type V-I Cas12i2 – *In vitro screen*

Type V-I  Cas12i2 – *In vitro screen*

Type V-I  Cas12i – *in vivo constructs*

Type V-I    Cas12i2 – indels & RNA Guide
designs

Representative Indels

PAM    +20bp

ACCCCCTTTCCAAAGCCCATTCCCTCTTTTC---GAGCCGGGGTGTGC    (SEQ ID NO: 550)
ACCCCCTTTCCAAAGCCCATTCCCTCTTTTT---GAGCCGGGGTGTGC    (SEQ ID NO: 551)
ACCCCCTTTCCAAAGCCCATTCCCTGTTTAT---GAGCCGGGGTGTGC    (SEQ ID NO: 552)
ACCCCCTTTCCAAAGCCCATACCCTCTTTA---AGAGCCGGGGTGTG    (SEQ ID NO: 553)
ACCCCCTTTCCAAAGCCCATTACCTCTTTA---AGAGCCGGGGTGTG    (SEQ ID NO: 554)
ACCCCCTTTCCAAAGCCCATTCCCTCTGTA---AGAGCCGGGGTGTG    (SEQ ID NO: 555)

FIG 41B

SEQUENCE LISTING

<160> NUMBER OF SEQ ID NOS: 621

<210> SEQ ID NO 1
<211> LENGTH: 1046
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 1

Met Val Ser Glu Ser Thr Ile Arg Pro Tyr Thr Ser Lys Leu Ala Pro
1               5                   10                  15

Asn Asp Pro Lys Leu Lys Met Leu Asn Asp Thr Phe Asn Trp Leu Asp
            20                  25                  30

His Ala Tyr Lys Val Phe Phe Asp Val Ser Val Ala Leu Phe Gly Ala
            35                  40                  45

Ile Glu His Glu Thr Ala Gln Glu Leu Ile Gly Glu Lys Ser Lys Phe
    50                  55                  60

Asp Ala Asp Leu Leu Cys Ala Ile Met Trp Phe Arg Leu Glu Glu Lys
65                  70                  75                  80

Ser Asp Asn Pro Gly Pro Leu Gln Thr Val Glu Gln Arg Met Arg Leu
                85                  90                  95

Phe Gln Lys Tyr Ser Gly His Glu Pro Ser Ser Phe Thr Gln Glu Tyr
            100                 105                 110

Ile Lys Gly Asn Ile Asp Ser Glu Lys Tyr Gln Trp Val Asp Cys Arg
            115                 120                 125

Leu Lys Phe Ile Asp Leu Ala Arg Asn Ile Asn Thr Thr Gln Glu Ser
    130                 135                 140

Leu Lys Ile Asp Ala Tyr Thr Leu Phe Met Asn Lys Leu Ile Pro Val
145                 150                 155                 160

Ser Lys Asp Asp Glu Phe Asn Ala Tyr Gly Leu Ile Ser Gln Leu Phe
                165                 170                 175

Gly Thr Gly Lys Lys Glu Asp Arg Ser Ile Lys Ala Ser Met Leu Glu
            180                 185                 190

Glu Ile Ser Asn Ile Ile Glu Asp Lys Lys Pro Asn Thr Trp Glu Glu
            195                 200                 205

Tyr His Asp Leu Ile Lys Lys Thr Phe Asn Val Asp Asn Tyr Lys Glu
    210                 215                 220

Leu Lys Glu Lys Leu Ser Ala Gly Ser Ser Gly Arg Asp Ser Ser Leu
225                 230                 235                 240

Val Ile Asp Leu Lys Glu Glu Lys Thr Gly Leu Leu Gln Pro Asn Phe
                245                 250                 255

Ile Lys Asn Arg Ile Val Lys Phe Arg Glu Asp Ala Asp Lys Lys Arg
            260                 265                 270

Thr Val Phe Leu Leu Pro Asn Arg Met Lys Leu Arg Glu Phe Ile Ala
            275                 280                 285

Ser Gln Ile Gly Pro Phe Glu Gln Asn Ser Trp Ser Ala Val Leu Asn
    290                 295                 300

Arg Ser Met Ala Ala Ile Gln Ser Lys Asn Ser Ser Asn Ile Leu Tyr
305                 310                 315                 320

Thr Asn Glu Lys Glu Glu Arg Asn Asn Glu Ile Gln Glu Leu Leu Lys
                325                 330                 335

Lys Asp Ile Leu Ser Ala Ala Ser Ile Leu Gly Asp Phe Arg Arg Gly
            340                 345                 350

Glu Phe Asn Arg Ser Val Val Ser Lys Asn His Leu Gly Ala Arg Leu
            355                 360                 365

Asn Glu Leu Phe Glu Ile Trp Gln Glu Leu Thr Met Asp Asp Gly Ile
    370                 375                 380

Lys Lys Tyr Val Asp Leu Cys Lys Asp Lys Phe Ser Arg Arg Pro Val
385                 390                 395                 400

```
Lys Ala Leu Leu Gln Tyr Ile Tyr Pro Tyr Phe Asp Lys Ile Asn Ala
                405                 410                 415

Lys Gln Phe Leu Asp Ala Ala Ser Tyr Asn Thr Leu Val Glu Thr Asn
                420                 425                 430

Asn Arg Lys Lys Ile His Pro Thr Val Thr Gly Pro Thr Val Cys Asn
                435                 440                 445

Trp Gly Pro Lys Ser Thr Ile Asn Gly Ser Ile Thr Pro Pro Asn Gln
    450                 455                 460

Met Val Lys Gly Arg Pro Ala Gly Ser His Gly Met Ile Trp Val Thr
465                 470                 475                 480

Met Thr Val Ile Asp Asn Gly Arg Trp Ile Lys His His Leu Pro Phe
                485                 490                 495

His Asn Ser Arg Tyr Tyr Glu Glu His Tyr Cys Tyr Arg Glu Gly Leu
                500                 505                 510

Pro Thr Lys Asn Lys Pro Arg Thr Lys Gln Leu Gly Thr Gln Val Gly
                515                 520                 525

Ser Thr Ile Ser Ala Pro Ser Leu Ala Ile Leu Lys Ser Gln Glu Glu
                530                 535                 540

Gln Asp Arg Arg Asn Asp Arg Lys Asn Arg Phe Lys Ala His Lys Ser
545                 550                 555                 560

Ile Ile Arg Ser Gln Glu Asn Ile Glu Tyr Asn Val Ala Phe Asp Lys
                565                 570                 575

Ser Thr Asn Phe Asp Val Thr Arg Lys Asn Gly Glu Phe Phe Ile Thr
                580                 585                 590

Ile Ser Ser Arg Val Ala Thr Pro Lys Tyr Ser Tyr Lys Leu Asn Ile
                595                 600                 605

Gly Asp Met Ile Met Gly Leu Asp Asn Asn Gln Thr Ala Pro Cys Thr
    610                 615                 620

Tyr Ser Ile Trp Arg Val Val Glu Lys Asp Thr Glu Gly Ser Phe Phe
625                 630                 635                 640

His Asn Lys Ile Trp Leu Gln Leu Val Thr Asp Gly Lys Val Thr Ser
                645                 650                 655

Ile Val Asp Asn Asn Arg Gln Val Asp Gln Leu Ser Tyr Ala Gly Ile
                660                 665                 670

Glu Tyr Ser Asn Phe Ala Glu Trp Arg Lys Asp Arg Arg Gln Phe Leu
                675                 680                 685

Arg Ser Ile Asn Glu Asp Tyr Val Lys Lys Ser Asp Asn Trp Arg Asn
    690                 695                 700

Met Asn Leu Tyr Gln Trp Asn Ala Glu Tyr Ser Arg Leu Leu Leu Asp
705                 710                 715                 720

Val Met Lys Glu Asn Lys Gly Lys Asn Ile Gln Asn Thr Phe Arg Ala
                725                 730                 735

Glu Ile Glu Glu Leu Ile Cys Gly Lys Phe Gly Ile Arg Leu Gly Ser
                740                 745                 750

Leu Phe His His Ser Leu Gln Phe Leu Thr Asn Cys Lys Ser Leu Ile
                755                 760                 765

Ser Ser Tyr Phe Met Leu Asn Asn Lys Lys Glu Glu Tyr Asp Gln Glu
    770                 775                 780

Leu Phe Asp Ser Asp Phe Phe Arg Leu Met Lys Ser Ile Gly Asp Lys
785                 790                 795                 800

Arg Val Arg Lys Arg Lys Glu Lys Ser Ser Arg Ile Ser Ser Thr Val
                805                 810                 815

Leu Gln Ile Ala Arg Glu Asn Asn Val Lys Ser Leu Cys Val Glu Gly
```

```
                    820                 825                 830

Tyr Leu Pro Thr Ser Thr Lys Lys Thr Lys Pro Lys Gln Asn Gln Lys
        835                 840                 845

Ser Ile Asp Trp Cys Ala Arg Ala Val Val Lys Lys Leu Asn Asp Gly
    850                 855                 860

Cys Lys Val Leu Gly Ile Asn Leu Gln Ala Ile Asp Pro Arg Asp Thr
865                 870                 875                 880

Ser His Leu Asp Pro Phe Val Tyr Tyr Gly Lys Lys Ser Thr Lys Val
                885                 890                 895

Gly Lys Glu Ala Arg Tyr Thr Ile Val Glu Pro Ser Asn Ile Lys Glu
        900                 905                 910

Tyr Met Thr Asn Arg Phe Asp Asp Trp His Arg Gly Val Thr Lys Lys
        915                 920                 925

Ser Lys Lys Gly Asp Val Gln Thr Ser Thr Thr Val Leu Leu Tyr Gln
    930                 935                 940

Glu Ala Leu Arg Gln Phe Ala Ser His Tyr Lys Leu Asp Phe Asp Ser
945                 950                 955                 960

Leu Pro Lys Met Lys Phe Tyr Glu Leu Ala Lys Ile Leu Gly Asp His
                965                 970                 975

Glu Lys Val Ile Ile Pro Cys Arg Gly Gly Arg Ala Tyr Leu Ser Thr
            980                 985                 990

Tyr Pro Val Thr Lys Asp Ser Ser  Lys Ile Thr Phe Asn  Gly Arg Glu
        995                 1000                1005

Arg Trp  Tyr Asn Glu Ser Asp  Val Val Ala Ala Val  Asn Ile Val
    1010                1015                1020

Leu Arg  Gly Ile Ile Asp Glu  Asp Glu Gln Pro Asp  Gly Ala Lys
    1025                1030                1035

Lys Gln  Ala Leu Ala Arg Thr  Lys
    1040                1045
```

```
<210> SEQ ID NO 2
<211> LENGTH: 1091
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Phe Thr Leu Leu Leu Ser Asp Ile Ser Gln Gln Asn Phe Asn Lys
1               5                   10                  15

Phe Leu Lys Asn Phe Phe Phe Thr Arg Asn Lys Thr Val Val His Cys
            20                  25                  30

Ser Ser Glu Ile Arg His Lys Gly Tyr Arg Ser Asn Val Met Val Ser
        35                  40                  45

Glu Ser Thr Ile Arg Pro Tyr Thr Ser Lys Leu Ala Pro Asn Asp Pro
    50                  55                  60

Lys Leu Lys Met Leu Asn Asp Thr Phe Asn Trp Leu Asp His Ala Tyr
65                  70                  75                  80

Lys Val Phe Phe Asp Val Ser Val Ala Leu Phe Gly Ala Ile Glu His
                85                  90                  95

Glu Thr Ala Gln Glu Leu Ile Gly Glu Lys Ser Lys Phe Asp Ala Asp
            100                 105                 110

Leu Leu Cys Ala Ile Met Trp Phe Arg Leu Glu Glu Lys Ser Asp Asn
        115                 120                 125
```

```
Pro Gly Pro Leu Gln Thr Val Glu Gln Arg Met Arg Leu Phe Gln Lys
    130                 135                 140

Tyr Ser Gly His Glu Pro Ser Ser Phe Thr Gln Glu Tyr Ile Lys Gly
145                 150                 155                 160

Asn Ile Asp Ser Glu Lys Tyr Gln Trp Val Asp Cys Arg Leu Lys Phe
                165                 170                 175

Ile Asp Leu Ala Arg Asn Ile Asn Thr Thr Gln Glu Ser Leu Lys Ile
            180                 185                 190

Asp Ala Tyr Thr Leu Phe Met Asn Lys Leu Ile Pro Val Ser Lys Asp
            195                 200                 205

Asp Glu Phe Asn Ala Tyr Gly Leu Ile Ser Gln Leu Phe Gly Thr Gly
    210                 215                 220

Lys Lys Glu Asp Arg Ser Ile Lys Ala Ser Met Leu Glu Glu Ile Ser
225                 230                 235                 240

Asn Ile Ile Glu Asp Lys Lys Pro Asn Thr Trp Glu Glu Tyr His Asp
                245                 250                 255

Leu Ile Lys Lys Thr Phe Asn Val Asp Asn Tyr Lys Glu Leu Lys Glu
            260                 265                 270

Lys Leu Ser Ala Gly Ser Ser Gly Arg Asp Ser Ser Leu Val Ile Asp
            275                 280                 285

Leu Lys Glu Glu Lys Thr Gly Leu Leu Gln Pro Asn Phe Ile Lys Asn
    290                 295                 300

Arg Ile Val Lys Phe Arg Glu Asp Ala Asp Lys Lys Arg Thr Val Phe
305                 310                 315                 320

Leu Leu Pro Asn Arg Met Lys Leu Arg Glu Phe Ile Ala Ser Gln Ile
                325                 330                 335

Gly Pro Phe Glu Gln Asn Ser Trp Ser Ala Val Leu Asn Arg Ser Met
            340                 345                 350

Ala Ala Ile Gln Ser Lys Asn Ser Ser Asn Ile Leu Tyr Thr Asn Glu
            355                 360                 365

Lys Glu Glu Arg Asn Asn Glu Ile Gln Glu Leu Leu Lys Lys Asp Ile
    370                 375                 380

Leu Ser Ala Ala Ser Ile Leu Gly Asp Phe Arg Arg Gly Glu Phe Asn
385                 390                 395                 400

Arg Ser Val Val Ser Lys Asn His Leu Gly Ala Arg Leu Asn Glu Leu
                405                 410                 415

Phe Glu Ile Trp Gln Glu Leu Thr Met Asp Asp Gly Ile Lys Lys Tyr
            420                 425                 430

Val Asp Leu Cys Lys Asp Lys Phe Ser Arg Arg Pro Val Lys Ala Leu
            435                 440                 445

Leu Gln Tyr Ile Tyr Pro Tyr Phe Asp Lys Ile Asn Ala Lys Gln Phe
    450                 455                 460

Leu Asp Ala Ala Ser Tyr Asn Thr Leu Val Glu Thr Asn Asn Arg Lys
465                 470                 475                 480

Lys Ile His Pro Thr Val Thr Gly Pro Thr Val Cys Asn Trp Gly Pro
                485                 490                 495

Lys Ser Thr Ile Asn Gly Ser Ile Thr Pro Pro Asn Gln Met Val Lys
            500                 505                 510

Gly Arg Pro Ala Gly Ser His Gly Met Ile Trp Val Thr Met Thr Val
            515                 520                 525

Ile Asp Asn Gly Arg Trp Ile Lys His His Leu Pro Phe His Asn Ser
    530                 535                 540
```

```
Arg Tyr Tyr Glu Glu His Tyr Cys Tyr Arg Glu Gly Leu Pro Thr Lys
545             550             555             560

Asn Lys Pro Arg Thr Lys Gln Leu Gly Thr Gln Val Gly Ser Thr Ile
                565             570             575

Ser Ala Pro Ser Leu Ala Ile Leu Lys Ser Gln Glu Glu Gln Asp Arg
                580             585             590

Arg Asn Asp Arg Lys Asn Arg Phe Lys Ala His Lys Ser Ile Ile Arg
                595             600             605

Ser Gln Glu Asn Ile Glu Tyr Asn Val Ala Phe Asp Lys Ser Thr Asn
        610             615             620

Phe Asp Val Thr Arg Lys Asn Gly Glu Phe Phe Ile Thr Ile Ser Ser
625             630             635             640

Arg Val Ala Thr Pro Lys Tyr Ser Tyr Lys Leu Asn Ile Gly Asp Met
                645             650             655

Ile Met Gly Leu Asp Asn Asn Gln Thr Ala Pro Cys Thr Tyr Ser Ile
                660             665             670

Trp Arg Val Val Glu Lys Asp Thr Glu Gly Ser Phe Phe His Asn Lys
        675             680             685

Ile Trp Leu Gln Leu Val Thr Asp Gly Lys Val Thr Ser Ile Val Asp
        690             695             700

Asn Asn Arg Gln Val Asp Gln Leu Ser Tyr Ala Gly Ile Glu Tyr Ser
705             710             715             720

Asn Phe Ala Glu Trp Arg Lys Asp Arg Arg Gln Phe Leu Arg Ser Ile
                725             730             735

Asn Glu Asp Tyr Val Lys Lys Ser Asp Asn Trp Arg Asn Met Asn Leu
                740             745             750

Tyr Gln Trp Asn Ala Glu Tyr Ser Arg Leu Leu Leu Asp Val Met Lys
        755             760             765

Glu Asn Lys Gly Lys Asn Ile Gln Asn Thr Phe Arg Ala Glu Ile Glu
        770             775             780

Glu Leu Ile Cys Gly Lys Phe Gly Ile Arg Leu Gly Ser Leu Phe His
785             790             795             800

His Ser Leu Gln Phe Leu Thr Asn Cys Lys Ser Leu Ile Ser Ser Tyr
                805             810             815

Phe Met Leu Asn Asn Lys Lys Glu Glu Tyr Asp Gln Glu Leu Phe Asp
                820             825             830

Ser Asp Phe Phe Arg Leu Met Lys Ser Ile Gly Asp Lys Arg Val Arg
                835             840             845

Lys Arg Lys Glu Lys Ser Ser Arg Ile Ser Ser Thr Val Leu Gln Ile
        850             855             860

Ala Arg Glu Asn Asn Val Lys Ser Leu Cys Val Glu Gly Tyr Leu Pro
865             870             875             880

Thr Ser Thr Lys Lys Thr Lys Pro Lys Gln Asn Gln Lys Ser Ile Asp
                885             890             895

Trp Cys Ala Arg Ala Val Val Lys Lys Leu Asn Asp Gly Cys Lys Val
                900             905             910

Leu Gly Ile Asn Leu Gln Ala Ile Asp Pro Arg Asp Thr Ser His Leu
        915             920             925

Asp Pro Phe Val Tyr Tyr Gly Lys Lys Ser Thr Lys Val Gly Lys Glu
        930             935             940

Ala Arg Tyr Thr Ile Val Glu Pro Ser Asn Ile Lys Glu Tyr Met Thr
945             950             955             960

Asn Arg Phe Asp Asp Trp His Arg Gly Val Thr Lys Lys Ser Lys Lys
```

```
                   965              970              975
Gly Asp Val Gln Thr Ser Thr Thr Val Leu Leu Tyr Gln Glu Ala Leu
            980              985              990

Arg Gln Phe Ala Ser His Tyr Lys  Leu Asp Phe Asp Ser  Leu Pro Lys
        995              1000             1005

Met Lys  Phe Tyr Glu Leu Ala  Lys Ile Leu Gly Asp  His Glu Lys
    1010             1015             1020

Val Ile  Ile Pro Cys Arg Gly  Gly Arg Ala Tyr Leu  Ser Thr Tyr
    1025             1030             1035

Pro Val  Thr Lys Asp Ser Ser  Lys Ile Thr Phe Asn  Gly Arg Glu
    1040             1045             1050

Arg Trp  Tyr Asn Glu Ser Asp  Val Val Ala Ala Val  Asn Ile Val
    1055             1060             1065

Leu Arg  Gly Ile Ile Asp Glu  Asp Glu Gln Pro Asp  Gly Ala Lys
    1070             1075             1080

Lys Gln  Ala Leu Ala Arg Thr  Lys
    1085             1090

<210> SEQ ID NO 3
<211> LENGTH: 1093
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Ser Asn Lys Glu Lys Asn Ala Ser Glu Thr Arg Lys Ala Tyr Thr
1               5               10              15

Thr Lys Met Ile Pro Arg Ser His Asp Arg Met Lys Leu Leu Gly Asn
            20              25              30

Phe Met Asp Tyr Leu Met Asp Gly Thr Pro Ile Phe Phe Glu Leu Trp
        35              40              45

Asn Gln Phe Gly Gly Gly Ile Asp Arg Asp Ile Ile Ser Gly Thr Ala
    50              55              60

Asn Lys Asp Lys Ile Ser Asp Asp Leu Leu Leu Ala Val Asn Trp Phe
65              70              75              80

Lys Val Met Pro Ile Asn Ser Lys Pro Gln Gly Val Ser Pro Ser Asn
            85              90              95

Leu Ala Asn Leu Phe Gln Gln Tyr Ser Gly Ser Glu Pro Asp Ile Gln
            100             105             110

Ala Gln Glu Tyr Phe Ala Ser Asn Phe Asp Thr Glu Lys His Gln Trp
        115             120             125

Lys Asp Met Arg Val Glu Tyr Glu Arg Leu Leu Ala Glu Leu Gln Leu
    130             135             140

Ser Arg Ser Asp Met His His Asp Leu Lys Leu Met Tyr Lys Glu Lys
145             150             155             160

Cys Ile Gly Leu Ser Leu Ser Thr Ala His Tyr Ile Thr Ser Val Met
            165             170             175

Phe Gly Thr Gly Ala Lys Asn Asn Arg Gln Thr Lys His Gln Phe Tyr
            180             185             190

Ser Lys Val Ile Gln Leu Leu Glu Glu Ser Thr Gln Ile Asn Ser Val
        195             200             205

Glu Gln Leu Ala Ser Ile Ile Leu Lys Ala Gly Asp Cys Asp Ser Tyr
    210             215             220
```

-continued

```
Arg Lys Leu Arg Ile Arg Cys Ser Arg Lys Gly Ala Thr Pro Ser Ile
225             230             235             240

Leu Lys Ile Val Gln Asp Tyr Glu Leu Gly Thr Asn His Asp Asp Glu
            245             250             255

Val Asn Val Pro Ser Leu Ile Ala Asn Leu Lys Glu Lys Leu Gly Arg
            260             265             270

Phe Glu Tyr Glu Cys Glu Trp Lys Cys Met Glu Lys Ile Lys Ala Phe
            275             280             285

Leu Ala Ser Lys Val Gly Pro Tyr Tyr Leu Gly Ser Tyr Ser Ala Met
            290             295             300

Leu Glu Asn Ala Leu Ser Pro Ile Lys Gly Met Thr Thr Lys Asn Cys
305             310             315             320

Lys Phe Val Leu Lys Gln Ile Asp Ala Lys Asn Asp Ile Lys Tyr Glu
            325             330             335

Asn Glu Pro Phe Gly Lys Ile Val Glu Gly Phe Phe Asp Ser Pro Tyr
            340             345             350

Phe Glu Ser Asp Thr Asn Val Lys Trp Val Leu His Pro His His Ile
            355             360             365

Gly Glu Ser Asn Ile Lys Thr Leu Trp Glu Asp Leu Asn Ala Ile His
    370             375             380

Ser Lys Tyr Glu Glu Asp Ile Ala Ser Leu Ser Glu Asp Lys Lys Glu
385             390             395             400

Lys Arg Ile Lys Val Tyr Gln Gly Asp Val Cys Gln Thr Ile Asn Thr
            405             410             415

Tyr Cys Glu Glu Val Gly Lys Glu Ala Lys Thr Pro Leu Val Gln Leu
            420             425             430

Leu Arg Tyr Leu Tyr Ser Arg Lys Asp Asp Ile Ala Val Asp Lys Ile
            435             440             445

Ile Asp Gly Ile Thr Phe Leu Ser Lys Lys His Lys Val Glu Lys Gln
    450             455             460

Lys Ile Asn Pro Val Ile Gln Lys Tyr Pro Ser Phe Asn Phe Gly Asn
465             470             475             480

Asn Ser Lys Leu Leu Gly Lys Ile Ile Ser Pro Lys Asp Lys Leu Lys
            485             490             495

His Asn Leu Lys Cys Asn Arg Asn Gln Val Asp Asn Tyr Ile Trp Ile
            500             505             510

Glu Ile Lys Val Leu Asn Thr Lys Thr Met Arg Trp Glu Lys His His
    515             520             525

Tyr Ala Leu Ser Ser Thr Arg Phe Leu Glu Glu Val Tyr Tyr Pro Ala
    530             535             540

Thr Ser Glu Asn Pro Pro Asp Ala Leu Ala Ala Arg Phe Arg Thr Lys
545             550             555             560

Thr Asn Gly Tyr Glu Gly Lys Pro Ala Leu Ser Ala Glu Gln Ile Glu
            565             570             575

Gln Ile Arg Ser Ala Pro Val Gly Leu Arg Lys Val Lys Lys Arg Gln
            580             585             590

Met Arg Leu Glu Ala Ala Arg Gln Gln Asn Leu Leu Pro Arg Tyr Thr
    595             600             605

Trp Gly Lys Asp Phe Asn Ile Asn Ile Cys Lys Arg Gly Asn Asn Phe
    610             615             620

Glu Val Thr Leu Ala Thr Lys Val Lys Lys Lys Glu Lys Asn Tyr
625             630             635             640
```

-continued

```
Lys Val Val Leu Gly Tyr Asp Ala Asn Ile Val Arg Lys Asn Thr Tyr
              645                 650                 655

Ala Ala Ile Glu Ala His Ala Asn Gly Asp Gly Val Ile Asp Tyr Asn
              660                 665                 670

Asp Leu Pro Val Lys Pro Ile Glu Ser Gly Phe Val Thr Val Glu Ser
              675                 680                 685

Gln Val Arg Asp Lys Ser Tyr Asp Gln Leu Ser Tyr Asn Gly Val Lys
      690                 695                 700

Leu Leu Tyr Cys Lys Pro His Val Glu Ser Arg Arg Ser Phe Leu Glu
705                 710                 715                 720

Lys Tyr Arg Asn Gly Thr Met Lys Asp Asn Arg Gly Asn Asn Ile Gln
              725                 730                 735

Ile Asp Phe Met Lys Asp Phe Glu Ala Ile Ala Asp Asp Glu Thr Ser
              740                 745                 750

Leu Tyr Tyr Phe Asn Met Lys Tyr Cys Lys Leu Leu Gln Ser Ser Ile
              755                 760                 765

Arg Asn His Ser Ser Gln Ala Lys Glu Tyr Arg Glu Glu Ile Phe Glu
      770                 775                 780

Leu Leu Arg Asp Gly Lys Leu Ser Val Leu Lys Leu Ser Ser Leu Ser
785                 790                 795                 800

Asn Leu Ser Phe Val Met Phe Lys Val Ala Lys Ser Leu Ile Gly Thr
              805                 810                 815

Tyr Phe Gly His Leu Leu Lys Lys Pro Lys Asn Ser Lys Ser Asp Val
              820                 825                 830

Lys Ala Pro Pro Ile Thr Asp Glu Asp Lys Gln Lys Ala Asp Pro Glu
              835                 840                 845

Met Phe Ala Leu Arg Leu Ala Leu Glu Glu Lys Arg Leu Asn Lys Val
      850                 855                 860

Lys Ser Lys Lys Glu Val Ile Ala Asn Lys Ile Val Ala Lys Ala Leu
865                 870                 875                 880

Glu Leu Arg Asp Lys Tyr Gly Pro Val Leu Ile Lys Gly Glu Asn Ile
              885                 890                 895

Ser Asp Thr Thr Lys Lys Gly Lys Lys Ser Ser Thr Asn Ser Phe Leu
              900                 905                 910

Met Asp Trp Leu Ala Arg Gly Val Ala Asn Lys Val Lys Glu Met Val
              915                 920                 925

Met Met His Gln Gly Leu Glu Phe Val Glu Val Asn Pro Asn Phe Thr
      930                 935                 940

Ser His Gln Asp Pro Phe Val His Lys Asn Pro Glu Asn Thr Phe Arg
945                 950                 955                 960

Ala Arg Tyr Ser Arg Cys Thr Pro Ser Glu Leu Thr Glu Lys Asn Arg
              965                 970                 975

Lys Glu Ile Leu Ser Phe Leu Ser Asp Lys Pro Ser Lys Arg Pro Thr
              980                 985                 990

Asn Ala Tyr Tyr Asn Glu Gly Ala  Met Ala Phe Leu Ala  Thr Tyr Gly
              995                 1000                 1005

Leu Lys  Lys Asn Asp Val Leu  Gly Val Ser Leu Glu  Lys Phe Lys
      1010                 1015                 1020

Gln Ile  Met Ala Asn Ile Leu  His Gln Arg Ser Glu  Asp Gln Leu
      1025                 1030                 1035

Leu Phe  Pro Ser Arg Gly Gly  Met Phe Tyr Leu Ala  Thr Tyr Lys
      1040                 1045                 1050

Leu Asp  Ala Asp Ala Thr Ser  Val Asn Trp Asn Gly  Lys Gln Phe
```

-continued

```
          1055                1060                1065

Trp Val  Cys Asn Ala Asp Leu  Val Ala Ala Tyr Asn  Val Gly Leu
          1070                1075                1080

Val Asp  Ile Gln Lys Asp Phe  Lys Lys Lys
          1085                1090
```

```
<210> SEQ ID NO 4
<211> LENGTH: 1033
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Met Ser Asp Asn Ile Ile Leu Pro Tyr Asn Ser Lys Leu Ala Pro
1               5                   10                  15

Asp Glu Arg Lys Gln Arg Leu Leu Asn Asp Thr Phe Asn Trp Phe Asp
            20                  25                  30

Met Cys Asn Glu Val Phe Phe Asp Phe Val Lys Asn Leu Tyr Gly Gly
            35                  40                  45

Val Lys His Glu His Leu Ile Leu Val Asn Phe Ala Glu Lys Pro Lys
        50                  55                  60

Lys Val Ser Asn Ser Lys Lys Pro Lys Lys Asp Gln Glu Val Asn
65                  70                  75                  80

Ile His Val Glu Pro Asn Gln Ala Glu Trp Val Asp Asn Ala Cys Ala
                85                  90                  95

Thr Phe Trp Phe Arg Leu Gln Ala Lys Ser Thr Val Gln Leu Asp Gln
            100                 105                 110

Ser Val Gln Thr Ala Glu Glu Arg Ile Arg Arg Phe Arg Asp Tyr Ala
            115                 120                 125

Gly His Glu Pro Ser Ser Phe Ala Lys Ser Tyr Leu Asn Gly Asn Tyr
        130                 135                 140

Asp Pro Glu Lys Thr Glu Trp Val Asp Cys Arg Leu Leu Tyr Val Asn
145                 150                 155                 160

Phe Cys Arg Asn Leu Asn Val Asn Leu Asp Ala Asp Ile Arg Thr Met
                165                 170                 175

Val Glu His Asn Leu Leu Pro Val Leu Pro Gly Gln Asp Phe Lys Thr
            180                 185                 190

Asn Asn Val Phe Ser Asn Ile Phe Gly Val Gly Asn Lys Glu Asp Lys
            195                 200                 205

Gly Gln Lys Thr Asn Trp Leu Asn Thr Val Ser Glu Gly Leu Gln Ser
        210                 215                 220

Lys Glu Ile Trp Asn Trp Asp Glu Tyr Arg Asp Leu Ile Ser Arg Ser
225                 230                 235                 240

Thr Gly Cys Ser Thr Ala Ala Glu Leu Arg Ser Glu Ser Ile Gly Arg
                245                 250                 255

Pro Ser Met Leu Ala Val Asp Phe Ala Ser Glu Lys Ser Gly Gln Ile
            260                 265                 270

Ser Gln Glu Trp Leu Ala Glu Arg Val Lys Ser Phe Arg Ala Ala Ala
            275                 280                 285

Ser Gln Lys Ser Lys Ile Tyr Asp Met Pro Asn Arg Leu Val Leu Lys
        290                 295                 300

Glu Tyr Ile Ala Ser Lys Ile Gly Pro Phe Lys Leu Glu Arg Trp Ser
305                 310                 315                 320
```

```
Ala Ala Ala Val Ser Ala Tyr Lys Asp Val Arg Ser Lys Asn Ser Ile
            325             330             335

Asn Leu Leu Tyr Ser Lys Glu Arg Leu Trp Arg Cys Lys Glu Ile Ala
            340             345             350

Gln Ile Leu Val Asp Asn Thr Gln Val Ala Glu Ala Gln Gln Ile Leu
            355             360             365

Val Asn Tyr Ser Ser Gly Asp Thr Asn Ser Phe Thr Val Glu Asn Arg
            370             375             380

His Met Gly Asp Leu Thr Val Leu Phe Lys Ile Trp Glu Lys Met Asp
385             390             395             400

Met Asp Ser Gly Ile Glu Gln Tyr Ser Glu Ile Tyr Arg Asp Glu Tyr
            405             410             415

Ser Arg Asp Pro Ile Thr Glu Leu Leu Arg Tyr Leu Tyr Asn His Arg
            420             425             430

His Ile Ser Ala Lys Thr Phe Arg Ala Ala Ala Arg Leu Asn Ser Leu
            435             440             445

Leu Leu Lys Asn Asp Arg Lys Lys Ile His Pro Thr Ile Ser Gly Arg
            450             455             460

Thr Ser Val Ser Phe Gly His Ser Thr Ile Lys Gly Cys Ile Thr Pro
465             470             475             480

Pro Asp His Ile Val Lys Asn Arg Lys Glu Asn Ala Gly Ser Thr Gly
            485             490             495

Met Ile Trp Val Thr Met Gln Leu Ile Asp Asn Gly Arg Trp Ala Asp
            500             505             510

His His Ile Pro Phe His Asn Ser Arg Tyr Tyr Arg Asp Phe Tyr Ala
            515             520             525

Tyr Arg Ala Asp Leu Pro Thr Ile Ser Asp Pro Arg Arg Lys Ser Phe
            530             535             540

Gly His Arg Ile Gly Asn Asn Ile Ser Asp Thr Arg Met Ile Asn His
545             550             555             560

Asp Cys Lys Lys Ala Ser Lys Met Tyr Leu Arg Thr Ile Gln Asn Met
            565             570             575

Thr His Asn Val Ala Phe Asp Gln Gln Thr Gln Phe Ala Val Arg Arg
            580             585             590

Tyr Ala Asp Asn Asn Phe Thr Ile Thr Ile Gln Ala Arg Val Val Gly
            595             600             605

Arg Lys Tyr Lys Lys Glu Ile Ser Val Gly Asp Arg Val Met Gly Val
            610             615             620

Asp Gln Asn Gln Thr Thr Ser Asn Thr Tyr Ser Val Trp Glu Val Val
625             630             635             640

Ala Glu Gly Thr Glu Asn Ser Tyr Pro Tyr Lys Gly Asn Asn Tyr Arg
            645             650             655

Leu Val Glu Asp Gly Phe Ile Arg Ser Glu Cys Ser Gly Arg Asp Gln
            660             665             670

Leu Ser Tyr Asp Gly Leu Asp Phe Gln Asp Phe Ala Gln Trp Arg Arg
            675             680             685

Glu Arg Tyr Ala Phe Leu Ser Ser Val Gly Cys Ile Leu Asn Asp Glu
            690             695             700

Ile Glu Pro Gln Ile Pro Val Ser Ala Glu Lys Ala Lys Lys Lys Lys
705             710             715             720

Lys Phe Ser Lys Trp Arg Gly Cys Ser Leu Tyr Ser Trp Asn Leu Cys
            725             730             735
```

```
Tyr Ala Tyr Tyr Leu Lys Gly Leu Met His Glu Asn Leu Ala Asn Asn
            740                 745                 750

Pro Ala Gly Phe Arg Gln Glu Ile Leu Asn Phe Ile Gln Gly Ser Arg
            755                 760                 765

Gly Val Arg Leu Cys Ser Leu Asn His Thr Ser Phe Arg Leu Leu Ser
            770                 775                 780

Lys Ala Lys Ser Leu Ile His Ser Phe Phe Gly Leu Asn Asn Ile Lys
785                 790                 795                 800

Asp Pro Glu Ser Gln Arg Asp Phe Asp Pro Glu Ile Tyr Asp Ile Met
                805                 810                 815

Val Asn Leu Thr Gln Arg Lys Thr Asn Lys Arg Lys Glu Lys Ala Asn
            820                 825                 830

Arg Ile Thr Ser Ser Ile Leu Gln Ile Ala Asn Arg Leu Asn Val Ser
            835                 840                 845

Arg Ile Val Ile Glu Asn Asp Leu Pro Asn Ala Ser Ser Lys Asn Lys
            850                 855                 860

Ala Ser Ala Asn Gln Arg Ala Thr Asp Trp Cys Ala Arg Asn Val Ser
865                 870                 875                 880

Glu Lys Leu Glu Tyr Ala Cys Lys Met Leu Gly Ile Ser Leu Trp Gln
                885                 890                 895

Ile Asp Pro Arg Asp Thr Ser His Leu Asp Pro Phe Val Val Gly Lys
                900                 905                 910

Glu Ala Arg Phe Met Lys Ile Lys Val Ser Asp Ile Asn Glu Tyr Thr
            915                 920                 925

Ile Ser Asn Phe Lys Lys Trp His Ala Asn Ile Ala Thr Thr Ser Thr
            930                 935                 940

Thr Ala Pro Leu Tyr His Asp Ala Leu Lys Ala Phe Ser Ser His Tyr
945                 950                 955                 960

Gly Ile Asp Trp Asp Asn Leu Pro Glu Met Lys Phe Trp Glu Leu Lys
                965                 970                 975

Asn Ala Leu Lys Asp His Lys Glu Val Phe Ile Pro Asn Arg Gly Gly
            980                 985                 990

Arg Cys Tyr Leu Ser Thr Leu Pro  Val Thr Ser Thr Ser  Glu Lys Ile
            995                 1000                1005

Val Phe  Asn Gly Arg Glu Arg  Trp Leu Asn Ala Ser  Asp Ile Val
    1010                1015                1020

Ala Gly  Val Asn Ile Val Leu  Arg Ser Val
    1025                1030
```

<210> SEQ ID NO 5
<211> LENGTH: 1054
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Met Ser Ser Ala Ile Lys Ser Tyr Lys Ser Val Leu Arg Pro Asn Glu
1                   5                   10                  15

Arg Lys Asn Gln Leu Leu Lys Ser Thr Ile Gln Cys Leu Glu Asp Gly
                20                  25                  30

Ser Ala Phe Phe Phe Lys Met Leu Gln Gly Leu Phe Gly Gly Ile Thr
            35                  40                  45

Pro Glu Ile Val Arg Phe Ser Thr Glu Gln Glu Lys Gln Gln Gln Asp
```

-continued

```
             50                   55                   60

Ile Ala Leu Trp Cys Ala Val Asn Trp Phe Arg Pro Val Ser Gln Asp
65                   70                   75                   80

Ser Leu Thr His Thr Ile Ala Ser Asp Asn Leu Val Glu Lys Phe Glu
                85                   90                   95

Glu Tyr Tyr Gly Gly Thr Ala Ser Asp Ala Ile Lys Gln Tyr Phe Ser
                100                  105                  110

Ala Ser Ile Gly Glu Ser Tyr Tyr Trp Asn Asp Cys Arg Gln Gln Tyr
                115                  120                  125

Tyr Asp Leu Cys Arg Glu Leu Gly Val Glu Val Ser Asp Leu Thr His
        130                  135                  140

Asp Leu Glu Ile Leu Cys Arg Glu Lys Cys Leu Ala Val Ala Thr Glu
145                  150                  155                  160

Ser Asn Gln Asn Asn Ser Ile Ile Ser Val Leu Phe Gly Thr Gly Glu
                165                  170                  175

Lys Glu Asp Arg Ser Val Lys Leu Arg Ile Thr Lys Lys Ile Leu Glu
                180                  185                  190

Ala Ile Ser Asn Leu Lys Glu Ile Pro Lys Asn Val Ala Pro Ile Gln
                195                  200                  205

Glu Ile Ile Leu Asn Val Ala Lys Ala Thr Lys Glu Thr Phe Arg Gln
        210                  215                  220

Val Tyr Ala Gly Asn Leu Gly Ala Pro Ser Thr Leu Glu Lys Phe Ile
225                  230                  235                  240

Ala Lys Asp Gly Gln Lys Glu Phe Asp Leu Lys Lys Leu Gln Thr Asp
                245                  250                  255

Leu Lys Lys Val Ile Arg Gly Lys Ser Lys Glu Arg Asp Trp Cys Cys
                260                  265                  270

Gln Glu Glu Leu Arg Ser Tyr Val Glu Gln Asn Thr Ile Gln Tyr Asp
        275                  280                  285

Leu Trp Ala Trp Gly Glu Met Phe Asn Lys Ala His Thr Ala Leu Lys
        290                  295                  300

Ile Lys Ser Thr Arg Asn Tyr Asn Phe Ala Lys Gln Arg Leu Glu Gln
305                  310                  315                  320

Phe Lys Glu Ile Gln Ser Leu Asn Asn Leu Leu Val Val Lys Lys Leu
                325                  330                  335

Asn Asp Phe Phe Asp Ser Glu Phe Phe Ser Gly Glu Glu Thr Tyr Thr
                340                  345                  350

Ile Cys Val His His Leu Gly Gly Lys Asp Leu Ser Lys Leu Tyr Lys
                355                  360                  365

Ala Trp Glu Asp Asp Pro Ala Asp Pro Glu Asn Ala Ile Val Val Leu
        370                  375                  380

Cys Asp Asp Leu Lys Asn Asn Phe Lys Lys Glu Pro Ile Arg Asn Ile
385                  390                  395                  400

Leu Arg Tyr Ile Phe Thr Ile Arg Gln Glu Cys Ser Ala Gln Asp Ile
                405                  410                  415

Leu Ala Ala Ala Lys Tyr Asn Gln Gln Leu Asp Arg Tyr Lys Ser Gln
                420                  425                  430

Lys Ala Asn Pro Ser Val Leu Gly Asn Gln Gly Phe Thr Trp Thr Asn
                435                  440                  445

Ala Val Ile Leu Pro Glu Lys Ala Gln Arg Asn Asp Arg Pro Asn Ser
        450                  455                  460

Leu Asp Leu Arg Ile Trp Leu Tyr Leu Lys Leu Arg His Pro Asp Gly
465                  470                  475                  480
```

-continued

```
Arg Trp Lys Lys His His Ile Pro Phe Tyr Asp Thr Arg Phe Phe Gln
            485             490             495

Glu Ile Tyr Ala Ala Gly Asn Ser Pro Val Asp Thr Cys Gln Phe Arg
            500             505             510

Thr Pro Arg Phe Gly Tyr His Leu Pro Lys Leu Thr Asp Gln Thr Ala
            515             520             525

Ile Arg Val Asn Lys Lys His Val Lys Ala Ala Lys Thr Glu Ala Arg
    530             535             540

Ile Arg Leu Ala Ile Gln Gln Gly Thr Leu Pro Val Ser Asn Leu Lys
545             550             555             560

Ile Thr Glu Ile Ser Ala Thr Ile Asn Ser Lys Gly Gln Val Arg Ile
                565             570             575

Pro Val Lys Phe Asp Val Gly Arg Gln Lys Gly Thr Leu Gln Ile Gly
            580             585             590

Asp Arg Phe Cys Gly Tyr Asp Gln Asn Gln Thr Ala Ser His Ala Tyr
            595             600             605

Ser Leu Trp Glu Val Val Lys Glu Gly Gln Tyr His Lys Glu Leu Gly
    610             615             620

Cys Phe Val Arg Phe Ile Ser Ser Gly Asp Ile Val Ser Ile Thr Glu
625             630             635             640

Asn Arg Gly Asn Gln Phe Asp Gln Leu Ser Tyr Glu Gly Leu Ala Tyr
            645             650             655

Pro Gln Tyr Ala Asp Trp Arg Lys Lys Ala Ser Lys Phe Val Ser Leu
            660             665             670

Trp Gln Ile Thr Lys Lys Asn Lys Lys Glu Ile Val Thr Val Glu
            675             680             685

Ala Lys Glu Lys Phe Asp Ala Ile Cys Lys Tyr Gln Pro Arg Leu Tyr
            690             695             700

Lys Phe Asn Lys Glu Tyr Ala Tyr Leu Leu Arg Asp Ile Val Arg Gly
705             710             715             720

Lys Ser Leu Val Glu Leu Gln Gln Ile Arg Gln Glu Ile Phe Arg Phe
                725             730             735

Ile Glu Gln Asp Cys Gly Val Thr Arg Leu Gly Ser Leu Ser Leu Ser
            740             745             750

Thr Leu Glu Thr Val Lys Ala Val Lys Gly Ile Ile Tyr Ser Tyr Phe
            755             760             765

Ser Thr Ala Leu Asn Ala Ser Lys Asn Asn Pro Ile Ser Asp Glu Gln
    770             775             780

Arg Lys Glu Phe Asp Pro Glu Leu Phe Ala Leu Leu Glu Lys Leu Glu
785             790             795             800

Leu Ile Arg Thr Arg Lys Lys Lys Gln Lys Val Glu Arg Ile Ala Asn
            805             810             815

Ser Leu Ile Gln Thr Cys Leu Glu Asn Asn Ile Lys Phe Ile Arg Gly
            820             825             830

Glu Gly Asp Leu Ser Thr Thr Asn Asn Ala Thr Lys Lys Lys Ala Asn
            835             840             845

Ser Arg Ser Met Asp Trp Leu Ala Arg Gly Val Phe Asn Lys Ile Arg
    850             855             860

Gln Leu Ala Pro Met His Asn Ile Thr Leu Phe Gly Cys Gly Ser Leu
865             870             875             880

Tyr Thr Ser His Gln Asp Pro Leu Val His Arg Asn Pro Asp Lys Ala
                885             890             895
```

```
Met Lys Cys Arg Trp Ala Ala Ile Pro Val Lys Asp Ile Gly Asp Trp
            900                 905                 910

Val Leu Arg Lys Leu Ser Gln Asn Leu Arg Ala Lys Asn Ile Gly Thr
        915                 920                 925

Gly Glu Tyr Tyr His Gln Gly Val Lys Glu Phe Leu Ser His Tyr Glu
    930                 935                 940

Leu Gln Asp Leu Glu Glu Glu Leu Leu Lys Trp Arg Ser Asp Arg Lys
945                 950                 955                 960

Ser Asn Ile Pro Cys Trp Val Leu Gln Asn Arg Leu Ala Glu Lys Leu
                965                 970                 975

Gly Asn Lys Glu Ala Val Val Tyr Ile Pro Val Arg Gly Gly Arg Ile
            980                 985                 990

Tyr Phe Ala Thr His Lys Val Ala  Thr Gly Ala Val Ser  Ile Val Phe
        995                 1000                1005

Asp Gln  Lys Gln Val Trp Val  Cys Asn Ala Asp His  Val Ala Ala
    1010                1015                1020

Ala Asn  Ile Ala Leu Thr Val  Lys Gly Ile Gly Glu  Gln Ser Ser
    1025                1030                1035

Asp Glu  Glu Asn Pro Asp Gly  Ser Arg Ile Lys Leu  Gln Leu Thr
    1040                1045                1050

Ser
```

```
<210> SEQ ID NO 6
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
cccacaatac ctgagaaatc cgtcctacgt tgacgg                               36

<210> SEQ ID NO 7
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
aatttttgtg cccatcgttg gcac                                           24

<210> SEQ ID NO 8
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ctctcaatgc cttagaaatc cgtccttggt tgacgg                              36

<210> SEQ ID NO 9
<211> LENGTH: 34
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"

<400> SEQUENCE: 9
gcaacaccta agaaatccgt ctttcattga cggg                                    34

<210> SEQ ID NO 10
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
gttgcaaaac ccaagaaatc cgtctttcat tgacgg                                  36

<210> SEQ ID NO 11
<211> LENGTH: 1080
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Pro Arg Asn Tyr Phe Leu Gly Ile Phe Ser Leu Gln Lys Asn Lys
1               5                   10                  15

Ser Val Val His Cys Ser Val Glu Ile Arg His Lys Gly Tyr Arg Ser
            20                  25                  30

Ser Val Met Val Ser Asp Ser Thr Ile Arg Pro Tyr Ala Ser Lys Leu
        35                  40                  45

Ala Pro Asn Asp Pro Lys Leu Lys Met Leu Asn Asp Thr Phe Asn Trp
    50                  55                  60

Leu Asp His Ala Tyr Lys Val Phe Phe Asp Val Ser Val Ala Leu Phe
65                  70                  75                  80

Gly Ala Ile Glu His Glu Thr Ala Gln Glu Leu Ile Gly Glu Lys Ser
                85                  90                  95

Lys Phe Asp Ala Asp Leu Ile Cys Ala Ile Met Trp Phe Arg Leu Glu
            100                 105                 110

Glu Lys Ser Asp Asn Pro Gly Pro Leu Gln Thr Val Glu Gln Arg Met
            115                 120                 125

Arg Leu Phe Gln Lys Tyr Ser Gly His Glu Pro Ser Ser Phe Thr Gln
        130                 135                 140

Glu Tyr Ile Lys Gly Asn Ile Asp Ser Glu Lys Tyr Glu Trp Val Asp
145                 150                 155                 160

Cys Arg Leu Lys Phe Ile Asp Leu Ala Arg Asn Ile Asn Thr Thr Gln
                165                 170                 175

Glu Ser Leu Lys Ile Asp Ala Tyr Thr Leu Phe Met Asn Lys Leu Ile
            180                 185                 190

Pro Val Ser Lys Asp Asp Glu Phe Asn Ala Tyr Gly Leu Ile Ser Gln
            195                 200                 205

Leu Phe Gly Thr Gly Lys Lys Glu Asp Arg Ser Ile Lys Ala Ala Met
    210                 215                 220

Leu Glu Glu Ile Ser Asn Ile Leu Ala Asp Lys Lys Pro Asp Thr Trp
225                 230                 235                 240

-continued

```
Glu Glu Tyr His Asp Leu Ile Lys Lys Asn Phe Asn Val Asp Asn Tyr
            245             250             255

Lys Glu Leu Lys Glu Lys Leu Ser Ala Gly Ser Ser Gly Arg Asp Ser
            260             265             270

Ser Leu Val Ile Asp Leu Lys Glu Glu Lys Thr Gly Leu Leu Gln Pro
            275             280             285

Asn Phe Ile Lys Asn Arg Ile Val Lys Phe Arg Glu Asp Ala Asp Lys
            290             295             300

Lys Lys Thr Val Phe Leu Leu Pro Asn Arg Met Lys Leu Arg Glu Phe
305             310             315             320

Ile Ala Ser Gln Ile Gly Pro Phe Glu Gln Asn Ser Trp Ser Ala Val
            325             330             335

Leu Asn Arg Ser Met Ala Ala Ile Gln Ser Lys Asn Ser Ser Asn Ile
            340             345             350

Leu Tyr Thr Asn Glu Lys Glu Glu Arg Asn Asn Glu Ile Gln Glu Leu
            355             360             365

Leu Lys Lys Asp Ile Leu Ser Ala Ala Ser Ile Leu Gly Asp Phe Arg
            370             375             380

Arg Gly Glu Phe Asn Arg Ser Val Val Ser Lys Asn His Leu Gly Ala
385             390             395             400

Arg Leu Asn Glu Leu Phe Glu Ile Trp Gln Asp Leu Thr Met Asp Asp
            405             410             415

Gly Ile Arg Lys Tyr Val Asp Leu Cys Lys Asp Lys Phe Ser Arg Arg
            420             425             430

Pro Val Lys Ala Leu Leu Gln Tyr Ile Tyr Pro Tyr Phe Asp Lys Ile
            435             440             445

Thr Ala Lys Gln Phe Leu Asp Ala Ala Ser Tyr Asn Thr Leu Val Glu
            450             455             460

Thr Asn Asn Arg Lys Lys Ile His Pro Thr Val Thr Gly Pro Thr Val
465             470             475             480

Cys Asn Trp Gly Pro Lys Ser Thr Ile Asn Gly Ser Ile Thr Pro Pro
            485             490             495

Asn Gln Met Val Lys Gly Arg Pro Ala Gly Ser His Gly Met Ile Trp
            500             505             510

Val Thr Met Thr Val Ile Asp Asn Gly Arg Trp Ile Lys His His Leu
            515             520             525

Pro Phe Tyr Asn Ser Arg Tyr Tyr Glu Glu His Tyr Cys Tyr Arg Glu
            530             535             540

Gly Leu Pro Thr Lys Asn Gln Pro Arg Thr Lys Gln Leu Gly Thr Gln
545             550             555             560

Val Gly Ser Thr Ile Ser Ala Thr Ser Leu Ala Ala Leu Lys Ser Gln
            565             570             575

Glu Glu Gln Asp Arg Arg Asn Asp Arg Lys Asn Arg Phe Lys Ala His
            580             585             590

Lys Ser Ile Ile Arg Ser Gln Glu Asn Ile Glu Tyr Asn Val Ala Phe
            595             600             605

Asp Lys Ser Thr Asn Phe Asp Val Thr Arg Lys Asn Gly Glu Phe Phe
            610             615             620

Ile Thr Ile Ser Ser Arg Val Ala Thr Pro Lys Tyr Ser Tyr Lys Leu
625             630             635             640

Asn Ile Gly Asp Met Ile Met Gly Leu Asp Asn Asn Gln Thr Ala Pro
            645             650             655
```

```
Cys Thr Tyr Ser Ile Trp Arg Val Val Glu Lys Asp Thr Glu Gly Ser
            660             665                 670

Phe Phe His Asn Lys Ile Trp Leu Gln Leu Val Thr Asp Gly Lys Ile
        675             680                 685

Thr Ser Ile Val Asp Asn Asn Arg Gln Val Asp Gln Leu Ser Tyr Ala
        690             695             700

Gly Ile Glu Tyr Ser Asn Phe Ala Glu Trp Arg Lys Asp Arg Arg Gln
705             710             715                 720

Phe Leu Arg Ser Ile Asn Glu Asp Tyr Val Lys Lys Ser Asp Asn Trp
            725             730                 735

Arg Asn Met Asn Leu Tyr Gln Trp Asn Ala Glu Tyr Ser Arg Leu Leu
            740             745             750

Leu Asp Val Met Lys Glu Asn Lys Gly Lys Asn Ile Gln Asn Thr Phe
        755             760             765

Arg Ala Glu Ile Glu Glu Leu Ile Cys Gly Lys Phe Gly Ile Arg Leu
        770             775             780

Gly Ser Leu Phe His His Ser Leu Gln Phe Leu Thr Asn Cys Lys Ser
785             790             795                 800

Leu Ile Ser Ser Tyr Phe Met Leu Asn Asn Lys Lys Glu Glu Tyr Asp
            805             810             815

Gln Glu Leu Phe Asp Ser Asp Phe Phe Arg Leu Met Lys Ser Ile Gly
            820             825             830

Asp Lys Arg Val Arg Lys Arg Lys Glu Lys Ser Ser Arg Ile Ser Ser
            835             840             845

Thr Val Leu Gln Ile Ala Arg Glu Asn Asn Ile Lys Ser Leu Cys Val
        850             855             860

Glu Gly Asp Leu Pro Thr Ala Thr Lys Lys Thr Lys Pro Lys Gln Asn
865             870             875                 880

Gln Lys Ser Ile Asp Trp Cys Ala Arg Ala Val Val Lys Lys Leu Asn
            885             890             895

Asp Gly Cys Lys Val Leu Gly Ile Asn Leu Gln Ala Ile Asp Pro Arg
            900             905             910

Asp Thr Ser His Leu Asp Pro Phe Val Tyr Tyr Gly Lys Lys Ser Thr
            915             920             925

Lys Val Gly Lys Glu Ala Arg Tyr Thr Ile Val Glu Pro Ser Asn Ile
        930             935             940

Lys Glu Tyr Met Thr Asn Arg Phe Asp Asp Trp His Arg Gly Val Thr
945             950             955                 960

Lys Lys Ser Lys Lys Gly Asp Val Gln Thr Ser Thr Thr Val Leu Leu
            965             970                 975

Tyr Gln Glu Ala Leu Arg Gln Phe Ala Ser His Tyr Glu Leu Asp Phe
            980             985                 990

Asp Ser Leu Pro Lys Met Lys Phe  Tyr Asp Leu Ala Lys  Arg Leu Gly
        995             1000                1005

Asp His  Glu Lys Val Ile Ile  Pro Cys Arg Gly Gly  Arg Ala Tyr
    1010             1015             1020

Leu Ser  Thr Tyr Pro Val Thr  Lys Asp Ser Ser Lys  Ile Thr Phe
    1025             1030             1035

Asn Gly  Arg Glu Arg Trp Tyr  Asn Glu Ser Asp Val  Val Ala Ala
    1040             1045             1050

Val Asn  Ile Val Leu Arg Gly  Ile Arg Asp Glu Asp  Glu Gln Pro
    1055             1060             1065

Asp Asp  Ala Lys Lys Gln Ala  Leu Ala Arg Thr Lys
```

-continued

```
       1070              1075              1080
```

<210> SEQ ID NO 12
<211> LENGTH: 1046
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Val Ser Asp Ser Thr Ile Arg Pro Tyr Ala Ser Lys Leu Ala Pro
1               5                   10                  15

Asn Asp Pro Lys Leu Lys Met Leu Asn Asp Thr Phe Asn Trp Leu Asp
            20                  25                  30

His Ala Tyr Lys Val Phe Phe Asp Val Ser Val Ala Leu Phe Gly Ala
        35                  40                  45

Ile Glu His Glu Thr Ala Gln Glu Leu Ile Gly Glu Lys Ser Lys Phe
    50                  55                  60

Asp Ala Asp Leu Ile Cys Ala Ile Met Trp Phe Arg Leu Glu Glu Lys
65                  70                  75                  80

Ser Asp Asn Pro Gly Pro Leu Gln Thr Val Glu Gln Arg Met Arg Leu
                85                  90                  95

Phe Gln Lys Tyr Ser Gly His Glu Pro Ser Ser Phe Thr Gln Glu Tyr
            100                 105                 110

Ile Lys Gly Asn Ile Asp Ser Glu Lys Tyr Glu Trp Val Asp Cys Arg
        115                 120                 125

Leu Lys Phe Ile Asp Leu Ala Arg Asn Ile Asn Thr Thr Gln Glu Ser
    130                 135                 140

Leu Lys Ile Asp Ala Tyr Thr Leu Phe Met Asn Lys Leu Ile Pro Val
145                 150                 155                 160

Ser Lys Asp Asp Glu Phe Asn Ala Tyr Gly Leu Ile Ser Gln Leu Phe
                165                 170                 175

Gly Thr Gly Lys Lys Glu Asp Arg Ser Ile Lys Ala Ala Met Leu Glu
            180                 185                 190

Glu Ile Ser Asn Ile Leu Ala Asp Lys Lys Pro Asp Thr Trp Glu Glu
            195                 200                 205

Tyr His Asp Leu Ile Lys Lys Asn Phe Asn Val Asp Asn Tyr Lys Glu
        210                 215                 220

Leu Lys Glu Lys Leu Ser Ala Gly Ser Ser Gly Arg Asp Ser Ser Leu
225                 230                 235                 240

Val Ile Asp Leu Lys Glu Glu Lys Thr Gly Leu Leu Gln Pro Asn Phe
                245                 250                 255

Ile Lys Asn Arg Ile Val Lys Phe Arg Glu Asp Ala Asp Lys Lys Lys
            260                 265                 270

Thr Val Phe Leu Leu Pro Asn Arg Met Lys Leu Arg Glu Phe Ile Ala
            275                 280                 285

Ser Gln Ile Gly Pro Phe Glu Gln Asn Ser Trp Ser Ala Val Leu Asn
        290                 295                 300

Arg Ser Met Ala Ala Ile Gln Ser Lys Asn Ser Ser Asn Ile Leu Tyr
305                 310                 315                 320

Thr Asn Glu Lys Glu Glu Arg Asn Asn Glu Ile Gln Glu Leu Leu Lys
                325                 330                 335

Lys Asp Ile Leu Ser Ala Ala Ser Ile Leu Gly Asp Phe Arg Arg Gly
            340                 345                 350
```

-continued

```
Glu Phe Asn Arg Ser Val Val Ser Lys Asn His Leu Gly Ala Arg Leu
        355             360             365

Asn Glu Leu Phe Glu Ile Trp Gln Asp Leu Thr Met Asp Asp Gly Ile
        370             375             380

Arg Lys Tyr Val Asp Leu Cys Lys Asp Lys Phe Ser Arg Arg Pro Val
385             390             395             400

Lys Ala Leu Leu Gln Tyr Ile Tyr Pro Tyr Phe Asp Lys Ile Thr Ala
            405             410             415

Lys Gln Phe Leu Asp Ala Ala Ser Tyr Asn Thr Leu Val Glu Thr Asn
            420             425             430

Asn Arg Lys Lys Ile His Pro Thr Val Thr Gly Pro Thr Val Cys Asn
            435             440             445

Trp Gly Pro Lys Ser Thr Ile Asn Gly Ser Ile Thr Pro Pro Asn Gln
        450             455             460

Met Val Lys Gly Arg Pro Ala Gly Ser His Gly Met Ile Trp Val Thr
465             470             475             480

Met Thr Val Ile Asp Asn Gly Arg Trp Ile Lys His His Leu Pro Phe
            485             490             495

Tyr Asn Ser Arg Tyr Tyr Glu Glu His Tyr Cys Tyr Arg Glu Gly Leu
            500             505             510

Pro Thr Lys Asn Gln Pro Arg Thr Lys Gln Leu Gly Thr Gln Val Gly
            515             520             525

Ser Thr Ile Ser Ala Thr Ser Leu Ala Ala Leu Lys Ser Gln Glu Glu
        530             535             540

Gln Asp Arg Arg Asn Asp Arg Lys Asn Arg Phe Lys Ala His Lys Ser
545             550             555             560

Ile Ile Arg Ser Gln Glu Asn Ile Glu Tyr Asn Val Ala Phe Asp Lys
            565             570             575

Ser Thr Asn Phe Asp Val Thr Arg Lys Asn Gly Glu Phe Phe Ile Thr
            580             585             590

Ile Ser Ser Arg Val Ala Thr Pro Lys Tyr Ser Tyr Lys Leu Asn Ile
        595             600             605

Gly Asp Met Ile Met Gly Leu Asp Asn Asn Gln Thr Ala Pro Cys Thr
        610             615             620

Tyr Ser Ile Trp Arg Val Val Glu Lys Asp Thr Glu Gly Ser Phe Phe
625             630             635             640

His Asn Lys Ile Trp Leu Gln Leu Val Thr Asp Gly Lys Ile Thr Ser
            645             650             655

Ile Val Asp Asn Asn Arg Gln Val Asp Gln Leu Ser Tyr Ala Gly Ile
            660             665             670

Glu Tyr Ser Asn Phe Ala Glu Trp Arg Lys Asp Arg Arg Gln Phe Leu
            675             680             685

Arg Ser Ile Asn Glu Asp Tyr Val Lys Lys Ser Asp Asn Trp Arg Asn
        690             695             700

Met Asn Leu Tyr Gln Trp Asn Ala Glu Tyr Ser Arg Leu Leu Leu Asp
705             710             715             720

Val Met Lys Glu Asn Lys Gly Lys Asn Ile Gln Asn Thr Phe Arg Ala
            725             730             735

Glu Ile Glu Glu Leu Ile Cys Gly Lys Phe Gly Ile Arg Leu Gly Ser
            740             745             750

Leu Phe His His Ser Leu Gln Phe Leu Thr Asn Cys Lys Ser Leu Ile
            755             760             765
```

```
Ser Ser Tyr Phe Met Leu Asn Asn Lys Lys Glu Glu Tyr Asp Gln Glu
    770                 775                 780

Leu Phe Asp Ser Asp Phe Phe Arg Leu Met Lys Ser Ile Gly Asp Lys
785                 790                 795                 800

Arg Val Arg Lys Arg Lys Glu Lys Ser Ser Arg Ile Ser Ser Thr Val
                805                 810                 815

Leu Gln Ile Ala Arg Glu Asn Asn Ile Lys Ser Leu Cys Val Glu Gly
                820                 825                 830

Asp Leu Pro Thr Ala Thr Lys Lys Thr Lys Pro Lys Gln Asn Gln Lys
                835                 840                 845

Ser Ile Asp Trp Cys Ala Arg Ala Val Val Lys Lys Leu Asn Asp Gly
    850                 855                 860

Cys Lys Val Leu Gly Ile Asn Leu Gln Ala Ile Asp Pro Arg Asp Thr
865                 870                 875                 880

Ser His Leu Asp Pro Phe Val Tyr Tyr Gly Lys Lys Ser Thr Lys Val
                885                 890                 895

Gly Lys Glu Ala Arg Tyr Thr Ile Val Glu Pro Ser Asn Ile Lys Glu
                900                 905                 910

Tyr Met Thr Asn Arg Phe Asp Asp Trp His Arg Gly Val Thr Lys Lys
                915                 920                 925

Ser Lys Lys Gly Asp Val Gln Thr Ser Thr Thr Val Leu Leu Tyr Gln
    930                 935                 940

Glu Ala Leu Arg Gln Phe Ala Ser His Tyr Glu Leu Asp Phe Asp Ser
945                 950                 955                 960

Leu Pro Lys Met Lys Phe Tyr Asp Leu Ala Lys Arg Leu Gly Asp His
                965                 970                 975

Glu Lys Val Ile Ile Pro Cys Arg Gly Gly Arg Ala Tyr Leu Ser Thr
                980                 985                 990

Tyr Pro Val Thr Lys Asp Ser Ser  Lys Ile Thr Phe Asn  Gly Arg Glu
                995                 1000                1005

Arg Trp  Tyr Asn Glu Ser Asp  Val Val Ala Ala Val  Asn Ile Val
    1010                1015                1020

Leu Arg  Gly Ile Arg Asp Glu  Asp Glu Gln Pro Asp  Asp Ala Lys
    1025                1030                1035

Lys Gln  Ala Leu Ala Arg Thr  Lys
    1040                1045
```

```
<210> SEQ ID NO 13
<211> LENGTH: 1046
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Val Ser Glu Ser Thr Ile Arg Pro Tyr Thr Ser Lys Leu Ala Pro
1               5                   10                  15

Asn Asp Ser Lys Leu Lys Met Leu Asn Asp Thr Phe Asn Trp Leu Asp
                20                  25                  30

His Ala Tyr Lys Val Phe Phe Asp Val Ser Val Ala Leu Phe Gly Ala
        35                  40                  45

Ile Glu His Glu Thr Ala Gln Glu Leu Ile Gly Glu Lys Ser Lys Phe
    50                  55                  60

Asp Ala Asp Leu Leu Cys Ala Ile Met Trp Phe Arg Leu Glu Glu Lys
```

```
65                    70                    75                    80

Ser Asp Asn Pro Gly Pro Leu Gln Thr Val Glu Gln Arg Met Arg Leu
                85                    90                    95

Phe Gln Lys Tyr Ser Gly His Glu Pro Ser Ser Phe Thr Gln Glu Tyr
                100                   105                   110

Ile Lys Gly Asn Ile Asp Ser Glu Lys Tyr Gln Trp Val Asp Cys Arg
                115                   120                   125

Leu Lys Phe Ile Asp Leu Ala Arg Asn Ile Asn Thr Thr Gln Glu Ser
    130                   135                   140

Leu Lys Ile Asp Ala Tyr Thr Leu Phe Met Asn Lys Leu Ile Pro Val
145                   150                   155                   160

Ser Lys Asp Asp Glu Phe Asn Ala Tyr Gly Leu Ile Ser Gln Leu Phe
                165                   170                   175

Gly Thr Gly Lys Lys Glu Asp Arg Ser Ile Lys Ala Ser Met Leu Glu
                180                   185                   190

Glu Ile Ser Asn Ile Leu Ala Asp Lys Asn Pro Asn Thr Trp Glu Glu
                195                   200                   205

Tyr Gln Asp Leu Ile Lys Lys Thr Phe Asn Val Asp Asn Tyr Lys Glu
    210                   215                   220

Leu Lys Glu Lys Leu Ser Ala Gly Ser Ser Gly Arg Asp Gly Ser Leu
225                   230                   235                   240

Val Ile Asp Leu Lys Glu Glu Lys Thr Gly Leu Leu Gln Pro Asn Phe
                245                   250                   255

Ile Lys Asn Arg Ile Val Lys Phe Arg Glu Asp Ala Asp Lys Lys Arg
                260                   265                   270

Thr Val Phe Leu Leu Pro Asn Arg Met Lys Leu Arg Glu Phe Ile Ala
                275                   280                   285

Ser Gln Ile Gly Pro Phe Glu Gln Asn Ser Trp Ser Ala Val Leu Asn
    290                   295                   300

Arg Ser Met Ala Ala Ile Gln Ser Lys Asn Ser Ser Asn Ile Leu Tyr
305                   310                   315                   320

Thr Asn Glu Lys Glu Glu Arg Asn Asn Glu Ile Gln Glu Leu Leu Lys
                325                   330                   335

Lys Asp Ile Leu Ser Ala Ala Ser Ile Leu Gly Asp Phe Arg Arg Gly
                340                   345                   350

Glu Phe Asn Arg Ser Val Val Ser Lys Asn His Leu Gly Ala Arg Leu
                355                   360                   365

Asn Glu Leu Phe Glu Ile Trp Gln Glu Leu Thr Met Asp Asp Gly Ile
    370                   375                   380

Lys Lys Tyr Val Asp Leu Cys Lys Asp Lys Phe Ser Arg Arg Pro Val
385                   390                   395                   400

Lys Ala Leu Leu Gln Tyr Ile Tyr Pro Tyr Phe Asp Lys Ile Asn Ala
                405                   410                   415

Lys Gln Phe Leu Asp Ala Ala Ser Tyr Asn Thr Leu Val Glu Thr Asn
                420                   425                   430

Asn Arg Lys Lys Ile His Pro Thr Val Thr Gly Pro Thr Val Cys Asn
                435                   440                   445

Trp Gly Pro Lys Ser Thr Ile Asn Gly Ser Ile Thr Pro Pro Asn Gln
    450                   455                   460

Met Val Lys Gly Arg Pro Ala Gly Ser His Gly Met Ile Trp Val Thr
465                   470                   475                   480

Met Thr Val Ile Asp Asn Gly Arg Trp Ile Lys His His Leu Pro Phe
                485                   490                   495
```

-continued

```
His Asn Ser Arg Tyr Tyr Glu Glu His Tyr Cys Tyr Arg Glu Gly Leu
            500                 505                 510

Pro Thr Lys Asn Lys Pro Arg Thr Lys Gln Leu Gly Thr Gln Val Gly
            515                 520                 525

Ser Thr Ile Ser Ala Pro Ser Leu Ala Ile Leu Lys Ser Gln Glu Glu
            530                 535                 540

Gln Asp Arg Arg Asn Asp Arg Lys Asn Arg Phe Lys Ala His Lys Ser
545                 550                 555                 560

Ile Ile Arg Ser Gln Glu Asn Ile Glu Tyr Asn Val Ala Phe Asp Lys
                565                 570                 575

Ser Thr Asn Phe Asp Val Thr Arg Lys Asn Gly Glu Phe Phe Ile Thr
            580                 585                 590

Ile Ser Ser Arg Val Ala Thr Pro Lys Tyr Ser Tyr Lys Leu Asn Ile
            595                 600                 605

Gly Asp Met Ile Met Gly Leu Asp Asn Asn Gln Thr Ala Pro Cys Thr
            610                 615                 620

Tyr Ser Ile Trp Arg Val Val Glu Lys Asp Thr Glu Gly Ser Phe Phe
625                 630                 635                 640

His Asn Lys Ile Trp Leu Gln Leu Val Thr Asp Gly Lys Val Thr Ser
                645                 650                 655

Ile Val Asp Asn Asn Arg Gln Val Asp Gln Leu Ser Tyr Ala Gly Ile
                660                 665                 670

Glu Tyr Ser Asn Phe Ala Glu Trp Arg Lys Asp Arg Arg Gln Phe Leu
            675                 680                 685

Arg Ser Ile Asn Glu Asp Tyr Val Lys Lys Ser Asp Asn Trp Arg Asn
690                 695                 700

Met Asn Leu Tyr Gln Trp Asn Ala Glu Tyr Ser Arg Leu Leu Leu Asp
705                 710                 715                 720

Val Met Lys Glu Asn Lys Gly Lys Asn Ile Gln Asn Thr Phe Arg Ala
                725                 730                 735

Glu Ile Glu Glu Leu Ile Cys Gly Lys Phe Gly Ile Arg Leu Gly Ser
            740                 745                 750

Leu Phe His His Ser Leu Gln Phe Leu Thr Asn Cys Lys Ser Leu Ile
            755                 760                 765

Ser Ser Tyr Phe Met Leu Asn Asn Lys Lys Glu Glu Tyr Asp Gln Glu
            770                 775                 780

Leu Phe Asp Ser Asp Phe Phe Arg Leu Met Lys Ser Ile Gly Asp Lys
785                 790                 795                 800

Arg Val Arg Lys Arg Lys Glu Lys Ser Ser Arg Ile Ser Ser Thr Val
                805                 810                 815

Leu Gln Ile Ala Arg Glu Asn Asn Val Lys Ser Leu Cys Val Glu Gly
            820                 825                 830

Tyr Leu Pro Thr Ser Thr Lys Lys Thr Lys Pro Lys Gln Asn Gln Lys
            835                 840                 845

Ser Ile Asp Trp Cys Ala Arg Ala Val Val Lys Lys Leu Asn Asp Gly
            850                 855                 860

Cys Lys Val Leu Gly Ile Tyr Leu Gln Ala Ile Asp Pro Arg Asp Thr
865                 870                 875                 880

Ser His Leu Asp Pro Phe Val Tyr Tyr Gly Lys Lys Ser Thr Lys Val
                885                 890                 895

Gly Lys Glu Ala Arg His Thr Ile Val Glu Pro Ser Asn Ile Lys Glu
            900                 905                 910
```

```
Tyr Met Thr Asn Arg Phe Asp Asp Trp His Arg Gly Val Thr Lys Lys
        915                 920             925

Ser Lys Lys Gly Asp Val Gln Thr Ser Thr Thr Val Leu Leu Tyr Gln
        930                 935             940

Glu Ala Leu Arg Gln Phe Ala Ser His Tyr Lys Leu Asp Phe Asp Ser
945                 950             955                 960

Leu Pro Lys Met Lys Phe Tyr Glu Leu Ala Lys Ile Leu Gly Asp His
                965             970             975

Glu Lys Val Ile Ile Pro Cys Arg Gly Gly Arg Ala Tyr Leu Ser Thr
                980             985             990

Tyr Pro Val Thr Lys Asp Ser Ser  Lys Ile Thr Phe Asn  Gly Arg Glu
        995             1000            1005

Arg Trp  Tyr Asn Glu Ser Asp  Val Val Ala Ala Val  Asn Ile Val
        1010            1015            1020

Leu Arg  Gly Ile Ile Asp Glu  Asp Glu Gln Pro Asp  Gly Ala Lys
        1025            1030            1035

Lys Gln  Ala Thr Thr Arg Arg  Thr
        1040            1045

<210> SEQ ID NO 14
<211> LENGTH: 1098
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Ser Ile Ser Asn Asn Asn Ile Leu Pro Tyr Asn Pro Lys Leu Leu
1               5               10              15

Pro Asp Asp Arg Lys His Lys Met Leu Val Asp Thr Phe Asn Gln Leu
                20              25              30

Asp Leu Ile Arg Asn Asn Leu His Asp Met Ile Ile Ala Leu Tyr Gly
        35              40              45

Ala Leu Lys Tyr Asp Asn Ile Lys Gln Phe Ala Ser Lys Glu Lys Pro
        50              55              60

His Ile Ser Ala Asp Ala Leu Cys Ser Ile Asn Trp Phe Arg Leu Val
65              70              75              80

Lys Thr Asn Glu Arg Lys Pro Ala Ile Glu Ser Asn Gln Ile Ile Ser
                85              90              95

Lys Phe Ile Gln Tyr Ser Gly His Thr Pro Asp Lys Tyr Ala Leu Ser
        100             105             110

His Ile Thr Gly Asn His Glu Pro Ser His Lys Trp Ile Asp Cys Arg
        115             120             125

Glu Tyr Ala Ile Asn Tyr Ala Arg Ile Met His Leu Ser Phe Ser Gln
        130             135             140

Phe Gln Asp Leu Ala Thr Ala Cys Leu Asn Cys Lys Ile Leu Ile Leu
145             150             155             160

Asn Gly Thr Leu Thr Ser Ser Trp Ala Trp Gly Ala Asn Ser Ala Leu
                165             170             175

Phe Gly Gly Ser Asp Lys Glu Asn Phe Ser Val Lys Ala Lys Ile Leu
        180             185             190

Asn Ser Phe Ile Glu Asn Leu Lys Asp Glu Met Asn Thr Thr Lys Phe
        195             200             205

Gln Val Val Glu Lys Val Cys Gln Gln Ile Gly Ser Ser Asp Ala Ala
```

-continued

```
          210                  215                  220
Asp Leu Phe Asp Leu Tyr Arg Ser Thr Val Lys Asp Gly Asn Arg Gly
225                  230                  235                  240

Pro Ala Thr Gly Arg Asn Pro Lys Val Met Asn Leu Phe Ser Gln Asp
                245                  250                  255

Gly Glu Ile Ser Ser Glu Gln Arg Glu Asp Phe Ile Glu Ser Phe Gln
                260                  265                  270

Lys Val Met Gln Glu Lys Asn Ser Lys Gln Ile Ile Pro His Leu Asp
                275                  280                  285

Lys Leu Lys Tyr His Leu Val Lys Gln Ser Gly Leu Tyr Asp Ile Tyr
                290                  295                  300

Ser Trp Ala Ala Ala Ile Lys Asn Ala Asn Ser Thr Ile Val Ala Ser
305                  310                  315                  320

Asn Ser Ser Asn Leu Asn Thr Ile Leu Asn Lys Thr Glu Lys Gln Gln
                325                  330                  335

Thr Phe Glu Glu Leu Arg Lys Asp Glu Lys Ile Val Ala Cys Ser Lys
                340                  345                  350

Ile Leu Leu Ser Val Asn Asp Thr Leu Pro Glu Asp Leu His Tyr Asn
                355                  360                  365

Pro Ser Thr Ser Asn Leu Gly Lys Asn Leu Asp Val Phe Phe Asp Leu
                370                  375                  380

Leu Asn Glu Asn Ser Val His Thr Ile Glu Asn Lys Glu Glu Lys Asn
385                  390                  395                  400

Lys Ile Val Lys Glu Cys Val Asn Gln Tyr Met Glu Glu Cys Lys Gly
                405                  410                  415

Leu Asn Lys Pro Pro Met Pro Val Leu Leu Thr Phe Ile Ser Asp Tyr
                420                  425                  430

Ala His Lys His Gln Ala Gln Asp Phe Leu Ser Ala Ala Lys Met Asn
                435                  440                  445

Phe Ile Asp Leu Lys Ile Lys Ser Ile Lys Val Val Pro Thr Val His
                450                  455                  460

Gly Ser Ser Pro Tyr Thr Trp Ile Ser Asn Leu Ser Lys Lys Asn Lys
465                  470                  475                  480

Asp Gly Lys Met Ile Arg Thr Pro Asn Ser Ser Leu Ile Gly Trp Ile
                485                  490                  495

Ile Pro Pro Glu Glu Ile His Asp Gln Lys Phe Ala Gly Gln Asn Pro
                500                  505                  510

Ile Ile Trp Ala Val Leu Arg Val Tyr Cys Asn Asn Lys Trp Glu Met
                515                  520                  525

His His Phe Pro Phe Ser Asp Ser Arg Phe Phe Thr Glu Val Tyr Ala
                530                  535                  540

Tyr Lys Pro Asn Leu Pro Tyr Leu Pro Gly Gly Glu Asn Arg Ser Lys
545                  550                  555                  560

Arg Phe Gly Tyr Arg His Ser Thr Asn Leu Ser Asn Glu Ser Arg Gln
                565                  570                  575

Ile Leu Leu Asp Lys Ser Lys Tyr Ala Lys Ala Asn Lys Ser Val Leu
                580                  585                  590

Arg Cys Met Glu Asn Met Thr His Asn Val Val Phe Asp Pro Lys Thr
                595                  600                  605

Ser Leu Asn Ile Arg Ile Lys Thr Asp Lys Asn Asn Ser Pro Val Leu
                610                  615                  620

Asp Asp Lys Gly Arg Ile Thr Phe Val Met Gln Ile Asn His Arg Ile
625                  630                  635                  640
```

```
Leu Glu Lys Tyr Asn Asn Thr Lys Ile Glu Ile Gly Asp Arg Ile Leu
            645                 650                 655

Ala Tyr Asp Gln Asn Gln Ser Glu Asn His Thr Tyr Ala Ile Leu Gln
            660                 665                 670

Arg Thr Glu Glu Gly Ser His Ala His Gln Phe Asn Gly Trp Tyr Val
            675                 680                 685

Arg Val Leu Glu Thr Gly Lys Val Thr Ser Ile Val Gln Gly Leu Ser
        690                 695                 700

Gly Pro Ile Asp Gln Leu Asn Tyr Asp Gly Met Pro Val Thr Ser His
705                 710                 715                 720

Lys Phe Asn Cys Trp Gln Ala Asp Arg Ser Ala Phe Val Ser Gln Phe
                725                 730                 735

Ala Ser Leu Lys Ile Ser Glu Thr Glu Thr Phe Asp Glu Ala Tyr Gln
            740                 745                 750

Ala Ile Asn Ala Gln Gly Ala Tyr Thr Trp Asn Leu Phe Tyr Leu Arg
            755                 760                 765

Ile Leu Arg Lys Ala Leu Arg Val Cys His Met Glu Asn Ile Asn Gln
    770                 775                 780

Phe Arg Glu Glu Ile Leu Ala Ile Ser Lys Asn Arg Leu Ser Pro Met
785                 790                 795                 800

Ser Leu Gly Ser Leu Ser Gln Asn Ser Leu Lys Met Ile Arg Ala Phe
                805                 810                 815

Lys Ser Ile Ile Asn Cys Tyr Met Ser Arg Met Ser Phe Val Asp Glu
            820                 825                 830

Leu Gln Lys Lys Glu Gly Asp Leu Glu Leu His Thr Ile Met Arg Leu
            835                 840                 845

Thr Asp Asn Lys Leu Asn Asp Lys Arg Val Glu Lys Ile Asn Arg Ala
    850                 855                 860

Ser Ser Phe Leu Thr Asn Lys Ala His Ser Met Gly Cys Lys Met Ile
865                 870                 875                 880

Val Gly Glu Ser Asp Leu Pro Val Ala Asp Ser Lys Thr Ser Lys Lys
                885                 890                 895

Gln Asn Val Asp Arg Met Asp Trp Cys Ala Arg Ala Leu Ser His Lys
            900                 905                 910

Val Glu Tyr Ala Cys Lys Leu Met Gly Leu Ala Tyr Arg Gly Ile Pro
            915                 920                 925

Ala Tyr Met Ser Ser His Gln Asp Pro Leu Val His Leu Val Glu Ser
    930                 935                 940

Lys Arg Ser Val Leu Arg Pro Arg Phe Val Val Ala Asp Lys Ser Asp
945                 950                 955                 960

Val Lys Gln His His Leu Asp Asn Leu Arg Arg Met Leu Asn Ser Lys
                965                 970                 975

Thr Lys Val Gly Thr Ala Val Tyr Tyr Arg Glu Ala Val Glu Leu Met
            980                 985                 990

Cys Glu Glu Leu Gly Ile His Lys  Thr Asp Met Ala Lys  Gly Lys Val
            995                 1000                1005

Ser Leu  Ser Asp Phe Val Asp  Lys Phe Ile Gly Glu  Lys Ala Ile
    1010                1015                1020

Phe Pro  Gln Arg Gly Gly Arg  Phe Tyr Met Ser Thr  Lys Arg Leu
    1025                1030                1035

Thr Thr  Gly Ala Lys Leu Ile  Cys Tyr Ser Gly Ser  Asp Val Trp
    1040                1045                1050
```

-continued

```
Leu Ser  Asp Ala Asp Glu Ile  Ala Ala Ile Asn Ile  Gly Met Phe
    1055              1060               1065

Val Val  Cys Asp Gln Thr Gly  Ala Phe Lys Lys Lys  Lys Lys Glu
    1070              1075               1080

Lys Leu  Asp Asp Glu Glu Cys  Asp Ile Leu Pro Phe  Arg Pro Met
    1085              1090               1095
```

```
<210> SEQ ID NO 15
<211> LENGTH: 1088
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15
```

```
Met Ser Ser Gln Val Val Arg Pro Tyr Asn Ala Lys Phe Leu Pro Asp
1               5               10              15

Asp Arg Lys His Lys Met Leu Thr Asp Thr Ile Asn Gln Leu Asp Lys
        20              25              30

Ile Ser Ser Lys His Phe Asp Leu Leu Val Ala Phe Tyr Gly Ser Ile
        35              40              45

Gln His Lys His Val Ser Ile Asn Asp Lys Gln Glu Glu His Ile Thr
    50              55              60

Pro Asp Ser Val Cys Ala Ile Asn Trp Phe Arg Pro Met Ser Lys Asp
65              70              75              80

Tyr Ala Lys Tyr Gln Val Lys Ile Asp Ser Met Ile Thr Asn Phe Lys
            85              90              95

Glu Tyr Ala Gly His Ile Pro Asp Lys Tyr Ala Ile Glu Tyr Met Gly
        100             105             110

Ser Asn Ile Asp Thr Asp Arg Phe Val Trp Val Asp Cys Arg Asn Phe
        115             120             125

Ala Lys Asp Tyr Val Arg Asn Met Asp Met Ser Phe Ser Glu Phe Gln
        130             135             140

Asn Leu Val Asp Ala Leu Val Phe Cys Lys Ile Leu Ala Leu Asn Glu
145             150             155             160

Ser Thr Ser Thr Asn Trp Ala Trp Gly Ala Ile Ser Ala Ile Tyr Gly
            165             170             175

Gly Gly Asp Lys Glu Asp Ser Gln Phe Lys Ala Lys Val Leu Asn Thr
            180             185             190

Phe Val Lys Ala Leu Asn Asp Glu Asn Asn Lys Thr Lys Phe Asp Val
            195             200             205

Ile Asn Lys Val Cys Ser Asp Leu Gly Tyr Asn Asp His Leu Ser Leu
    210             215             220

Ile Glu Asp Phe Arg Ser Thr Ile Asp Glu Asn Gly Asn Lys Lys Ser
225             230             235             240

Ala Ser Gly Ser Pro Pro Ala Ile Ala Lys Phe Thr Glu Asp Gly Glu
            245             250             255

Ile Ser Asp Asn Tyr Arg Arg Ala Cys Ile Ser Ser Phe Ser Lys Thr
            260             265             270

Ala Lys Glu Lys Gln Asp Lys Lys Ser Ile Pro His Leu Asp Ile Leu
        275             280             285

Lys Thr His Met Ile Ala Met Cys Gly Glu Tyr Asn Thr Tyr Ala Trp
    290             295             300

Thr Glu Ala Ile Lys Asn Ala Asn Thr Asp Ile Thr Ser Arg Asn Thr
```

-continued

```
305                 310                 315                 320

Arg Asn Met Thr Phe Ile Lys Glu Lys Ile Glu Ser Arg Asn Ser Leu
                325                 330                 335

Lys Ile Tyr Asp Thr Glu Glu Asn Met Lys Ala Ala Lys Ile Leu Asn
                340                 345                 350

Gly Ile Asn His Lys Leu Thr Pro Asp Leu His Tyr Thr Pro Ala Pro
                355                 360                 365

Lys His Leu Gly Lys Asn Leu Lys Asp Leu Phe Glu Met Leu Glu Glu
                370                 375                 380

Lys Asn Ile Leu Ala Gln Asn Glu Lys Glu Lys Lys Ala Ala Leu Asp
385                 390                 395                 400

Glu Cys Ile Lys Gln Tyr Ile Asp Asp Cys Lys Gly Leu Asn Gln Gln
                405                 410                 415

Pro Ile Ala Ser Leu Leu Ala His Ile Ser Asn Tyr His Lys Glu Ile
                420                 425                 430

Thr Ala Glu Asn Phe Leu Asp Gly Ala Lys Leu Leu Val Leu Leu Gln
                435                 440                 445

Lys Ile Asn Arg Gln Lys Ala His Pro Ser Val Phe Ser Pro Lys Ala
                450                 455                 460

Tyr Thr Trp Gly Ser Lys Leu Glu Lys Asn Arg Arg Ala Ala Asn Ser
465                 470                 475                 480

Ala Leu Leu Gly Trp Ile Val Pro Pro Glu Glu Lys His Lys Asp Arg
                485                 490                 495

His Ala Gly Gln His Pro Val Met Trp Val Thr Met Thr Leu Leu Asn
                500                 505                 510

Asn Gly Lys Trp Glu Lys His His Val Pro Phe Thr Asn Ser Arg Phe
                515                 520                 525

Phe Ser Glu Val Tyr Ala Tyr Gln Pro Glu Leu Pro Tyr Lys Glu Gly
                530                 535                 540

Gly Tyr Ala Arg Asn Ser Lys Thr Ala Thr Lys Pro Ser Gln Ile Met
545                 550                 555                 560

Leu Pro Ala Tyr Ala Glu Ser Met Arg His His Ile Ala Thr Lys Gly
                565                 570                 575

Asn Gly His Lys Lys Ser Glu Lys Ile Val Leu Arg Ala Leu Ser Asn
                580                 585                 590

Ile Arg His Asn Val Arg Phe Asp Pro Ser Thr Ser Phe Phe Val Arg
                595                 600                 605

Ile Met Arg Asp Lys Lys Gly Asn His Arg Leu Asp Thr Lys Gly Arg
                610                 615                 620

Ile Thr Phe Gly Leu Gln Ile Asn His Arg Ile Thr Val Gly Lys Thr
625                 630                 635                 640

Lys Ser Glu Ile Asn Ile Gly Asp Arg Leu Leu Ala Phe Asp Gln Asn
                645                 650                 655

Gln Ser Glu Asn His Thr Phe Ala Ile Met Gln Arg Val Glu Glu Asn
                660                 665                 670

Thr Pro Asn Ser His Gln Phe Asn Gly Trp Asn Ile Arg Val Leu Glu
                675                 680                 685

Thr Gly Lys Val Val Ser Met Thr Lys Gly Ile Glu Ser Tyr Tyr Asp
                690                 695                 700

Gln Leu Ser Tyr Asp Gly Val Pro Tyr Glu Thr Lys Lys Phe Glu Asp
705                 710                 715                 720

Trp Arg Asn Glu Arg Lys Ala Phe Val Lys Lys Asn Lys Asp Ile Val
                725                 730                 735
```

```
Ile Lys Glu Glu Lys Thr Phe Gly Gln Met Phe Ala Glu Ile Lys Lys
            740                 745                 750

Ser Ser Leu Tyr Lys Trp Asn Leu Ser Tyr Leu Lys Ile Leu Arg Met
            755                 760                 765

Ala Ile Arg Ala Lys Ser Gly Asp Thr Val Ser Leu Phe Arg Glu Glu
            770                 775                 780

Leu Ile Ser Ile Ala Lys Asn Arg Phe Gly Pro Leu Gly Leu Gly Ser
        785                 790                 795                 800

Leu Ser Ala Ser Ser Leu Lys Met Leu Gly Ala Phe Cys Gly Val Ile
                    805                 810                 815

Gln Ser Tyr Phe Ser Val Leu Asn Cys Leu Asp Asp Lys Asp Lys Ser
            820                 825                 830

Asn Phe Asp Ser Glu Leu Tyr Phe Tyr Leu Val Ser Ala Phe Glu Lys
            835                 840                 845

Arg Val Phe Lys Arg Asn Glu Lys Thr Ser Arg Ala Ser Ser Phe Ile
        850                 855                 860

Met Ala Met Ala Tyr Asn His Gly Cys Lys Met Ile Val Cys Glu Asp
865                 870                 875                 880

Asp Leu Pro Thr Ala Gly Ala Gly Ala Asn Lys Arg Gln Asn Ser Asp
                885                 890                 895

Arg Met Asp Trp Cys Ala Arg Ser Leu Ala Gln Lys Ile Lys Thr Gly
            900                 905                 910

Cys Glu Ala Met Ser Ile Ala Tyr Arg Ala Ile Pro Ala Tyr Met Ser
            915                 920                 925

Ser His Gln Asp Pro Leu Val His Leu Ala Asp Gly Lys Thr Ser Val
            930                 935                 940

Leu Cys Pro Arg Phe Ala Leu Val Ser Lys Asp Asp Ile Lys Gln Tyr
945                 950                 955                 960

Gln Leu Asp Gly Met Arg Arg Met Leu Asn Ser Lys Ser Lys Ile Gly
                965                 970                 975

Thr Ala Val Tyr Tyr Arg Ala Ala Val Glu Leu Leu Cys Lys Glu Leu
            980                 985                 990

Gly Ile Asn Lys Thr Asp Ile Ala  Lys Gly Lys Leu Ser  Val Ser Gln
            995                 1000                1005

Phe Ala  Asp Ile Val Asn Gly  Glu Ile Leu Leu Pro  Gln Arg Gly
        1010                1015                1020

Gly Arg  Val Tyr Leu Ala Thr  Lys Glu Leu Thr Asn  Gly Ala Lys
        1025                1030                1035

Leu Val  Ser Tyr Asn Gly Ser  Asp Val Trp Leu Ser  Asn Ala Asp
        1040                1045                1050

Glu Ile  Ala Ala Ile Asn Ile  Gly Met Phe Val Val  Cys Thr Gln
        1055                1060                1065

Thr Gly  Val Phe Gly Lys Lys  Lys Lys Lys Asp Glu  Gln Asp Gly
        1070                1075                1080

Asp Ile  Glu Ile Ala
        1085
```

<210> SEQ ID NO 16
<211> LENGTH: 1074
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Ala Ser Ile Ser Arg Pro Tyr Gly Thr Lys Leu Arg Pro Asp Ala
1               5                   10                  15

Arg Lys Lys Glu Met Leu Asp Lys Phe Phe Asn Thr Leu Thr Lys Gly
                20                  25                  30

Gln Arg Val Phe Ala Asp Leu Ala Leu Cys Ile Tyr Gly Ser Leu Thr
            35                  40                  45

Leu Glu Met Ala Lys Ser Leu Glu Pro Glu Ser Asp Ser Glu Leu Val
        50                  55                  60

Cys Ala Ile Gly Trp Phe Arg Leu Val Asp Lys Thr Ile Trp Ser Lys
65                  70                  75                  80

Asp Gly Ile Lys Gln Glu Asn Leu Val Lys Gln Tyr Glu Ala Tyr Ser
                85                  90                  95

Gly Lys Glu Ala Ser Glu Val Val Lys Thr Tyr Leu Asn Ser Pro Ser
            100                 105                 110

Ser Asp Lys Tyr Val Trp Ile Asp Cys Arg Gln Lys Phe Leu Arg Phe
            115                 120                 125

Gln Arg Glu Leu Gly Thr Arg Asn Leu Ser Glu Asp Phe Glu Cys Met
        130                 135                 140

Leu Phe Glu Gln Tyr Ile Arg Leu Thr Lys Gly Glu Ile Glu Gly Tyr
145                 150                 155                 160

Ala Ala Ile Ser Asn Met Phe Gly Asn Gly Glu Lys Glu Asp Arg Ser
                165                 170                 175

Lys Lys Arg Met Tyr Ala Thr Arg Met Lys Asp Trp Leu Glu Ala Asn
            180                 185                 190

Glu Asn Ile Thr Trp Glu Gln Tyr Arg Glu Ala Leu Lys Asn Gln Leu
            195                 200                 205

Asn Ala Lys Asn Leu Glu Gln Val Val Ala Asn Tyr Lys Gly Asn Ala
        210                 215                 220

Gly Gly Ala Asp Pro Phe Phe Lys Tyr Ser Phe Ser Lys Glu Gly Met
225                 230                 235                 240

Val Ser Lys Lys Glu His Ala Gln Gln Leu Asp Lys Phe Lys Thr Val
            245                 250                 255

Leu Lys Asn Lys Ala Arg Asp Leu Asn Phe Pro Asn Lys Glu Lys Leu
            260                 265                 270

Lys Gln Tyr Leu Glu Ala Glu Ile Gly Ile Pro Val Asp Ala Asn Val
        275                 280                 285

Tyr Ser Gln Met Phe Ser Asn Gly Val Ser Glu Val Gln Pro Lys Thr
        290                 295                 300

Thr Arg Asn Met Ser Phe Ser Asn Glu Lys Leu Asp Leu Leu Thr Glu
305                 310                 315                 320

Leu Lys Asp Leu Asn Lys Gly Asp Gly Phe Glu Tyr Ala Arg Glu Val
            325                 330                 335

Leu Asn Gly Phe Phe Asp Ser Glu Leu His Thr Thr Glu Asp Lys Phe
            340                 345                 350

Asn Ile Thr Ser Arg Tyr Leu Gly Gly Asp Lys Ser Asn Arg Leu Ser
        355                 360                 365

Lys Leu Tyr Lys Ile Trp Lys Lys Glu Gly Val Asp Cys Glu Glu Gly
        370                 375                 380

Ile Gln Gln Phe Cys Glu Ala Val Lys Asp Lys Met Gly Gln Ile Pro
385                 390                 395                 400

Ile Arg Asn Val Leu Lys Tyr Leu Trp Gln Phe Arg Glu Thr Val Ser

```
                      405                    410                    415

Ala Glu Asp Phe Glu Ala Ala Ala Lys Ala Asn His Leu Glu Glu Lys
            420                    425                    430

Ile Ser Arg Val Lys Ala His Pro Ile Val Ile Ser Asn Arg Tyr Trp
            435                    440                    445

Ala Phe Gly Thr Ser Ala Leu Val Gly Asn Ile Met Pro Ala Asp Lys
        450                    455                    460

Arg His Gln Gly Glu Tyr Ala Gly Gln Asn Phe Lys Met Trp Leu Glu
    465                    470                    475                    480

Ala Glu Leu His Tyr Asp Gly Lys Lys Ala Lys His His Leu Pro Phe
                485                    490                    495

Tyr Asn Ala Arg Phe Phe Glu Glu Val Tyr Cys Tyr His Pro Ser Val
                500                    505                    510

Ala Glu Ile Thr Pro Phe Lys Thr Lys Gln Phe Gly Cys Glu Ile Gly
            515                    520                    525

Lys Asp Ile Pro Asp Tyr Val Ser Val Ala Leu Lys Asp Asn Pro Tyr
        530                    535                    540

Lys Lys Ala Thr Lys Arg Ile Leu Arg Ala Ile Tyr Asn Pro Val Ala
    545                    550                    555                    560

Asn Thr Thr Gly Val Asp Lys Thr Thr Asn Cys Ser Phe Met Ile Lys
                565                    570                    575

Arg Glu Asn Asp Glu Tyr Lys Leu Val Ile Asn Arg Lys Ile Ser Val
                580                    585                    590

Asp Arg Pro Lys Arg Ile Glu Val Gly Arg Thr Ile Met Gly Tyr Asp
            595                    600                    605

Arg Asn Gln Thr Ala Ser Asp Thr Tyr Trp Ile Gly Arg Leu Val Pro
        610                    615                    620

Pro Gly Thr Arg Gly Ala Tyr Arg Ile Gly Glu Trp Ser Val Gln Tyr
    625                    630                    635                    640

Ile Lys Ser Gly Pro Val Leu Ser Ser Thr Gln Gly Val Asn Asn Ser
                645                    650                    655

Thr Thr Asp Gln Leu Val Tyr Asn Gly Met Pro Ser Ser Ser Glu Arg
            660                    665                    670

Phe Lys Ala Trp Lys Lys Ala Arg Met Ala Phe Ile Arg Lys Leu Ile
            675                    680                    685

Arg Gln Leu Asn Asp Glu Gly Leu Glu Ser Lys Gly Gln Asp Tyr Ile
        690                    695                    700

Pro Glu Asn Pro Ser Ser Phe Asp Val Arg Gly Glu Thr Leu Tyr Val
    705                    710                    715                    720

Phe Asn Ser Asn Tyr Leu Lys Ala Leu Val Ser Lys His Arg Lys Ala
                725                    730                    735

Lys Lys Pro Val Glu Gly Ile Leu Asp Glu Ile Glu Ala Trp Thr Ser
            740                    745                    750

Lys Asp Lys Asp Ser Cys Ser Leu Met Arg Leu Ser Ser Leu Ser Asp
            755                    760                    765

Ala Ser Met Gln Gly Ile Ala Ser Leu Lys Ser Leu Ile Asn Ser Tyr
        770                    775                    780

Phe Asn Lys Asn Gly Cys Lys Thr Ile Glu Asp Lys Glu Lys Phe Asn
    785                    790                    795                    800

Pro Val Leu Tyr Ala Lys Leu Val Glu Val Glu Gln Arg Arg Thr Asn
                805                    810                    815

Lys Arg Ser Glu Lys Val Gly Arg Ile Ala Gly Ser Leu Glu Gln Leu
            820                    825                    830
```

```
Ala Leu Leu Asn Gly Val Glu Val Val Ile Gly Glu Ala Asp Leu Gly
        835                 840                 845

Glu Val Glu Lys Gly Lys Ser Lys Lys Gln Asn Ser Arg Asn Met Asp
    850                 855                 860

Trp Cys Ala Lys Gln Val Ala Gln Arg Leu Glu Tyr Lys Leu Ala Phe
865                 870                 875                 880

His Gly Ile Gly Tyr Phe Gly Val Asn Pro Met Tyr Thr Ser His Gln
                885                 890                 895

Asp Pro Phe Glu His Arg Arg Val Ala Asp His Ile Val Met Arg Ala
            900                 905                 910

Arg Phe Glu Glu Val Asn Val Glu Asn Ile Ala Glu Trp His Val Arg
        915                 920                 925

Asn Phe Ser Asn Tyr Leu Arg Ala Asp Ser Gly Thr Gly Leu Tyr Tyr
    930                 935                 940

Lys Gln Ala Thr Met Asp Phe Leu Lys His Tyr Gly Leu Glu Glu His
945                 950                 955                 960

Ala Glu Gly Leu Glu Asn Lys Lys Ile Lys Phe Tyr Asp Phe Arg Lys
                965                 970                 975

Ile Leu Glu Asp Lys Asn Leu Thr Ser Val Ile Ile Pro Lys Arg Gly
            980                 985                 990

Gly Arg Ile Tyr Met Ala Thr Asn Pro Val Thr Ser Asp Ser Thr Pro
        995                 1000                1005

Ile Thr Tyr Ala Gly Lys Thr Tyr Asn Arg Cys Asn Ala Asp Glu
    1010                1015                1020

Val Ala Ala Ala Asn Ile Val Ile Ser Val Leu Ala Pro Arg Ser
    1025                1030                1035

Lys Lys Asn Glu Glu Gln Asp Asp Ile Pro Leu Ile Thr Lys Lys
    1040                1045                1050

Ala Glu Ser Lys Ser Pro Pro Lys Asp Arg Lys Arg Ser Lys Thr
    1055                1060                1065

Ser Gln Leu Pro Gln Lys
    1070
```

```
<210> SEQ ID NO 17
<211> LENGTH: 1031
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Val Ser Asp Ser Thr Ile Arg Pro Tyr Thr Ser Lys Leu Ala Pro
1               5                   10                  15

Asn Asp Pro Lys Arg Lys Met Leu Asn Asp Thr Phe Asn Trp Leu Asp
            20                  25                  30

His Ala Tyr Lys Val Phe Phe Asp Val Ser Val Ala Leu Phe Gly Gly
        35                  40                  45

Ile Asp Tyr Glu Ala Ala Glu Glu Leu Ile Asp Glu Lys Ser Thr Phe
    50                  55                  60

Asp Ala Asp Leu Leu Cys Ala Ile Met Trp Phe Arg Leu Glu Glu Lys
65                  70                  75                  80

Ser Asn Asn Pro Gly Pro Leu Gln Thr Thr Glu Gln Arg Thr Arg Leu
                85                  90                  95
```

Phe Gln Lys Tyr Ser Gly His Glu Pro Ser Ser Phe Ala Gln Glu Tyr
              100                 105                 110

Ile Lys Gly Asn Thr Asp Thr Glu Lys Tyr Glu Trp Val Asp Cys Arg
              115                 120                 125

Leu Lys Phe Ala Asp Leu Ala Arg Asn Ile His Thr Thr Gln Glu Ser
          130                 135                 140

Leu Lys Thr Asp Ala Tyr Thr Leu Phe Met Asn Lys Leu Ile Pro Val
145                 150                 155                 160

Ser Lys Asp Asp Glu Phe Asn Ala Tyr Gly Phe Ile Ser Gln Leu Phe
                  165                 170                 175

Gly Thr Gly Lys Lys Glu Asp Arg Ser Val Lys Ala Ser Met Leu Glu
              180                 185                 190

Glu Ile Ser Asn Ile Ile Glu Asp Lys Lys Pro Asn Thr Trp Glu Glu
              195                 200                 205

Tyr Gln Asp Leu Ile Lys Lys Thr Phe Asn Val Ser Asn Tyr Lys Glu
          210                 215                 220

Leu Lys Glu Lys Leu Ser Ala Gly Ser Ser Gly Arg Asp Gly Ser Leu
225                 230                 235                 240

Val Ile Asp Leu Lys Glu Glu Lys Thr Gly Leu Leu Gln Pro Asn Phe
                  245                 250                 255

Ile Lys Asn Arg Ile Val Lys Phe Arg Glu Asp Ala Asp Lys Lys Arg
              260                 265                 270

Thr Val Phe Ser Leu Pro Asn Arg Met Lys Leu Arg Glu Phe Ile Ser
              275                 280                 285

Ser Gln Ile Gly Pro Phe Glu Gln Asn Ser Trp Ser Ala Val Leu Asn
          290                 295                 300

Arg Ser Met Ala Ala Ile Gln Ser Lys Asn Ser Ser Asn Ile Leu Tyr
305                 310                 315                 320

Thr Asn Gln Lys Gln Glu Arg Asn Asn Glu Ile Gln Glu Leu Leu Lys
                  325                 330                 335

Glu Asp Ile Leu Ser Ala Ala Ser Ile Leu Asn Asp Phe Arg Arg Gly
              340                 345                 350

Glu Phe Asn Ser Ser Val Val Ser Lys Asn His Leu Gly Ser Arg Leu
          355                 360                 365

Asn Glu Leu Phe Glu Met Trp Gln Ala Leu Lys Met Asn Asp Gly Ile
      370                 375                 380

Glu Lys Tyr Thr Asp Leu Cys Lys Asp Asn Phe Ser Arg Arg Pro Val
385                 390                 395                 400

Ser Ala Leu Leu Gln Tyr Ile Tyr Pro Tyr Phe Asp Lys Ile Thr Ala
                  405                 410                 415

Lys Gln Phe Leu Asp Ala Ala Ser Tyr Asn Thr Leu Val Glu Thr Asn
              420                 425                 430

Asn Arg Lys Lys Ile His Pro Thr Val Thr Gly Pro Thr Val Cys Asn
          435                 440                 445

Trp Gly Pro Lys Ser Thr Ile Asn Gly Ser Ile Thr Pro Pro Asn Gln
      450                 455                 460

Met Val Lys Asp Arg Pro Ala Gly Ser His Gly Met Ile Trp Val Thr
465                 470                 475                 480

Met Thr Val Arg Asp Asn Gly Arg Trp Val Lys His His Leu Pro Phe
                  485                 490                 495

His Asn Ser Arg Tyr Tyr Glu Glu His Tyr Cys Tyr Arg Glu Gly Leu
              500                 505                 510

Pro Thr Lys Asn Gln Pro Arg Thr Lys Gln Leu Gly Thr Gln Val Gly

-continued

```
                515                 520                 525

Ser Ile Ile Ser Ala Pro Ser Leu Ala Ile Leu Lys Ser Gln Glu Glu
    530                 535                 540

Gln Asp Arg Arg Asn Asp Arg Lys Ser Arg Phe Lys Ala His Lys Ser
545                 550                 555                 560

Ile Ile Arg Ser Gln Glu Asn Ile Lys Tyr Asn Val Ala Phe Asp Lys
                565                 570                 575

Ser Thr Asn Phe Asp Val Thr Arg Lys Asn Gly Glu Phe Phe Ile Thr
                580                 585                 590

Ile Ser Ser Arg Val Thr Thr Pro Lys Tyr Ser His Lys Leu Asn Val
                595                 600                 605

Gly Asp Ile Ile Met Gly Leu Asp Asn Asn Gln Thr Ala Pro Cys Thr
    610                 615                 620

Tyr Ser Ile Trp Arg Ile Val Glu Lys Asp Thr Glu Gly Ser Phe Phe
625                 630                 635                 640

His Asn Lys Ile Trp Leu Gln Leu Val Thr Asp Gly Lys Ile Thr Ser
                645                 650                 655

Ile Val Asp Asn Asn Arg Gln Val Asp Gln Leu Ser Tyr Ala Gly Val
                660                 665                 670

Glu Tyr Ser Asn Phe Ala Glu Trp Arg Lys Asp Arg Arg Gln Phe Leu
                675                 680                 685

Arg Ser Ile Asn Glu Asp Tyr Val Lys Lys Ser Asp Asn Trp Leu Asn
    690                 695                 700

Met Asn Leu Tyr Gln Trp Asn Ala Glu Tyr Ser Arg Leu Leu Leu Gly
705                 710                 715                 720

Val Met Lys Asp Asn Lys Asp Lys Asn Ile Gln Asn Thr Phe Arg Ala
                725                 730                 735

Glu Ile Glu Glu Leu Ile Cys Gly Lys Phe Gly Ile Arg Leu Gly Ser
                740                 745                 750

Leu Ser His His Ser Leu Gln Phe Leu Thr Asn Cys Lys Ser Leu Ile
                755                 760                 765

Ser Ser Tyr Phe Met Leu Asn Asn Lys Lys Glu Glu His Asp Gln Glu
    770                 775                 780

Ser Phe Asp Ser Asp Phe Phe Arg Leu Met Arg Ser Ile Asp Asp Lys
785                 790                 795                 800

Arg Ile Arg Lys Arg Lys Glu Lys Ser Ser Arg Ile Ser Ser Ser Val
                805                 810                 815

Leu Gln Ile Ala Arg Glu Asn Asn Val Lys Ser Leu Cys Val Glu Gly
                820                 825                 830

Asp Leu Pro Thr Ala Thr Lys Lys Thr Lys Pro Lys Gln Asn Gln Lys
                835                 840                 845

Ser Ile Asp Trp Cys Ala Arg Ala Val Val Lys Lys Leu Asn Asp Gly
    850                 855                 860

Cys Lys Val Leu Gly Ile Asn Leu Gln Ala Ile Asp Pro Arg Asp Thr
865                 870                 875                 880

Ser His Leu Asp Pro Phe Val Tyr Tyr Gly Lys Lys Ser Thr Lys Val
                885                 890                 895

Gly Lys Glu Ala Arg Tyr Val Ile Val Glu Pro Ser Asn Ile Lys Glu
                900                 905                 910

Tyr Met Thr Lys Lys Phe Thr Asp Trp His Arg Gly Val Ser Lys Lys
                915                 920                 925

Ser Lys Lys Gly Asp Val Gln Thr Ser Thr Thr Ala Pro Leu Tyr Gln
    930                 935                 940
```

```
Glu Ala Leu Lys Gln Phe Ala Asp His Tyr Lys Leu Asp Phe Asp Ser
945                 950                 955                 960

Leu Pro Lys Met Lys Phe Tyr Glu Leu Ala Lys Ile Leu Glu Asp His
                965                 970                 975

Lys Gln Val Ile Ile Pro Cys Arg Gly Gly Arg Ala Tyr Leu Ser Thr
                980                 985                 990

Tyr Pro Ile Thr Lys Asp Ser Ser  Lys Ile Asn Phe Asn  Gly Arg Glu
            995             1000                1005

Arg Trp  Tyr Asn Gln Ser Asp  Val Val Ala Ala Val  Asn Ile Val
    1010                1015                1020

Leu Arg  Gly Ile Arg Asp Glu  Asn
    1025                1030
```

```
<210> SEQ ID NO 18
<211> LENGTH: 1066
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Pro Asp Pro Ile Lys Ser Tyr Lys Ser Pro Ile Ile Ile Asp Pro
1               5                   10                  15

Asn Asn Ala His Asp Val Glu Lys Leu Asp Phe Leu Arg Glu Thr Phe
                20                  25                  30

Val Tyr Leu Ser Asn Gly Thr Lys Cys Phe Met His Val Phe Leu Ser
                35                  40                  45

Leu Leu Gly Gly Met Asn Glu Thr Leu Ala Lys Lys Ile Val Ser Leu
        50                  55                  60

Glu Thr Pro Lys Lys Glu Lys Lys Lys Ser Asn Lys Pro Ser His
65                  70                  75                  80

Lys Ile Glu Leu Phe Leu Ala Ile Cys Trp Phe Arg Leu Val Lys Ile
                85                  90                  95

Ser Lys Asn Glu Ser Ser Val Leu Pro Ala Leu Leu Gly Asn Arg Phe
                100                 105                 110

Glu Lys Tyr Phe Gly Ala Lys Ala Thr Pro Glu Val Met Glu Tyr Phe
                115                 120                 125

Ser Ala Asn Tyr Asp Glu Ala Thr Tyr Ala Trp Lys Asp Met Arg Glu
        130                 135                 140

Glu Phe Val Ser Leu Lys Ser Lys Leu Lys Val Ser Glu Lys Asp Leu
145                 150                 155                 160

Ile Ser Asp Ile Gly Ser Met Ile Asn Glu Arg Tyr Ile Gly Leu Lys
                165                 170                 175

Phe Gly Lys Pro Trp Gly Ile Ile Ser Gly Leu Phe Gly Glu Gly Lys
                180                 185                 190

Lys Val Asp Arg Ser Leu Lys Val Glu Leu Leu Lys Asn Val Leu Glu
                195                 200                 205

Glu Ile Glu Lys Asn Pro Pro Lys Thr Lys Asp Gln Leu Ala Lys Met
        210                 215                 220

Ile Leu Lys Cys Ala Asp Cys Lys Asn Gly Gln Glu Ile His Ala Lys
225                 230                 235                 240

Cys Gly Lys Ile Gly Arg Met Ser Ser Val Ser Asn Trp Ala Asp Glu
                245                 250                 255
```

```
Val Gly Ser Glu Lys Glu Ile Val Leu Ser Phe Val Lys Ser Lys Ile
            260                 265                 270

Ser Gln Asp Leu Ala Lys Gln Ser Asn Glu Arg Asn Trp Lys Cys Val
            275                 280                 285

Asn Ala Leu Lys Ser Tyr Ile Leu Ser Glu Ile Gly Asn Cys Phe Asp
            290                 295                 300

Gln Ser Ser Trp Ser Glu Met Leu Asn Asn Ser Leu Ser Val Ile Gln
305                 310                 315                 320

Ser Lys Thr Thr Arg Asn Tyr Asn Phe Cys Ile Glu Gln Leu Glu Glu
            325                 330                 335

Lys Lys Asn Leu Asn Gln Asn His Arg Lys Phe Gly Thr Met Ile Glu
            340                 345                 350

Asp Tyr Phe Ser Ser Arg Phe Phe Thr Gly Glu Asn Lys Phe Ile Ile
            355                 360                 365

Cys Asn Phe His Val Gly Asp Lys Asp Lys Val Ser Ala Leu Leu Ala
            370                 375                 380

Ser Cys Glu Gly Leu Ser Glu Glu Glu Leu Glu Glu Lys Ile Gln Asn
385                 390                 395                 400

Phe Cys Glu Ser Gln Lys Gln Glu Ser Lys Met Pro Ile Pro Ala Leu
            405                 410                 415

Leu Met Tyr Leu Asn Ser Leu Lys Asp Ser Ile Thr Val Asp Gln Met
            420                 425                 430

Phe Gln Gly Ile Leu Tyr Asn Lys Ile Arg Asp Lys Ile Glu Arg Gln
            435                 440                 445

Lys Leu His Pro Ile Val Pro Asn Asn Asp Ser Phe Asp Trp Gly Met
            450                 455                 460

Ser Ser Lys Ile Asn Gly Arg Ile Ile Ser Pro Lys Glu Lys Ala Lys
465                 470                 475                 480

His Asn Ala Gln Asn Asn Arg Ser Leu Tyr Asp Ser Gly Ile Trp Ile
            485                 490                 495

Glu Ile Ser Val Leu Lys Asn Lys Glu Trp Ala Lys His His Tyr Lys
            500                 505                 510

Ile Ser Asn Thr Arg Phe Val Glu Glu Phe Tyr Tyr Pro Ser Ser Asn
            515                 520                 525

Asp Glu Asn Ser Leu Asp Gln Val Phe Arg Thr Gly Arg Asn Gly Phe
            530                 535                 540

Asn Asn Pro Ala Lys Asn Asn Leu Ser Leu Glu Gln Val Ser Asn Ile
545                 550                 555                 560

Lys Asn Ala Pro Lys Asn Arg Arg Arg Ala Ile Lys Arg Gln Met Arg
            565                 570                 575

Val Glu Ala Ala His Gln Gln Asn Val Leu Pro His Val Lys Trp Asp
            580                 585                 590

Asp Asn Tyr Cys Ile Thr Ile Ser Lys Tyr Gly Asp Lys Phe Val Thr
            595                 600                 605

Phe Ile Ser Lys Lys Phe Lys Ser Lys Lys Ser Lys Glu Tyr Val Val
            610                 615                 620

Phe Leu Gly Phe Asp Gln Asn Gln Thr Ala Ser His Thr Phe Ala Ala
625                 630                 635                 640

Val Gln Ile Cys Asp Ser Lys Asp Glu Asn Val Ile Pro Tyr Cys Gly
            645                 650                 655

Leu Phe Val Lys Pro Leu Glu Cys Gly His Ile Thr Ser Val Gln Lys
            660                 665                 670

Val Lys Asp Arg Ser Ile Asp Gln Leu Ser Tyr Ser Gly Leu Pro Trp
```

-continued

```
          675                    680                    685

Lys Asp Phe Ile Ser Trp Ser Gln Glu Arg Lys Glu Phe Val Ser Lys
     690                    695                    700

Trp Arg Met Val Glu Val Lys Thr Arg Asn Gly Glu Lys Leu Asp Asp
705                    710                    715                    720

Leu Thr Val Lys Ile Asn Lys Leu Asp Glu Asn Lys His Gly Leu Tyr
                    725                    730                    735

Ala Tyr Asn Ser Lys Tyr Phe Trp Tyr Leu Lys Ser Ile Met Arg Lys
                    740                    745                    750

Lys Thr Lys Asp Glu Leu Phe Glu Ile Arg Lys Glu Leu Leu Thr Val
                    755                    760                    765

Ile Lys Thr Gly Arg Leu Cys Val Leu Arg Leu Ser Ser Leu Asn His
     770                    775                    780

Ser Ser Phe Leu Met Leu Lys Asn Ala Lys Ser Ala Ile Ser Cys Tyr
785                    790                    795                    800

Phe Asn Asn Leu Leu Lys Gly Val Ser Asn Asp Gln Glu Lys Tyr Glu
                    805                    810                    815

Ala Asp Pro Glu Met Phe Glu Leu Arg Arg Glu Val Glu Ala Lys Arg
               820                    825                    830

Gln Asn Lys Cys Met Ser Lys Lys Asn Leu Ile Ser Ser Gln Ile Val
               835                    840                    845

Ser Lys Ala Ile Glu Leu Arg Gly Asn Tyr Gly Ser Val Ala Ile Ile
     850                    855                    860

Gly Glu Asp Leu Ser Asp Tyr Val Pro Asp Lys Gly Lys Lys Ser Thr
865                    870                    875                    880

Gln Asn Ala Asn Leu Leu Asp Trp Leu Ser Arg Gly Val Ala Asn Lys
               885                    890                    895

Val Lys Gln Ile Ala Asn Met His Asp Asn Ile Ser Phe Lys Asp Val
               900                    905                    910

Ser Pro Gln Trp Thr Ser His Gln Asp Ser Phe Val Asp Arg Asn Pro
               915                    920                    925

Asn Ser Ala Leu Arg Val Arg Phe Gly Ser Cys Asp Pro Glu Glu Met
     930                    935                    940

Tyr Glu Lys Asp Phe Glu Ser Leu Ile Lys Phe Leu Lys Glu Asp Cys
945                    950                    955                    960

Gly His Tyr Thr Asn Ser Met Asn Asp Phe Leu Ser His Tyr Gly Val
               965                    970                    975

Ser Arg Lys Asp Met Leu Glu Ile Lys Phe Ser Ala Phe Lys Ile Leu
               980                    985                    990

Met Lys Asn Ile Leu Asn Lys Thr  Gly Glu Lys Ser Leu  Leu Tyr Pro
               995                    1000                   1005

Lys Arg  Gly Gly Arg Leu Tyr  Leu Ala Thr His Lys  Leu Gly Gln
     1010                   1015                   1020

Cys Thr  Arg Arg Thr Tyr Asn  Gly Val Asp Phe Trp  Glu Cys Asp
     1025                   1030                   1035

Ala Asp  Cys Val Ala Ala Phe  Asn Ile Ala Leu Ser  Gly Ile Arg
     1040                   1045                   1050

Lys Tyr  Tyr Gly Ile Lys Ser  Glu Ala Val Ser Pro  Val
     1055                   1060                   1065
```

<210> SEQ ID NO 19
<211> LENGTH: 36
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 19
ctagcaatga cctaatagtg tgtccttagt tgacat                                36

<210> SEQ ID NO 20
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
tctcaacgat agtcagacat gtgtcctcag tgacac                                36

<210> SEQ ID NO 21
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cctacaatac ctaagaaatc cgtcctaagt tgacgg                                36

<210> SEQ ID NO 22
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
gtagcaatca gtacatattg tgcctttcat tggcaca                               37

<210> SEQ ID NO 23
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
gtagcaatca gtacatattg tgcctttcat tggcac                                36

<210> SEQ ID NO 24
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
gttggaatga ctaatttttg tgcccaccgt tggcac                                36
```

-continued

```
<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36
```

```
<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47
```

-continued

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

-continued

```
<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000
```

-continued

```
<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
```

-continued

```
<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92
```

```
000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
auuuuugugc ccaucguugg cac                                                 23

<210> SEQ ID NO 101
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
agaaauccgu cuuucauuga cgg                                                 23
```

-continued

```
<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113
```

```
<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124
```

-continued

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

```
<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000
```

```
<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 106
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(70)
<223> OTHER INFORMATION: a, c, u, g, unknown or other

<400> SEQUENCE: 150
cuagcaauga ccuaauagug uguccuuagu ugacaunnnn nnnnnnnnnn nnnnnnnnnn      60
nnnnnnnnnn cuagcaauga ccuaauagug uguccuuagu ugacau                   106

<210> SEQ ID NO 151
<211> LENGTH: 107
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(71)
<223> OTHER INFORMATION: a, c, u, g, unknown or other

<400> SEQUENCE: 151
cuagcaauga ccuaauagug uguccuuagu ugacaunnnn nnnnnnnnnn nnnnnnnnnn      60
nnnnnnnnnn ncuagcaaug accuaauagu guguccuuag uugacau                  107

<210> SEQ ID NO 152
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(72)
<223> OTHER INFORMATION: a, c, u, g, unknown or other

<400> SEQUENCE: 152
ucucaacgau agucagacau guguccucag ugacacnnnn nnnnnnnnnn nnnnnnnnnn      60
nnnnnnnnnn nnucucaacg auagucagac augguguccuc agugacac             108
```

<210> SEQ ID NO 153
<211> LENGTH: 107
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(71)
<223> OTHER INFORMATION: a, c, u, g, unknown or other

<400> SEQUENCE: 153
ccuacaauac cuaagaaauc cguccuaagu ugacggnnnn nnnnnnnnnn nnnnnnnnnn      60
nnnnnnnnnn nccuacaaua ccuaagaaau ccguccuaag uugacgg                  107

<210> SEQ ID NO 154
<211> LENGTH: 107
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (38)..(70)
<223> OTHER INFORMATION: a, c, u, g, unknown or other

<400> SEQUENCE: 154
guagcaauca guacauauug ugccuuucau uggcacannn nnnnnnnnnn nnnnnnnnnn      60
nnnnnnnnnn guagcaauca guacauauug ugccuuucau uggcaca                  107

<210> SEQ ID NO 155
<211> LENGTH: 106
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(70)
<223> OTHER INFORMATION: a, c, u, g, unknown or other

<400> SEQUENCE: 155
guagcaauca guacauauug ugccuuucau uggcacnnnn nnnnnnnnnn nnnnnnnnnn      60
nnnnnnnnnn guagcaauca guacauauug ugccuuucau uggcac                   106

<210> SEQ ID NO 156
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(72)
<223> OTHER INFORMATION: a, c, u, g, unknown or other

<400> SEQUENCE: 156
guuggaauga cuaauuuuug ugcccaccgu uggcacnnnn nnnnnnnnnn nnnnnnnnnn      60
nnnnnnnnnn nnguuggaau gacuaauuuu ugugcccacc guuggcac                    108

<210> SEQ ID NO 157
<211> LENGTH: 84
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (25)..(60)
<223> OTHER INFORMATION: a, c, u, g, unknown or other

<400> SEQUENCE: 157
aauuuuugug cccaucguug gcacnnnnnn nnnnnnnnnn nnnnnnnnnn nnnnnnnnnn    60
aauuuuugug cccaucguug gcac                                          84

<210> SEQ ID NO 158
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(72)
<223> OTHER INFORMATION: a, c, u, g, unknown or other

<400> SEQUENCE: 158
cccacaauac cugagaaauc cguccuacgu ugacggnnnn nnnnnnnnnn nnnnnnnnnn    60
nnnnnnnnnn nncccacaau accugagaaa uccguccuac guugacgg               108

<210> SEQ ID NO 159
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(72)
<223> OTHER INFORMATION: a, c, u, g, unknown or other

<400> SEQUENCE: 159
cccacaauac cugagaaauc cguccuacgu ugacggnnnn nnnnnnnnnn nnnnnnnnnn    60
nnnnnnnnnn nncccacaau accugagaaa uccguccuac guugacgg               108

<210> SEQ ID NO 160
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(72)
<223> OTHER INFORMATION: a, c, u, g, unknown or other

<400> SEQUENCE: 160
cucucaaugc cuuagaaauc cguccuuggu ugacggnnnn nnnnnnnnnn nnnnnnnnnn    60
nnnnnnnnnn nncucucaau gccuuagaaa uccguccuug guugacgg                    108

<210> SEQ ID NO 161
<211> LENGTH: 106
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(70)
<223> OTHER INFORMATION: a, c, u, g, unknown or other

<400> SEQUENCE: 161
cccacaauac cugagaaauc cguccuacgu ugacggnnnn nnnnnnnnnn nnnnnnnnnn      60
nnnnnnnnnn cccacaauac cugagaaauc cguccuacgu ugacgg                    106

<210> SEQ ID NO 162
<211> LENGTH: 92
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (35)..(58)
<223> OTHER INFORMATION: a, c, u, g, unknown or other

<400> SEQUENCE: 162
gcaacaccua agaaauccgu cuuucauuga cgggnnnnn nnnnnnnnnn nnnnnnnngc      60
aacaccuaag aaauccgucu uucauugacg gg                                    92

<210> SEQ ID NO 163
<211> LENGTH: 103
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (37)..(67)
<223> OTHER INFORMATION: a, c, u, g, unknown or other

<400> SEQUENCE: 163
guugcaaaac ccaagaaauc cgucuuucau ugacggnnnn nnnnnnnnnn nnnnnnnnnn      60
nnnnnnnguu gcaaaaccca agaaauccgu cuuucauuga cgg                       103

<210> SEQ ID NO 164

<400> SEQUENCE: 164

000

<210> SEQ ID NO 165

<400> SEQUENCE: 165

000

<210> SEQ ID NO 166

-continued

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

-continued

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

-continued

```
<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000
```

```
<210> SEQ ID NO 200
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Thr"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Leu"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 200

Ser Ser His Gln Asp Pro Phe
1               5

<210> SEQ ID NO 201
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Gly" or "Ser"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: VARIANT
<222> LOCATION: (6)..(6)
<223> OTHER INFORMATION: /replace="Ile"
<220> FEATURE:
<221> NAME/KEY: VARIANT
<222> LOCATION: (7)..(7)
<223> OTHER INFORMATION: /replace="Ser" or "Val"
<220> FEATURE:
<221> NAME/KEY: MOD_RES
<222> LOCATION: (8)..(10)
<223> OTHER INFORMATION: Any amino acid
<220> FEATURE:
<221> NAME/KEY: VARIANT
<222> LOCATION: (11)..(11)
<223> OTHER INFORMATION: /replace="Ala"
<220> FEATURE:
<221> NAME/KEY: SITE
<222> LOCATION: (1)..(11)
<223> OTHER INFORMATION: /note="Variant residues given in the sequence
      have no preference with respect to those in the annotations
      for variant positions"
```

<400> SEQUENCE: 201

Ala Xaa Asp Xaa Asn Gln Thr Xaa Xaa Xaa Thr
1               5                   10

<210> SEQ ID NO 202
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(11)
<223> OTHER INFORMATION: a, c, u, g, unknown or other

<400> SEQUENCE: 202
ccgucnnnnn nugacgg                                                          17

<210> SEQ ID NO 203
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(11)
<223> OTHER INFORMATION: a, c, u, g, unknown or other

<400> SEQUENCE: 203
gugccnnnnn nuggcac                                                          17

<210> SEQ ID NO 204
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(11)
<223> OTHER INFORMATION: a, c, u, g, unknown or other
<220> FEATURE:
<221> NAME/KEY: misc_feature
<222> LOCATION: (11)..(11)
<223> OTHER INFORMATION: May or may not be present

<400> SEQUENCE: 204
gugucnnnnn nugacay                                                          17

<210> SEQ ID NO 205
<211> LENGTH: 14
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
ucyuwvruug acgg                                                             14

-continued

```
<210> SEQ ID NO 206
<211> LENGTH: 14
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
ccywycruug gcac                                                        14

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Phe" or "Ile" or "Leu" or "Met" or
      "Pro" or "Val" or "Trp" or "Tyr"
<220> FEATURE:
<221> NAME/KEY: VARIANT
<222> LOCATION: (2)..(2)
<223> OTHER INFORMATION: /replace="Phe" or "Ile" or "Leu" or "Met" or
      "Pro" or "Arg" or "Val" or "Trp" or "Tyr"
<220> FEATURE:
<221> NAME/KEY: VARIANT
<222> LOCATION: (3)..(3)
<223> OTHER INFORMATION: /replace="Phe" or "Gly" or "Ile" or "Leu" or
      "Met" or "Pro" or "Val" or "Trp" or "Tyr"
<220> FEATURE:
<221> NAME/KEY: SITE
<222> LOCATION: (1)..(4)
<223> OTHER INFORMATION: /note="Variant residues given in the sequence
      have no preference with respect to those in the annotations
      for variant positions"

<400> SEQUENCE: 210

Cys Cys Cys Glu
1

<210> SEQ ID NO 211

<400> SEQUENCE: 211

000

<210> SEQ ID NO 212
```

-continued

```
<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223
```

-continued

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

```
<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000
```

-continued

```
<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257
```

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

-continued

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

-continued

```
<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290
<400> SEQUENCE: 290
000

<210> SEQ ID NO 291
```

```
<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 7
<212> TYPE: PRT
<213> ORGANISM: Simian virus 40

<400> SEQUENCE: 300

Pro Lys Lys Lys Arg Lys Val
1               5

<210> SEQ ID NO 301
<211> LENGTH: 16
<212> TYPE: PRT
<213> ORGANISM: Unknown
<220> FEATURE:
<221> NAME/KEY: source
```

<223> OTHER INFORMATION: /note="Description of Unknown:
      Nucleoplasmin bipartite NLS sequence"

<400> SEQUENCE: 301

Lys Arg Pro Ala Ala Thr Lys Lys Ala Gly Gln Ala Lys Lys Lys Lys
1               5                   10                  15

<210> SEQ ID NO 302
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      c-Myc NLS sequence"

<400> SEQUENCE: 302

Pro Ala Ala Lys Arg Val Lys Leu Asp
1               5

<210> SEQ ID NO 303
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      c-Myc NLS sequence"

<400> SEQUENCE: 303

Arg Gln Arg Arg Asn Glu Leu Lys Arg Ser Pro
1               5                   10

<210> SEQ ID NO 304
<211> LENGTH: 38
<212> TYPE: PRT
<213> ORGANISM: Homo sapiens

<400> SEQUENCE: 304

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 305
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 305

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 306
<211> LENGTH: 8

```
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 306

Val Ser Arg Lys Arg Pro Arg Pro
1               5

<210> SEQ ID NO 307
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 307

Pro Pro Lys Lys Ala Arg Glu Asp
1               5

<210> SEQ ID NO 308
<211> LENGTH: 8
<212> TYPE: PRT
<213> ORGANISM: Homo sapiens

<400> SEQUENCE: 308

Pro Gln Pro Lys Lys Lys Pro Leu
1               5

<210> SEQ ID NO 309
<211> LENGTH: 12
<212> TYPE: PRT
<213> ORGANISM: Mus sp.

<400> SEQUENCE: 309

Ser Ala Leu Ile Lys Lys Lys Lys Lys Met Ala Pro
1               5                   10

<210> SEQ ID NO 310
<211> LENGTH: 5
<212> TYPE: PRT
<213> ORGANISM: Influenza virus

<400> SEQUENCE: 310

Asp Arg Leu Arg Arg
1               5

<210> SEQ ID NO 311
<211> LENGTH: 7
<212> TYPE: PRT
<213> ORGANISM: Influenza virus

<400> SEQUENCE: 311

Pro Lys Gln Lys Lys Arg Lys
1               5

<210> SEQ ID NO 312
<211> LENGTH: 10
<212> TYPE: PRT
<213> ORGANISM: Hepatitis virus

<400> SEQUENCE: 312
```

Arg Lys Leu Lys Lys Lys Ile Lys Lys Leu
1               5                   10

<210> SEQ ID NO 313
<211> LENGTH: 10
<212> TYPE: PRT
<213> ORGANISM: Mus sp.

<400> SEQUENCE: 313

Arg Glu Lys Lys Lys Phe Leu Lys Arg Arg
1               5                   10

<210> SEQ ID NO 314
<211> LENGTH: 20
<212> TYPE: PRT
<213> ORGANISM: Homo sapiens

<400> SEQUENCE: 314

Lys Arg Lys Gly Asp Glu Val Asp Gly Val Asp Glu Val Ala Lys Lys
1               5                   10                  15

Lys Ser Lys Lys
            20

<210> SEQ ID NO 315
<211> LENGTH: 17
<212> TYPE: PRT
<213> ORGANISM: Homo sapiens

<400> SEQUENCE: 315

Arg Lys Cys Leu Gln Ala Gly Met Asn Leu Glu Ala Arg Lys Thr Lys
1               5                   10                  15

Lys

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

```
<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332
```

-continued

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

```
<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366
```

-continued

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

-continued

```
<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000
```

-continued

```
<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400
<211> LENGTH: 131
```

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 400
gggaauuuuu gugcccaucg uuggcacccu aaugcggaag uaguggguaa cccggaauuu     60
uugugcccau cguuggcacu ccgcaagaau ugauuggcuc caauucuaau uuuugugccc    120
aucguuggca c                                                        131

<210> SEQ ID NO 401
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
aauuuuugug cccaucguug gcac                                           24

<210> SEQ ID NO 402
<211> LENGTH: 28
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
ccuaaugcgg aaguaguggg uaacccgg                                       28

<210> SEQ ID NO 403
<211> LENGTH: 28
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
uccgcaagaa uugauuggcu ccaauucu                                       28

<210> SEQ ID NO 404
<211> LENGTH: 131
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 404
gggaauuuuu gugcccaucg uuggcacagg caucaucagc auuaaccacg caaacaauuu     60
uugugcccau cguuggcacg cgugcuggau ugcuucgaug gucugcgaau uuuugugccc    120
aucguuggca c                                                        131

<210> SEQ ID NO 405
<211> LENGTH: 24
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
aauuuuugug cccaucguug gcac                                                24

<210> SEQ ID NO 406
<211> LENGTH: 28
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
aggcaucauc agcauuaacc acgcaaac                                            28

<210> SEQ ID NO 407
<211> LENGTH: 28
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
gcgugcugga uugcuucgau ggucugcg                                            28

<210> SEQ ID NO 408
<211> LENGTH: 128
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 408
catgtggacc acattaggct gcaaaactgc gcatttacga aaacgcgaaa gtttgcgtgg        60
ttaatgctga tgatgcctta acaatgccga ttcgcggtgc ggatgaacgt aatttctcga       120
ggcgtatt                                                                128

<210> SEQ ID NO 409
<211> LENGTH: 128
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 409
catgtggacc acattaggct tggttgttgc tgccgacgac ggtgtgatgc cgcagaccat        60
cgaagcaatc cagcacgcga aagcggcgca ggtaccggtg gtggttgcgt aatttctcga       120
ggcgtatt                                                                128

<210> SEQ ID NO 410
<211> LENGTH: 128
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic polynucleotide"

<400> SEQUENCE: 410
aatacgcctc gagaaattac aaagtgatgc aggcgtttcc aggtgctttc cctaatgcgg      60
aagtagtggg taacccggtg cgtaccgatg tgttggcgct gccgttgcag cctaatgtgg     120
tccacatg                                                             128

<210> SEQ ID NO 411
<211> LENGTH: 171
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 411
gtgccaacga tgggcacaaa aattagaatt ggagccaatc aattcttgcg gagtgccaac      60
gatgggcaca aaaattagaa ttggagccaa tcaattcttg cggagtgcca acgatgggca     120
caaaaattcc ctatagtgag tcgtattact cgagggatcc ttattacatt t             171

<210> SEQ ID NO 412
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 412
taatacgact cactatag                                                   18

<210> SEQ ID NO 413
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 413
gtgccaacga tgggcacaaa aattagaatt ggagccaatc aattcttgcg ga             52

<210> SEQ ID NO 414
<211> LENGTH: 171
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 414
gtgccaacga tgggcacaaa aattcgcaga ccatcgaagc aatccagcac gcgtgccaac      60
gatgggcaca aaaattgttt gcgtggttaa tgctgatgat gcctgtgcca acgatgggca     120
caaaaattcc ctatagtgag tcgtattact cgagggatcc ttattacatt t             171

<210> SEQ ID NO 415
```

```
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 415
taatacgact cactatag                                               18

<210> SEQ ID NO 416
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 416
gtgccaacga tgggcacaaa aattcgcaga ccatcgaagc aatccagcac gc          52

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424
```

-continued

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

-continued

```
<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000
```

-continued

```
<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458
```

-continued

```
<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469
```

```
000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000
```

-continued

```
<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492
```

-continued

```
<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500
<211> LENGTH: 212
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 500
gggcagagcg cacatcgccc acagtccccg agaagttggg gggagggggtc ggcaattgat        60 ccggtgccta gagaaggtgg cgcgggggtaa actgggaaag tgatgtcgtg tactggctcc       120
gcctttttcc cgagggtggg ggagaaccgt atataagtgc agtagtcgcc gtgaacgttc       180
tttttcgcaa cgggtttgcc gccagaacac ag                                      212

<210> SEQ ID NO 501
<211> LENGTH: 3375
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic polynucleotide"

<400> SEQUENCE: 501
atgaaaatcg aagaaggtaa aggtcaccat caccatcacc acatgtctaa caaggagaag     60
aatgccagcg agacccggaa ggcctacacc acaaagatga tccccaggag ccacgaccgc    120
atgaagctgc tgggcaactt tatggactat ctgatggatg gcaccccat cttcttgag    180 ctgtggaatc agttcggcgg cggcatcgac agagatatca tcagcggcac agccaacaag    240
gataagatct ccgacgatct gctgctggcc gtgaactggt ttaaagtgat gccaatcaat    300
tctaagcccc agggcgtgtc cccttctaac ctggccaatc tgttccagca gtacagcgga    360
tccgagcctg acatccaggc acaggagtat ttcgcctcca actttgacac cgagaagcac    420
cagtggaagg atatgcgggt ggagtacgag agactgctgg ccgagctgca gctgtctagg    480
agcgacatgc atcacgatct gaagctgatg tacaaggaga agtgcatcgg cctgtccctg    540
tctaccgccc actatatcac aagcgtgatg tttggcaccg gcgccaagaa caatcgccag    600
acaaagcacc agttctattc caaagtgatc cagctgctgg aggagagcac ccagatcaat    660
tccgtggagc agctggcctc catcatcctg aaggccggcg actgcgattc ttacaggaag    720
ctgaggatca ggtgttcccg caagggagca accccatcta tcctgaagat cgtgcaggac    780
tatgagctgg gcacaaacca cgacgatgaa gtgaatgtgc cctccctgat cgccaacctg    840
aaggagaagc tgggcaggtt tgagtacgag tgcgagtgga agtgtatgga gaagatcaag    900
gccttcctgg cctctaaagt gggcccttac tatctgggca gctattccgc catgctggag    960
aatgccctga gcccaatcaa gggcatgacc acaaagaact gtaagttcgt gctgaagcag   1020
atcgacgcca gaacgatat caagtacgag aatgagccct tggcaagat cgtggagggc   1080 ttctttgact ctccttattt cgagagcgat accaatgtga agtgggtgct gcaccctcac   1140
cacatcggcg agtctaacat caagacactg tgggaggacc tgaatgccat ccacagcaag   1200
tacgaggagg acatcgcctc tctgagcgag gataagaagg agaagcggat caaggtgtac   1260
cagggcgatg tgtgccagac catcaacaca tattgtgagg aagtgggcaa ggaggccaag   1320
accccactgg tgcagctgct gaggtacctg tattcccgca aggacgatat cgccgtggac   1380
aagatcatcg atggcatcac attcctgtct aagaagcaca aggtggagaa gcagaagatc   1440
aacccagtga tccagaagta ccccagcttc aattttggca acaattccaa gctgctgggc   1500
aagatcatca gcccaaagga caagctgaag cacaacctga agtgcaacag aaatcaggtg   1560
gataattaca tctggatcga gatcaaggtg ctgaacacca agacaatgcg gtgggagaag   1620
caccactatg ccctgagctc caccagattt ctggaggagg tgtactatcc cgccacatcc   1680
gagaatccac ctgacgcact ggcagcacgg ttcagaacca agacaaacgg ctacgagggc   1740
aagccagccc tgtctgccga gcagatcgag cagatcagga gcgcaccagt gggactgaga   1800
aaggtgaaga agcggcagat gagactggag gcagcaaggc agcagaatct gctgccacgc   1860
tatacctggg gcaaggattt taacatcaat atctgtaaga ggggcaacaa tttcgaggtg   1920 acccctggcca caaaggtgaa gaagaagaag gagaagaact acaaggtggt gctgggctat   1980
gacgccaaca tcgtgcgcaa gaatacctac gcagcaatcg aggcacacgc aaacggcgat   2040
ggcgtgatcg actataatga tctgcctgtg aagccaatcg agtctggctt tgtgacagtg   2100
gagagccagg tgagggacaa gtcctacgat cagctgtctt ataacggcgt gaagctgctg   2160
```

-continued

```
tactgcaagc ctcacgtgga gagccggaga tccttcctgg agaagtatcg gaacggcacc      2220
atgaaggaca atagaggcaa caatatccag atcgacttca tgaaggattt tgaggccatc      2280
gccgacgatg agacaagcct gtactacttc aacatgaagt actgtaagct gctgcagtct      2340
agcatccgca accactcctc tcaggccaag gagtataggg aggagatctt cgagctgctg      2400
cgcgatggca agctgtccgt gctgaagctg agctccctgt ctaatctgag cttcgtgatg      2460
tttaaggtgg ccaagtctct gatcggcacc tactttggcc acctgctgaa gaagcctaag      2520
aactccaagt ctgacgtgaa ggccccaccc atcacagacg aggataagca gaaggccgat      2580
ccagagatgt tcgcactgcg gctggcactg gaggagaaga gactgaataa ggtgaagagc      2640
aagaaggaag tgatcgccaa caagatcgtg gccaaggcac tggagctgag ggacaagtac      2700
ggaccagtgc tgatcaaggg cgagaatatc agcgatacca caaagaaggg caagaagtct      2760
agcaccaatt ccttcctgat ggactggctg gccagaggcg tggccaacaa ggtgaaggag      2820
atggtcatga tgcaccaggg cctggagttc gtggaggtga accccaattt tacctcccac      2880
caggatcctt tcgtgcacaa gaacccgag aataccttcc gggcaaggta cagcaggtgc      2940
accccttccg agctgacaga gaagaaccgc aaggagatcc tgtccttcct gtctgacaag      3000
cccagcaagc ggcctactaa cgcctactat aatgagggcg ccatggcctt tctggccaca      3060
tatggcctga gaagaatga cgtgctgggc gtgtccctgg agaagttcaa gcagatcatg      3120
gccaacatcc tgcaccagcg gtccgaggat cagctgctgt ttccctctag aggcggcatg      3180
ttctacctgg ccacctataa gctggacgcc gatgccacaa gcgtgaactg gaatggcaag      3240
cagttttggg tgtgtaacgc cgacctggtg gccgcctaca atgtgggcct ggtggacatc      3300
cagaaggatt tcaagaagaa gaaaaggccg gcggccacga aaaaggccgg ccaggcaaaa      3360
aagaaaaagt aataa                                                       3375
```

<210> SEQ ID NO 502
<211> LENGTH: 3258
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 502

```
atgaaaatcg aagaaggtaa aggtcaccat caccatcacc acatgagctc cgccatcaag       60
tcctacaagt ctgtgctgcg gccaaacgag agaaagaatc agctgctgaa gagcaccatc      120
cagtgcctgg aggacggctc cgccttcttt ttcaagatgc tgcagggcct gtttggcggc      180
atcacccccg agatcgtgag attcagcaca gagcaggaga agcagcagca ggatatcgcc      240
ctgtggtgtg ccgtgaattg gttcaggcct gtgagccagg actccctgac ccacacaatc      300
gcctccgata acctggtgga gaagtttgag gagtactatg gcggcacagc cagcgacgcc      360
atcaagcagt acttcagcgc ctccatcggc gagtcctact attggaatga ctgccgccag      420
cagtactatg atctgtgtcg gggagctggg gtggaggtgt ctgacctgac ccacgatctg      480
gagatcctgt gccgggagaa gtgtctggcc gtggccacag agagcaacca gaacaattct      540
atcatcagcg tgctgtttgg caccggcgag aaggaggata ggtctgtgaa gctgcgcatc      600
acaaagaaga tcctggaggc catcagcaac ctgaaggaga tcccaaagaa tgtggccccc      660
atccaggaga tcatcctgaa tgtggccaag gccaccaagg agacattcag acaggtgtac      720
gcaggaaacc tgggagcacc atccacccctg gagaagttta cgccaagga cggccagaag      780
```

-continued

```
gagttcgatc tgaagaagct gcagacagac ctgaagaaag tgatccgggg caagtctaag      840
gagagagatt ggtgctgtca ggaggagctg aggagctacg tggagcagaa taccatccag      900
tatgacctgt gggcctgggg cgagatgttc aacaaggccc acaccgccct gaagatcaag      960
tccacaagaa actacaattt tgccaagcag aggctggagc agttcaagga gatccagtct     1020
ctgaacaatc tgctggtggt gaagaagctg aacgactttt tcgatagcga gttttttctcc   1080 ggcgaggaga cctacacaat ctgcgtgcac cacctgggcg gcaaggacct gtccaagctg     1140
tataaggcct gggaggacga tcccgccgat cctgagaatg ccatcgtggt gctgtgcgac     1200
gatctgaaga acaattttaa gaaggagcct atcaggaaca tcctgcgcta catcttcacc     1260
atccgccagg agtgtagcgc acaggacatc ctggcagcag caaagtacaa tcagcagctg     1320
gatcggtata agagccagaa ggccaaccca tccgtgctgg gcaatcaggg ctttacctgg     1380
acaaacgccg tgatcctgcc agagaaggcc cagcggaacg acagacccaa ttctctggat     1440
ctgcgcatct ggctgtacct gaagctgcgg caccctgacg gcagatggaa gaagcaccac     1500
atcccattct acgatacccg gttttttccag gagatctatg ccgccggcaa tagccctgtg     1560
gacacctgtc agtttaggac accccgcttc ggctatcacc tgcctaagct gaccgatcag     1620
acagccatcc gcgtgaacaa gaagcacgtg aaggcagcaa agaccgaggc acggatcaga     1680
ctggccatcc agcagggcac actgccagtg tccaatctga gatcaccga gatctccgcc      1740 acaatcaact ctaagggcca ggtgcgcatc cccgtgaagt ttgacgtggg aaggcagaag     1800
ggaaccctgc agatcggcga ccggttctgc ggctacgatc agaaccagac agcctctcac     1860
gcctatagcc tgtgggaggt ggtgaaggag ggccagtacc acaaggagct gggctgtttt     1920
gtgcgcttca tctctagcgg cgacatcgtg tccatcaccg agaaccgggg caatcagttt     1980
gatcagctgt cttatgaggg cctggcctac ccccagtatg ccgactggag aaagaaggcc     2040
tccaagttcg tgtctctgtg gcagatcacc aagaagaaca agaagaagga gatcgtgaca     2100
gtggaggcca aggagaagtt tgacgccatc tgcaagtacc agcctaggct gtataagttc     2160
aacaaggagt acgcctatct gctgcgggat atcgtgagag gcaagagcct ggtggagctg     2220
cagcagatca ggcaggagat cttttcgcttc atcgagcagg actgtggagt gacccgcctg     2280
ggatctctga gcctgtccac cctggagaca gtgaaggccg tgaagggcat catctactcc     2340
tattttctca cagccctgaa tgcctctaag aacaatccca tcagcgacga gcagcggaag     2400
gagtttgatc ctgagctgtt cgccctgctg gagaagctgg agctgatcag gactcggaag     2460
aagaagcaga aggtggagag aatcgccaat agcctgatcc agacatgcct ggagaacaat     2520
atcaagttca tcaggggcga gggcgacctg tccaccacaa acaatgccac caagaagaag     2580
gccaactcta ggagcatgga ttggctggcc agaggcgtgt ttaataagat ccggcagctg     2640
gccccaatgc acaacatcac cctgttcggc tgcggcagcc tgtacacatc ccaccaggac     2700
cctctggtgc acagaaaccc agataaggcc atgaagtgta gatgggcagc aatcccagtg     2760
aaggacatcg gcgattgggt gctgagaaag ctgtcccaga acctgagggc caagaatatc     2820
ggcaccggcg agtactatca ccagggcgtg aaggagttcc tgtctcacta tgagctgcag     2880
gacctggagg aggagctgct gaagtggcgg tctgatagaa agagcaacat cccttgctgg     2940
gtgctgcaga atagactggc cgagaagctg ggcaacaagg aggccgtggt gtacatccca     3000
gtgaggggcg gccgcatcta ttttgcaacc cacaaggtgg caacaggagc cgtgagcatc     3060
gtgttcgacc agaagcaagt gtgggtgtgt aatgcagatc acgtggcagc agcaaacatc     3120
```

-continued

```
gcactgaccg tgaagggcat cggcgagcag tcctctgacg aggagaaccc cgatggctcc      3180
aggatcaagc tgcagctgac atctaaaagg ccggcggcca cgaaaaaggc cggccaggca      3240
aaaaagaaaa agtaataa                                                    3258

<210> SEQ ID NO 503
<211> LENGTH: 228
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 503
cgactgtgcc ttctagttgc cagccatctg ttgtttgccc ctcccccgtg ccttccttga        60
ccctggaagg tgccactccc actgtccttt cctaataaaa tgaggaaatt gcatcgcatt       120
gtctgagtag gtgtcattct attctggggg gtggggtggg gcaggacagc aaggggagg        180 attgggaaga caatagcagg catgctgggg atgcggtggg ctctatgg                    228

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511
```

-continued

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

-continued

```
<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000
```

```
<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545
```

```
<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
accccctttc caaagcccat tccctctttt cgagccgggg tgtgc                      45

<210> SEQ ID NO 551
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
accccctttc caaagcccat tccctctttt tgagccgggg tgtgc                      45

<210> SEQ ID NO 552
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
accccctttc caaagcccat tccctgttta tgagccgggg tgtgc                      45

<210> SEQ ID NO 553
<211> LENGTH: 44
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 553 acccccttc caaagcccat tccctctttta agagccgggg tgtg                      44

<210> SEQ ID NO 554
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554 acccccttc caaagcccat tacctctttta agagccgggg tgtg                      44

<210> SEQ ID NO 555
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555 acccccttc caaagcccat tccctctgta agagccgggg tgtg                       44

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000
```

```
<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573
```

-continued

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

-continued

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

-continued

```
<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600
<211> LENGTH: 2
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 600

Gly Ser
1

<210> SEQ ID NO 601
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 601

Gly Ser Gly Gly Gly Gly Ser
1               5

<210> SEQ ID NO 602
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 602

Gly Gly Gly Gly Ser Gly Gly Gly Gly Ser Gly Gly Gly Gly Ser
1               5                   10                  15

<210> SEQ ID NO 603
<211> LENGTH: 18
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 603

Gly Gly Ser Gly Gly Ser Gly Gly Ser Gly Gly Ser Gly Gly Ser Gly
1               5                   10                  15

Gly Ser

<210> SEQ ID NO 604
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 604

Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
            20                  25                  30

<210> SEQ ID NO 605
<211> LENGTH: 167
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 605

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp
                165

<210> SEQ ID NO 606
<211> LENGTH: 167
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 606

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp
                165
```

<210> SEQ ID NO 607
<211> LENGTH: 198
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 607

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140
```

-continued

```
Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 608
<211> LENGTH: 208
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 608

```
Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
                20                  25                  30

Cys Tyr Val Leu Phe Glu Leu Lys Arg Arg Gly Glu Arg Arg Ala Cys
            35                  40                  45

Phe Trp Gly Tyr Ala Val Asn Lys Pro Gln Ser Gly Thr Glu Arg Gly
        50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
            115                 120                 125

Glu Lys Asn Ala Arg Asn Gln Ile Gly Leu Trp Asn Leu Arg Asp Asn
        130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
            195                 200                 205
```

<210> SEQ ID NO 609
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 609

```
Met Ser Ser Glu Thr Gly Pro Val Ala Val Asp Pro Thr Leu Arg Arg
1               5                   10                  15
```

-continued

```
Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
            85                  90                  95

Ser Arg Ala Ile Thr Glu Phe Leu Ser Arg Tyr Pro His Val Thr Leu
        100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
            165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
    210                 215                 220

Ala Thr Gly Leu Lys
225
```

```
<210> SEQ ID NO 610
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      KDEL motif sequence"

<400> SEQUENCE: 610

Lys Asp Glu Leu
1
```

```
<210> SEQ ID NO 611
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 611

Glu Ala Ala Ala Lys
1               5
```

```
<210> SEQ ID NO 612
<211> LENGTH: 44
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: modified_base
<222> LOCATION: (24)..(44)
<223> OTHER INFORMATION: a, c, t, g, unknown or other

<400> SEQUENCE: 612
atttttgtgc ccatcgttgg cacnnnnnnn nnnnnnnnnn nnnn                         44

<210> SEQ ID NO 613
<211> LENGTH: 44
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (24)..(44)
<223> OTHER INFORMATION: a, c, u, g, unknown or other

<400> SEQUENCE: 613
agaaauccgu cuuucauuga cggnnnnnnn nnnnnnnnnn nnnn                         44

<210> SEQ ID NO 614
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
ttcgcgtgct ggattgcttc gatggtctgc ggcatc                                 36

<210> SEQ ID NO 615
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
gatgccgcag accatcgaag caatccagca cgcgaa                                 36

<210> SEQ ID NO 616
<211> LENGTH: 28
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
gcgugcugga uugcuucgau ggucugcg                                          28

<210> SEQ ID NO 617
<211> LENGTH: 34
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

```
     Synthetic oligonucleotide"

<400> SEQUENCE: 617
gcaacaccua agaaauccgu cuuucauuga cggg                                   34

<210> SEQ ID NO 618
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 618
guugcaaaac ccaagaaauc cgucuuucau ugacgg                                 36

<210> SEQ ID NO 619
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 619
aauuuuugug cccaucguug gcac                                              24

<210> SEQ ID NO 620
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 620
cucucaaugc cuuagaaauc cguccuuggu ugacgg                                 36

<210> SEQ ID NO 621
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 621
cccacaauac cugagaaauc cguccuacgu ugacgg                                 36
```

CRISPR DNA TARGETING ENZYMES AND SYSTEMS

CROSS REFERENCE TO RELATED APPLICATIONS

This application is a divisional of U.S. application Ser. No. 16/680,104, filed Nov. 11, 2019, now U.S. Pat. No. 10,808,245, which is a continuation of International Application No. PCT/US2019/022375, filed Mar. 14, 2019, which claims the benefit of priority of U.S. Application No. 62/642,919, filed Mar. 14, 2018; U.S. Application No. 62/666,397, filed May 3, 2018; U.S. Application No. 62/672,489, filed May 16, 2018; U.S. Application No. 62/679,628, filed Jun. 1, 2018; U.S. Application No. 62/703,857, filed Jul. 26, 2018; U.S. Application No. 62/740,856, filed Oct. 3, 2018; U.S. Application No. 62/746,528, filed Oct. 16, 2018; U.S. Application No. 62/772,038, filed Nov. 27, 2018; and U.S. Application No. 62/775,885, filed Dec. 5, 2018. The content of each of the foregoing applications is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 29, 2019, is named 45138-0011WO1_SL.txt and is 185,394 bytes in size.

FIELD OF THE INVENTION

The present disclosure relates to systems, methods, and compositions used for the control of gene expression involving sequence targeting and nucleic acid editing, which uses vector systems related to Clustered Regularly Interspaced Short Palindromic Repeats (CRISPR) and components thereof.

BACKGROUND

Recent application of advances in genome sequencing technologies and analysis have yielded significant insights into the genetic underpinning of biological activities in many diverse areas of nature, ranging from prokaryotic biosynthetic pathways to human pathologies. To fully understand and evaluate the vast quantities of information produced by genetic sequencing technologies, equivalent increases in the scale, efficacy, and ease of technologies for genome and epigenome manipulation are needed. These novel genome and epigenome engineering technologies will accelerate the development of novel applications in numerous areas, including biotechnology, agriculture, and human therapeutics.

Clustered Regularly Interspaced Short Palindromic Repeats (CRISPR) and the CRISPR-associated (Cas) genes, collectively known as the CRISPR-Cas or CRISPR/Cas systems, are currently understood to provide immunity to bacteria and archaea against phage infection. The CRISPR-Cas systems of prokaryotic adaptive immunity are an extremely diverse group of proteins effectors, non-coding elements, as well as loci architectures, some examples of which have been engineered and adapted to produce important biotechnologies.

The components of the system involved in host defense include one or more effector proteins capable of modifying DNA or RNA and an RNA guide element that is responsible to targeting these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

CRISPR-Cas systems can be broadly classified into two classes: Class 1 systems are composed of multiple effector proteins that together form a complex around a crRNA, and Class 2 systems consist of a single effector protein that complexes with the RNA guide to target DNA or RNA substrates. The single-subunit effector composition of the Class 2 systems provides a simpler component set for engineering and application translation, and have thus far been an important source of programmable effectors. Thus, the discovery, engineering, and optimization of novel Class 2 systems may lead to widespread and powerful programmable technologies for genome engineering and beyond.

CRISPR-Cas systems are adaptive immune systems in archaea and bacteria that defend the species against foreign genetic elements. The characterization and engineering of Class 2 CRISPR-Cas systems, exemplified by CRISPR-Cas9, have paved the way for a diverse array of biotechnology applications in genome editing and beyond. Nevertheless, there remains a need for additional programmable effectors and systems for modifying nucleic acids and polynucleotides (i.e., DNA, RNA, or any hybrid, derivative, or modification) beyond the current CRISPR-Cas systems that enable novel applications through their unique properties.

Citation or identification of any document in this application is not an admission that such document is available as prior art to the present invention.

SUMMARY

This disclosure provides non-naturally-occurring, engineered systems and compositions for new single-effector Class 2 CRISPR-Cas systems, together with methods for computational identification from genomic databases, development of the natural loci into an engineered system, and experimental validation and application translation. These new effectors are divergent in sequence to orthologs and homologs of existing Class 2 CRISPR effectors, and also have unique domain organizations. They provide additional features that include, but are not limited to, 1) novel DNA/RNA editing properties and control mechanisms, 2) smaller size for greater versatility in delivery strategies, 3) genotype triggered cellular processes such as cell death, and 4) programmable RNA-guided DNA insertion, excision, and mobilization. Adding the novel DNA-targeting systems described herein to the toolbox of techniques for genome and epigenome manipulation enables broad applications for specific, programmed perturbations.

In general, this disclosure relates to new CRISPR-Cas systems including newly discovered enzymes and other components used to create minimal systems that can be used in non-natural environments, e.g., in bacteria other than those in which the system was initially discovered.

In one aspect, the disclosure provides engineered, non-naturally occurring CRISPR-Cas systems that include: i) one or more Type V-I (CLUST.029130) RNA guides or one or more nucleic acids encoding the one or more Type V-I RNA guides, wherein a Type V-I RNA guide includes or consists of a direct repeat sequence and a spacer sequence capable of hybridizing to a target nucleic acid; and ii) a Type V-I (CLUST.029130) CRISPR-Cas effector protein or a nucleic acid encoding the Type V-I CRISPR-Cas effector protein, wherein the Type V-I CRISPR-Cas effector protein is capable of binding to a Type V-I RNA guide and of targeting the target nucleic acid sequence complementary to the spacer sequence, wherein the target nucleic acid is a DNA. As used herein, the Type V-I (CLUST.029130) CRISPR-Cas effector proteins are also referred to as Cas12i effector proteins, and these two terms are used interchangeably in this disclosure.

In some embodiments of any of the systems described herein, the Type V-I CRISPR-Cas effector protein is about 1100 amino acids or less in length (excluding any amino acid signal sequence or peptide tag fused thereto) and includes at least one RuvC domain. In some embodiments, none, one, or more of the RuvC domains are catalytically inactivated. In some embodiments, the Type V-I CRISPR-Cas effector protein includes or consists of the amino acid sequence $X_1SHX_4DX_6X_7$ (SEQ ID NO: 200), wherein $X_1$ is S or T, $X_4$ is Q or L, $X_6$ is P or S, and $X_7$ is F or L.

In some embodiments, the Type V-I CRISPR-Cas effector protein includes or consists of the amino acid sequence $X_1XDXNX_6X_7XXXX_{11}$ (SEQ ID NO: 201), wherein $X_1$ is A or G or S, X is any amino acid, $X_6$ is Q or I, $X_7$ is T or S or V, and $X_{10}$ is T or A. In some embodiments, the Type V-I CRISPR-Cas effector protein includes or consists of the amino acid sequence $X_1X_2X_3E$ (SEQ ID NO: 210), wherein $X_1$ is C or F or I or L or M or P or V or W or Y, $X_2$ C or F or I or L or M or P or R or V or W or Y, and $X_3$ C or F or G or I or L or M or P or V or W or Y.

In some embodiments, the Type V-I CRISPR-Cas effector protein includes more than one sequence from the set SEQ ID NO: 200, SEQ ID NO: 201, and SEQ ID NO: 210. In some embodiments, the Type V-I CRISPR-Cas effector protein includes or consists of an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence provided in Table 4 (e.g., SEQ ID NOs: 1-5, and 11-18).

In some embodiments of any of the systems described herein, the Type V-I CRISPR-Cas effector protein includes or consists of an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of Cas12i1 (SEQ ID NO: 3) or Cas12i2 (SEQ ID NO: 5). In some embodiments, the Type V-I CRISPR-Cas effector protein is Cas12i1 (SEQ ID NO: 3) or Cas12i2 (SEQ ID NO: 5).

In some embodiments, the Type V-I CRISPR-Cas effector protein is capable of recognizing a protospacer adjacent motif (PAM), and the target nucleic acid includes or consists of a PAM including or consisting of the nucleic acid sequence 5'-TTN-3' or 5'-TTH-3' or 5'-TTY-3' or 5'-TTC-3'.

In some embodiments of any of the systems described herein, the Type V-I CRISPR-Cas effector protein includes one or more amino acid substitutions within at least one of the RuvC domains. In some embodiments, the one or more amino acid substitutions include a substitution, e.g., an alanine substitution, at an amino residue corresponding to D647 or E894 or D948 of SEQ ID NO: 3. In some embodiments, the one or more amino acid substitutions include an alanine substitution at an amino residue corresponding to D599 or E833 or D886 of SEQ ID NO: 5. In some embodiments, the one or more amino acid substitutions result in a reduction of the nuclease activity of the Type V-I CRISPR- Cas effector protein as compared to the nuclease activity of the Type V-I CRISPR-Cas effector protein without the one or more amino acid substitutions.

In some embodiments of any of the systems described herein, the Type V-I RNA guide includes a direct repeat sequence that includes a stem-loop structure proximal to the 3' end (immediately adjacent to the spacer sequence). In some embodiments, the Type V-I RNA guide direct repeat includes a stem loop proximal to the 3' end where the stem is 5 nucleotides in length. In some embodiments, the Type V-I RNA guide direct repeat includes a stem loop proximal to the 3' end where the stem is 5 nucleotides in length and the loop is 7 nucleotides in length. In some embodiments, the Type V-I RNA guide direct repeat includes a stem loop proximal to the 3' end where the stem is 5 nucleotides in length and the loop is 6, 7, or 8 nucleotides in length.

In some embodiments, the Type V-I RNA guide direct repeat includes the sequence 5'-CCGUCNNNNN-NUGACGG-3' (SEQ ID NO: 202) proximal to the 3' end, wherein N refers to any nucleobase. In some embodiments, the Type V-I RNA guide direct repeat includes the sequence 5'-GUGCCNNNNNNUGGCAC-3' (SEQ ID NO: 203) proximal to the 3' end, wherein N refers to any nucleobase.

In some embodiments, the Type V-I RNA guide direct repeat includes the sequence 5'-GUGUCN$_{5-6}$UGACAX$_1$-3' (SEQ ID NO: 204) proximal to the 3' end, wherein N$_{5-6}$ refers to a contiguous sequence of any 5 or 6 nucleobases, and $X_1$ refers to C or T or U. In some embodiments, the Type V-I RNA guide direct repeat includes the sequence 5'-UCX$_3$UX$_5$X$_6$X$_7$UUGACGG-3' (SEQ ID NO: 205) proximal to the 3' end, wherein $X_3$ refers to C or T or U, $X_5$ refers to A or T or U, $X_6$ refers to A or C or G, and $X_7$ refers to A or G. In some embodiments, the Type V-I RNA guide direct repeat includes the sequence 5'-CCX$_3$X$_4$X$_5$CX-UUGGCAC-3' (SEQ ID NO: 206) proximal to the 3' end, wherein $X_3$ refers to C or T or U, $X_4$ refers to A or T or U, $X_5$ refers to C or T or U, and $X_7$ refers to A or G.

In some embodiments, the Type V-I RNA guide includes a direct repeat sequence including or consisting of a nucleotide sequence that is at least 80% identical, e.g., 85%, 90%, 91%, 92%, 93%, 94%, 95%, 96%, 97%, 98%, 99%, or 100% identical, to a nucleotide sequence provided in Table 5A (e.g., SEQ ID NOs: 6-19, and 19-24).

In some embodiments, the Type V-I RNA guide includes or consists of a nucleotide sequence or subsequence thereof provided in Table 5B (e.g., SEQ ID Nos: 150-163). In some embodiments, the Type V-I RNA guide includes or consists of a nucleotide sequence constructed by the concatenation of a direct repeat, spacer, direct repeat sequence wherein the direct repeat sequence is provided in Table 5A and the length of the spacer is provided in the Spacer Lens 1 column in Table 5B. In some embodiments, the Type V-I RNA guide includes or consists of a nucleotide sequence constructed by the concatenation of a direct repeat, spacer, direct repeat sequence wherein the direct repeat sequence is provided in Table 5A and the length of the spacer is provided in the Spacer Lens 2 column in Table 5B. In some embodiments, the Type V-I RNA guide includes or consists of a nucleotide sequence constructed by the concatenation of a direct repeat, spacer, direct repeat sequence wherein the direct repeat sequence is provided in Table 5A and the length of the spacer is provided in the Spacer Lens 3 column in Table 5B.

In some embodiments of any of the systems described herein, the spacer sequence of the Type V-I RNA guide includes or consists of between about 15 to about 34 nucleotides (e.g., 16, 17, 18, 19, 20, 21, or 22 nucleotides).

In some embodiments of any of the systems described herein, the spacer is between 17 nucleotides and 31 nucleotides in length.

In some embodiments of any of the systems provided herein, the target nucleic acid is a DNA. In some embodiments of any of the systems described herein, the target nucleic acid includes a protospacer adjacent motif (PAM), e.g., a PAM including or consisting of the nucleic acid sequence 5'-TTN-3' or 5'-TTH-3' or 5'-TTY-3' or 5'-TTC-3'.

In certain embodiments of any of the systems provided herein, the targeting of the target nucleic acid by the Type V-I CRISPR-Cas effector protein and RNA guide results in a modification (e.g., a single-stranded or a double-stranded cleavage event) in the target nucleic acid. In some embodiments, the modification is a deletion event. In some embodiments, the modification is an insertion event. In some embodiments, the modification results in cell toxicity and/or cell death.

In some embodiments, the Type V-I CRISPR-Cas effector protein has non-specific (i.e., "collateral") nuclease (e.g., DNase) activity. In certain embodiments of any of the systems provided herein, the system further includes a donor template nucleic acid (e.g., a DNA or a RNA).

In some embodiments of any of the systems provided herein, the system is within a cell (e.g., a eukaryotic cell (e.g., a mammalian cell) or a prokaryotic cell (e.g., a bacterial cell)).

In another aspect, the disclosure provides methods of targeting and editing a target nucleic acid, wherein the methods include contacting the target nucleic acid with any of the systems described herein. These can be carried out ex vivo or in vitro methods. In some embodiments, the methods described herein do not modify the germ line genetic identity of a human being.

In other aspects, the disclosure provides methods of targeting the insertion of a payload nucleic acid at a site of a target nucleic acid, wherein the methods include contacting the target nucleic acid with any of the systems described herein.

In yet another aspect, the disclosure provides methods of targeting the excision of a payload nucleic acid from a site at a target nucleic acid, wherein the methods include contacting the target nucleic acid with any of the systems described herein.

In another aspect, the disclosure provides methods of targeting and nicking a non-target strand (non-spacer complementary strand) of a double-stranded target DNA upon recognition of a target strand (spacer complementary strand) of the double-stranded target DNA. The method includes contacting the double-stranded target DNA with any of the systems described herein.

In yet another aspect, the disclosure provides methods of targeting and cleaving a double-stranded target DNA, the method including contacting the double-stranded target DNA with any of the systems described herein.

In some embodiments of the methods of targeting and cleaving a double-stranded target DNA, a non-target strand (non-spacer complementary strand) of the double-stranded target DNA is nicked before a target strand (spacer complementary strand) of the double-stranded target nucleic acid is nicked.

In yet another aspect, the disclosure provides methods of specifically editing a double-stranded nucleic acid, the methods including: contacting (a) a Type V-I effector protein and one other enzyme with sequence-specific nicking activity; (b) a Type V-I RNA guide that guides the Type V-I effector protein to nick the opposing strand relative to the activity of the other sequence-specific nickase; and (c) the double-stranded nucleic acid, wherein the method results in reduced likelihood of off-target modification.

In some embodiments, the Type V-I effector protein further includes a linker sequence. In some embodiments, the Type V-I effector protein includes one or more mutations or amino acid substitutions that render the CRISPR-associated protein unable to cleave DNA.

In yet another aspect, the disclosure provides methods of base editing a double-stranded nucleic acid, the method including: contacting (a) a fusion protein comprising a Type V-I effector protein and a protein domain with DNA modifying activity (e.g., cytidine deamination); (b) a Type V-I RNA guide targeting the double-stranded nucleic acid, and (c) the double-stranded nucleic acid. The Type V-I effector of the fusion protein can be modified to nick non-target strand of the double-stranded nucleic acid. In some embodiments, the Type V-I effector of the fusion protein can be modified to be nuclease deficient. zzz In another aspect, the disclosure provides methods of modifying a DNA molecule, the methods including contacting the DNA molecule with a system described herein.

In some embodiments of any of the methods described herein (and compositions for use in such methods), the cell is a eukaryotic cell. In some embodiments, the cell is an animal cell. In some embodiments, the cell is a cancer cell (e.g., a tumor cell). In some embodiments, the cell is an infectious agent cell or a cell infected with an infectious agent. In some embodiments, the cell is a bacterial cell, a cell infected with a virus, a cell infected with a prion, a fungal cell, a protozoan, or a parasite cell.

In another aspect, the disclosure provides methods of treating a condition or disease in a subject in need thereof and compositions for use in such methods. The methods include administering to the subject a system described herein, wherein the spacer sequence is complementary to at least 15 nucleotides of a target nucleic acid associated with the condition or disease, wherein the Type V-I CRISPR-Cas effector protein associates with the RNA guide to form a complex, wherein the complex binds to a target nucleic acid sequence that is complementary to the at least 15 nucleotides of the spacer sequence, and wherein upon binding of the complex to the target nucleic acid sequence the Type V-I CRISPR-Cas effector protein cleaves or silences the target nucleic acid, thereby treating the condition or disease in the subject.

In some embodiments of the methods described herein (and compositions for use in such methods), the condition or disease is a cancer or an infectious disease. In some embodiments, the condition or disease is cancer, wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In some embodiments, the Type V-I effector protein includes or consists of at least one (e.g., two, three, four, five, six, or more) nuclear localization signal (NLS). In some embodiments, the Type V-I effector protein includes or consists of at least one (e.g., two, three, four, five, six, or more) nuclear export signal (NES). In some embodiments, the Type V-I effector protein includes at least one (e.g., two, three, four, five, six, or more) NLS and at least one (e.g., two, three, four, five, six, or more) NES.

In some embodiments, the systems described herein include a nucleic acid encoding one or more RNA guides. In some embodiments, the nucleic acid encoding the one or more RNA guides is operably linked to a promoter (e.g., a constitutive promoter or an inducible promoter).

In some embodiments, the systems described herein include a nucleic acid encoding a target nucleic acid (e.g., a target DNA). In some embodiments, the nucleic acid encoding the target nucleic acid is operably linked to a promoter (e.g., a constitutive promoter or an inducible promoter).

In some embodiments, the systems described herein include a nucleic acid encoding a Type V-I CRISPR-Cas effector protein in a vector. In some embodiments, the system further includes one or more nucleic acids encoding an RNA guide present in the vector.

In some embodiments, the vectors included in the systems are viral vectors (e.g., retroviral vectors, lentiviral vectors, adenoviral vectors, adeno-associated vectors, and herpes simplex vectors. In some embodiments, the vectors included in the system are phage vectors.

In some embodiments, the systems provided herein are in a delivery system. In some embodiments, the delivery system is a nanoparticle, a liposome, an exosome, a microvesicle, and a gene-gun.

The disclosure also provides a cell (e.g., a eukaryotic cell or a prokaryotic cell (e.g., a bacterial cell)) comprising a system described herein. In some embodiments, the eukaryotic cell is a mammalian cell (e.g., a human cell) or a plant cell. The disclosure also provides animal models (e.g., rodent, rabbit, dog, monkey, or ape models) and plant model that include the cells. In some embodiments, the methods are used to treat a subject, e.g., a mammal, such as a human patient. The mammalian subject can also be a domesticated mammal, such as a dog, cat, horse, monkey, rabbit, rat, mouse, cow, goat, or sheep In yet another aspect, the disclosure provides methods of detecting a target nucleic acid (e.g., DNA or RNA) in a sample, the methods including: (a) contacting the sample with a system provided herein and a labeled reporter nucleic acid, wherein hybridization of the crRNA to the target nucleic acid causes cleavage of the labeled reporter nucleic acid; and (b) measuring a detectable signal produced by cleavage of the labeled reporter nucleic acid, thereby detecting the presence of the target nucleic acid in the sample.

In some embodiments, the methods of detecting a target nucleic acid can also include comparing a level of the detectable signal with a reference signal level, and determining an amount of target nucleic acid in the sample based on the level of the detectable signal.

In some embodiments, the measuring is performed using gold nanoparticle detection, fluorescence polarization, colloid phase transition/dispersion, electrochemical detection, or semiconductor based-sensing.

In some embodiments, the labeled reporter nucleic acid can include a fluorescence-emitting dye pair, a fluorescence resonance energy transfer (FRET) pair, or a quencher/fluorophore pair, wherein cleavage of the labeled reporter nucleic acid by the effector protein results in an increase or a decrease of the amount of signal produced by the labeled reporter nucleic acid.

Turning to another aspect, the disclosure includes methods of modifying a target DNA, which include contacting the target DNA with a complex comprising a Cas12i effector protein and an engineered Type V-I RNA guide, which is designed to hybridize with (e.g., is at least 70%, 75%, 80%, 85%, 90%, 95%, 96%, 97%, 98%, 99%, or 100% complementary to) a target sequence of the target DNA, and the system is distinguished by (a) the lack of a tracrRNA in the system, and (b) the Cas12i effector protein and Type V-I RNA guide form a complex that associates with the target DNA, thereby modifying the target DNA.

In certain embodiments, modifying the target DNA includes cleaving at least one strand of the target DNA (e.g., creating a single-strand break or "nick," or creating a double strand break). Alternatively, or additionally, modification of the target DNA includes either (i) binding to the target DNA, thereby preventing the target DNA from associating with another biomolecule or complex, or (ii) unwinding a portion of the target DNA. In some instances, the target DNA includes a protospacer adjacent motif (PAM) sequence that is recognized by the Cas12i effector protein, such as 5'-TTN-3' or 5'-TTH-3' or 5'-TTY-3' or 5'-TTC-3'. The Cas12 effector protein is, in certain embodiments, a Cas12i1 effector protein or a Cas12i2 effector protein.

Continuing with this aspect of the disclosure, in certain embodiments the contacting of the target DNA with the complex occurs in a cell, for instance by (a) contacting the cell with the complex, which complex is formed in vitro, or (b) contacting the cell with one or more nucleic acids encoding the Cas 12i effector protein and the Type V-I RNA guide, which are then expressed by the cell and which form the complex within the cell. In some cases, the cell is a prokaryotic cell; in other cases, it is a eukaryotic cell.

In another aspect, this disclosure relates to methods of altering a target DNA, including contacting the target DNA within the cell with a genome editing system including a Cas12i protein and a Type V-I RNA guide (e.g., a crRNA, guide RNA or like structure, optionally comprising one or more nucleotide, nucleobase or backbone modifications) comprising a 15-24 nucleotide spacer sequence having at least 70%, 75%, 80%, 85%, 90%, 91%, 92%, 93%, 94%, 95%, 96%, 97%, 98%, 99%, or 100% complementarity to a sequence in the target DNA, but which system does not comprise a tracrRNA. In various embodiments, the Cas12i protein includes or consists of an amino acid sequence having at least 95%, e.g., 96%, 97%, 98%, 99%, or 100%, sequence identity to SEQ ID NO: 3 and the Type V-I RNA guide comprises a direct repeat sequence with at least 95%, e.g., 96%, 97%, 98%, 99%, or 100%, sequence identity to one of SEQ ID NOS: 7 or 24; or the Cas12i protein includes or consists of an amino acid sequence having at least 95%, e.g., 96%, 97%, 98%, 99%, or 100%, sequence identity to SEQ ID NO: 5 and the Type V-I RNA guide comprises a direct repeat sequence with at least 95% e.g., 96%, 97%, 98%, 99%, or 100%, sequence identity to one of SEQ ID NOS: 9 or 10. The target DNA is optionally a cellular DNA, and the contacting optionally occurs within a cell such as a prokaryotic cell or a eukaryotic cell (e.g., a mammalian cell, a plant cell, or a human cell).

In some embodiments, the Type V-I CRISPR-Cas effector protein comprises an amino acid sequence having at least 90%, or at least 95%, sequence identity to one of SEQ ID NOs: 1-5 or 11-18. According to certain embodiments, the Type V-I CRISPR-Cas effector protein comprises an amino acid sequence given by SEQ ID NO: 3, or an amino acid sequence given by SEQ ID NO: 5. The total length of the CRISPR-Cas effector protein according to certain embodiments is less than 1100 amino acids, excluding any amino acid signal sequence or peptide tag fused thereto. In some cases, the CRISPR-Cas effector protein comprises an amino acid substitution, for instance a substitution at an amino acid residue corresponding to D647, E894, or D948 of SEQ ID NO: 3 or a substitution at an amino acid residue corresponding to D599, E833, or D886 of SEQ ID NO: 5. The substitution is optionally an alanine.

In yet another aspect, this disclosure relates to an engineered, non-naturally occurring CRISPR-Cas systems, including or consisting of a Cas12i effector protein, and an engineered Type V-I RNA guide (e.g., a crRNA, guide RNA or like structure, optionally including one or more nucleotide, nucleobase or backbone modifications) having a 15-34 nucleotide spacer sequence that is at least 80%, e.g., 85%, 90%, 91%, 92%, 93%, 94%, 95%, 96%, 97%, 98%, 99%, or 100%, complementary to a target sequence. The systems do not include a tracrRNA, and the Cas12i effector protein and the Type V-I RNA guide form a complex that associates with the target sequence. In some instances, the complex of the Cas 12i effector protein and Type V-I RNA guide causes cleavage of at least one strand of a DNA comprising the target sequence. The target sequence can include a protospacer adjacent motif (PAM) sequence recognized by the Cas12i effector protein, which PAM sequence is optionally 5'-TTN-3', 5'-TTY-3' or 5'-TTH-3' or 5'-TTC-3'. The Type V-I RNA guide can include a direct repeat sequence having at least 95%, e.g., 96%, 97%, 98%, 99%, or 100%, sequence identity to one of SEQ ID NOS: 7, 9, 10, 24, 100, or 101.

In certain embodiments, the Cas 12i effector protein comprises an amino acid sequence having at least 95% sequence identity to SEQ ID NO: 3 and the direct repeat sequence has at least 95% sequence identity to SEQ ID NO: 100, or the Cas 12i effector protein comprises an amino acid sequence having at least 95% sequence identity to SEQ ID NO: 5 and the direct repeat sequence has at least 95% sequence identity to SEQ ID NO: 101. Alternatively, or additionally, the Cas12i effector protein comprises an amino acid substitution (optionally, an alanine substitution) selected from the group consisting of (a) a substitution at an amino acid residue corresponding to D647, E894, or D948 of SEQ ID NO: 3; and (b) a substitution at an amino acid residue corresponding to D599, E833, or D886 of SEQ ID NO: 5.

In still another aspect, this disclosure relates to a composition comprising one or more nucleic acids encoding a CRISPR-Cas system (or a genome editing system) according to one of the aspects of the disclosure. And in another aspect, the disclosure relates to a viral vector encoding a CRISPR-Cas system (or a genome editing system) according to one of the aspects of the disclosure.

The disclosure also includes methods of targeting and nicking a non-spacer complementary strand of a double-stranded target DNA upon recognition of a spacer complementary strand of the double-stranded target DNA, the method comprising contacting the double-stranded target DNA with any of the systems described herein.

In another aspect, the disclosure includes methods of targeting and cleaving a double-stranded target DNA, the method comprising contacting the double-stranded target DNA with a system as described herein. In these methods, a non-spacer complementary strand of the double-stranded target DNA is nicked before a spacer complementary strand of the double-stranded target nucleic acid is nicked.

In other embodiments, the disclosure includes methods of detecting a target nucleic acid in a sample, the method comprising: (a) contacting the sample with a system as described herein and a labeled reporter nucleic acid, wherein hybridization of the crRNA to the target nucleic acid causes cleavage of the labeled reporter nucleic acid; and (b) measuring a detectable signal produced by cleavage of the labeled reporter nucleic acid, thereby detecting the presence of the target nucleic acid in the sample. These methods can further include comparing a level of the detectable signal with a reference signal level, and determining an amount of target nucleic acid in the sample based on the level of the detectable signal. In some embodiments, the measuring is performed using gold nanoparticle detection, fluorescence polarization, colloid phase transition/dispersion, electrochemical detection, or semiconductor based-sensing. In some embodiments, the labeled reporter nucleic acid comprises a fluorescence-emitting dye pair, a fluorescence resonance energy transfer (FRET) pair, or a quencher/fluorophore pair, wherein cleavage of the labeled reporter nucleic acid by the effector protein results in an increase or a decrease of the amount of signal produced by the labeled reporter nucleic acid.

In another aspect, the methods herein include specifically editing a double-stranded nucleic acid, the method comprising contacting, under sufficient conditions and for a sufficient amount of time, (a) a Type V-I CRISPR-Cas effector and one other enzyme with sequence-specific nicking activity, and a crRNA that guides the Type V-I CRISPR-Cas effector to nick the opposing strand relative to the activity of the other sequence-specific nickase; and (b) the double-stranded nucleic acid; wherein the method results in the formation of a double-stranded break.

Another aspect includes methods of editing a double-stranded nucleic acid, the method comprising contacting, under sufficient conditions and for a sufficient amount of time, (a) a fusion protein comprising a the Type V-I CRISPR-Cas effector and a protein domain with DNA modifying activity and an RNA guide targeting the double-stranded nucleic acid; and (b) the double-stranded nucleic acid; wherein the Type V-I CRISPR-Cas effector of the fusion protein is modified to nick a non-target strand of the double-stranded nucleic acid.

Another aspect includes methods of inducing genotype-specific or transcriptional-state-specific cell death or dormancy in a cell, the method comprising contacting a cell, e.g., a prokaryotic or eukaryotic cell, with any system disclosed herein, wherein the RNA guide hybridizing to the target DNA causes a collateral DNase activity-mediated cell death or dormancy. For example, the cell can be a mammalian cell, e.g., a cancer cell. The cell can be an infectious cell or a cell infected with an infectious agent, e.g., a cell infected with a virus, a cell infected with a prion, a fungal cell, a protozoan, or a parasite cell.

In another aspect, the disclosure provides methods of treating a condition or disease in a subject in need thereof, the method comprising administering to the subject any of the systems described herein, wherein the spacer sequence is complementary to at least 15 nucleotides of a target nucleic acid associated with the condition or disease; wherein the Type V-I CRISPR-Cas effector protein associates with the RNA guide to form a complex; wherein the complex binds to a target nucleic acid sequence that is complementary to the at least 15 nucleotides of the spacer sequence; and wherein upon binding of the complex to the target nucleic acid sequence the Type V-I CRISPR-Cas effector protein cleaves the target nucleic acid, thereby treating the condition or disease in the subject. For example, the condition or disease can be a cancer or an infectious disease. For example, the condition or disease can be cancer, and wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

The disclosure also includes the systems or cells as described herein for use as a medicament, or for use in the treatment or prevention of a cancer or an infectious disease, e.g., wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

The disclosure also provides the use of the systems or cells as described herein in vitro or ex vivo methods of:

a) targeting and editing a target nucleic acid;

b) non-specifically degrading single-stranded DNA upon recognition of a DNA target nucleic acid;

c) targeting and nicking a non-spacer complementary strand of a double-stranded target DNA upon recognition of a spacer complementary strand of the double-stranded target DNA;

d) targeting and cleaving a double-stranded target DNA;

e) detecting a target nucleic acid in a sample;

f) specifically editing a double-stranded nucleic acid;

g) base editing a double-stranded nucleic acid;

h) inducing genotype-specific or transcriptional-state-specific cell death or dormancy in a cell.

i) creating an indel in a double-stranded target DNA;

j) inserting a sequence into a double-stranded target DNA, or k) deleting or inverting a sequence in a double-stranded target DNA.

In another aspect, the disclosure provides the use of the systems or cells described herein in methods of:

a) targeting and editing a target nucleic acid;

b) non-specifically degrading single-stranded DNA upon recognition of a DNA target nucleic acid;

c) targeting and nicking a non-spacer complementary strand of a double-stranded target DNA upon recognition of a spacer complementary strand of the double-stranded target DNA;

d) targeting and cleaving a double-stranded target DNA;

e) detecting a target nucleic acid in a sample;

f) specifically editing a double-stranded nucleic acid;

g) base editing a double-stranded nucleic acid;

h) inducing genotype-specific or transcriptional-state-specific cell death or dormancy in a cell;

i) creating an indel in a double-stranded target DNA;

j) inserting a sequence into a double-stranded target DNA, or k) deleting or inverting a sequence in a double-stranded target DNA, wherein the method does not comprise a process for modifying the germ line genetic identity of a human being and does not comprise a method of treatment of the human or animal body.

In the methods described herein, cleaving the target DNA or target nucleic acid results in the formation of an indel, or wherein cleaving the target DNA or target nucleic acid results in the insertion of a nucleic acid sequence, or, wherein cleaving the target DNA or target nucleic acid comprises cleaving the target DNA or target nucleic acid in two sites, and results in the deletion or inversion of a sequence between the two sites.

The various systems described herein can lack a tracrRNA. In some embodiments, the Type V-I CRISPR-Cas effector protein and Type V-I RNA guide form a complex that associates with the target nucleic acid, thereby modifying the target nucleic acid.

In some embodiments of the systems described herein, the spacer sequence is between 15 and 47 nucleotides in length, e.g., between 20 and 40 nucleotides in length, or between 24 and 38 nucleotides in length.

In another aspect, the disclosure provides eukaryotic cells, e.g., mammalian cells, e.g., human cells, comprising a modified target locus of interest, wherein the target locus of interest has been modified according to a method or via use of a composition of any one of the preceding claims. For example, the modification of the target locus of interest can result in:

(i) the eukaryotic cell comprising altered expression of at least one gene product;

(ii) the eukaryotic cell comprising altered expression of at least one gene product, wherein the expression of the at least one gene product is increased;

(iii) the eukaryotic cell comprising altered expression of at least one gene product, wherein the expression of the at least one gene product is decreased; or (iv) the eukaryotic cell comprising an edited genome.

In another aspect, the disclosure provides a eukaryotic cell line of or comprising the eukaryotic cells described herein, or progeny thereof, or a multicellular organism comprising one or more eukaryotic cells described herein.

The disclosure also provides plant or animal models comprising one or more cells as described herein.

In another aspect, the disclosure provides methods of producing a plant, having a modified trait of interest encoded by a gene of interest, the method comprising contacting a plant cell with any of the systems described herein, thereby either modifying or introducing said gene of interest, and regenerating a plant from the plant cell.

The disclosure also provides methods of identifying a trait of interest in a plant, wherein the trait of interest is encoded by a gene of interest, the method comprising contacting a plant cell with any of the systems described herein, thereby identifying the gene of interest. For example, the method can further comprising introducing the identified gene of interest into a plant cell or plant cell line or plant germ plasm and generating a plant therefrom, whereby the plant contains the gene of interest. The method can include having the plant exhibit the trait of interest.

The disclosure also includes methods of targeting and cleaving a single-stranded target DNA, the method comprising contacting the target nucleic acid with any of the systems described herein. The methods can include the condition or disease being infectious, and wherein the infectious agent is selected from the group consisting of human immunodeficiency virus (HIV), herpes simplex virus-1 (HSV1), and herpes simplex virus-2 (HSV2).

In some of the method described herein, both strands of target DNA can be cleaved at different sites, resulting in a staggered cut. In other embodiments, both strands of target DNA are cleaved at the same site, resulting in a blunt double-strand break (DSB).

In some of the therapeutic methods described herein, the condition or disease is selected from the group consisting of Cystic Fibrosis, Duchenne Muscular Dystrophy, Becker Muscular Dystrophy, Alpha-1-antitrypsin Deficiency, Pompe Disease, Myotonic Dystrophy, Huntington Disease, Fragile X Syndrome, Friedreich's ataxia, Amyotrophic Lateral Sclerosis, Frontotemporal Dementia, Hereditary Chronic Kidney Disease, Hyperlipidemia, Hypercholesterolemia, Leber Congenital Amaurosis, Sickle Cell Disease, and Beta Thalassemia.

The term "cleavage event," as used herein, refers to a DNA break in a target nucleic acid created by a nuclease of a CRISPR system described herein. In some embodiments, the cleavage event is a double-stranded DNA break. In some embodiments, the cleavage event is a single-stranded DNA break.

The term "CRISPR-Cas system," "Type V-I CRISPR-Cas system," or "Type V-I system" as used herein refers to a Type V-I CRISPR-Cas effector protein (i.e., Cas12i effector protein) and one or more Type V-I RNA guides, and/or nucleic acids encoding the Type V-I CRISPR-Cas effector protein or the one or more Type V-I RNA guides, and optionally promoters operably linked to the expression of the CRISPR effector or to the RNA guide or to both.

The term "CRISPR array" as used herein refers to the nucleic acid (e.g., DNA) segment that includes CRISPR repeats and spacers, starting with the first nucleotide of the first CRISPR repeat and ending with the last nucleotide of the last (terminal) CRISPR repeat. Typically, each spacer in a CRISPR array is located between two repeats. The terms "CRISPR repeat," or "CRISPR direct repeat," or "direct repeat," as used herein, refer to multiple short direct repeating sequences, which show very little or no sequence variation within a CRISPR array. Suitably, a Type V-I direct repeat may form a stem-loop structure.

A "stem-loop structure" refers to a nucleic acid having a secondary structure that includes a region of nucleotides that are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing. Thus, the stem may include one or more base mismatches. Alternatively, the base-pairing may be exact, i.e., not include any mismatches. The predicted stem loop structures of some Type V-I direct repeats are illustrated in FIG. 3. The stem for the Type V-I direct repeat contained within the RNA guide is composed of 5 complementary nucleobases that hybridize to each other, and the loop is 6, 7, or 9 nucleotides in length.

The term "CRISPR RNA" or "crRNA" as used herein refers to an RNA molecule comprising a guide sequence used by a CRISPR effector to target a specific nucleic acid sequence. Typically, crRNAs contains a spacer sequence that mediates target recognition and a direct repeat sequence (referred to herein as a direct repeat or "DR" sequence) that forms a complex with a CRISPR-Cas effector protein.

The term "donor template nucleic acid," as used herein refers to a nucleic acid molecule that can be used by one or more cellular proteins to alter the structure of a target nucleic acid after a CRISPR enzyme described herein has altered a target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

The term "CRISPR-Cas effector," "CRISPR effector," "effector," "CRISPR-associated protein," or "CRISPR enzyme," "Type V-I CRISPR-Cas effector protein," "Type V-I CRISPR-Cas effector," "Type V-I effector," or Cas12i effector protein" as used herein refers to a protein that carries out an enzymatic activity or that binds to a target site on a nucleic acid specified by an RNA guide. A CRISPR-Cas Type V-I effector protein associated within a Type V-I CRISPR-Cas system can also be referred to herein as "Cas12i" or "Cas12i enzyme." A Cas12i enzyme can recognize a short motif associated in the vicinity of a target DNA called a Protospacer Adjacent Motif (PAM). Suitably, a Cas12i enzyme of the present disclosure can recognize a PAM comprising or consisting of TTN, wherein N denotes any nucleotide. For example, the PAM may be TTN, TTH, TTY or TTC.

In some embodiments, a Type V-I CRISPR-Cas effector protein has endonuclease activity, nickase activity, and/or exonuclease activity.

The terms "CRISPR effector complex," "effector complex," "binary complex," or "surveillance complex" as used herein refer to a complex containing a Type V-I CRISPR-Cas effector protein and a Type V-I RNA guide.

The term "RNA guide" as used herein refers to any RNA molecule that facilitates the targeting of a protein described herein to a target nucleic acid. Exemplary "RNA guides" include, but are not limited to, crRNAs, pre-crRNAs (e g. DR-spacer-DR), and mature crRNAs (e.g. mature_DR-spacer, mature DR-spacer-mature_DR).

As used herein, the term "targeting" refers to the ability of a complex including a CRISPR-associated protein and an RNA guide, such as a crRNA, to preferentially or specifically bind to, e.g., hybridize to, a specific target nucleic acid compared to other nucleic acids that do not have the same or similar sequence as the target nucleic acid.

As used herein, the term "target nucleic acid" refers to a specific nucleic acid substrate that contains a nucleic acid sequence complementary to the entirety or a part of the spacer in an RNA guide. In some embodiments, the target nucleic acid comprises a gene or a sequence within a gene. In some embodiments, the target nucleic acid comprises a non-coding region (e.g., a promoter). In some embodiments, the target nucleic acid is single-stranded. In some embodiments, the target nucleic acid is double-stranded.

The terms "activated CRISPR complex," "activated complex," or "ternary complex" as used herein refer to a CRISPR effector complex after it has bound to or has modified a target nucleic acid.

The terms "collateral RNA" or "collateral DNA" as used herein refer to a nucleic acid substrate that is cleaved non-specifically by an activated CRISPR complex.

The term "collateral DNase activity," as used herein in reference to a CRISPR enzyme, refers to non-specific DNase activity of an activated CRISPR complex.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTION

The figures include a series of schematics and nucleic acid and amino acid sequences that represent the results of locus analysis of various protein clusters.

FIGS. 1A-B together depict a classification tree of Type V effectors (Cas12 proteins). The corresponding CRISPR-Cas loci organization is shown for each branch, with the need for a tracrRNA depicted by a white rectangle adjacent to a CRISPR array. CLUST.029130 (Type V-I) systems are depicted as Cas12i.

FIG. 2A is a schematic representation of the functional domains of the CLUST.029130 (Type V-I) effector, designated Cas12i. The solid grey shading indicates the location of the C-terminal RuvC domain, with the catalytic residues in the three conserved sequence motifs (I, II and III) indicated and shown to scale. The location of the bridge helix domain is indicated with the superscript h.

Figure 4A:
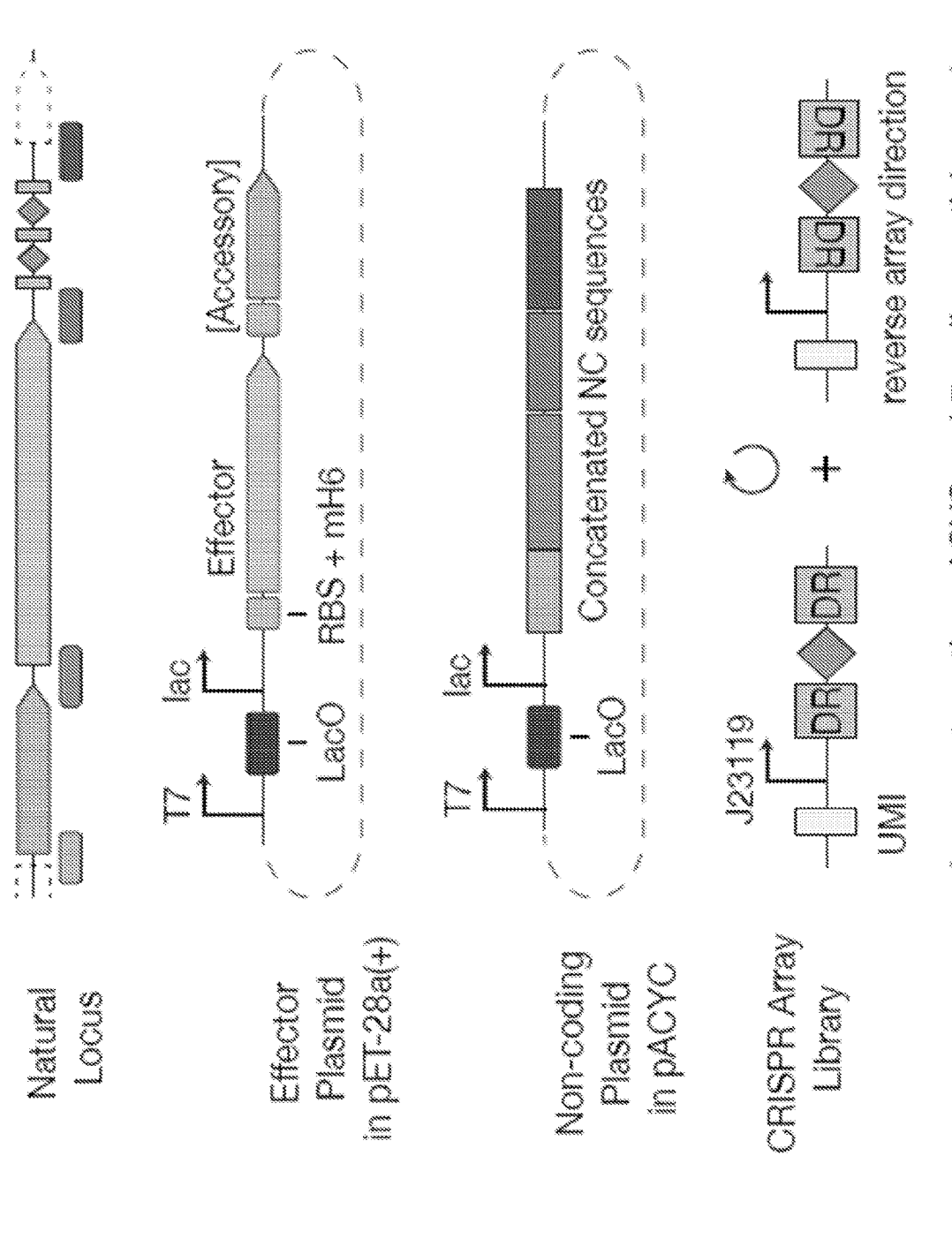
FIG. 4A is a schematic representation of the design of in vivo screen Effector and Non-coding Plasmids. CRISPR array libraries were designed including non-repetitive spacers uniformly sampled from both strands of pACYC184 or *E. coli* essential genes flanked by two DRs and expressed by J23119.
Figure 4B:
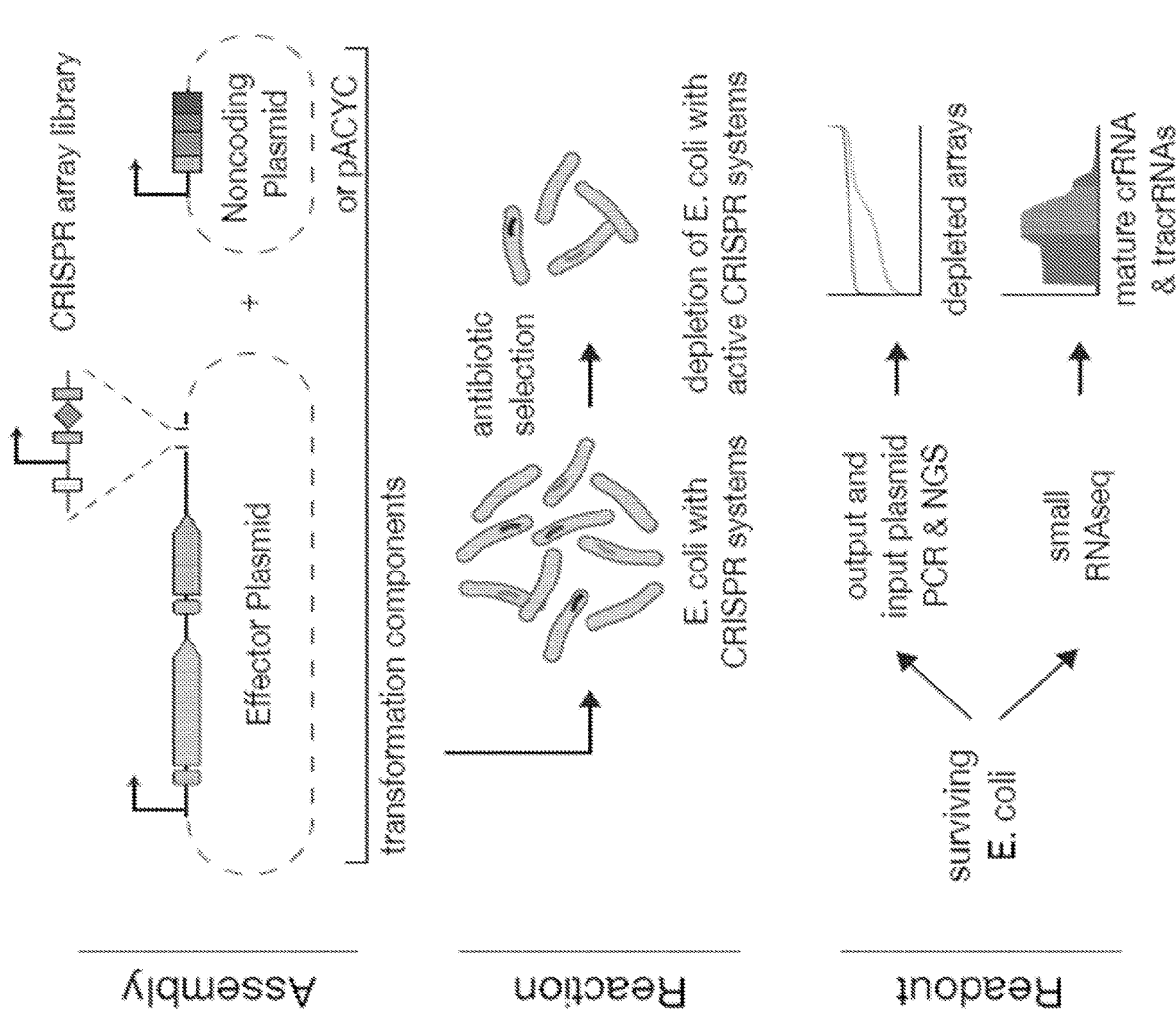
Figure 5A:
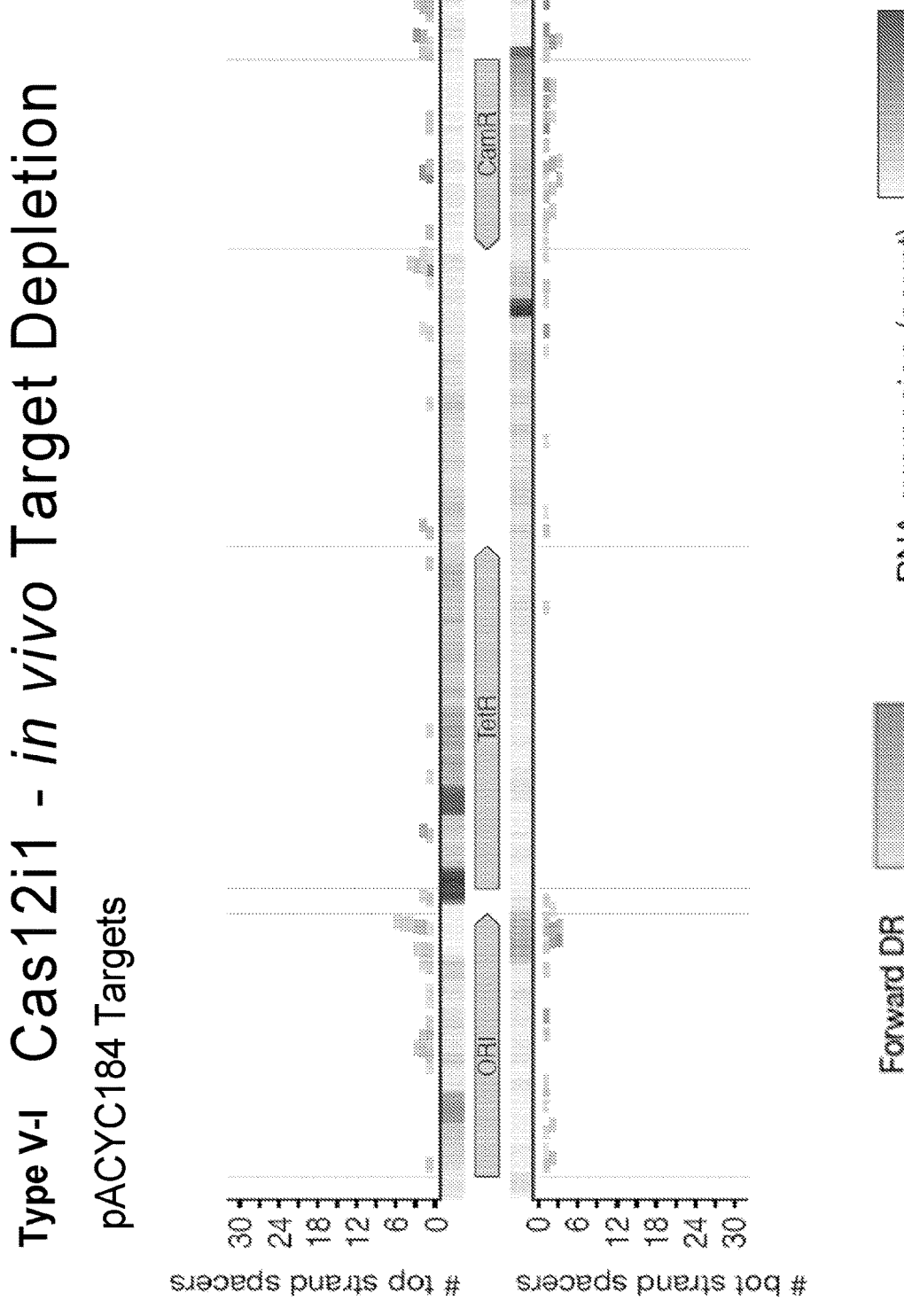
Figure 5B:
Figure 5C:
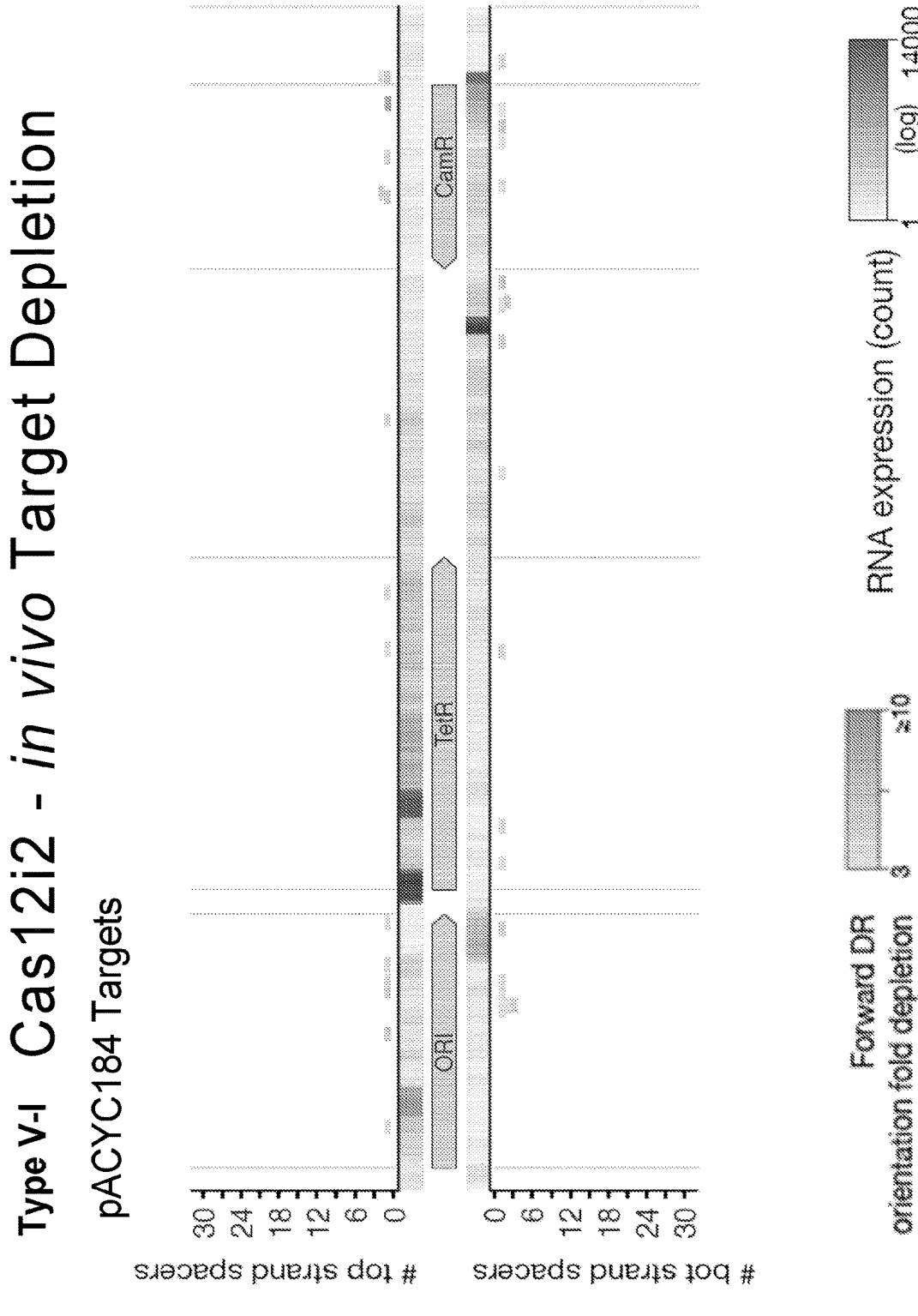
Figure 5D:
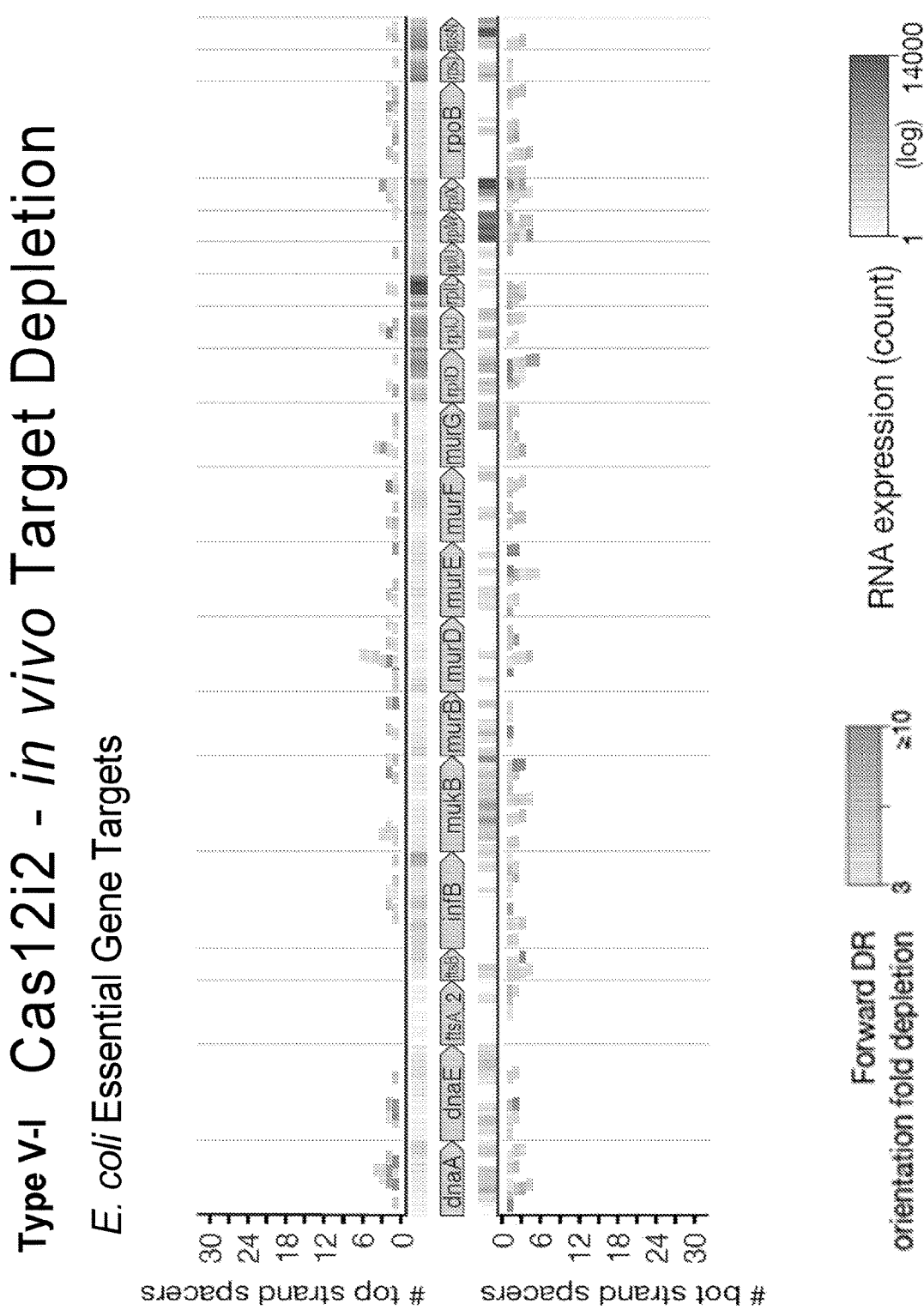

FIG. 4B is a schematic representation of the negative selection screening workflow; 1) CRISPR array libraries were cloned into the Effector Plasmid, 2) the Effector Plasmid and, when present, the Non-coding Plasmid were transformed into *E. coli* followed by outgrowth for negative selection of CRISPR arrays conferring interference against DNA or RNA transcripts from pACYC184 or *E. coli* essential genes, 3) Targeted sequencing of the Effector Plasmid was used to identify depleted CRISPR arrays and small RNA sequencing was used to identify mature crRNAs and tracrRNAs.

FIGS. 5A-B and FIGS. 5C-D are graphic representations that show the density of depleted and non-depleted targets for Cas12i1 and Cas12i2, respectively. Strongly depleted spacers targeting both pACYC184 and *E. coli* essential genes are depicted in separate plots. Targets on the top strand and bottom strand are shown separately, and in relation to the orientation of the annotated genes.

Figure 6A:
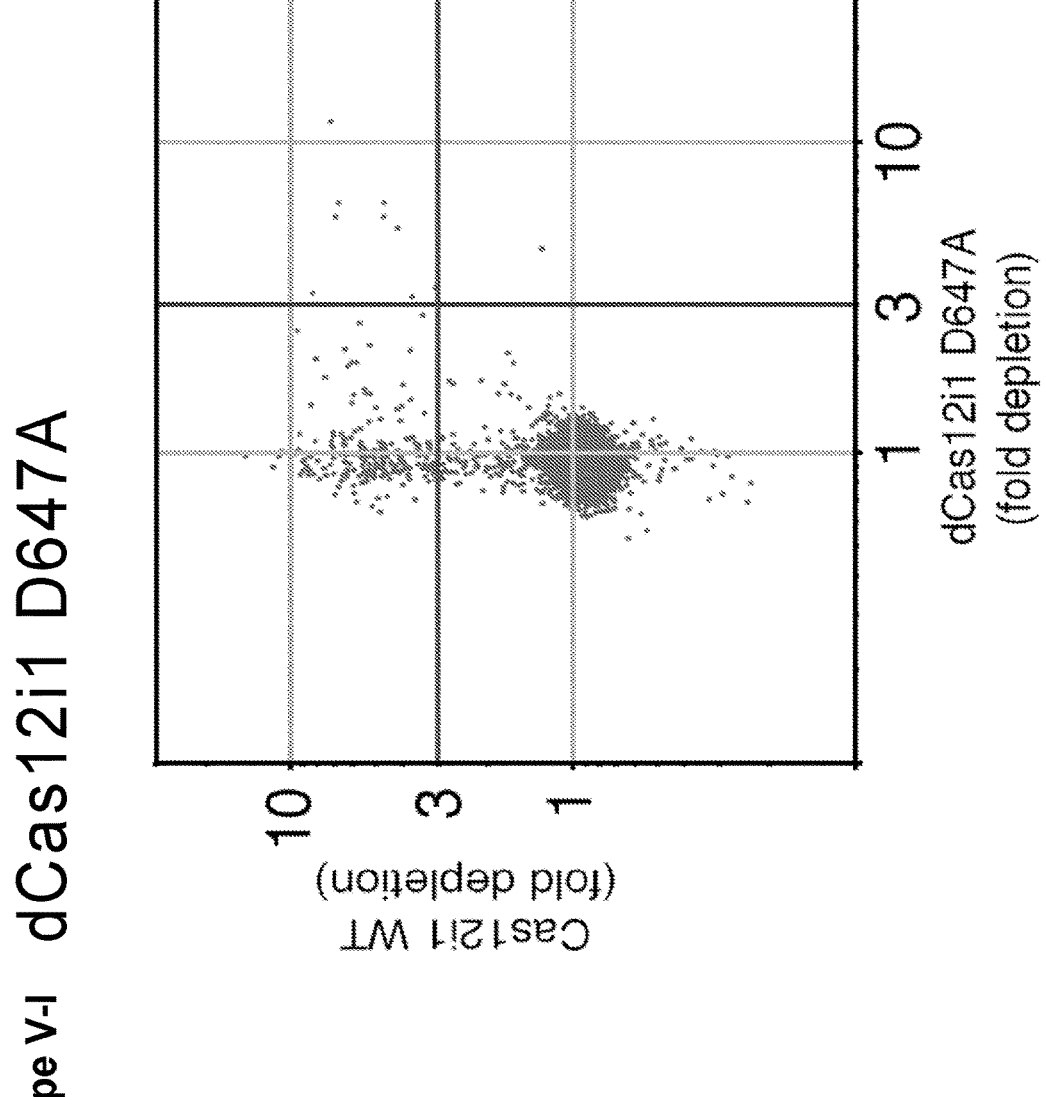
Figure 6B:
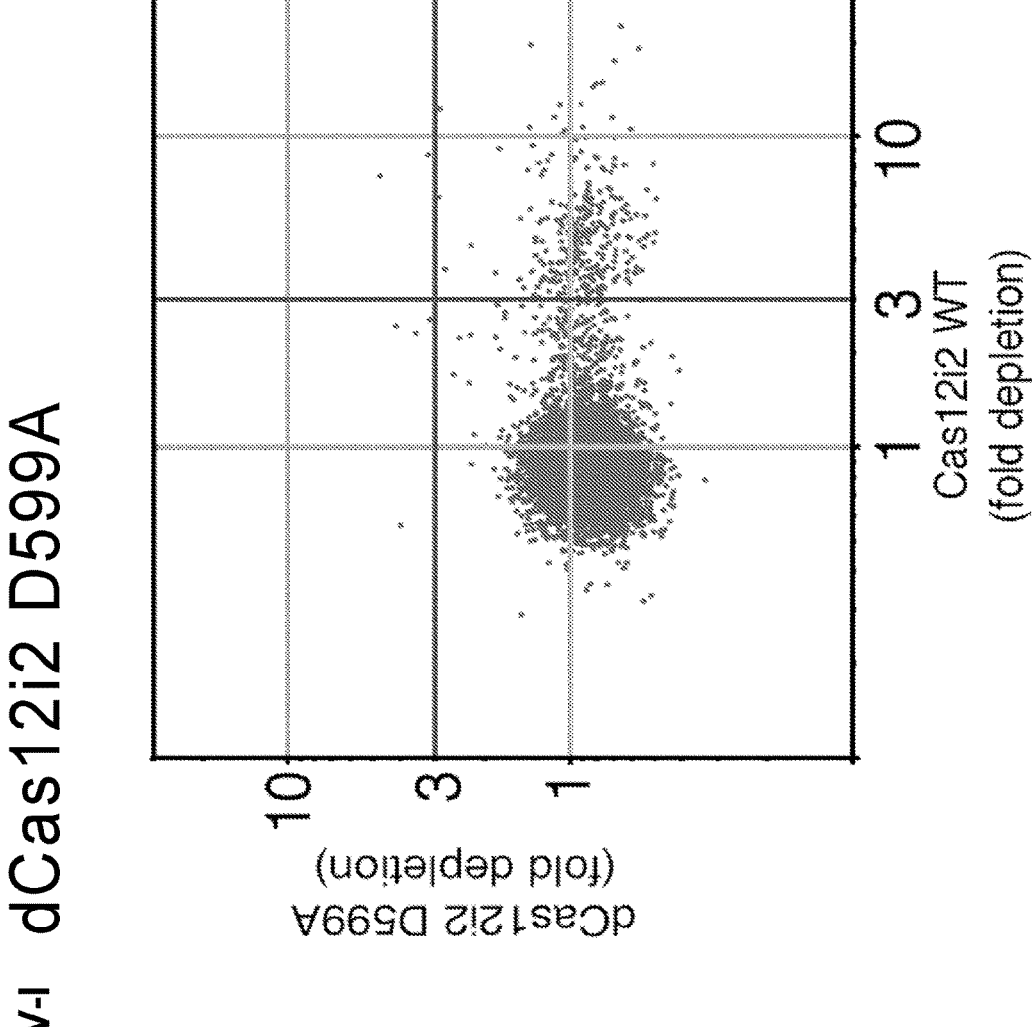

FIGS. 6A and 6B are scatter plots that show the effect of mutating the RuvC-I catalytic residue aspartate (in location 647 for Cas12i1, and 599 for Cas12i2) to alanine. Each point represents a spacer, and the value indicates the fold depletion under the condition specified for the axis (wild type vs mutant). Higher values indicate stronger depletion (i.e. fewer surviving colonies).

Figure 7A:
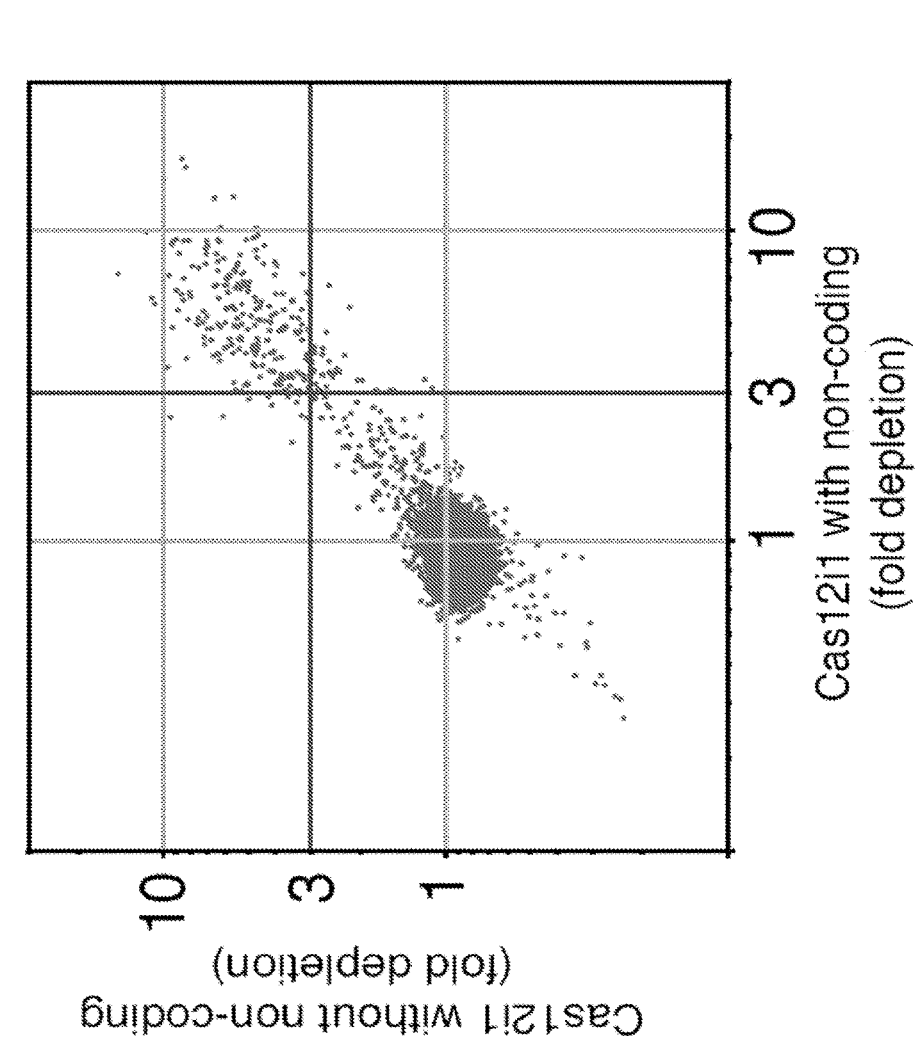
Figure 7B:
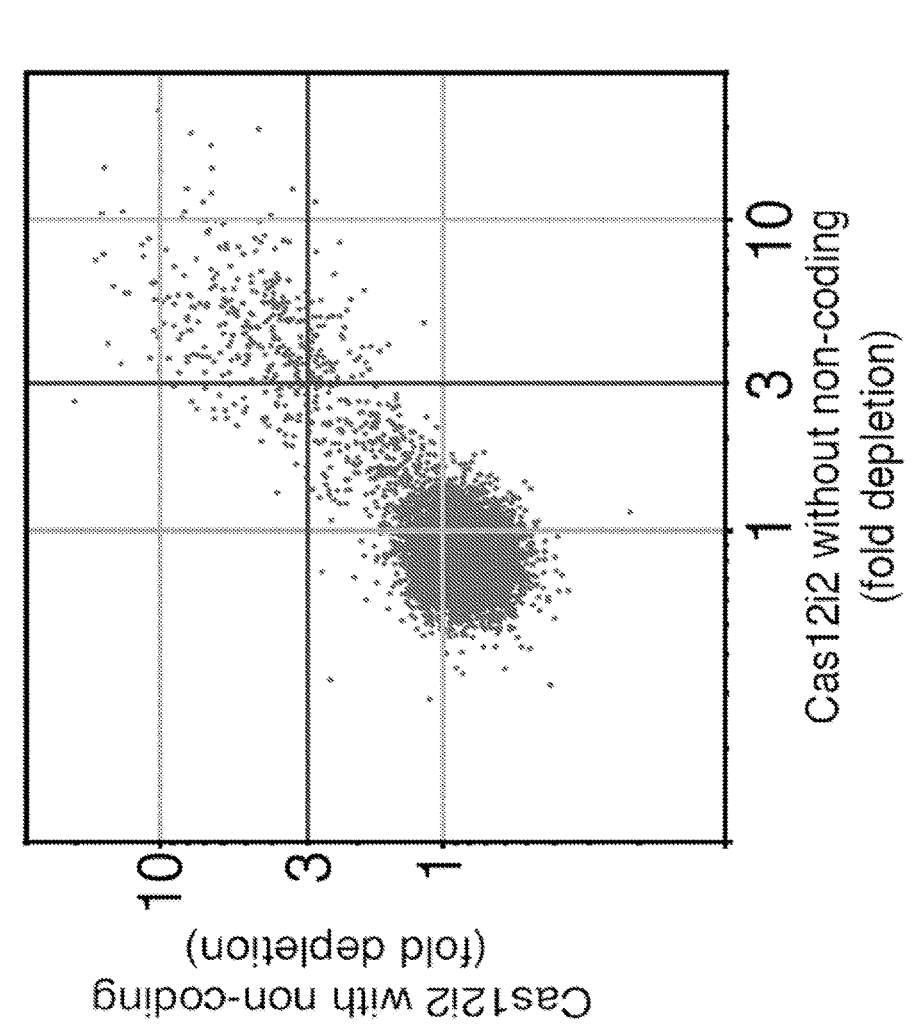

FIGS. 7A and 7B are scatter plots that show the effect of adding or removing the non-coding sequences to the Type V-I CRISPR-Cas system being screened. Each point represents a spacer, and the value indicates the fold depletion under the condition specified for the axis (wild type vs mutant). Higher values indicate stronger depletion (i.e., fewer surviving colonies).

Figure 8A:
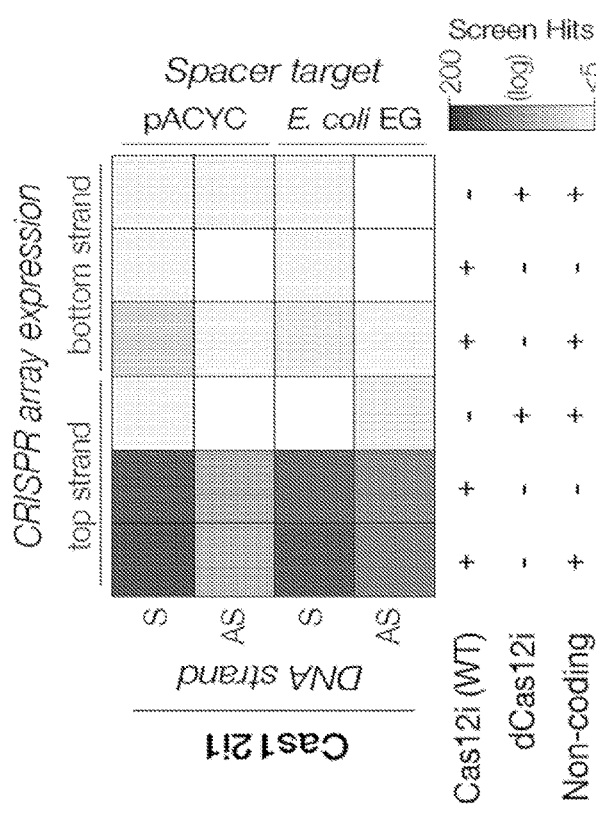
Figure 8B:
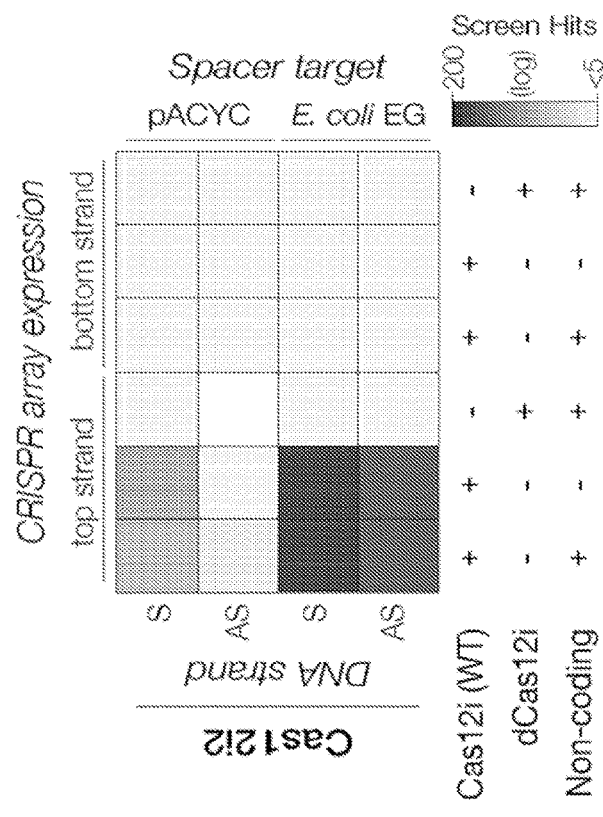

FIGS. 8A and 8B are heatmaps of the aggregate screening results for Cas12i1 and Cas12i2, respectively. The heatmap is decomposed into dependencies such as the orientation of the direct repeat, necessity of noncoding sequence, as well as the requirement of the intact RuvC domain (where dCas12i refers to a point mutant in a catalytically active residue of the RuvC-I domain). The Y-axis decomposes the library targets into the constituent features of targeting pACYC184, *E. coli* essential genes (*E. coli* EG), or strandedness of targeting (S, sense; AS, antisense). Cas12i1 and Cas 1212 in vivo screens were run in Endura Stb13 and E. CLONI® competent cell strains, respectively. CRISPR arrays strongly depleted in negative controls without Cas12i1 or Cas12i2 effectors are subtracted from the respective analyses.

Figure 9A:
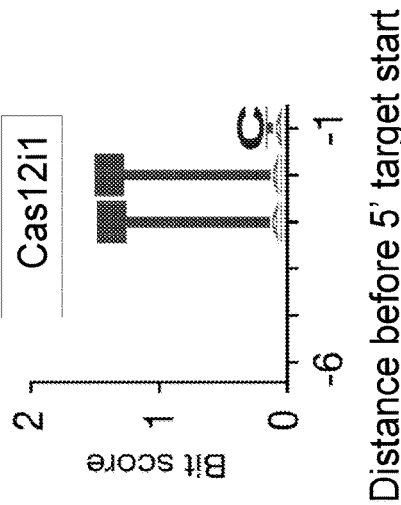
Figure 9B:
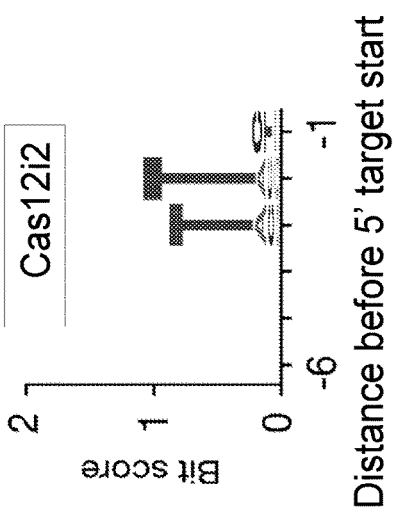

FIGS. 9A and 9B are weblogos of 5' PAM motifs identified from sequences flanking targets for strongly depleted spacers from Cas12i1 and Cas12i2 in vivo screens, respectively.

Figure 10A:
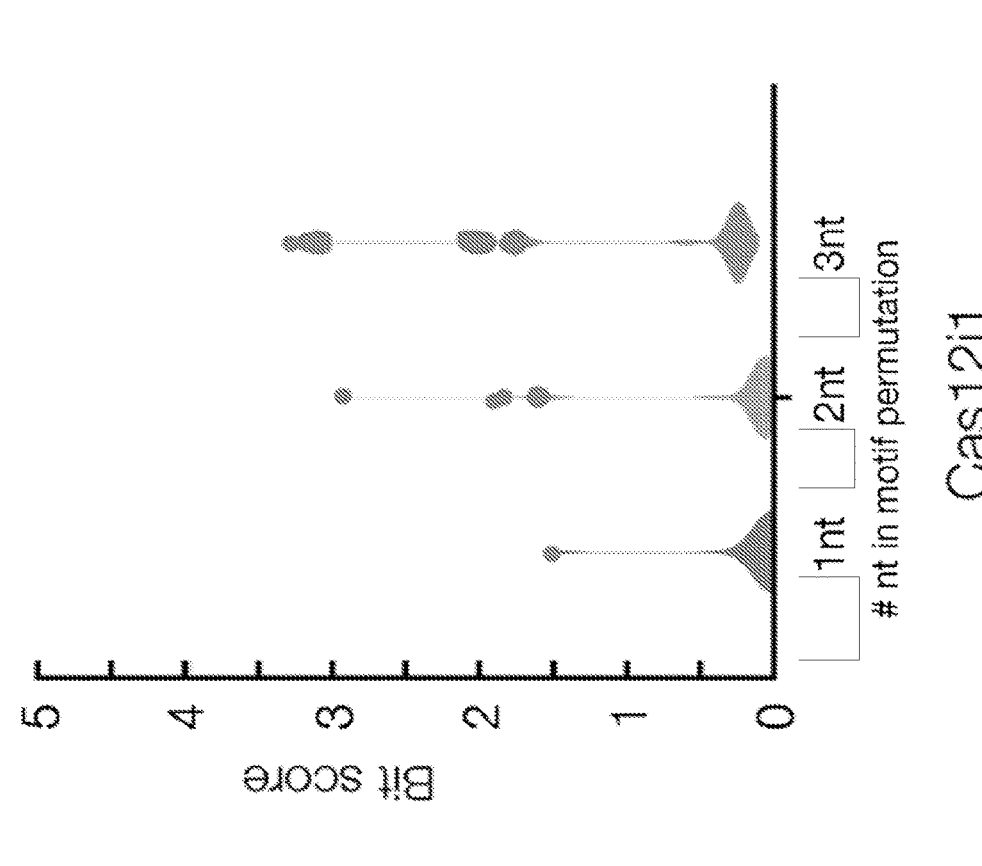
Figure 10B:
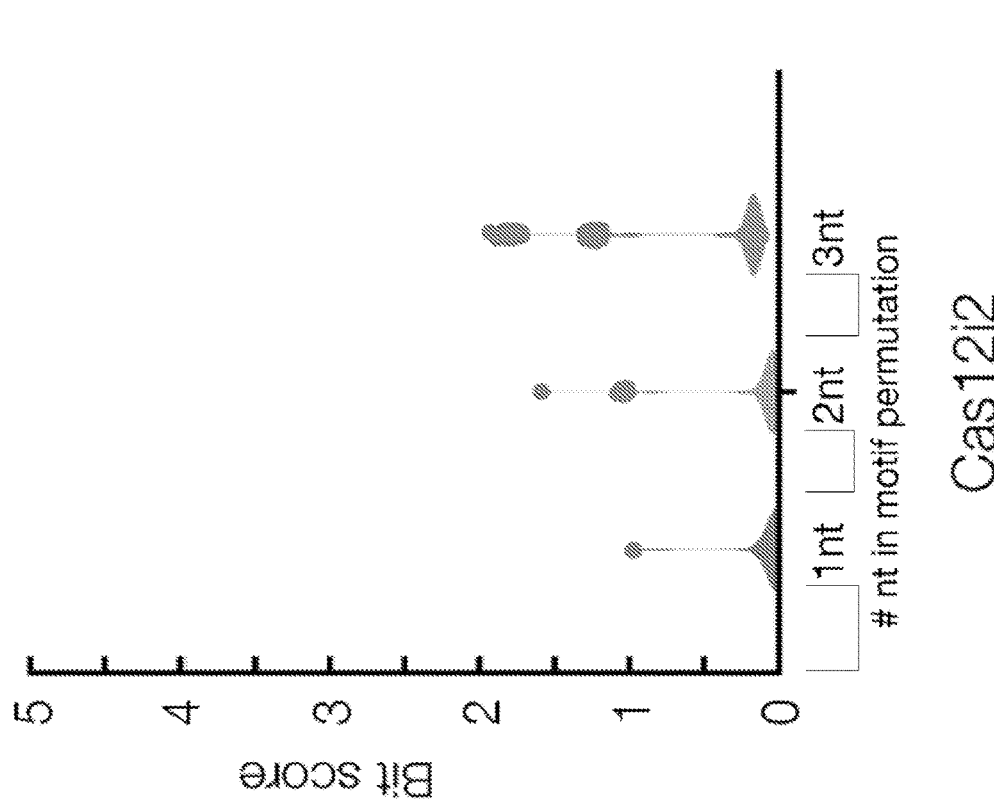

FIGS. 10A and 10B are violin plots of bit scores for all possible permutations of target and flanking nucleotides, confirming that Cas12i1 and Cas12i2 each have a preference for only a single 2-nt PAM motif at the 2nd and 3rd positions 5' of spacer targets.

Figure 11A:
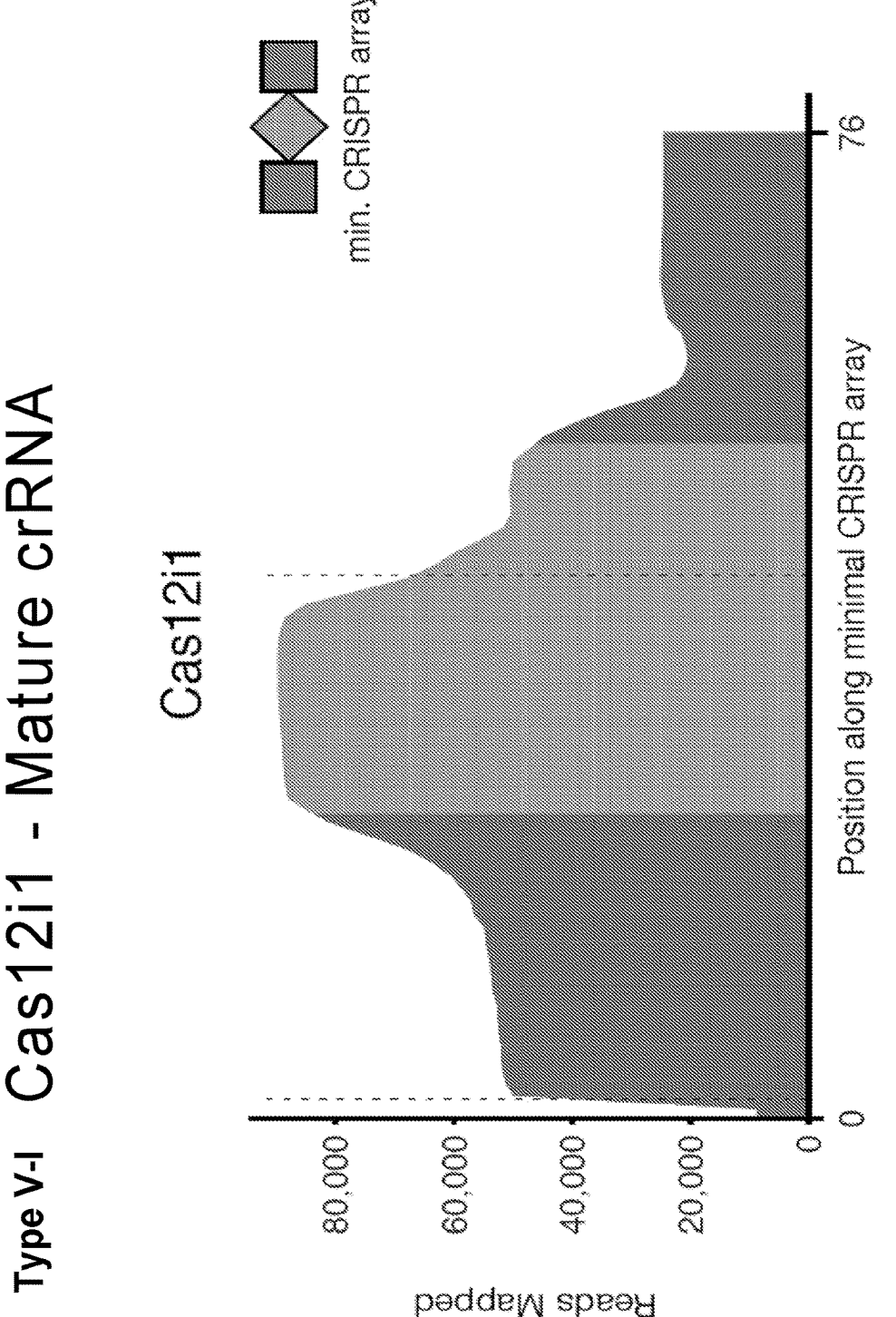
Figure 11B:
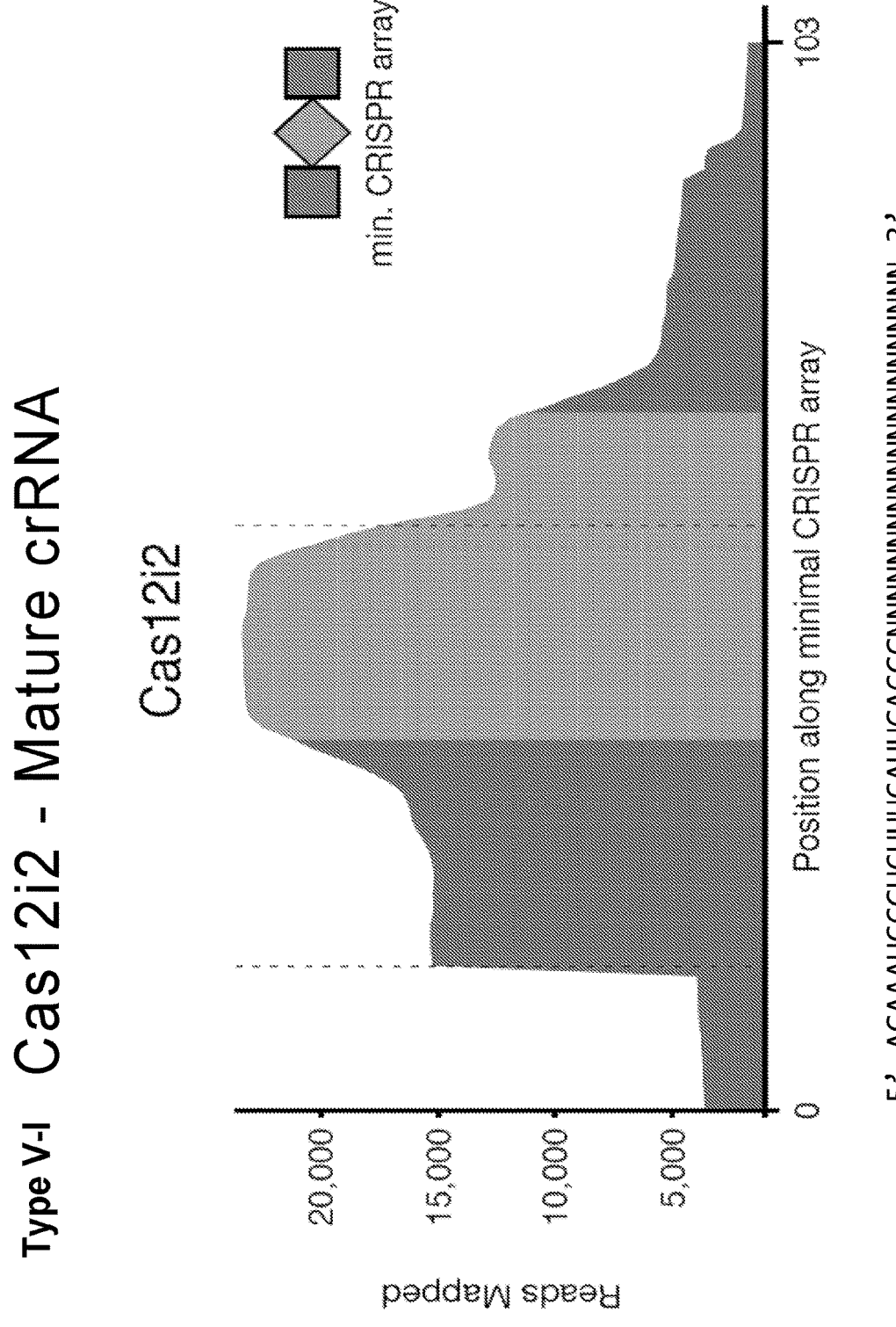

FIGS. 11A and 11B depict the read mapping of small RNA sequencing of in vivo screening samples of the minimal Cas12i systems, revealing the mature crRNA of Cas12i1 and Cas12i2 systems respectively.

Figure 12:

FIG. 12 is a denaturing gel showing pre-crRNA processing by Cas12i1 effector protein. Magnesium independent processing of pre-crRNA expressed from a minimal CRISPR array (repeat-spacer-repeat-spacer-repeat) with a 24 nt repeat and 28 nt spacer by Cas12i1. pre-crRNA was incubated with Cas12i1 for 30 minutes at 37° C. and analyzed on a 15% TBE-Urea gel.

Figure 13:
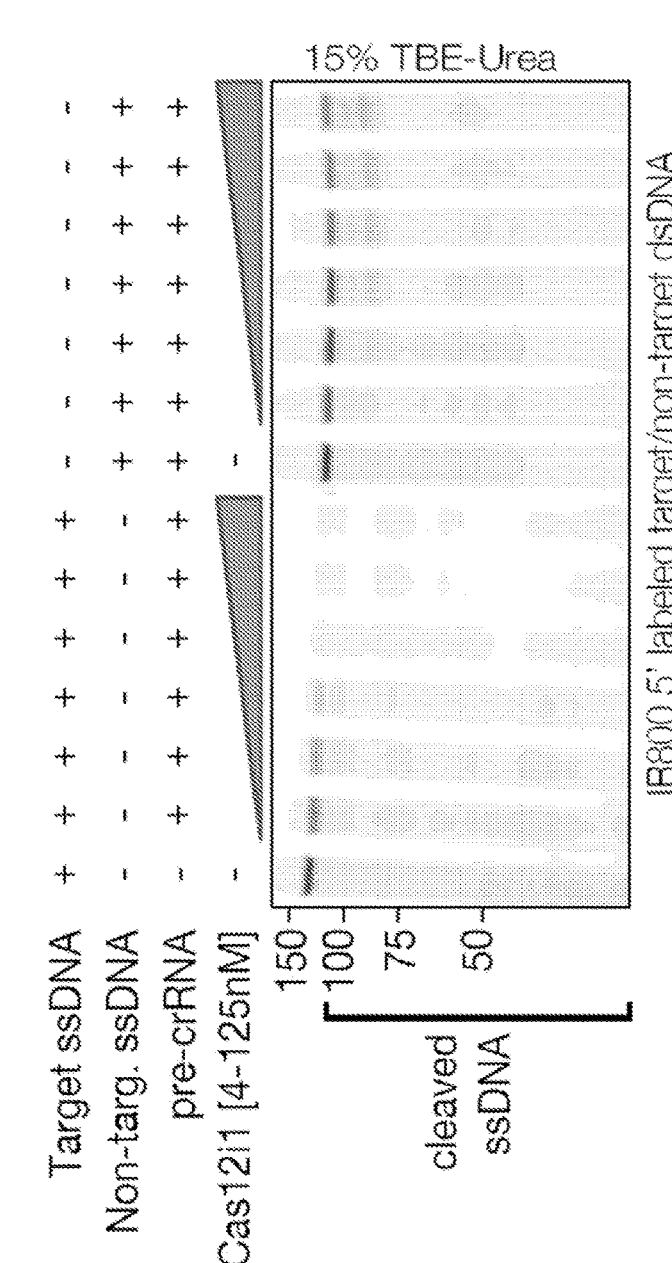

FIG. 13 is a representation of a gel that show the manipulation of IR800 dye-labeled target (left) or non-target (right) ssDNA by increasing doses of Cas12i1 binary complex. Samples were analyzed by 15% TBE-urea denaturing gel electrophoresis.

Figure 14:
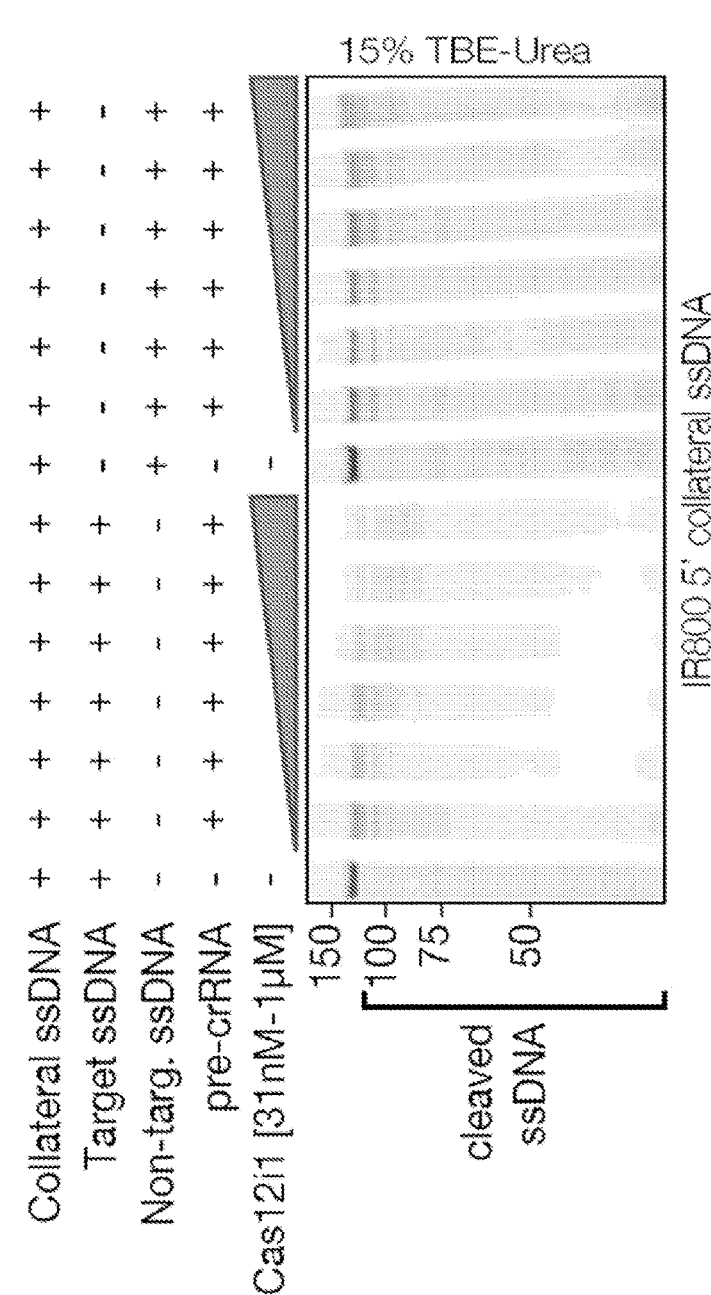

FIG. 14 is a representation of a gel that shows the manipulation of IR800 dye-labeled collateral ssDNA (with no sequence similarity to the target) in the presence of unlabeled target (left) or non-target (right) ssDNA by increasing doses of Cas12i1 binary complex. Samples were analyzed by 15% TBE-urea denaturing gel electrophoresis.

Figure 15:
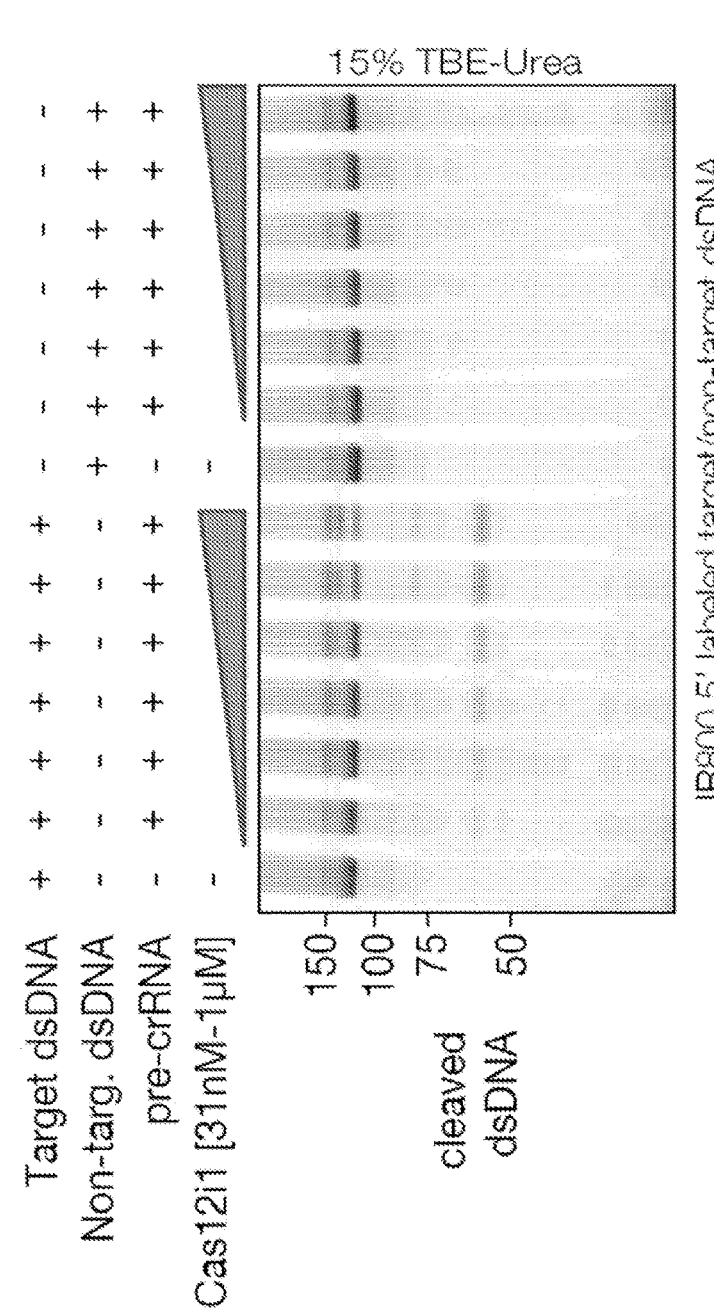

FIG. 15 is a representation of a gel that shows the manipulation of IR800 dye-labeled target (left) or non-target (right) dsDNA by increasing doses of Cas12i1 binary complex. Samples were analyzed by 15% TBE-urea denaturing gel electrophoresis.

Figure 16:
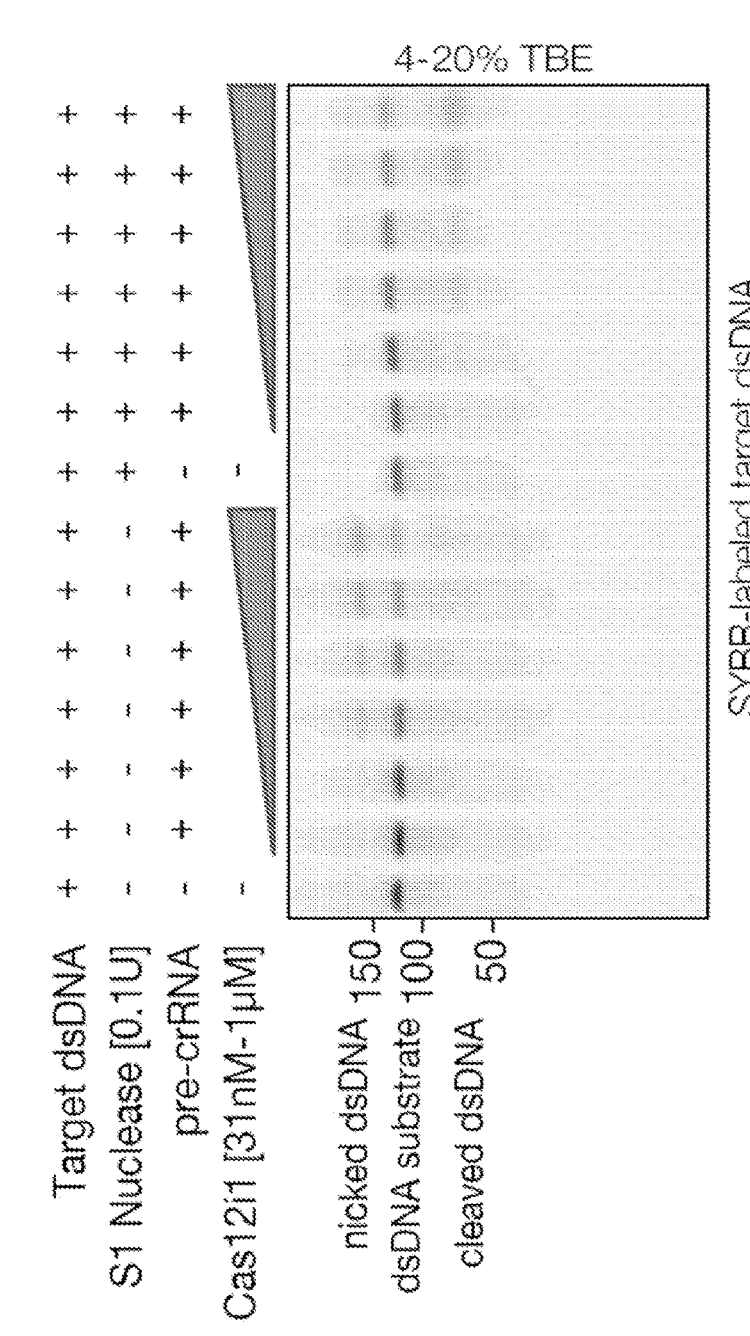

FIG. 16 is a representation of a gel that shows the manipulation of IR800 dye-labeled target dsDNA by increasing doses of Cas12i1 binary complex and quenched directly (left) or treated with SI nuclease before quenching (right). Samples were analyzed by 4-20% TBE non-denaturing gel electrophoresis.

Figure 17A:
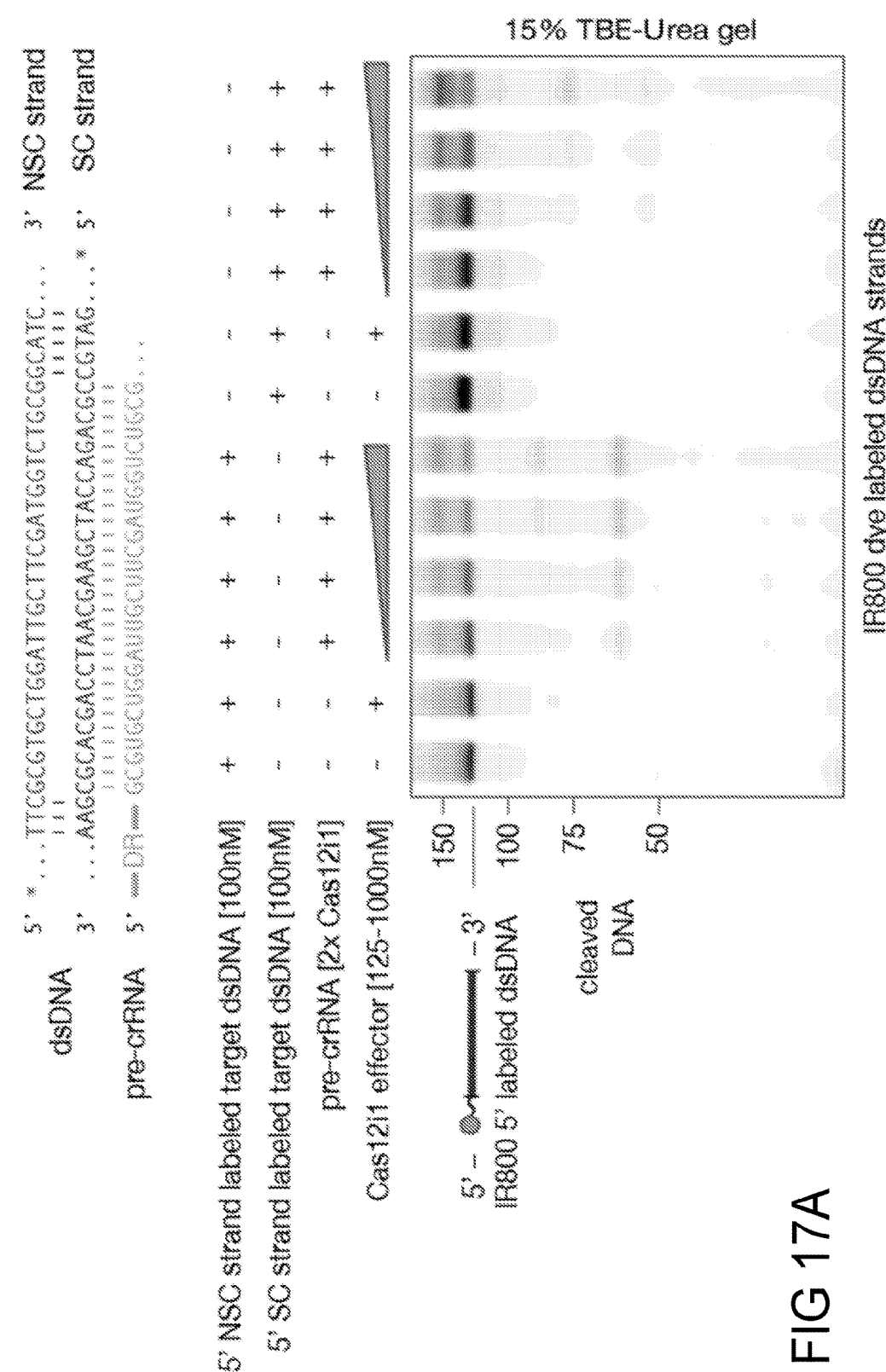
Figure 17B:
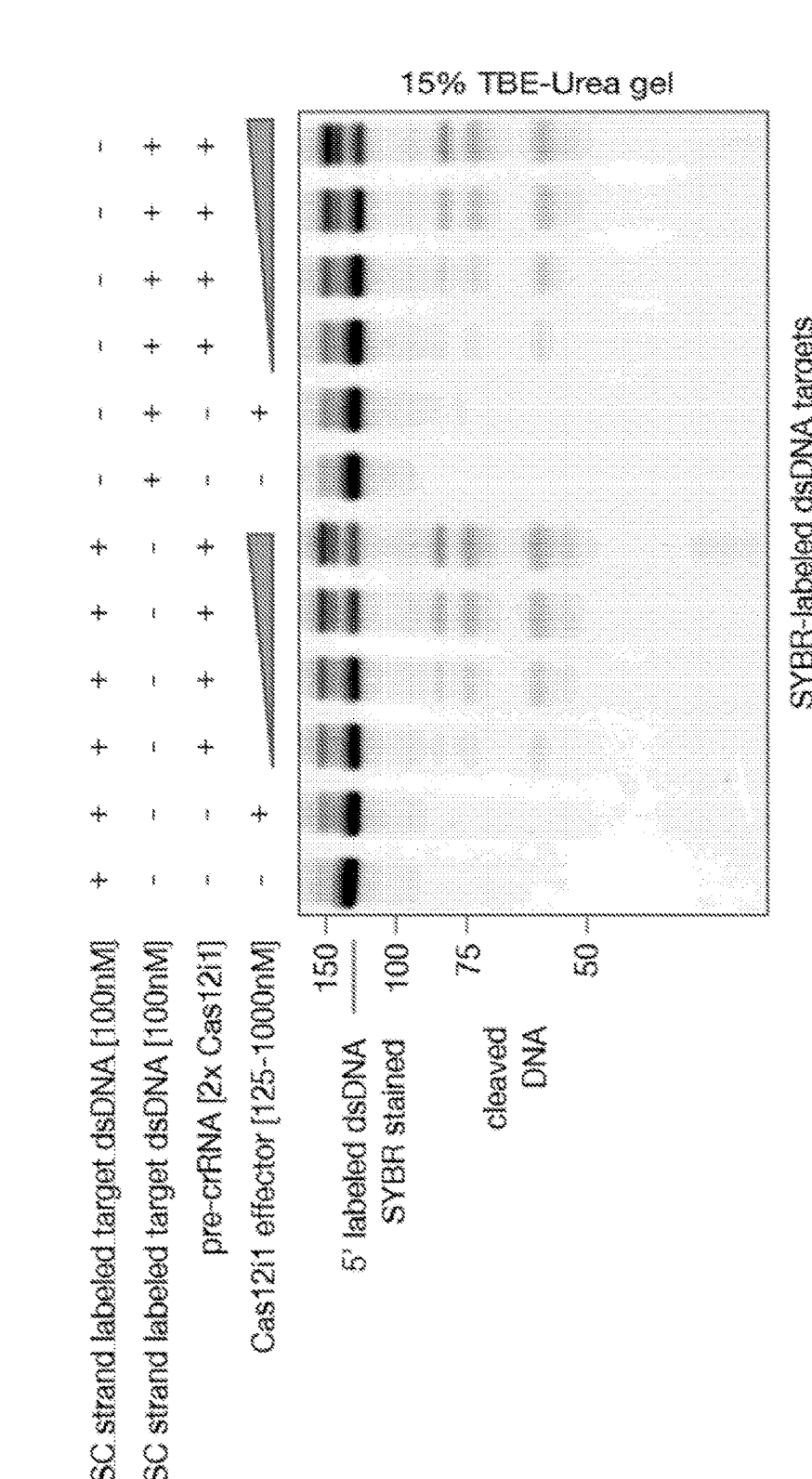

FIGS. 17A and 17B are representations of gels that show the asymmetric cleavage efficiency of dsDNA target strand (spacer complementary; "SC") versus non-target strand (non-spacer complementary; "NSC"). FIG. 17A is a denaturing gel imaged by IR800 (only labeled DNA), while FIG. 17B is a denaturing gel imaged by SYBR stain (total DNA). Each gel depicts cleavage or nicking activity on dsDNA with 5' IR800-labeled NSC strand (left), or 5' IR800-labeled SC strand (right), with increasing concentrations of Cas12i1 binary complex. Cas12i1 binary complex was formed by pre-incubating Cas12i1 with pre-crRNA for 10 minutes at 37° C. prior to adding to the substrates and incubating for 1 hour at 37° C.

Figure 18A:
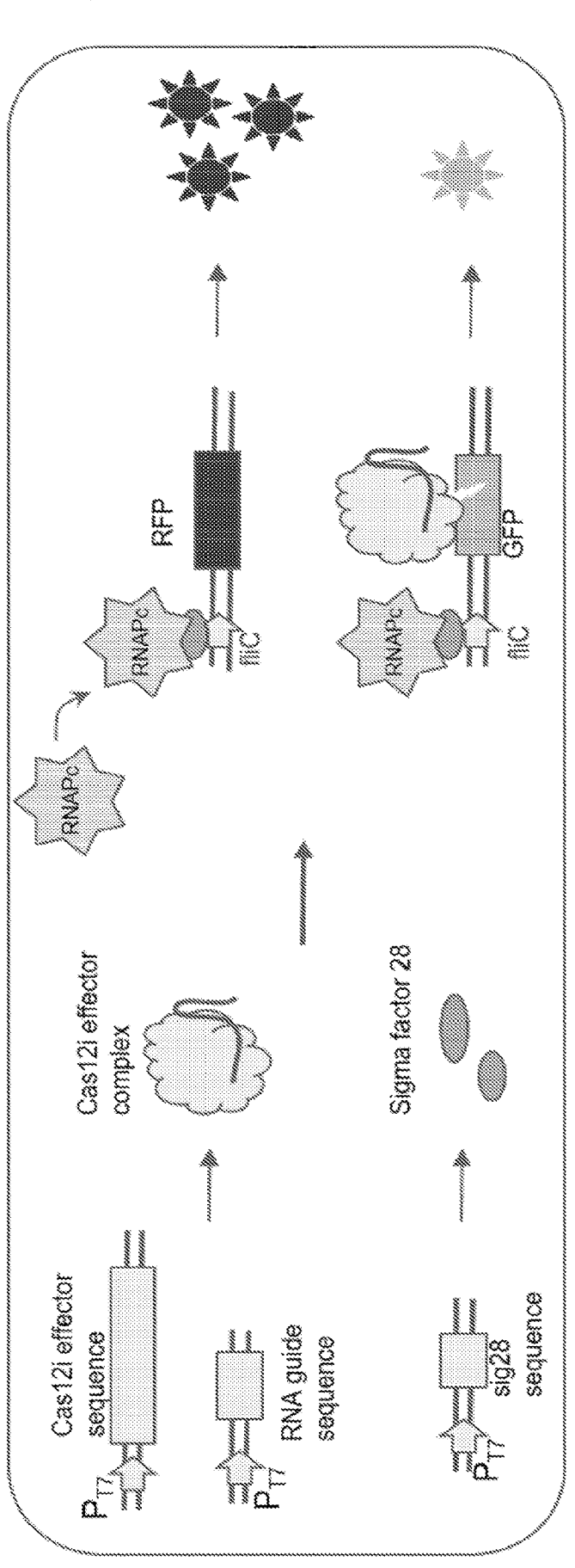

FIG. 18A is a schematic representation of the design of an in vitro assay to detect gene silencing. In a one pot reaction (depicted by the outer boundary), linear DNA templates encoding the Cas12i effector, RNA guide, and sigma factor 28 are combined with a reconstituted IVTT (in vitro transcription and translation) reagent and *E. coli* RNA polymerase core enzyme (denoted by RNAPc). A DNA plasmid encoding GFP targeted by the RNA guide is included, as is a non-target linear DNA template expressing RFP as an internal control. Both GFP and RFP are expressed from the sigma factor 28 promoter (fliC), and the GFP and RFP fluorescence is measured every 5 minutes for up to 12 hours.

Figure 18B:
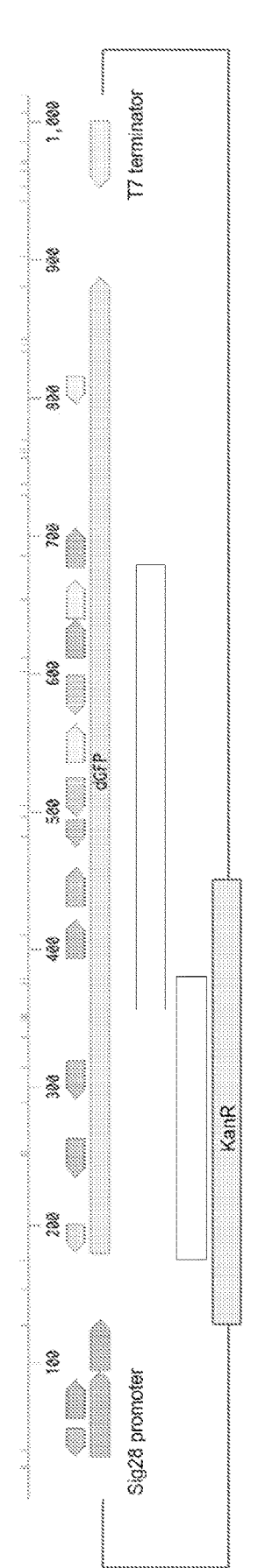

FIG. 18B is a schematic representation of the design of the GFP-encoding plasmid used as a substrate in the in vitro gene silencing assay. The plasmid encodes GFP under the sig28 promoter, and engineered RNA guides are designed to target both strands of the promoter region and the GFP gene (denoted by short chevrons in both orientations).

Figure 19A:
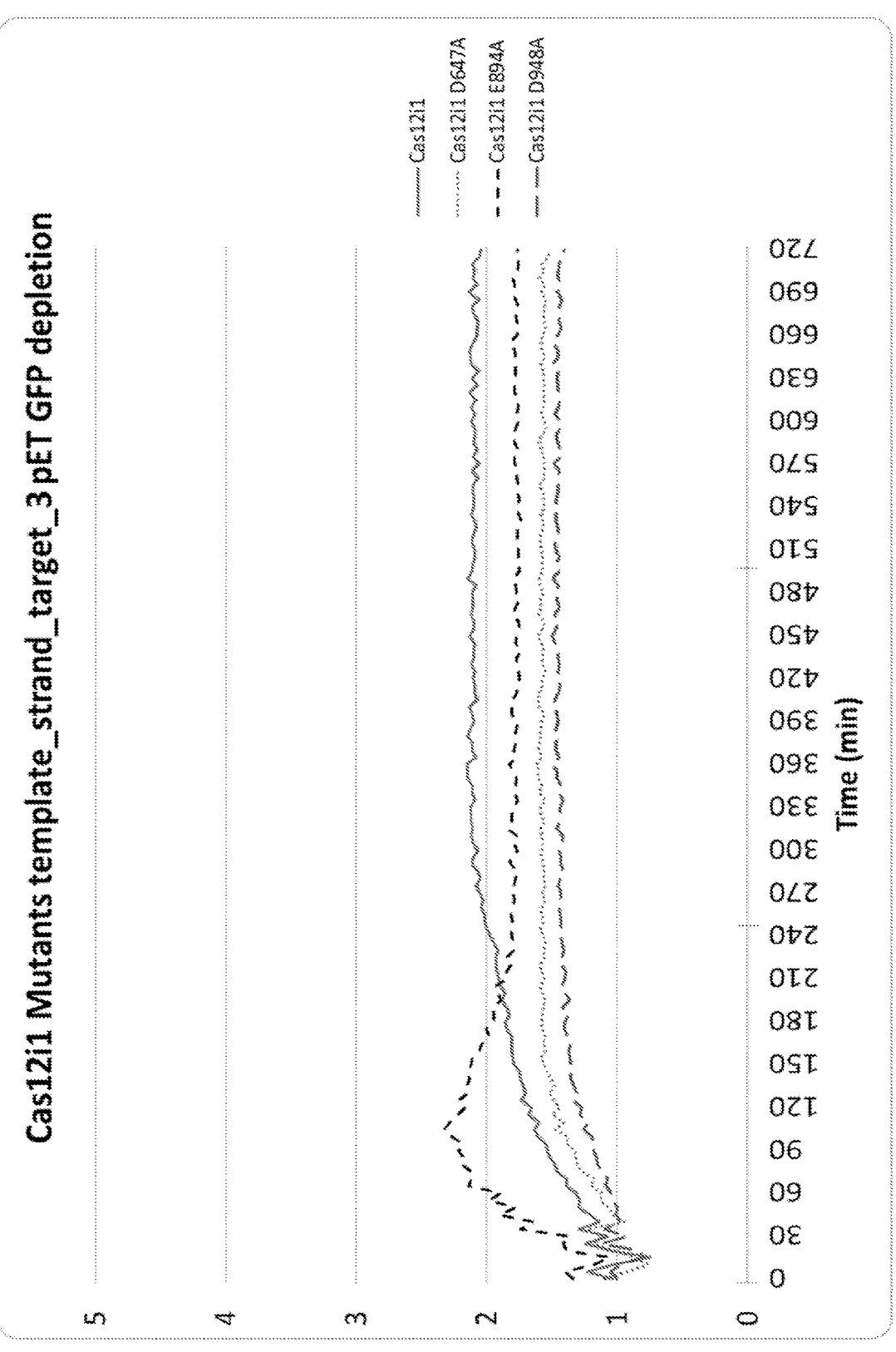
Figure 19B:
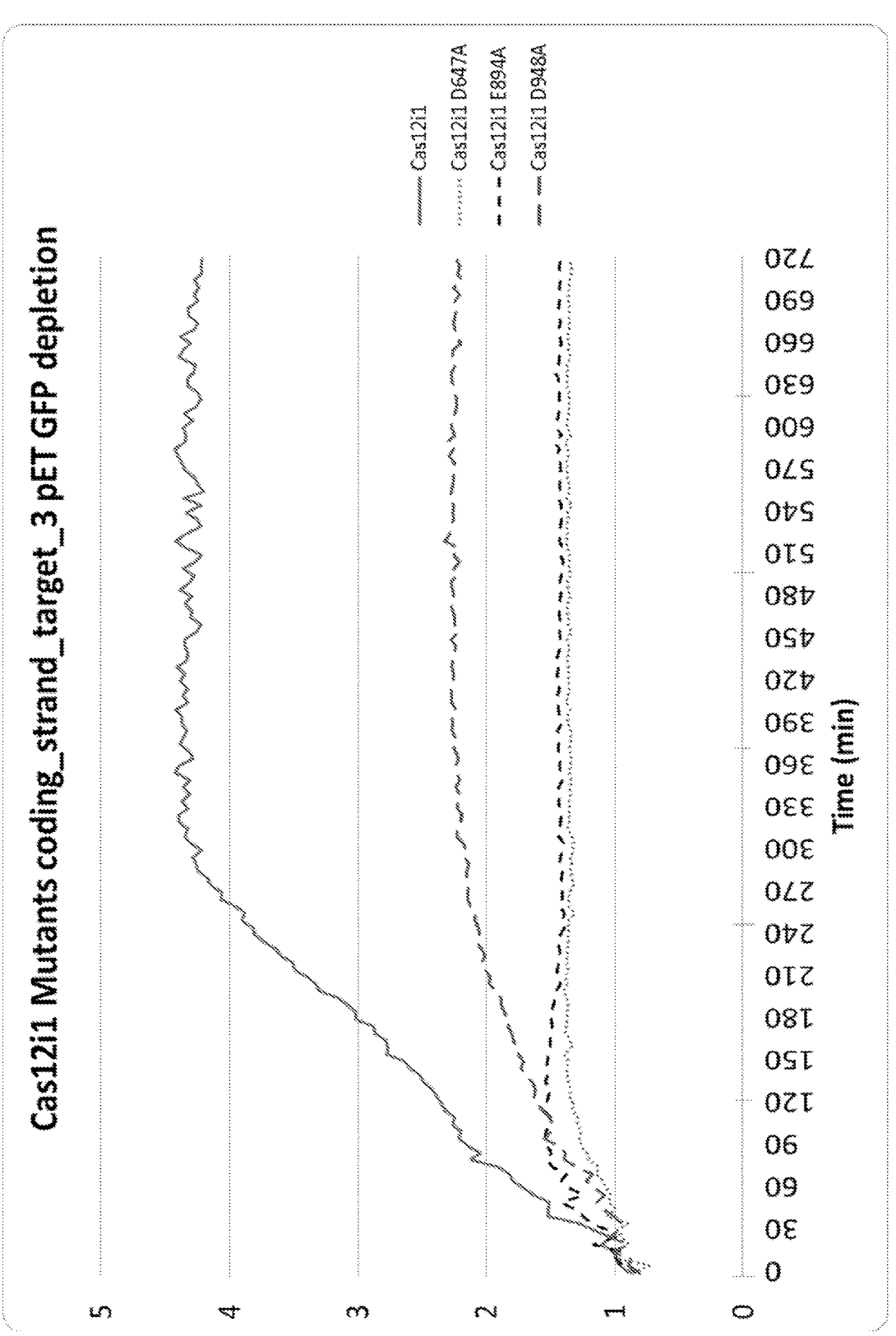

FIGS. 19A and 19B are graphs that show the GFP fluorescence fold depletion (y-axis) over 12 hours (720 minutes, x-axis) with the Type V-I effector as indicated in a complex with a guide containing a sequence complementary to the template strand (FIG. 19A) and coding strand (FIG. 19B) of the substrate GFP-coding region. GFP fluorescence fold depletion is calculated as the ratio of the normalized GFP fluorescence with the Type V-I effector in a complex with a non-target RNA guide over that of the Type V-I effector in a complex with a GFP-targeting RNA guide. Cas12i1 (solid line) shows greater depletion (gene silencing) compared to the activity of each of the mutant forms Cas12i1 D647A or Cas12i1 E894A or Cas12i1 D948A.

Figure 20:
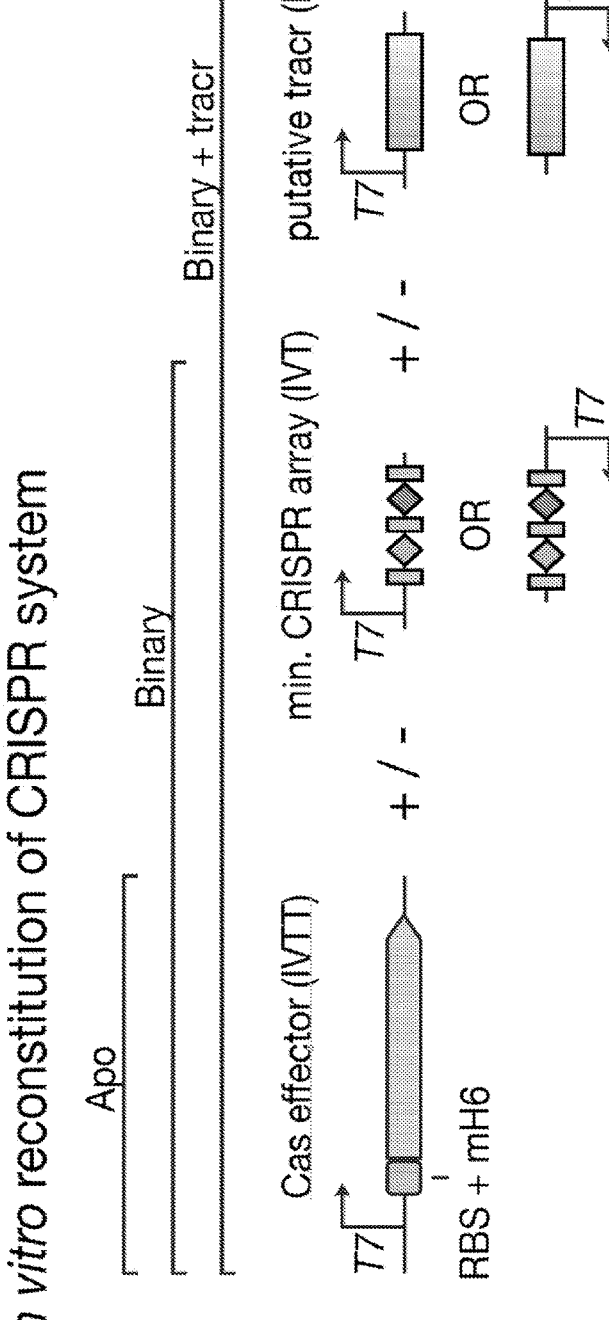

FIG. 20 shows the different forms of protein and/or RNAs in the in vitro reconstitution of the CRISPR-Cas system used in in vitro pooled screening. Transcriptional directions are indicated by the orientation of the T7 promoter arrow.

Figure 21:
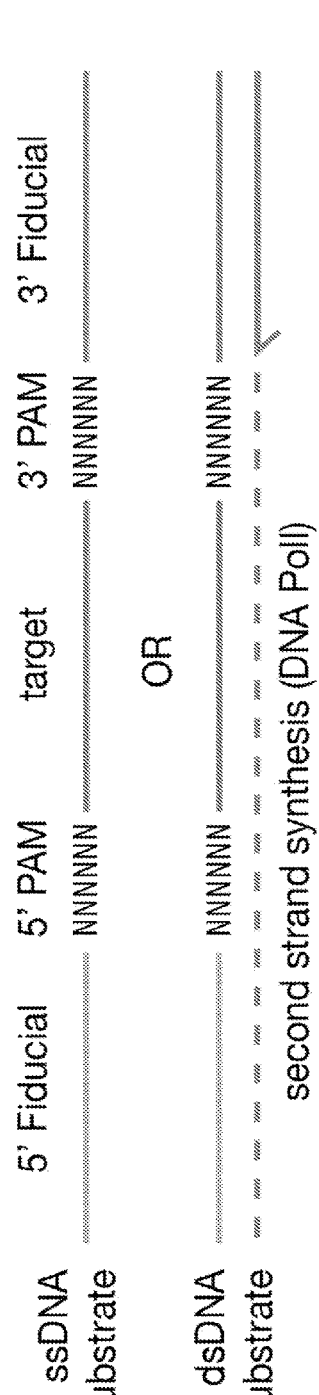

FIG. 21 shows one embodiment of the ssDNA and dsDNA substrates for in vitro pooled screening. The target sequence is flanked by 6 degenerate bases ("N") on both the 5' and 3' side, which are adjacent to a common region used as a fiducial mark for downstream data analysis following next generation sequencing. In the dsDNA substrate, the second strand synthesis is completed using a DNA polymerase I fill-in after annealing a primer to the 3' fiducial mark.

Figure 22:
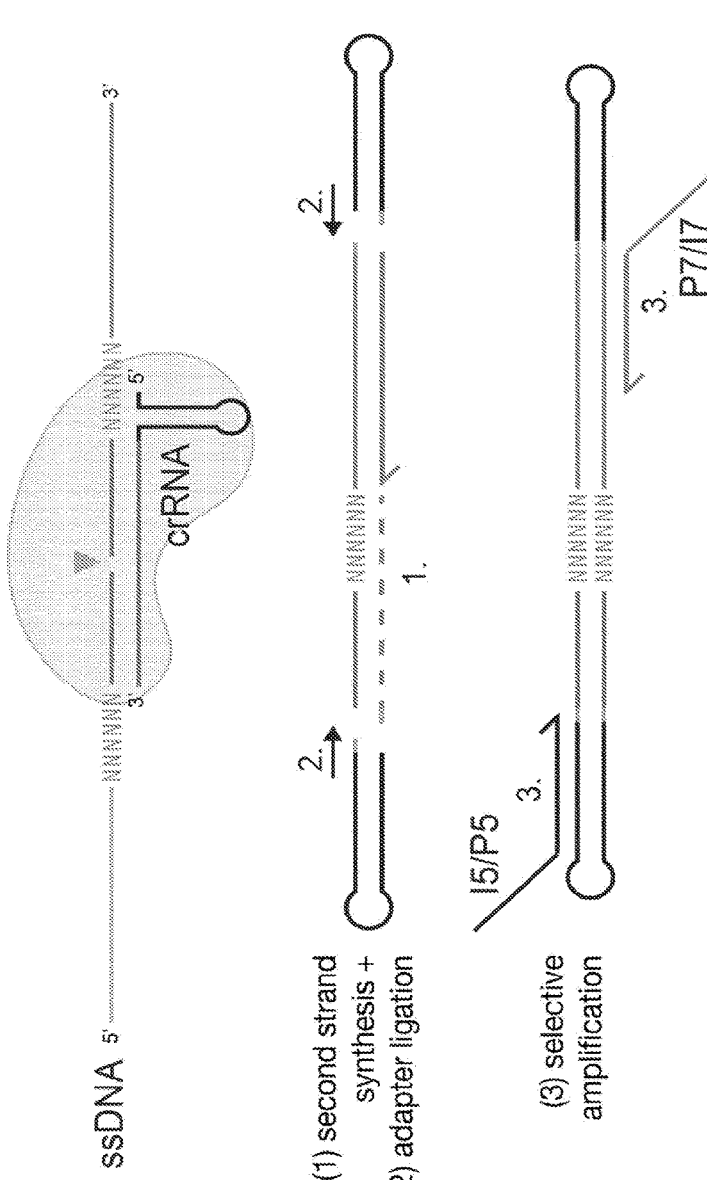

FIG. 22 displays a schematic of the unidirectional sequencing library preparation of the ssDNA fragments post incubation with the reconstituted CRISPR-Cas system.

Figure 23:
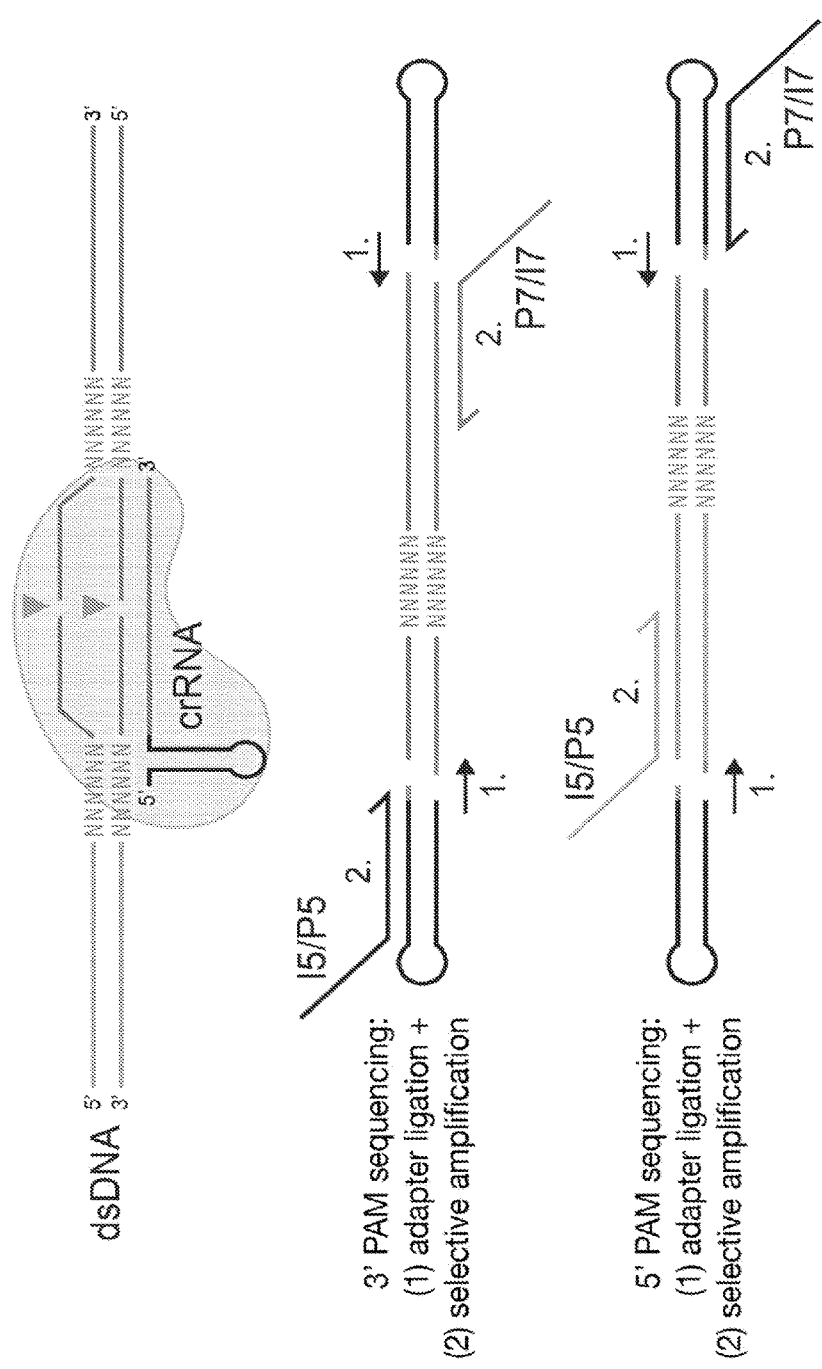

FIG. 23 displays a schematic of the bidirectional sequencing library preparation possible with the dsDNA fragments post incubation with the reconstituted CRISPR-Cas systems. The sequencing adaptor can be ligated to both cut fragments, and then selected for using a combination of primers common to the adaptor and common to the dsDNA substrate.

Figure 24A:
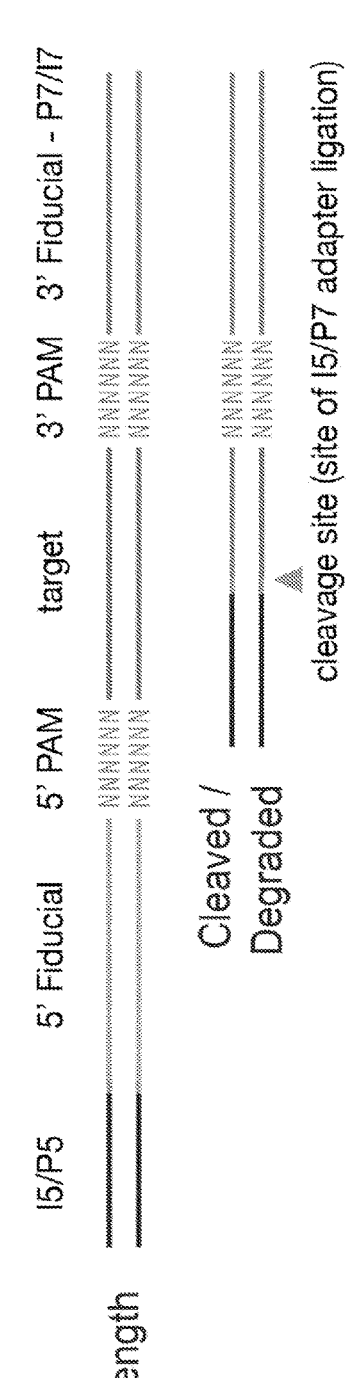
Figure 24B:
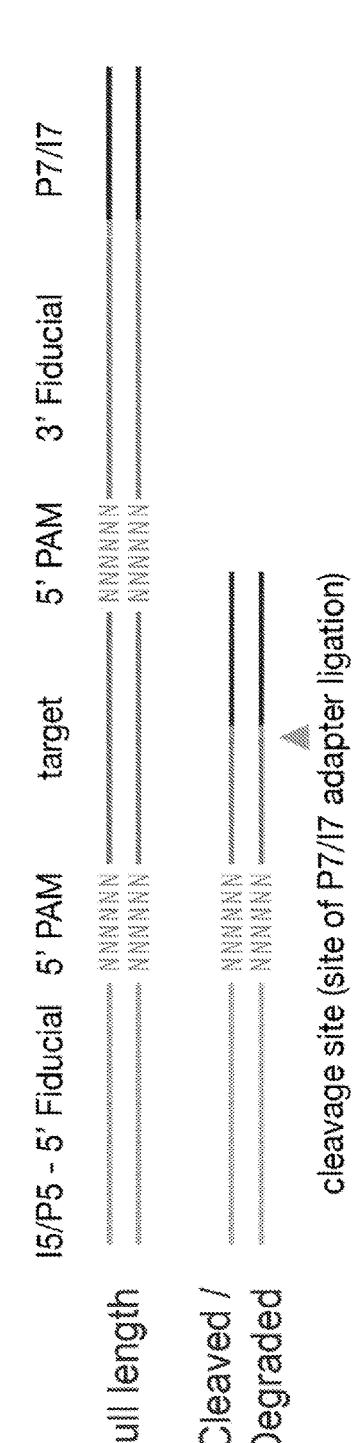

FIGS. 24A-B show the forms of the full length and cleaved products captured by the next generation sequencing library preparation and readout using A) I5/P5 ligation adapter and 3' fiducial for targeted amplification and addition of I7/P7, or B) I7/P7 ligation adapter and 5' fiducial for targeted amplification and addition of I5/P5.

Figure 25A:
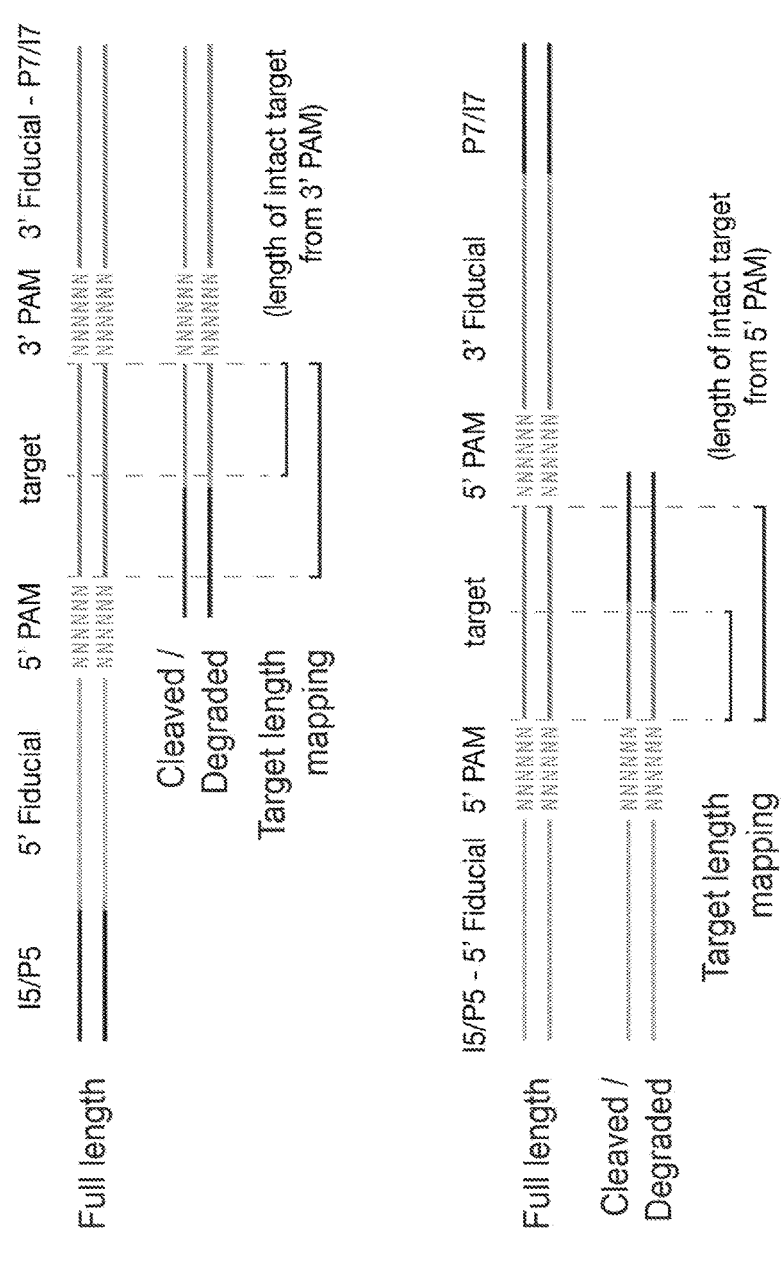
Figure 25B:
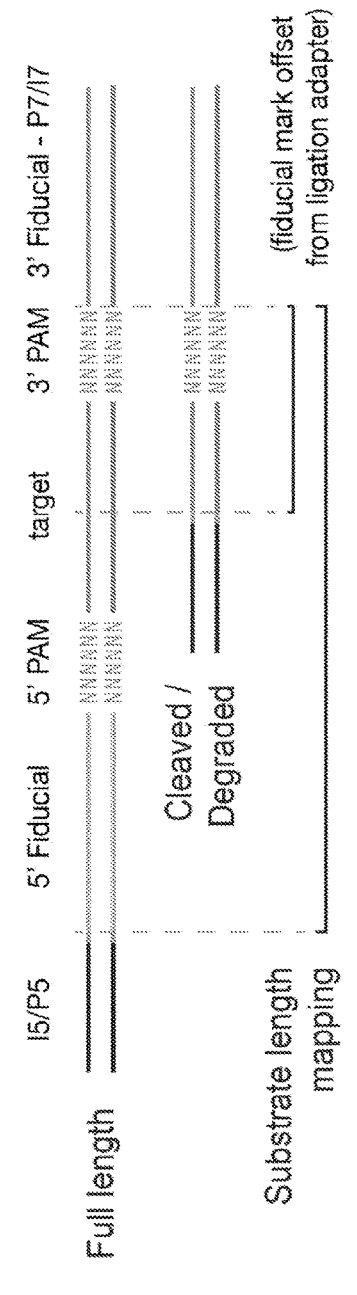
Figure 25B:
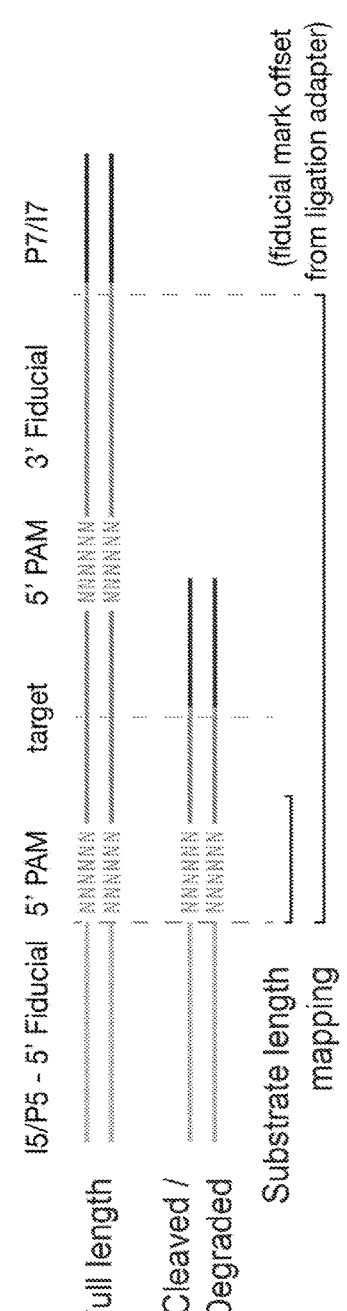

FIGS. 25A-B show a schematic for A) ssDNA target length mapping and B) substrate length mapping, respectively.

Figure 26A:
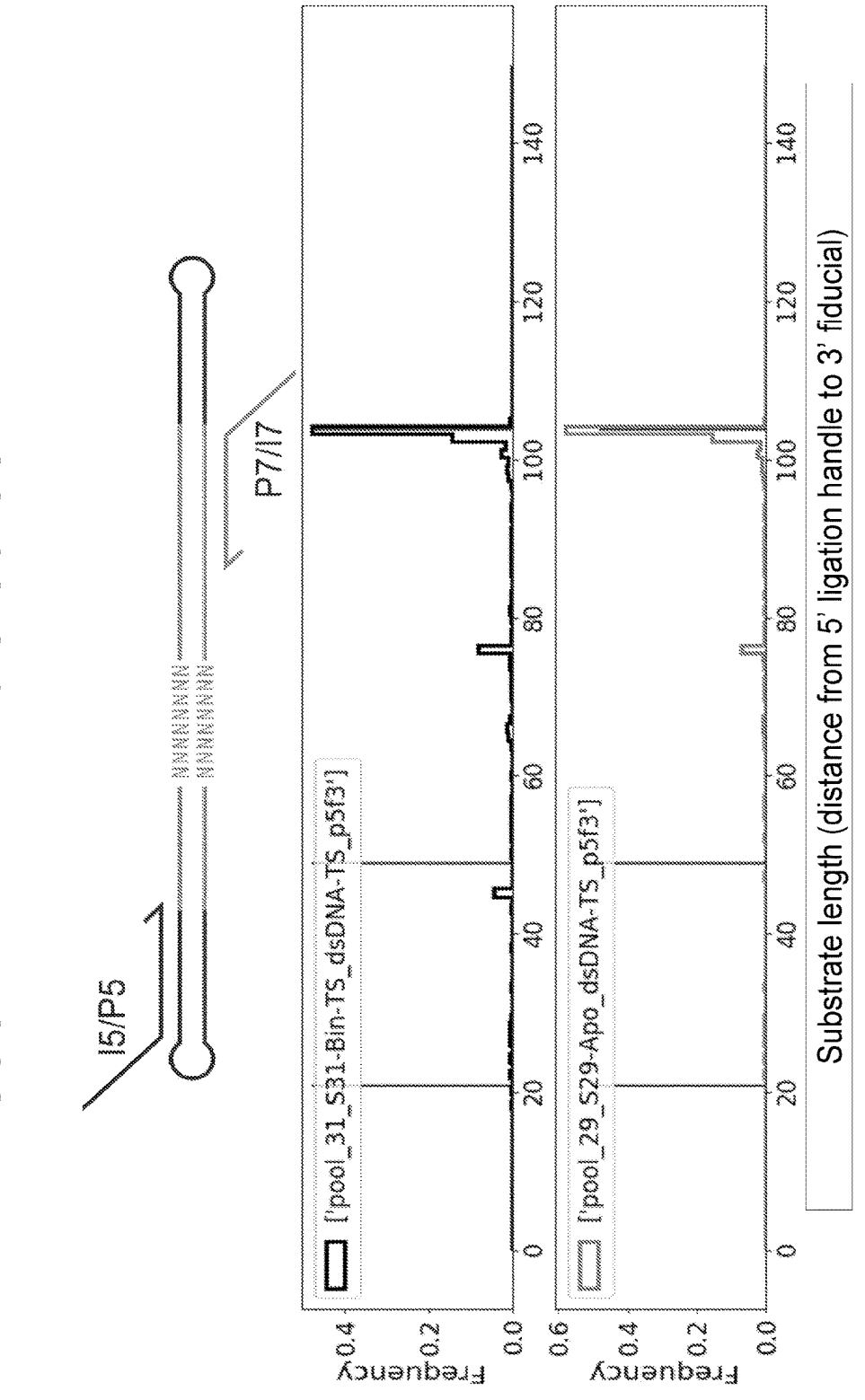
Figure 26B:
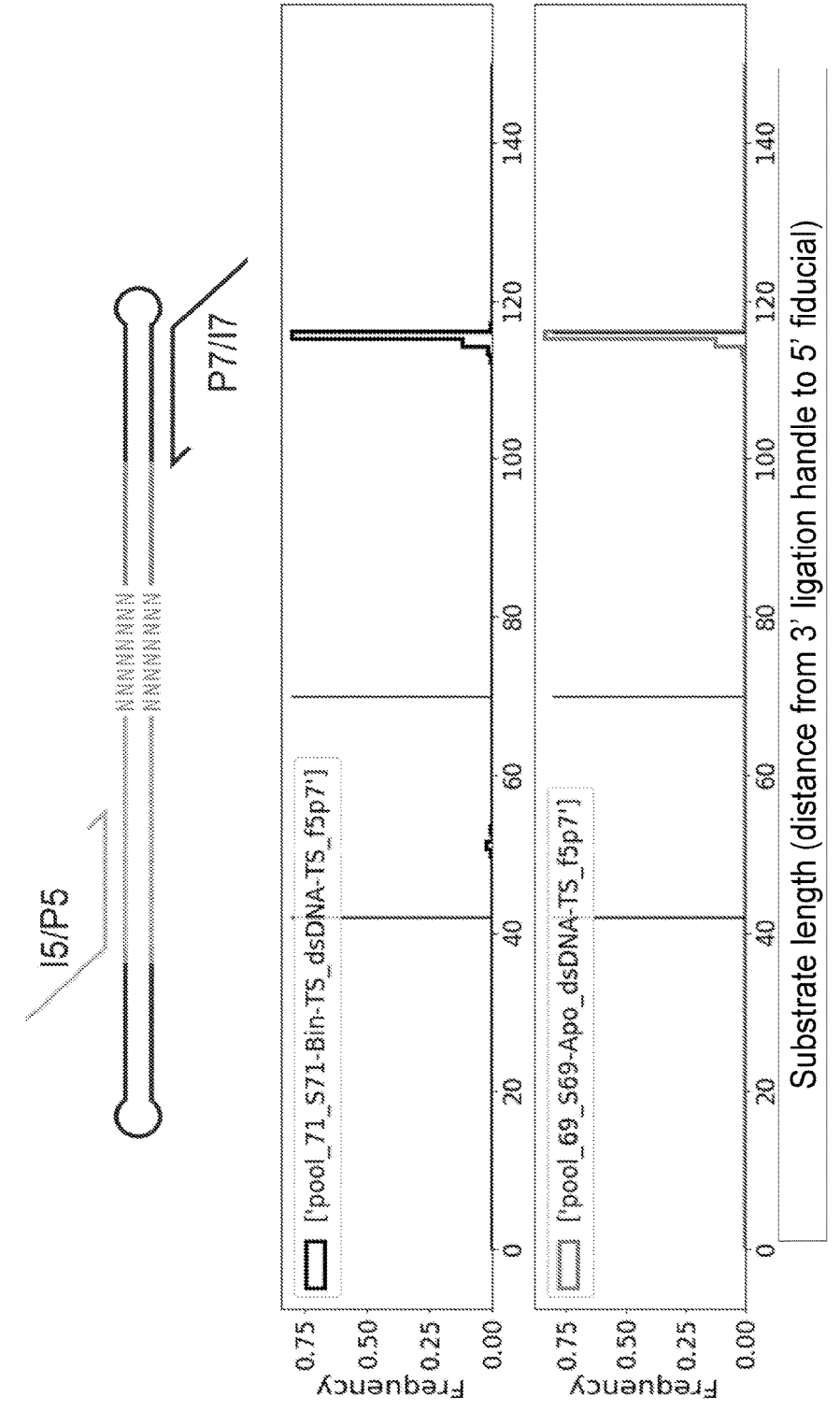

FIGS. 26A-B show the distribution of dsDNA substrate lengths for IVTT-expressed Cas12i1 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 27A:
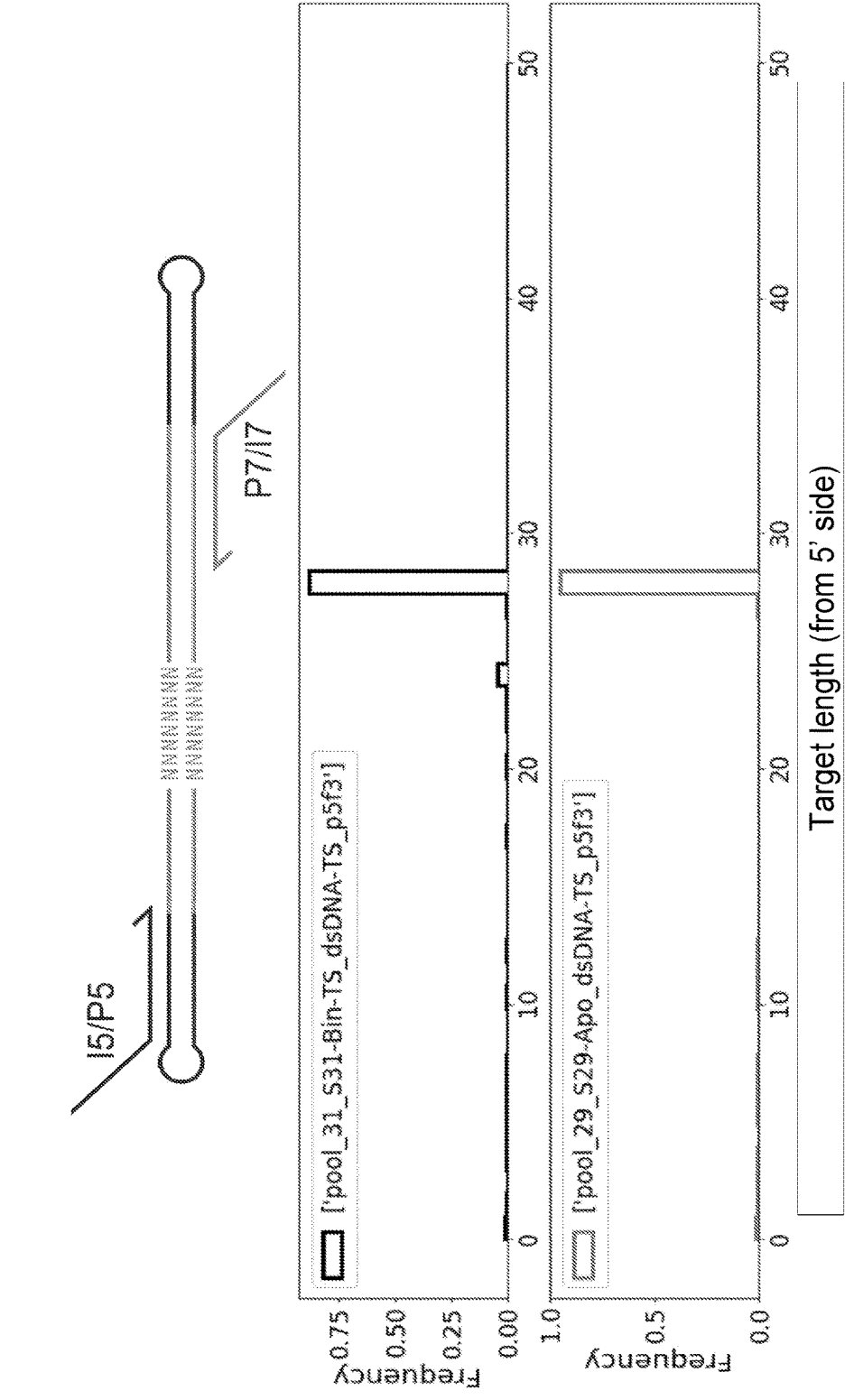
Figure 27B:
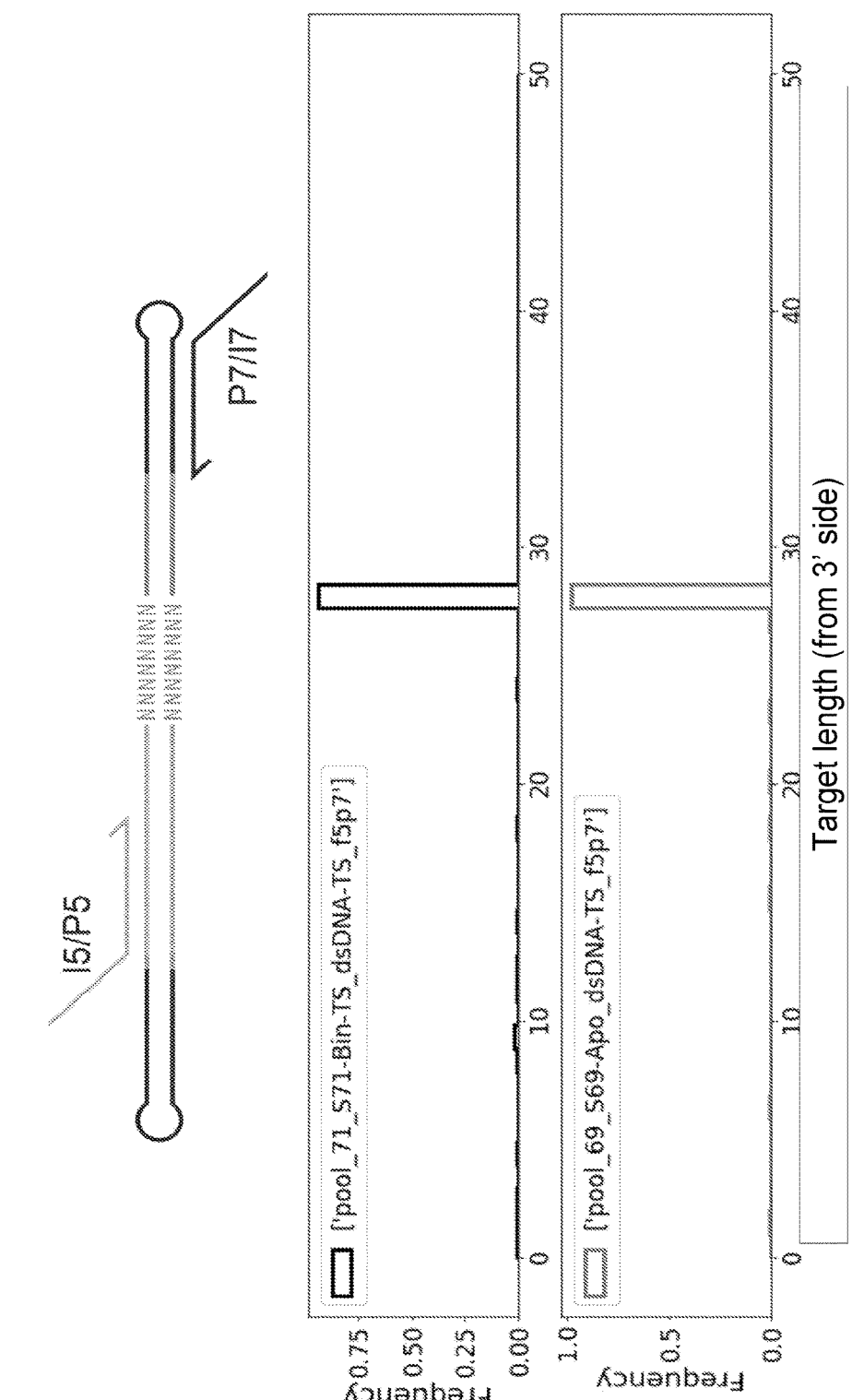

FIGS. 27A-B show the distribution of dsDNA target lengths for IVTT-expressed Cas12i1 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 28A:
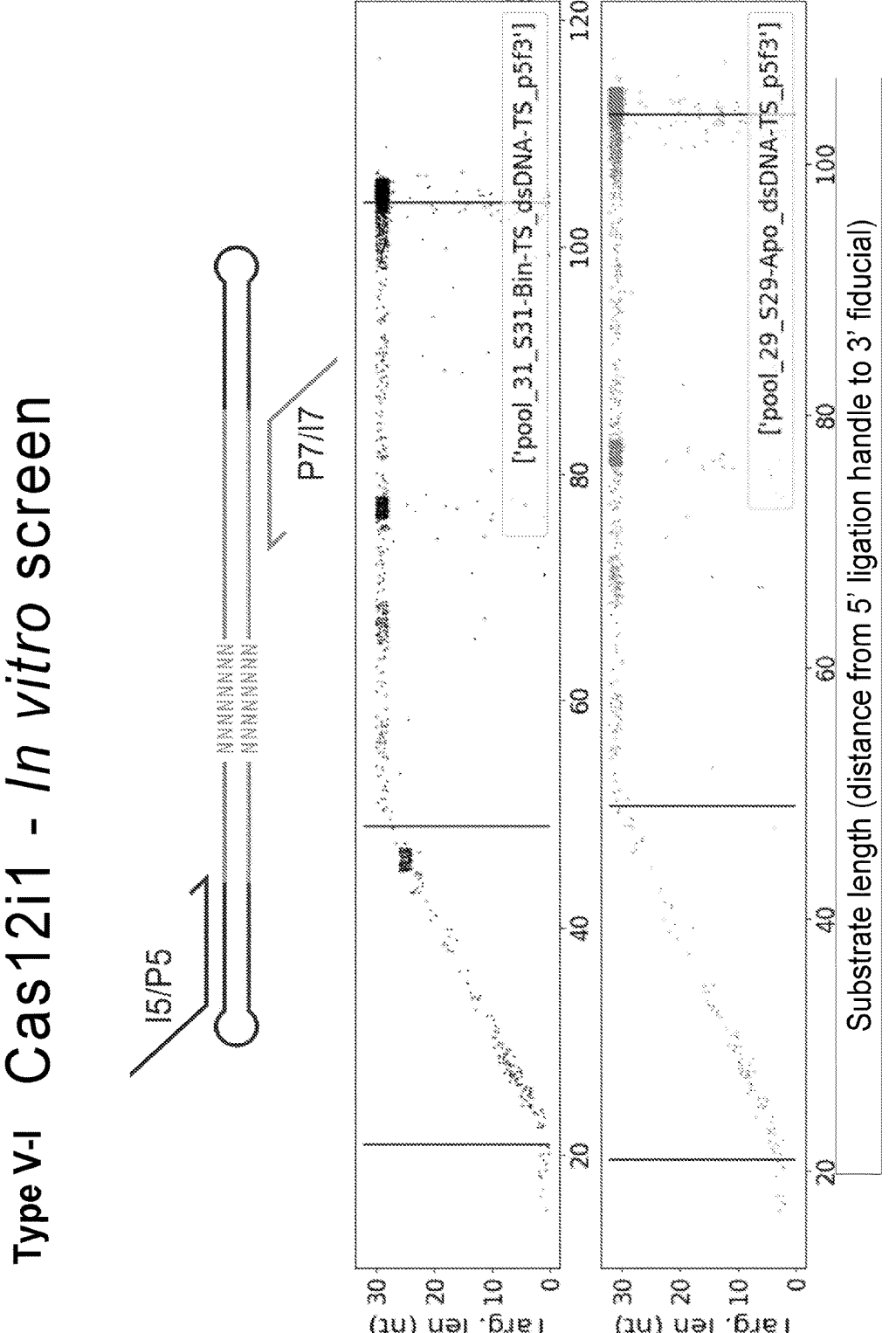
Figure 28B:
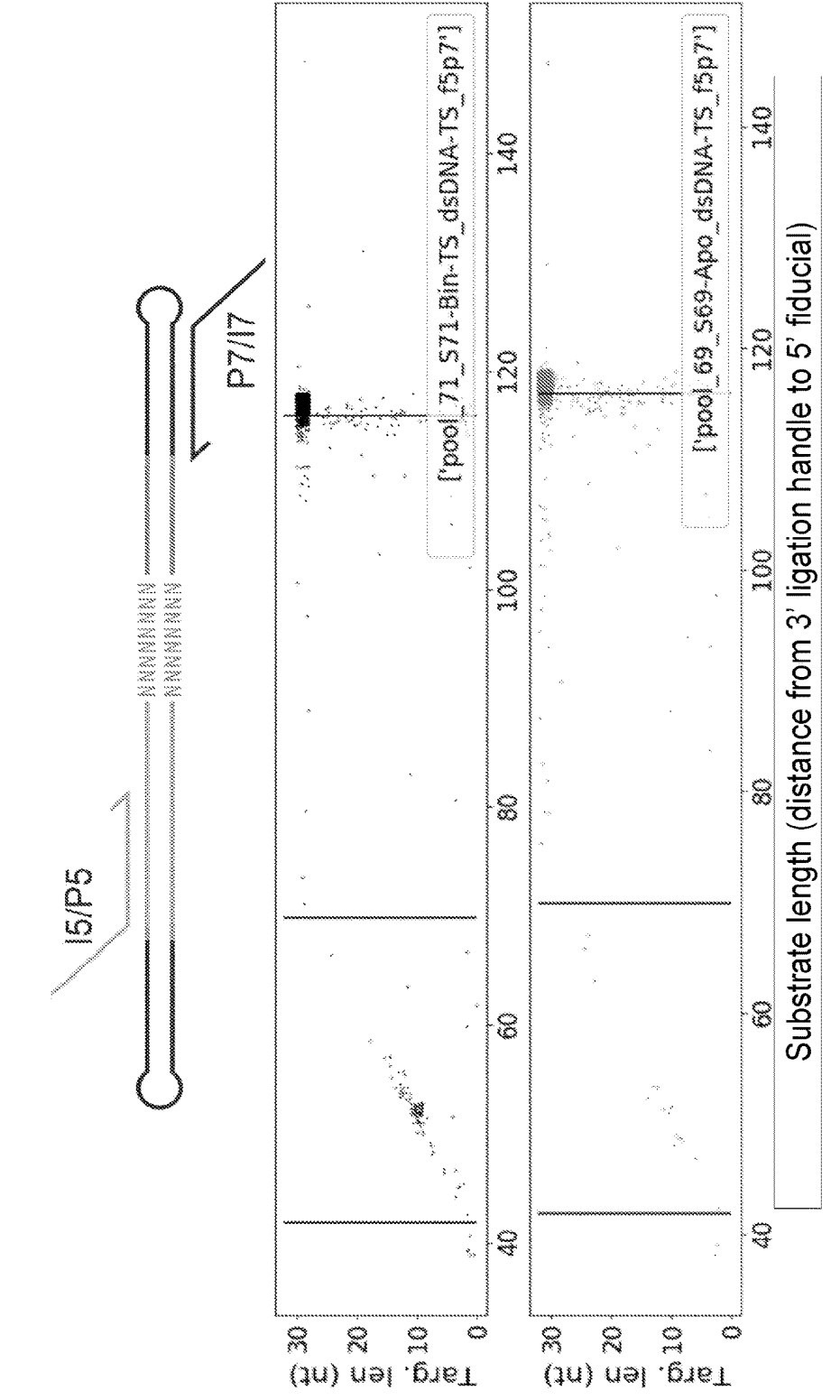

FIGS. 28A-B show the distribution of dsDNA substrate lengths (X) vs target lengths (Y) for IVTT-expressed Cas12i1 in complex with a top-strand (active orientation) crRNA targeting dsDNA (red) vs. apo (effector-only) controls (blue) (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 29:
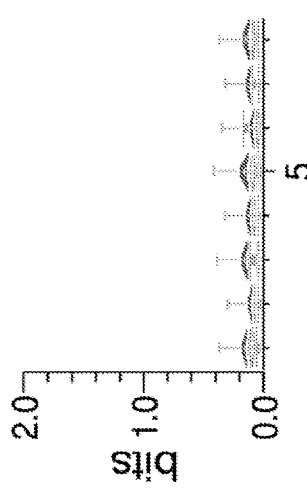
Figure 29:
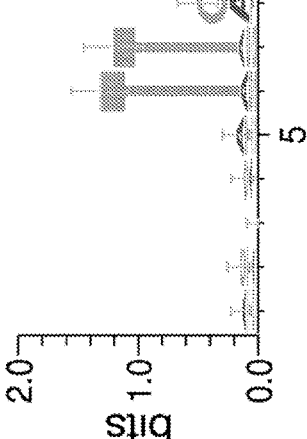

FIG. 29 shows a weblogo indicating a 5' TTN PAM motif (left of the target sequence) for Cas12i1 associated with non-target strand cleavage between the +24/+25 nucleotides relative to the PAM. No PAM sequence requirement is observed on the right side of the Cas12i1 target.

Figure 30:
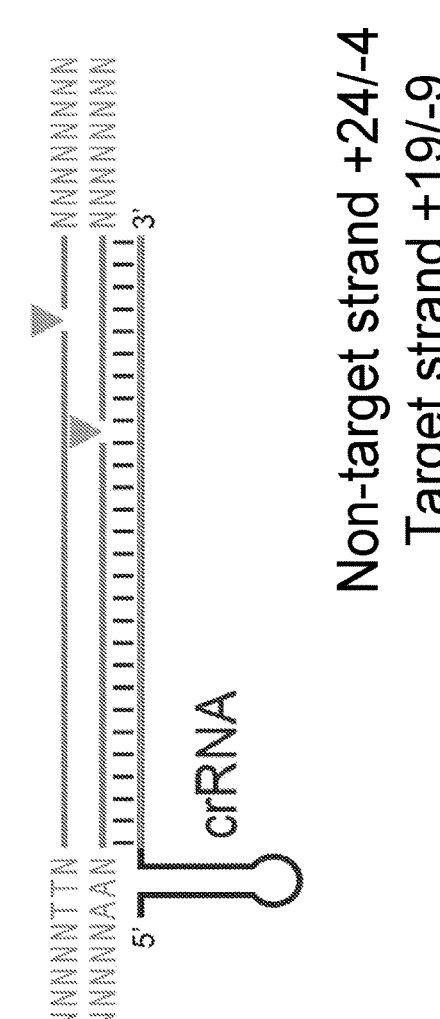

FIG. 30 shows a 5 nt 3' overhang associated with double stranded DNA cleavage by Cas12i1 indicated by cleavage observed between the +24/+25 nucleotides of the non-target strand relative to the PAM and cleavage between the +19/+20 nucleotides of the target strand relative to the PAM.

Figure 31A:
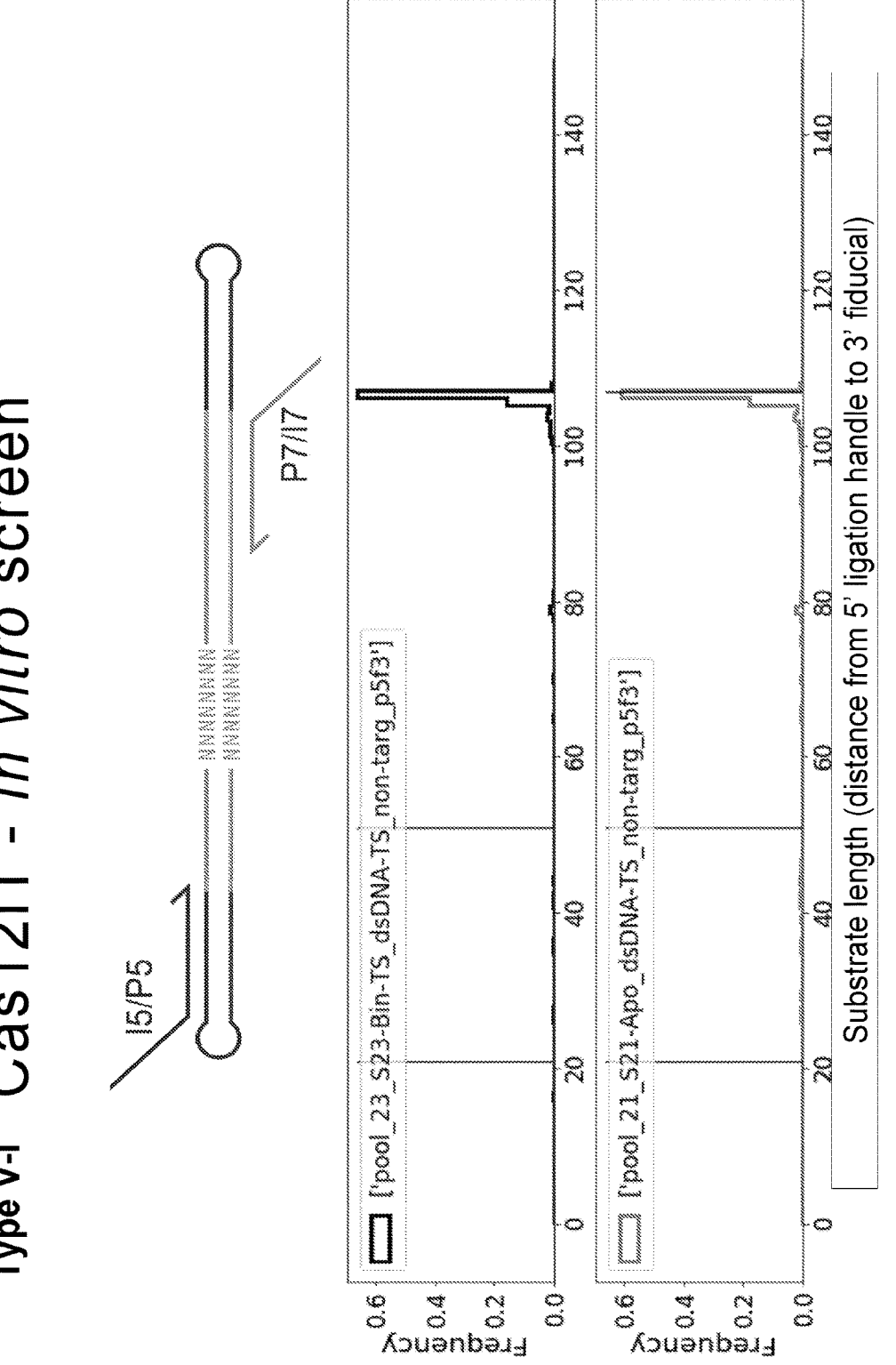
Figure 31B:
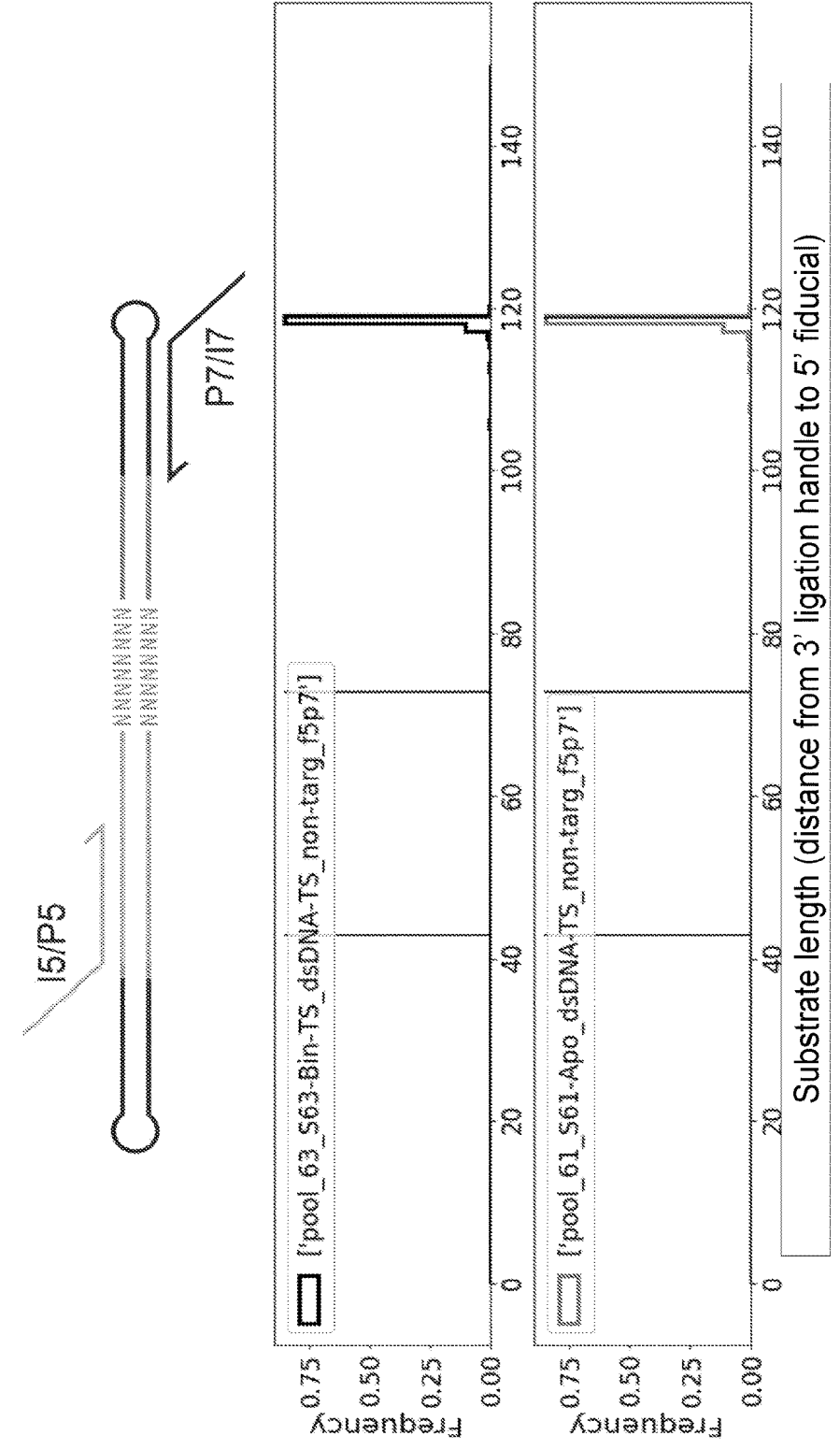

FIGS. 31A-B show the distribution of dsDNA substrate lengths for IVTT-expressed Cas12i1 in complex with a non-target crRNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 32A:
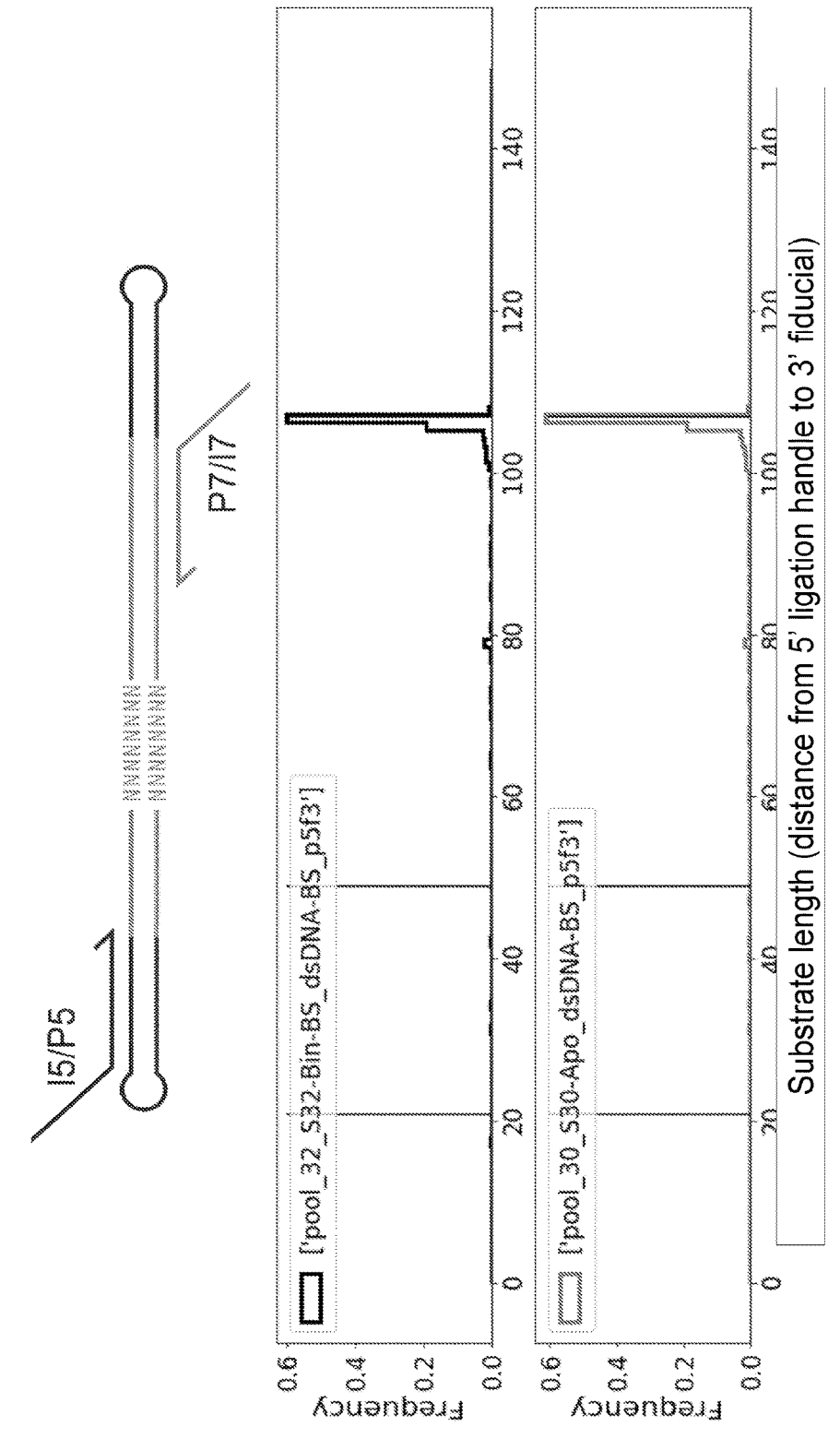
Figure 32B:
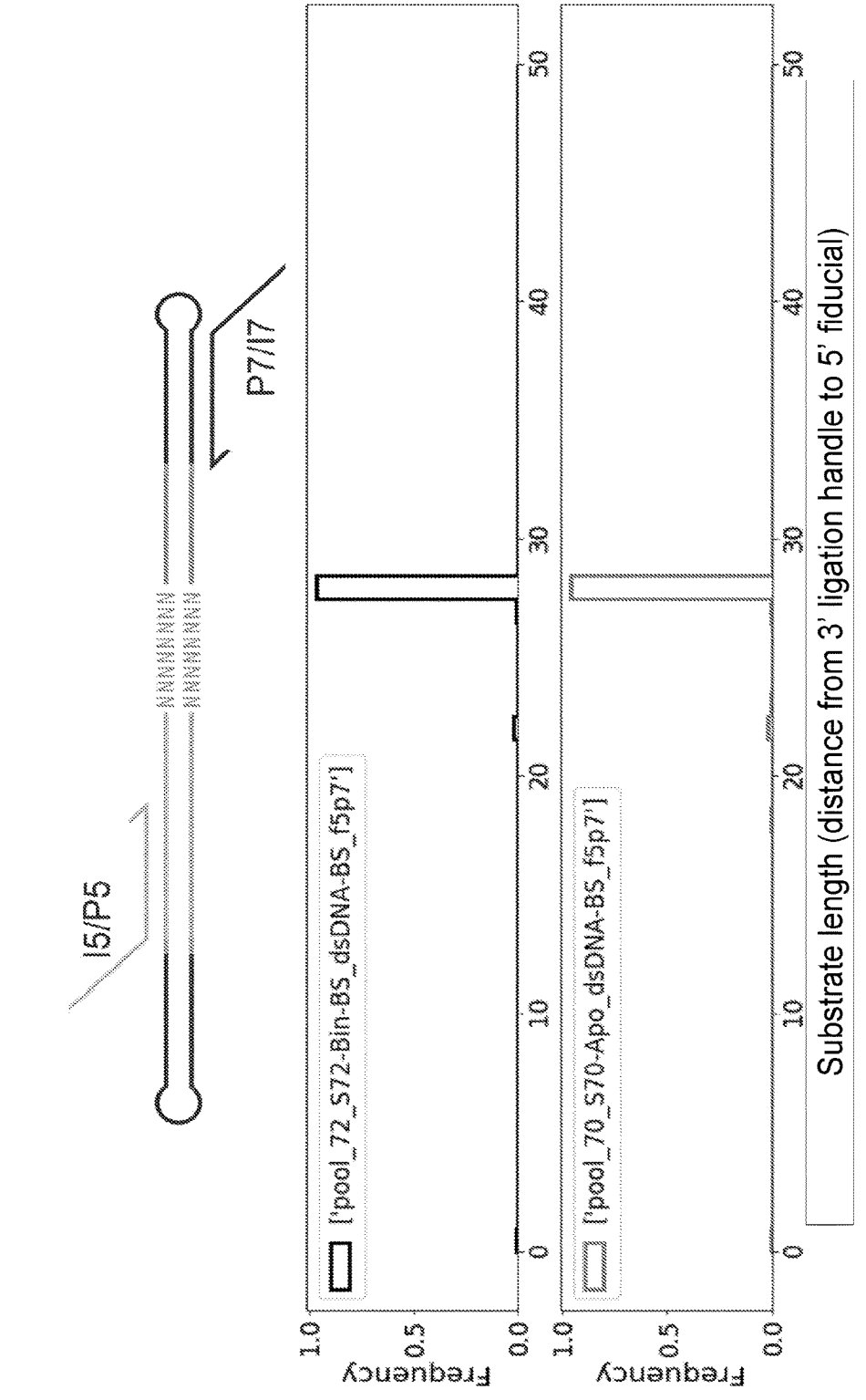

FIGS. 32A-B show the distribution of dsDNA substrate lengths for IVTT-expressed Cas12i1 in complex with a bottom-strand (inactive orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 33A:
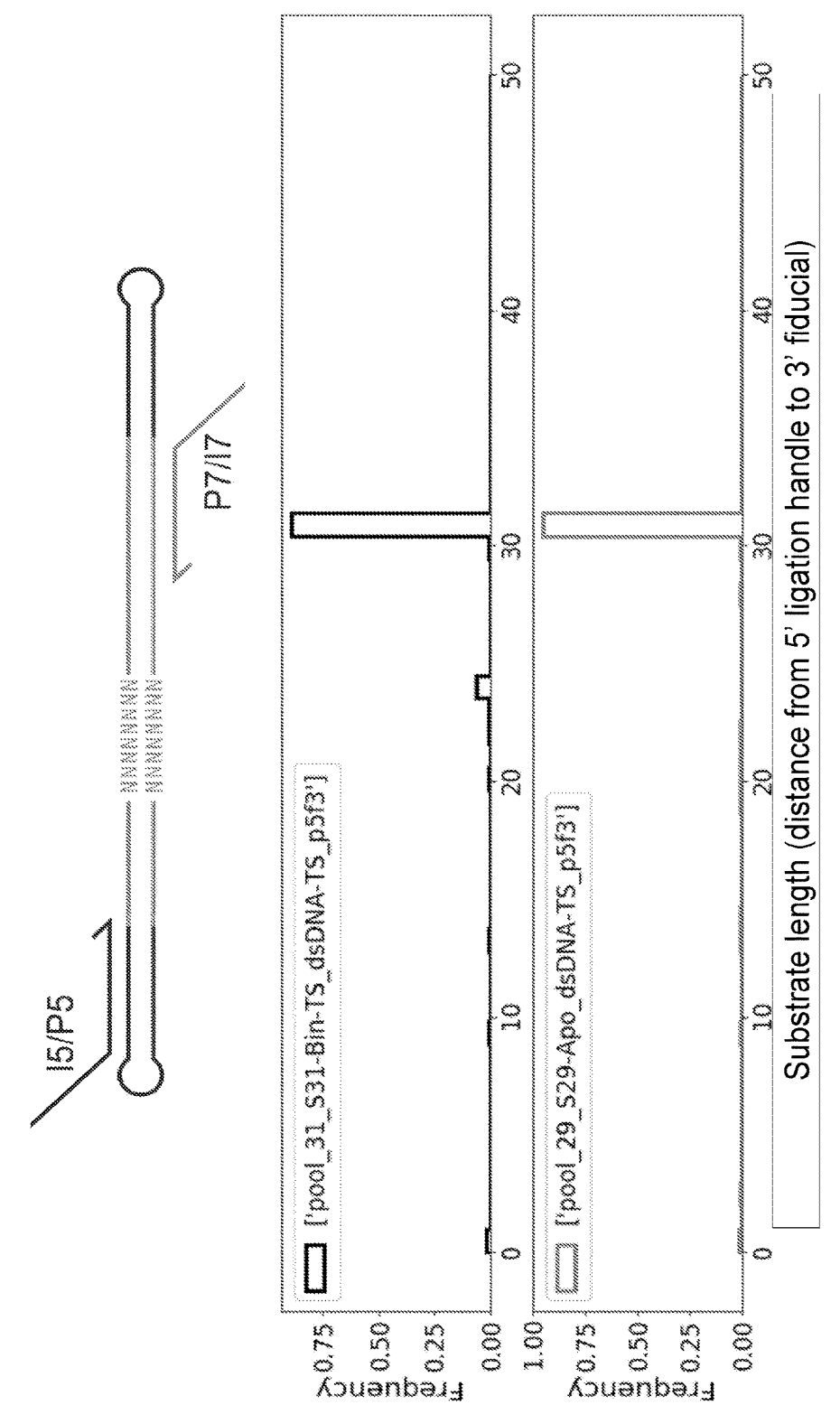
Figure 33B:
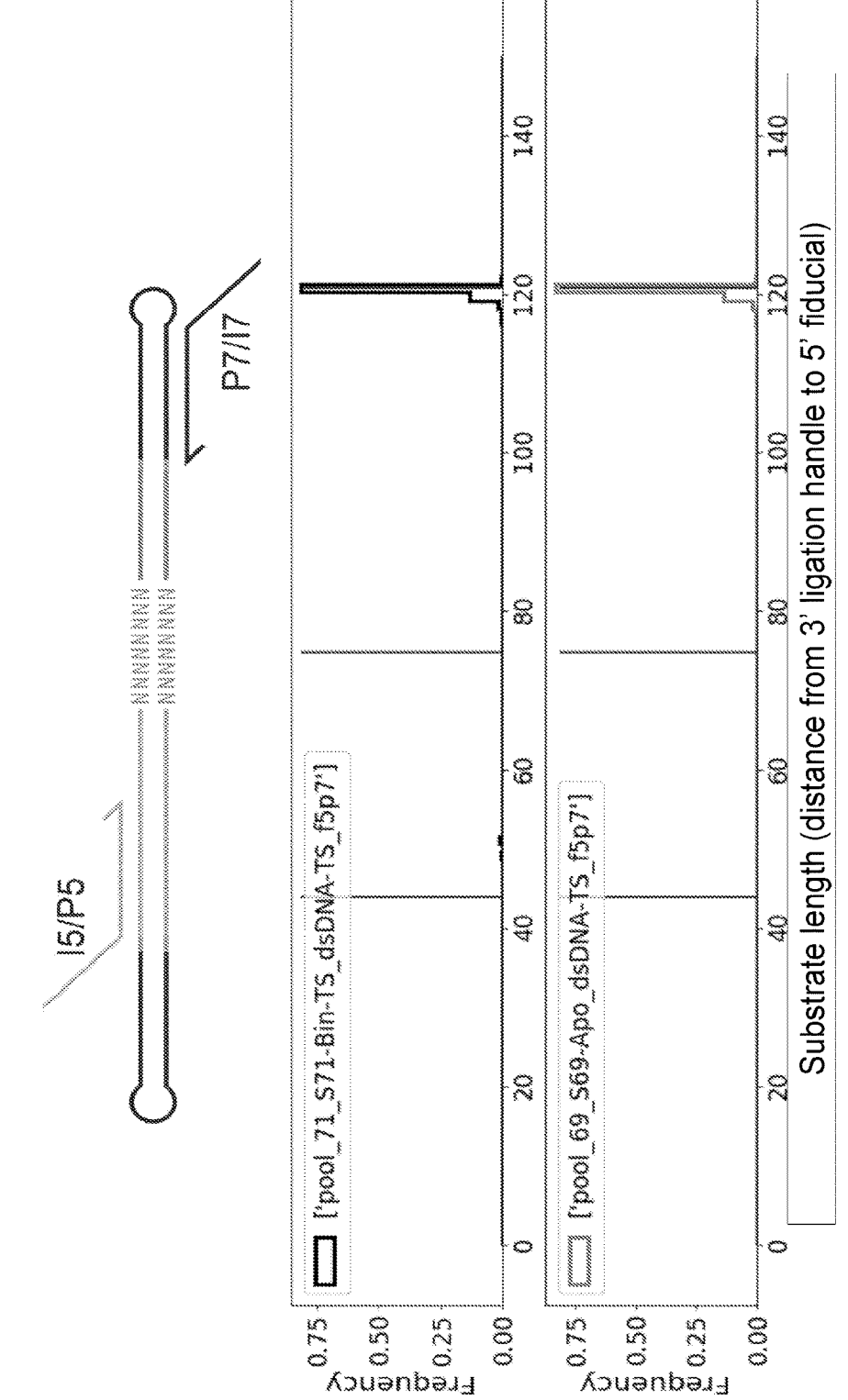

FIGS. 33A-B show the distribution of dsDNA substrate lengths for IVTT-expressed Cas12i2 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 34A:
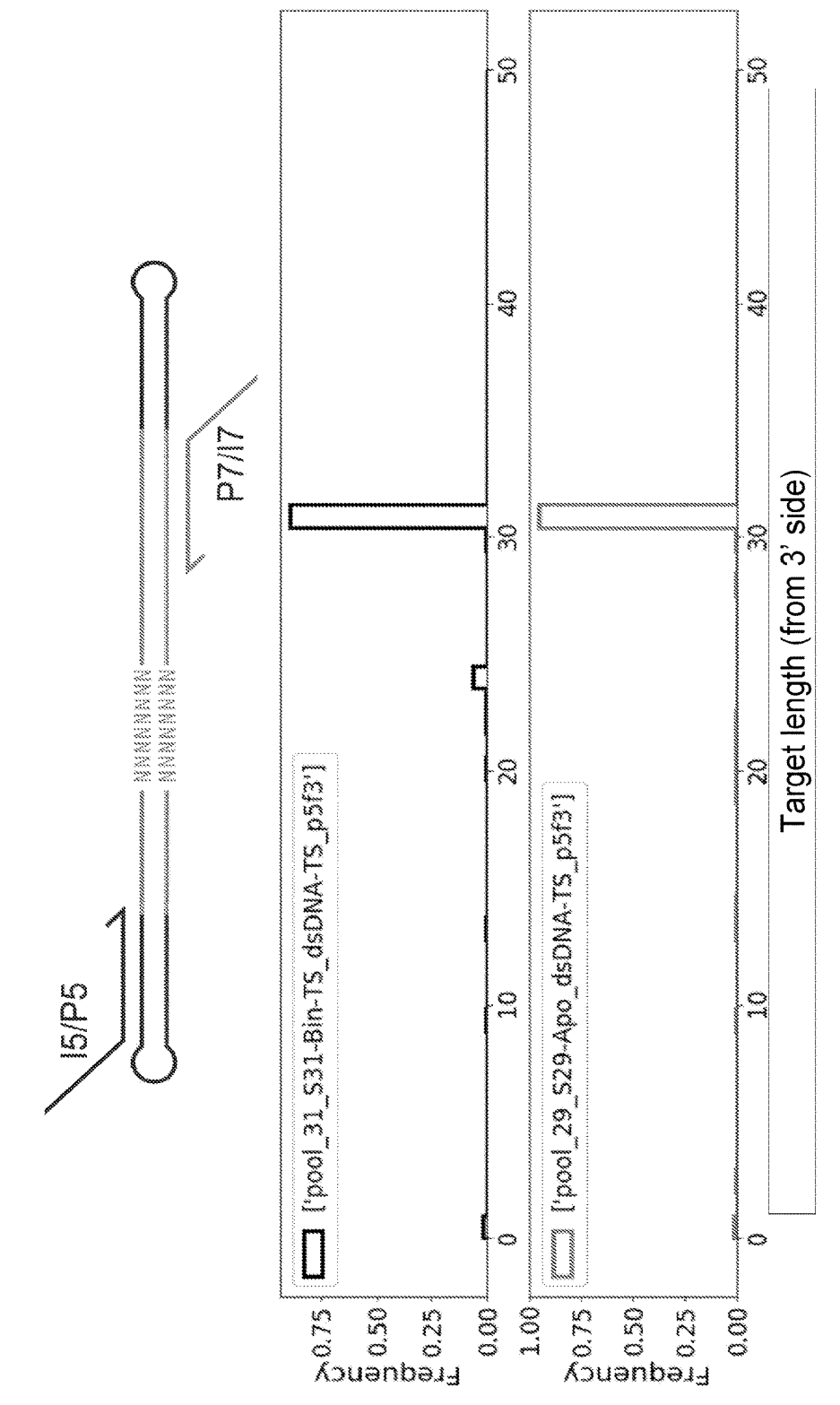
Figure 34B:
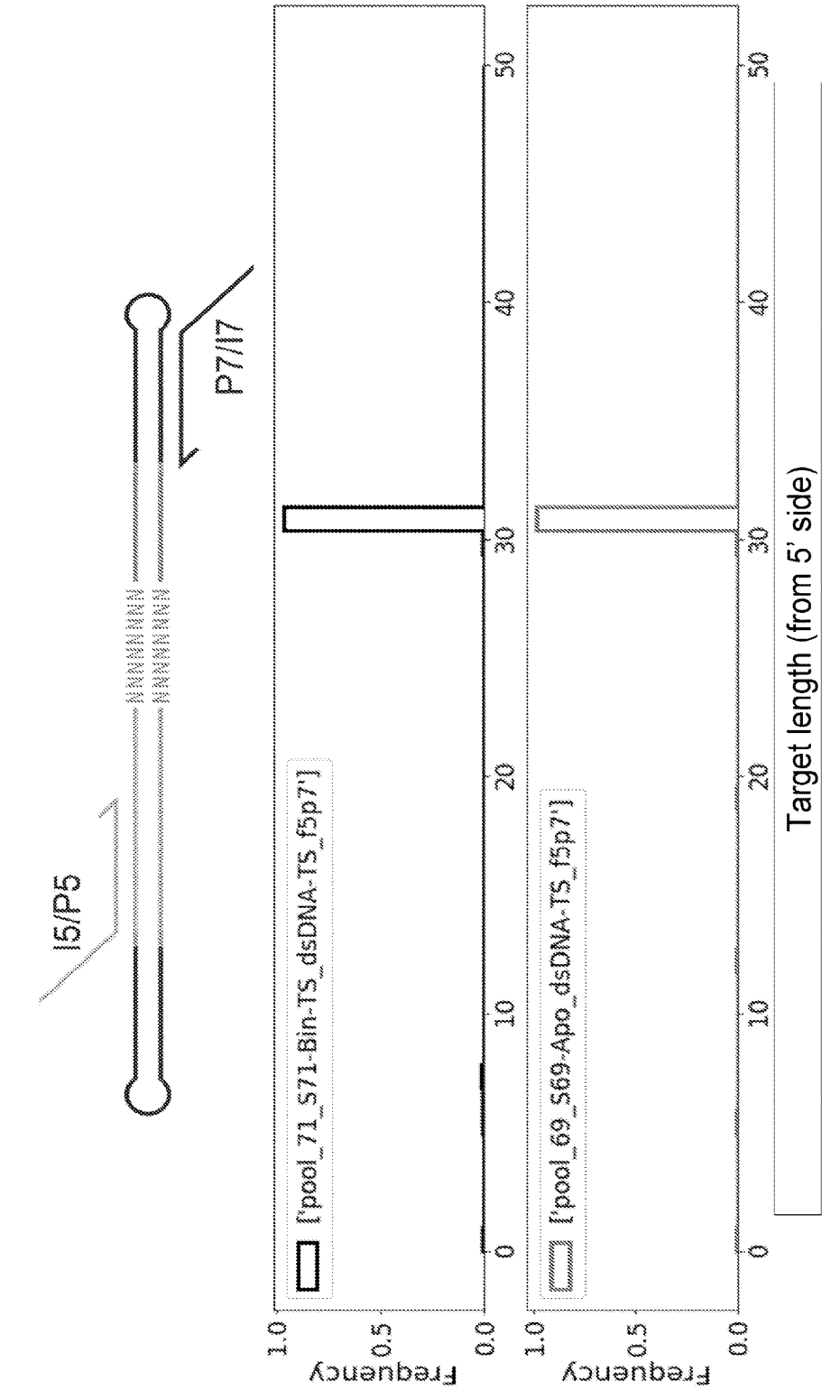

FIGS. 34A-B show the distribution of dsDNA target lengths for IVTT-expressed Cas12i2 in complex with a top-strand (active orientation) crRNA targeting dsDNA (red) vs. apo (effector-only) controls (blue). (A) Next generation sequencing libraries for readout were prepared with a first primer complementary to a handle ligated to the S' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 35A:
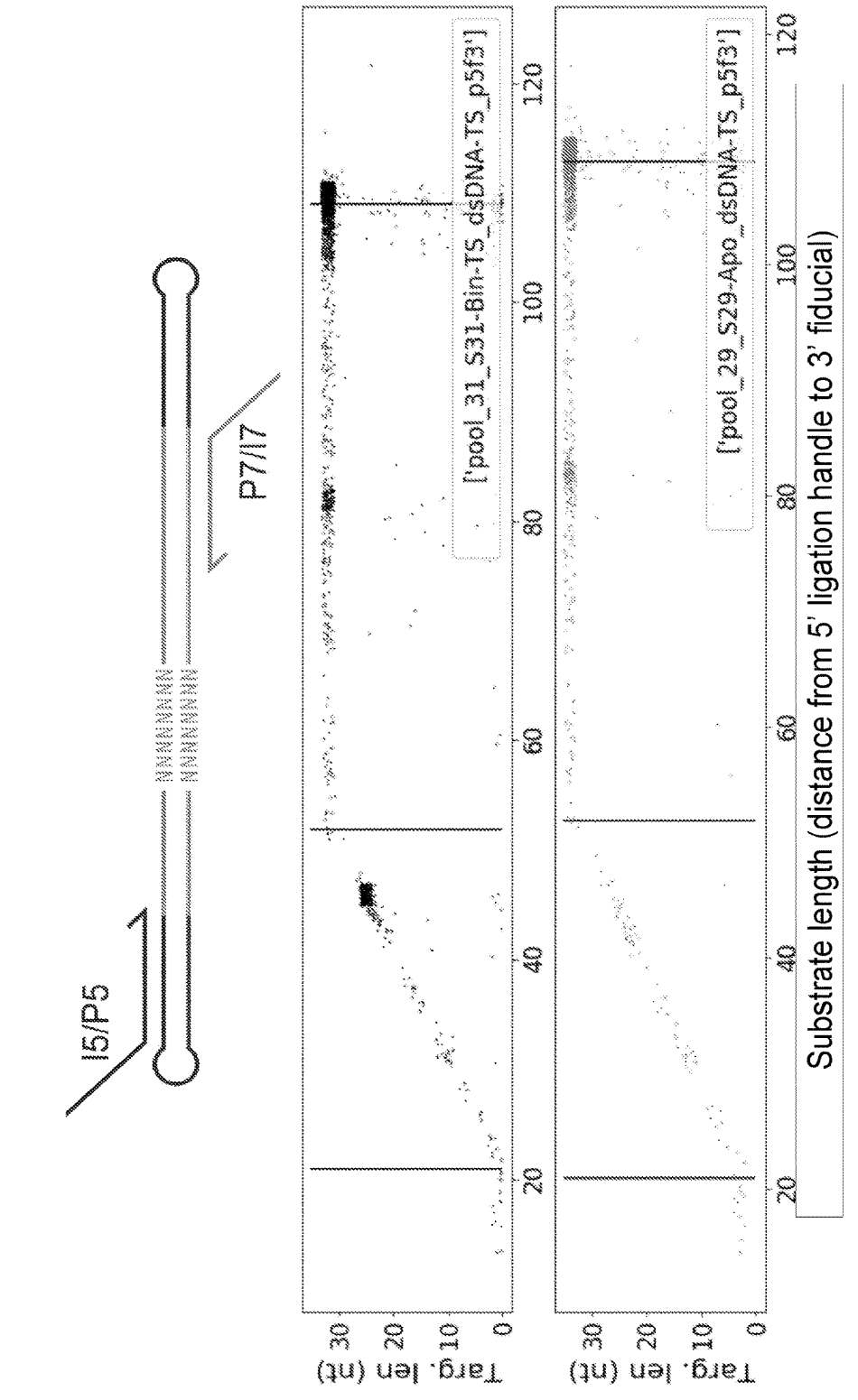
Figure 35B:
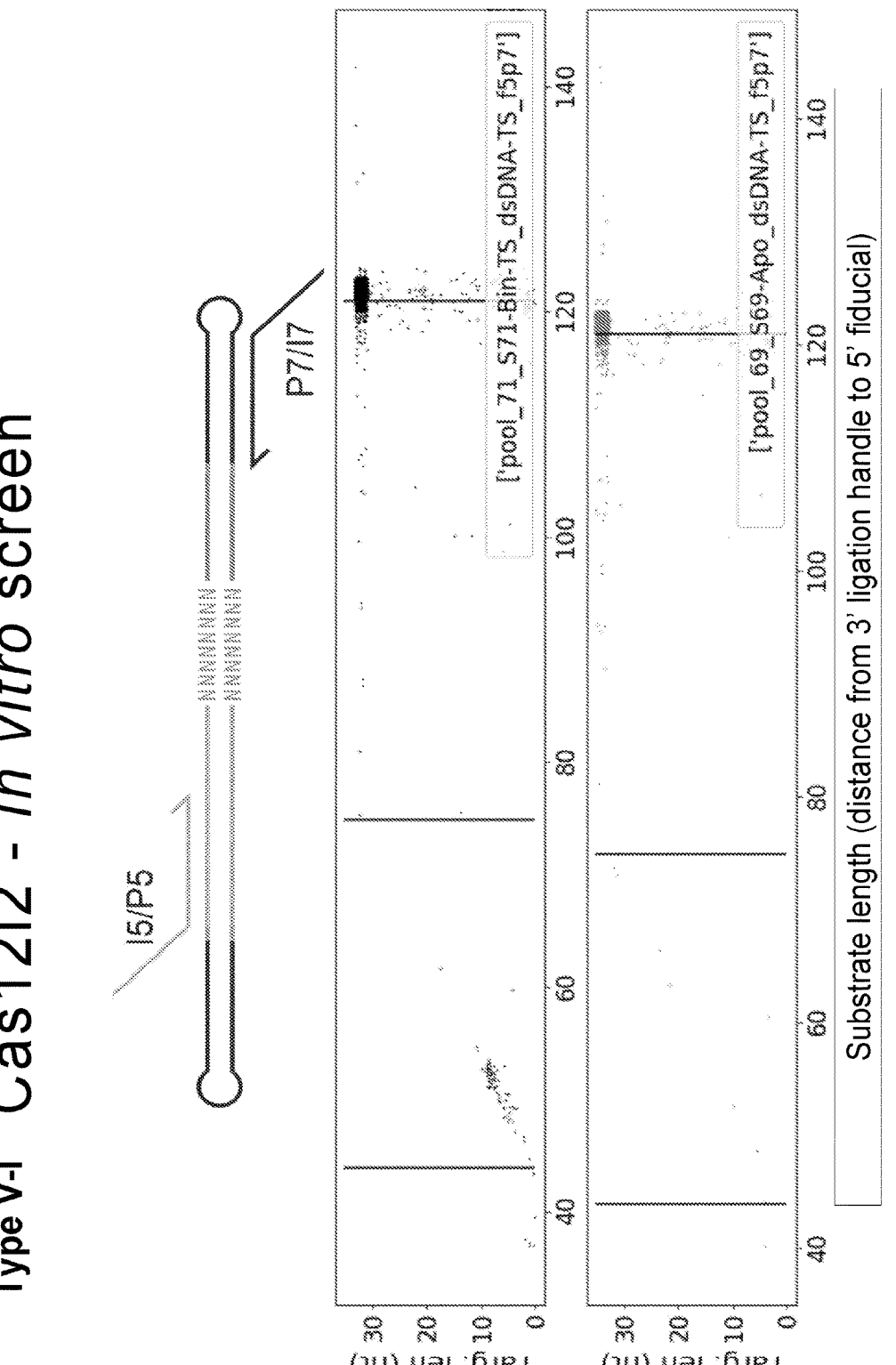

FIGS. 35A-B show the distribution of dsDNA substrate lengths (X) vs target lengths (Y) for IVTT-expressed Cas12i2 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 36:
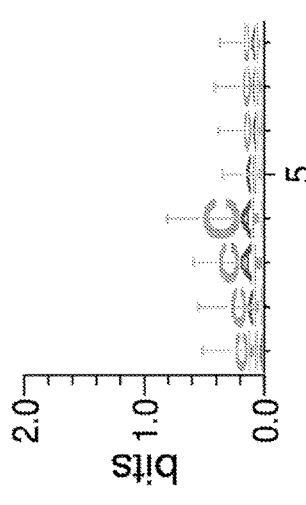
Figure 36:
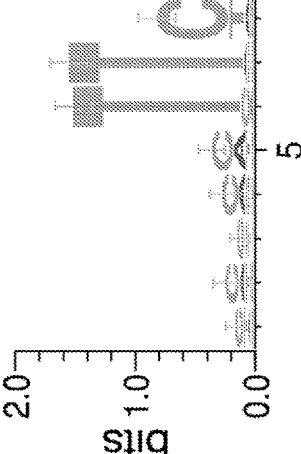
Figure 37:
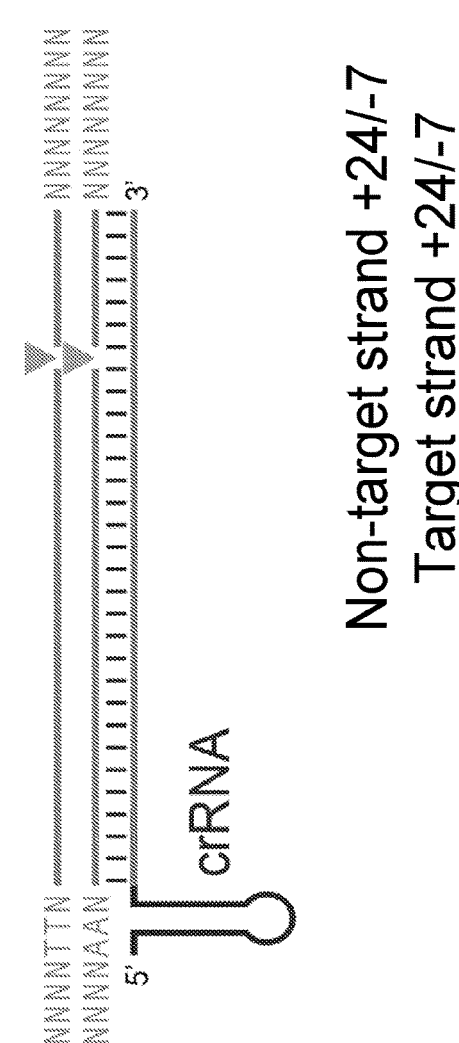

FIG. 36 shows a weblogo indicating a 5' TTN PAM motif (left of the target sequence) for Cas12i2 associated with non-target strand cleavage between the +24/+25 nucleotides relative to the PAM. No PAM sequence requirement is observed on the right side of the Cas12i2 target. FIG. 37 shows a blunt cut associated with double stranded DNA cleavage by Cas12i2 indicated by cleavage observed between the +24/+25 nucleotides of the non-target strand relative to the PAM and cleavage between the +24/+25 nucleotides of the target strand relative to the PAM.

Figure 38A:
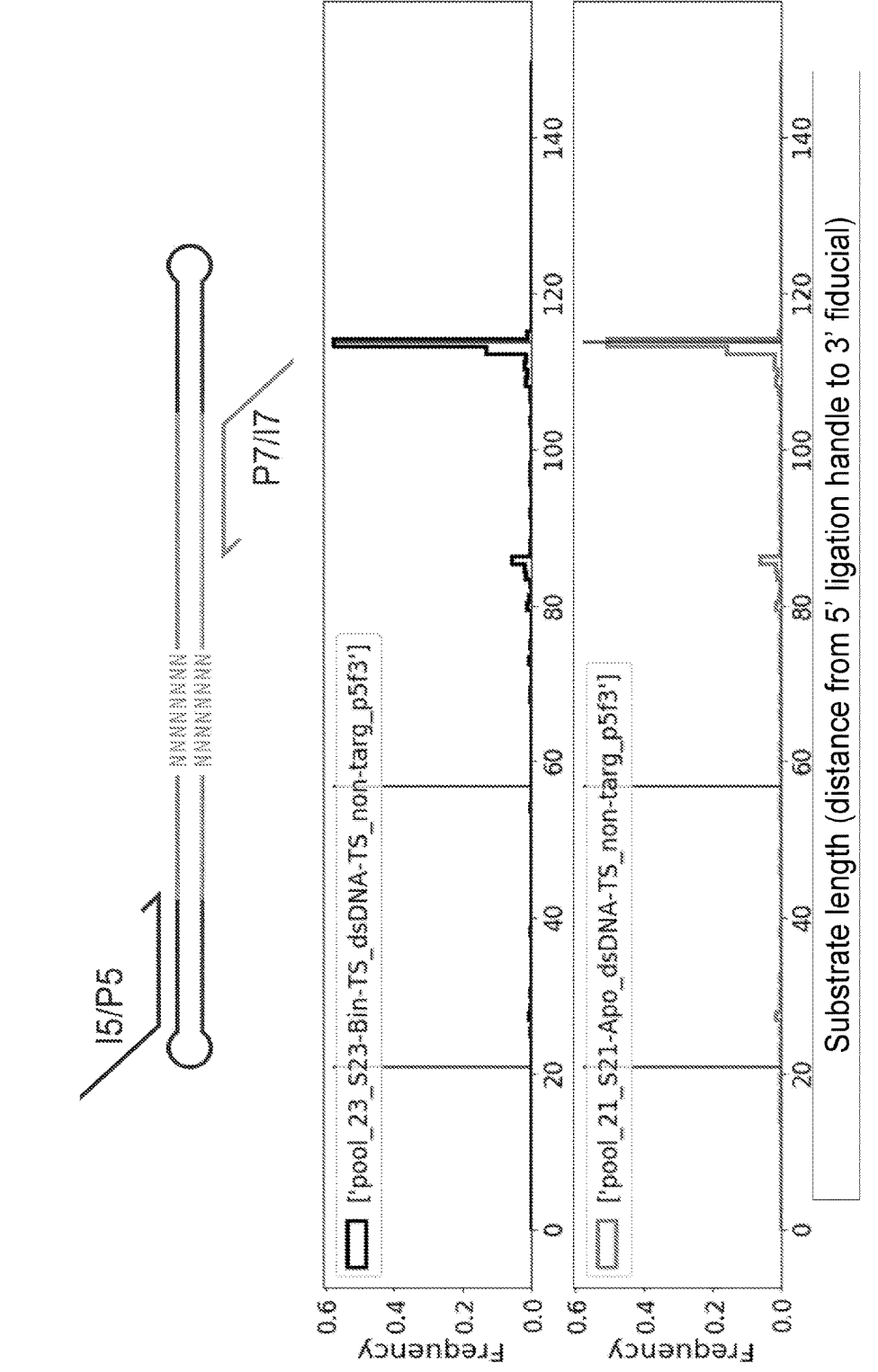
Figure 38B:
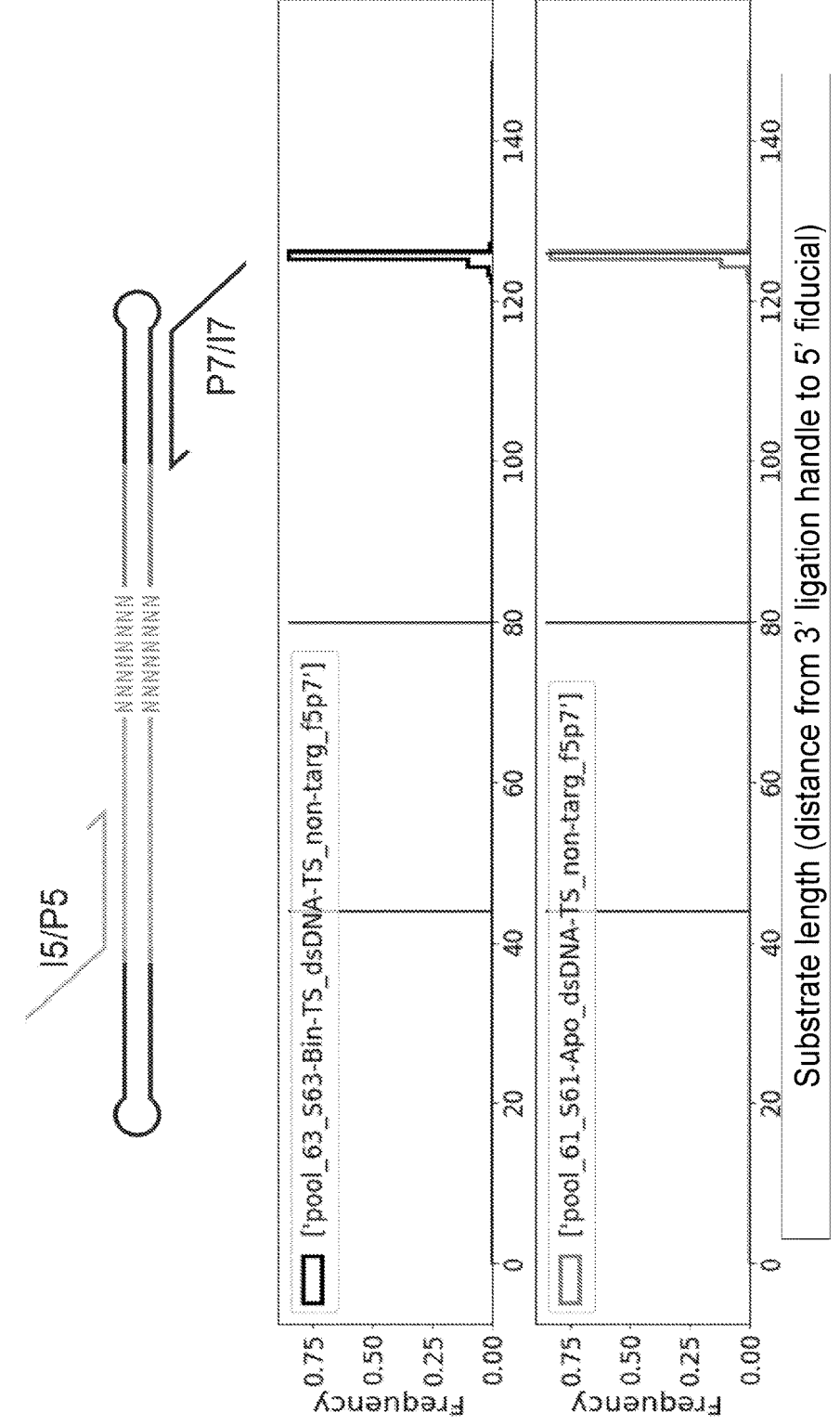

FIGS. 38A-B show the distribution of dsDNA substrate lengths for IVTT-expressed Cas12i2 in complex with a non-target crRNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences) (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 39A:
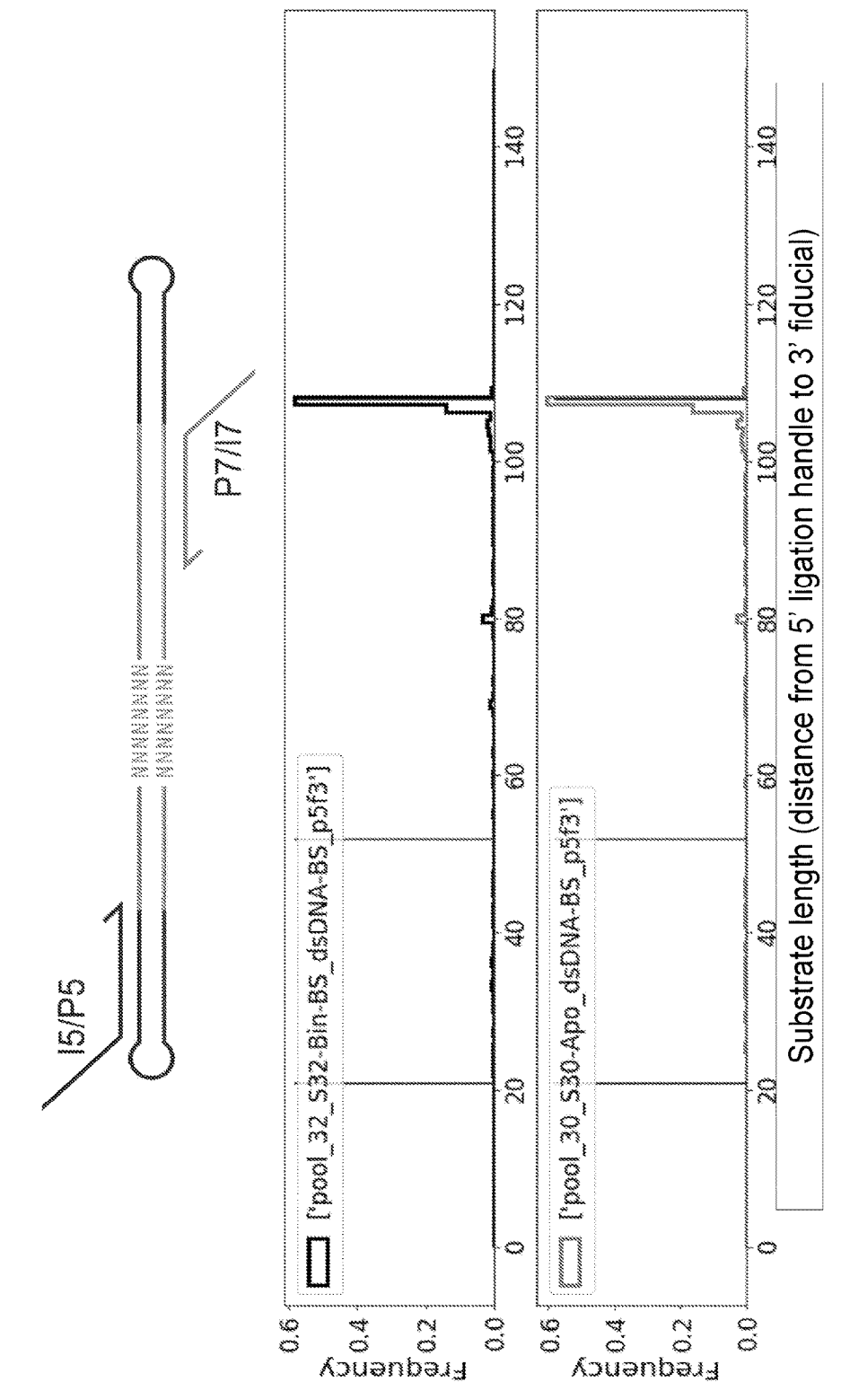
Figure 39B:
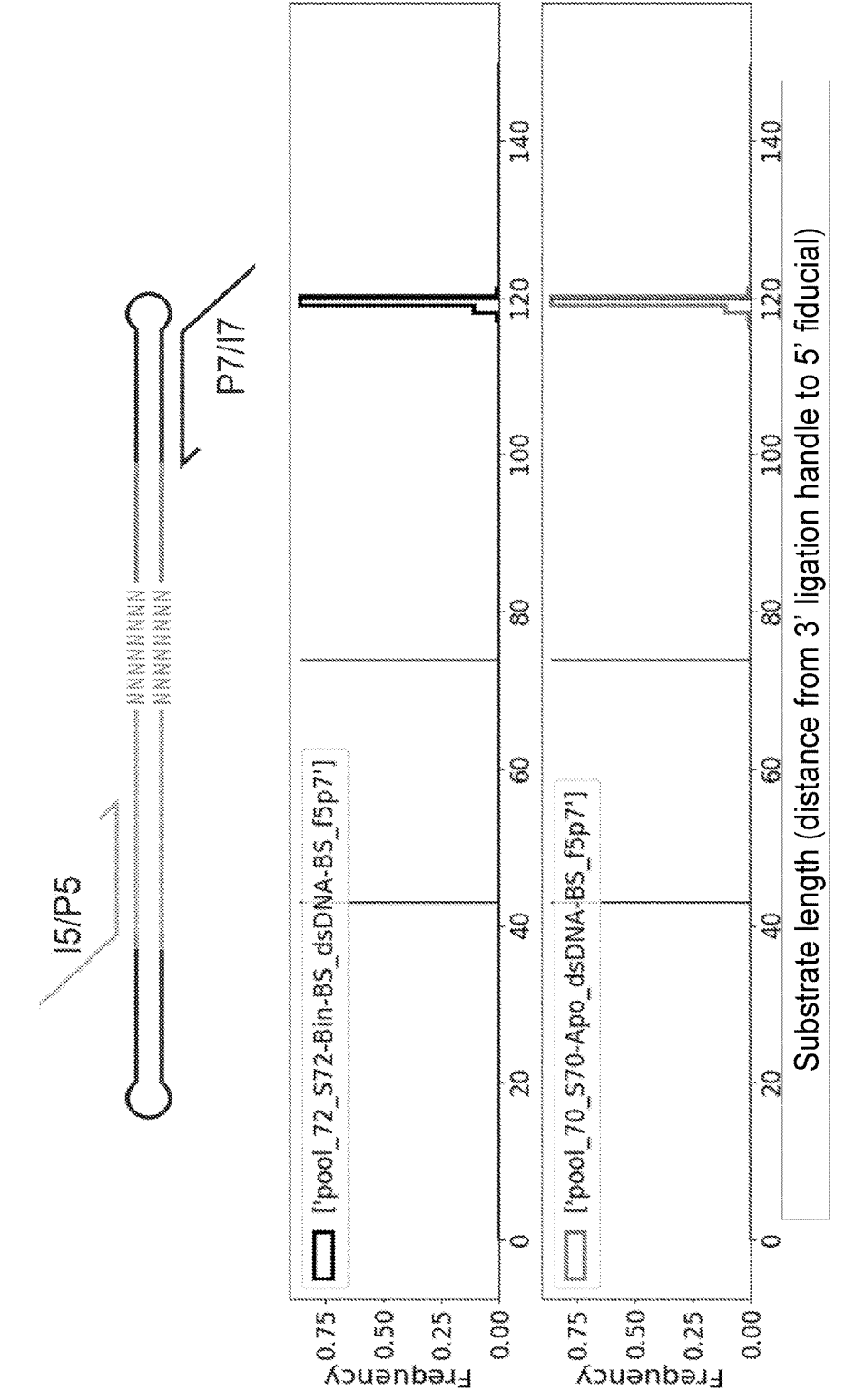

FIGS. 39A-B show the distribution of dsDNA substrate lengths for IVTT-expressed Cas12i2 in complex with a bottom-strand (inactive orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 40:
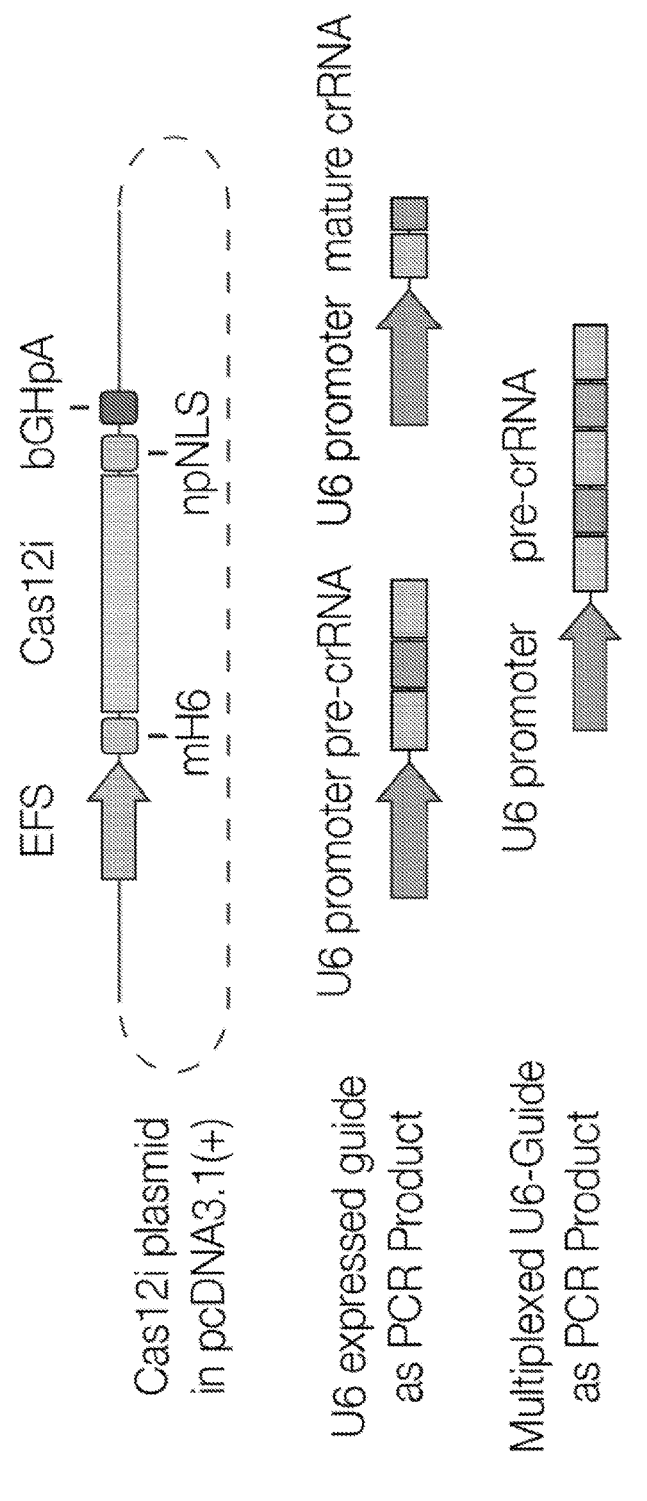

FIG. 40 is a schematic of the constructs used for mammalian validation of the Type V-I CRISPR systems as described herein. The effector is mammalian codon optimized and a nucleoplasmin nuclear localization sequence (npNLS) is appended to the C-terminus of the protein. Mammalian expression from the plasmid uses a EF1alpha-short promoter (EFS) and a poly A sequence from bGH (bGHpA). The RNA guide is expressed from a linear dsDNA fragment, driven by a RNA polymerase III promoter (U6). The schematic describes different implementations, with the RNA guide expressed as either a pre-crRNA bearing a single target, mature crRNA, or multiplexed with multiple targets in the shown configuration.

Figure 41A:
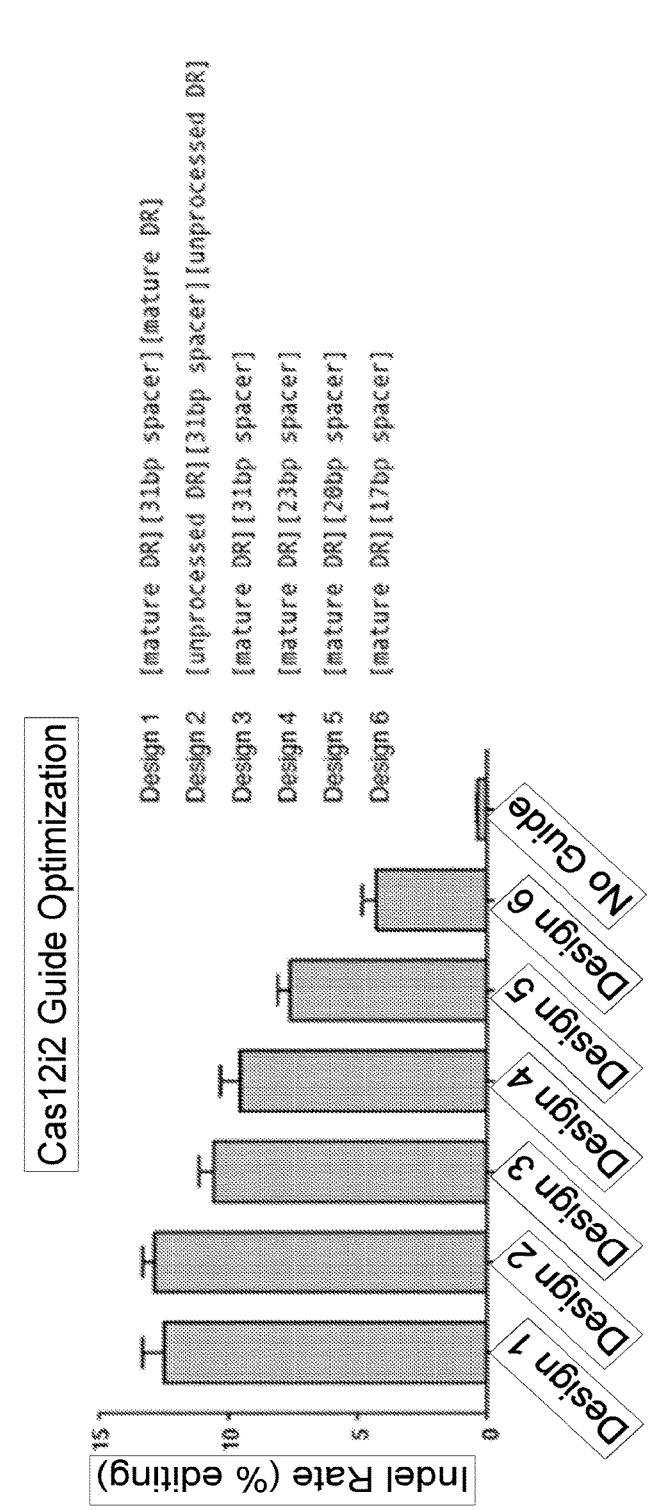

FIG. 41A is a bar graph that shows indel activity induced by the Cas12i2 CRISPR effector targeted to the VEGFA locus in the 293T cell line 72 hours post transient transfection of effector and RNA guide constructs described in FIG.

40. Different RNA guide designs were assayed and display varying degrees of efficacy. The error bars represent the S.E.M., with 3 replicates.

FIG. 41B is a representation of representative indels from next generation sequencing. Labeled are the TTC PAM sequence, and the representative indels occurring ≥20 bp downstream of the PAM.

DETAILED DESCRIPTION

The broad natural diversity of CRISPR-Cas defense systems contain a wide range of activity mechanisms and functional elements that can be harnessed for programmable biotechnologies. In a natural system, these mechanisms and parameters enable efficient defense against foreign DNA and viruses while providing self vs. non-self discrimination to avoid self-targeting. In an engineered system, the same mechanisms and parameters also provide a diverse toolbox of molecular technologies and define the boundaries of the targeting space. For instance, systems Cas9 and Cas13a have canonical DNA and RNA endonuclease activity and their targeting spaces are defined by the protospacer adjacent motif (PAM) on targeted DNA and protospacer flanking sites (PFS) on targeted RNA, respectively.

The methods described herein have been used to discover additional mechanisms and parameters within single subunit Class 2 effector systems that can expand the capabilities of RNA-programmable nucleic acid manipulation.

In one aspect, the disclosure relates to the use of computational methods and algorithms to search for and identify novel protein families that exhibit a strong co-occurrence pattern with certain other features within naturally occurring genome sequences. In certain embodiments, these computational methods are directed to identifying protein families that co-occur in close proximity to CRISPR arrays. However, the methods disclosed herein are useful in identifying proteins that naturally occur within close proximity to other features, both non-coding and protein-coding (e.g., fragments of phage sequences in non-coding areas of bacterial loci; or CRISPR Cas1 proteins). It is understood that the methods and calculations described herein may be performed on one or more computing devices.

In some embodiments, a set of genomic sequences is obtained from genomic or metagenomic databases. The databases comprise short reads, or contig level data, or assembled scaffolds, or complete genomic sequences of organisms. Likewise, the database may comprise genomic sequence data from prokaryotic organisms, or eukaryotic organisms, or may include data from metagenomic environmental samples. Examples of database repositories include the National Center for Biotechnology Information (NCBI) RefSeq, NCBI GenBank, NCBI Whole Genome Shotgun (WGS), and the Joint Genome Institute (JGI) Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify CRISPR arrays. In some embodiments, CRISPR arrays are identified by a heuristic that identifies nucleotide motifs repeated a minimum number of times (e.g. 2, 3, or 4 times), where the spacing between consecutive occurrences of a repeated motif does not exceed a specified length (e.g. 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form protein clusters. In certain other embodiments, mmseqs2 is used to form protein clusters.

To establish a pattern of strong co-occurrence between the members of a protein cluster with CRISPR arrays, a BLAST search of each member of the protein family may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the clusters of proteins within close proximity to CRISPR arrays are ranked or filtered by a metric to determine co-occurrence. One exemplary metric is the ratio of the number of elements in a protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR associated cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review, and may contain information including pairwise sequence similarity, phylogenetic tree, source organisms/environments, predicted functional domains, and a graphical depiction of locus structures. In some embodiments, the graphical depiction of locus structures may filter for nearby protein families that have a high representation. In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array, or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening

To efficiently validate the activity of the engineered novel CRISPR-Cas systems and simultaneously evaluate in an unbiased manner different activity mechanisms and functional parameters, a new pooled-screening approach is used in *E. coli*. First, from the computational identification of the conserved protein and noncoding elements of the novel CRISPR-Cas system, DNA synthesis and molecular cloning is used to assemble the separate components into a single artificial expression vector, which in one embodiment is based on a pET-28a+ backbone. In a second embodiment, the effectors and noncoding elements are transcribed on a single mRNA transcript, and different ribosomal binding sites are used to translate individual effectors.

Second, the natural crRNA and targeting spacers are replaced with a library of unprocessed crRNAs containing non-natural spacers targeting a second plasmid, pACYC184. This crRNA library is cloned into the vector backbone containing the protein effectors and noncoding elements (e.g. pET-28a+), and then subsequently transformed the library into *E. coli* along with the pACYC184 plasmid target. Consequently, each resulting *E. coli* cell contains no more than one targeting spacer. In an alternate embodiment, the library of unprocessed crRNAs containing non-natural spacers additionally target *E. coli* essential genes, drawn from resources such as those described in Baba et al. (2006) *Mol. Syst. Biol.* 2:2006.0008; and Gerdes et al. (2003). *J. Bacteriol.* 185 (19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets to add another dimension to the assay. In other embodiments, the non-coding sequences flanking the CRISPR array, putative effector or accessory open reading frames, and predicted anti-repeats indicative of tracrRNA elements were concatenated together and cloned into pACYC184 and expressed by lac and IPTG-inducible T7 promoters Third, the *E. coli* are grown under antibiotic selection. In one embodiment, triple antibiotic selection is used: kanamycin for ensuring successful transformation of the pET-28a+ vector containing the engineered CRISPR-Cas effector system, and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library. Examining the population of surviving cells at a later time point compared to an earlier time point typically provides a depleted signal compared to the inactive crRNAs. In some embodiments, double antibiotic selection is used. For example, withdrawal of either chloramphenicol or tetracycline to remove selective pressure can provide novel information about the targeting substrate, sequence specificity, and potency. In some embodiments, only kanamycin is used to ensure successful transformation of the pET-28a+ vector containing the engineered CRISPR-Cas effector system. This embodiment is suitable for libraries containing spacers targeting *E. coli* essential genes, as no additional selection beyond kanamycin is needed to observe growth alterations. In this embodiment, chloramphenicol and tetracycline dependence is removed, and their targets (if any) in the library provides an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters in a broad, hypothesis-agnostic manner. In this way, the features required for reconstituting the novel CRISPR-Cas system in a heterologous prokaryotic species can be more comprehensively tested and studied.

Certain important advantages of the in vivo pooled-screen described herein include:

(1) Versatility—plasmid design allows multiple effectors and/or noncoding elements to be expressed; library cloning strategy enables both transcriptional directions of the computationally predicted crRNA to be expressed;

(2) Comprehensive tests of activity mechanisms and functional parameters can be used to evaluate diverse interference mechanisms, including DNA or RNA cleavage; to examine co-occurrence of features such as transcription, plasmid DNA replication; and flanking sequences for a crRNA library to reliably determine PAMs with complexity equivalence of 4N's;

(3) Sensitivity—pACYC184 is a low copy plasmid, enabling high sensitivity for CRISPR-Cas activity, because even modest interference rates can eliminate the antibiotic resistance encoded by the plasmid; and (4) Efficiency—the pooled-screening includes optimized molecular biology steps that enable greater speed and throughput for RNA-sequencing and the protein expression samples can be directly harvested from the surviving cells in the screen.

As discussed in more detail in the Examples below, the novel CRISPR-Cas families described herein were evaluated using this in vivo pooled-screen to evaluate their operational elements, mechanisms and parameters, as well as their ability to be active and reprogrammed in an engineered system outside of their natural cellular environment.

In Vitro Pooled Screening

In vitro pooled screening approaches can also be used and are complementary to in vivo pooled screens. In vitro pooled screens enable rapid biochemical characterization and reduction of a CRISPR system to the essential components necessary for the system's activity. In one embodiment, a cell-free in vitro transcription and translation (IVTT) system is used to directly synthesize RNA and protein from DNA encoding the noncoding and effector proteins of the CRISPR system, thus enabling a faster and higher throughput method to evaluate a larger number of distinct separate CRISPR-Cas effector systems than conventional biochemical assays reliant on FPLC-purified proteins. In addition to enabling greater throughput and efficiency of biochemical reactions, the in vitro screening has several advantages that make it complementary to the in vivo pooled screening approach described above.

(1) Direct observation of both enrichment and depletion signals—in vitro pooled screening enables a readout of both cleavage enrichment, in which the cleavage products can be directly captured and sequenced to identify specific cut sites, cleavage patterns, and sequence motifs for active effector systems, as well as target depletion, in which the negative signal from the depletion of specific targets within the uncleaved population is used as a proxy for activity. As the in vivo pooled screen utilizes a target depletion readout, the enrichment mode offers additional insight into the effector activity.

(2) Greater control of the reaction components and environment—the well-defined components and activity of the proprietary IVTT enables precise control of the reaction components to identify the minimal components necessary for further activity translation, as compared to the complex E. coli cellular milieu for an in vivo screen. Additionally, non-natural modifications may be made to reaction components for enhanced activity or easier readout; for instance, adding phosphorothioated bonds onto the ssDNA and dsDNA substrates to reduce noise by limiting exonuclease degradation of substrates.

(3) Robustness to toxic/growth inhibiting proteins—for proteins that may be toxic to E. coli cell growth, the in vitro pooled screen enables functional screening without being subject to the growth constraints of a live cell. This ultimately enables greater versatility in protein selection and screening.

The novel CRISPR-Cas families described herein were evaluated using a combination of in vivo and in vitro pooled-screens to evaluate their operational elements, mechanisms and parameters, as well as their ability to be active and reprogrammed in an engineered system outside of their natural cellular environment.

Class 2 CRISPR-Cas Effectors Having a RuvC Domain

In one aspect, the disclosure provides Class 2 CRISPR-Cas systems referred to herein as CLUST.029130 (Type V-I) CRISPR-Cas systems. These Class 2 CRISPR-Cas systems include an isolated CRISPR-associated protein having a RuvC domain and an isolated crRNA, also referred to as an RNA guide, guide RNA, or gRNA, comprising a spacer sequence that is complementary to a target nucleic acid sequence such as a DNA sequence.

Suitably, a CRISPR-Cas effector protein having a RuvC domain may include one or motifs from the set of: the RuvC III motif, $X_1SHX_4DX_6X_7$ (SEQ ID NO: 200), wherein $X_1$ is S or T, $X_4$ is Q or L, $X_6$ is P or S, and $X_7$ is F or L; the RuvC I motif, $X_1XDXNX_6X_7XXXX_{11}$ (SEQ ID NO: 201), wherein $X_1$ is A or G or S, X is any amino acid, $X_6$ is Q or I, $X_7$ is T or S or V, and $X_{11}$ is T or A; and the RuvC II motif, $X_1X_2X_3E$ (SEQ ID NO: 210), wherein $X_1$ is C or F or I or L or M or P or V or W or Y, $X_2$ is C or F or I or L or M or P or R or V or W or Y, and $X_3$ is C or F or G or I or L or M or P or V or W or Y.

Suitably, a Type V-I CRISPR-Cas system includes a CRISPR-Cas effector having a RuvC domain and a Type V-I crRNA. Suitably, the Cas12i effector is about 1100 amino acids or less in length, and includes a functional PAM interacting domain that recognizes the PAM in the target DNA. Type V-I CRISPR-Cas effector proteins are capable of binding to a Type V-I RNA guide to form a Type V-I CRISPR-Cas system, wherein the Type V-I RNA guide includes a stem-loop structure with a 5-nucleotide stem and a loop of 6, 7, or 8 nucleotides. Type V-I CRISPR-Cas systems are capable of targeting and binding to sequence-specific DNA without the presence of a tracrRNA.

In some embodiments, the Type V-I CRISPR-Cas effector protein and the Type V-I RNA guide form a binary complex that may include other components. The binary complex is activated upon binding to a nucleic acid substrate that is complementary to a spacer sequence in the RNA guide (i.e., a sequence-specific substrate or target nucleic acid). In some embodiments, the sequence-specific substrate is a double-stranded DNA. In some embodiments, the sequence-specific substrate is a single-stranded DNA. In some embodiments, the sequence-specificity requires a complete match of the spacer sequence in the RNA guide (e.g., crRNA) to the target substrate. In other embodiments, the sequence specificity requires a partial (contiguous or non-contiguous) match of the spacer sequence in the RNA guide (e.g., crRNA) to the target substrate. Sequence specificity in certain embodiments further requires a complete match between a proto-spacer adjacent motif ("PAM") sequence proximate to the spacer sequence, and a canonical PAM sequence recognized by the CRISPR-associated protein. In some instances, a complete PAM sequence match is not required, and a partial match is sufficient for sequence-specific association of the binary complex and the DNA substrate.

In some embodiments, the target nucleic acid substrate is a double stranded DNA (dsDNA). In some embodiments, the target nucleic acid substrate is a dsDNA and includes a PAM. In some embodiments, the binary complex modifies the target sequence-specific dsDNA substrate upon binding to it. In some embodiments, the binary complex preferentially nicks the non-target strand of the target dsDNA substrate. In some embodiments, the binary complex cleaves both strands of the target dsDNA substrate it. In some embodiments, the binary complex cleaves both strands of target dsDNA substrate with a staggered cut. In some embodiments, the binary complex creates a blunt double-stranded break (DSB) on the target dsDNA substrate.

In some embodiments, the target nucleic acid substrate is a single stranded DNA (ssDNA). In some embodiments, the target nucleic acid substrate is a ssDNA and does not include a PAM. In some embodiments, the binary complex modifies the target sequence-specific ssDNA substrate upon binding to it. In some embodiments, the binary complex cleaves the target ssDNA substrate.

In some embodiments, the binary complex becomes activated upon binding to the target substrate. In some embodiments, the activated complex exhibits "multiple turnover" activity, whereby upon acting on (e.g., cleaving) the target substrate the activated complex remains in an activated state. In some embodiments, the binary complex exhibits "single turnover" activity, whereby upon acting on the target substrate the binary complex reverts to an inactive state. In some embodiments, the activated complex exhibits non-specific (i.e., "collateral") cleavage activity whereby the activated complex cleaves nucleic acids with no sequence similarity to the target. In some embodiments, the collateral nucleic acid substrate is a ssDNA.

CRISPR Enzyme Modifications

Nuclease-Deficient CRISPR Enzymes

Where the CRISPR enzymes described herein have nuclease activity, the CRISPR enzymes can be modified to have diminished nuclease activity, e.g., nuclease inactivation of at least 50%, at least 60%, at least 70%, at least 80%, at least 90%, at least 95%, at least 97%, or 100% as compared with the wild type CRISPR enzymes. The nuclease activity can be diminished by several methods, e.g., introducing mutations into the nuclease or PAM interacting domains of the CRISPR enzymes. In some embodiments, catalytic residues for the nuclease activities are identified, and these amino acid residues can be substituted by different amino acid residues (e.g., glycine or alanine) to diminish the nuclease activity. Examples of such mutations for Cas12i1 include D647A or E894A or D948A. Examples of such mutations for Cas12i2 include D599A or E833A or D886A.

The inactivated CRISPR enzymes can comprise (e.g., via fusion protein, linker peptides, Gly4Ser (GS) peptide linkers, etc.) or be associated (e.g., via co-expression of multiple proteins) with one or more functional domains. These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Krüppel associated box (KRAB), VP64, VP16, Fok1, P65, HSF1, MyoD1, and biotin-APEX.

The positioning of the one or more functional domains on the inactivated CRISPR enzymes allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR enzyme. In some embodiments, the functional domain is positioned at the C-terminus of the CRISPR enzyme. In some embodiments, the inactivated CRISPR enzyme is modified to comprise a first functional domain at the N-terminus and a second functional domain at the C-terminus.

Split Enzymes

The present disclosure also provides a split version of the CRISPR enzymes described herein. The split version of the CRISPR enzymes may be advantageous for delivery. In some embodiments, the CRISPR enzymes are split to two parts of the enzymes, which together substantially comprises a functioning CRISPR enzyme.

The split can be done in a way that the catalytic domain(s) are unaffected. The CRISPR enzymes may function as a nuclease or may be inactivated enzymes, which are essentially RNA-binding proteins with very little or no catalytic activity (e.g., due to mutation(s) in their catalytic domains).

In some embodiments, the nuclease lobe and α-helical lobe are expressed as separate polypeptides. Although the lobes do not interact on their own, the RNA guide recruits them into a complex that recapitulates the activity of full-length CRISPR enzymes and catalyzes site-specific DNA cleavage. The use of a modified RNA guide abrogates split-enzyme activity by preventing dimerization, allowing for the development of an inducible dimerization system. The split enzyme is described, e.g., in Wright, Addison V., et al. "Rational design of a split-Cas9 enzyme complex," Proc. Nat'l. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR enzyme for temporal control of CRISPR enzyme activity. The CRISPR enzymes can thus be rendered chemically inducible by being split into two fragments and rapamycin-sensitive dimerization domains can be used for controlled reassembly of the CRISPR enzymes.

The split point is typically designed in silico and cloned into the constructs. During this process, mutations can be introduced to the split enzyme and non-functional domains can be removed. In some embodiments, the two parts or fragments of the split CRISPR enzyme (i.e., the N-terminal and C-terminal fragments), can form a full CRISPR enzyme, comprising, e.g., at least 70%, at least 80%, at least 90%, at least 95%, or at least 99% of the sequence of the wild-type CRISPR enzyme.

Self-Activating or Inactivating Enzymes

The CRISPR enzymes described herein can be designed to be self-activating or self-inactivating. In some embodiments, the CRISPR enzymes are self-inactivating. For example, the target sequence can be introduced into the CRISPR enzyme coding constructs. Thus, the CRISPR enzymes can cleave the target sequence, as well as the construct encoding the enzyme thereby self-inactivating their expression. Methods of constructing a self-inactivating CRISPR system is described, e.g., in Epstein, Benjamin E., and David V. Schaffer. "Engineering a Self-Inactivating CRISPR System for AAV Vectors," Mol. Ther., 24 (2016): S50, which is incorporated herein by reference in its entirety.

In some other embodiments, an additional RNA guide, expressed under the control of a weak promoter (e.g., 7SK promoter), can target the nucleic acid sequence encoding the CRISPR enzyme to prevent and/or block its expression (e.g., by preventing the transcription and/or translation of the nucleic acid). The transfection of cells with vectors expressing the CRISPR enzyme, RNA guides, and RNA guides that target the nucleic acid encoding the CRISPR enzyme can lead to efficient disruption of the nucleic acid encoding the CRISPR enzyme and decrease the levels of CRISPR enzyme, thereby limiting the genome editing activity.

In some embodiments, the genome editing activity of the CRISPR enzymes can be modulated through endogenous RNA signatures (e.g., miRNA) in mammalian cells. The CRISPR enzyme switch can be made by using a miRNA-complementary sequence in the 5'-UTR of mRNA encoding the CRISPR enzyme. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa, Moe et al. "Cell-type-specific genome editing with a microRNA-responsive CRISPR-Cas9 switch," Nucl. Acids Res., 2017 Jul. 27; 45 (13): e118).

Inducible CRISPR Enzymes

The CRISPR enzymes can be inducible, e.g., light inducible or chemically inducible. This mechanism allows for activation of the functional domain in the CRISPR enzymes with a known trigger. Light inducibility can be achieved by various methods known in the art, e.g., by designing a fusion complex wherein CRY2 PHR/CIBN pairing is used in split CRISPR Enzymes (see, e.g., Konermann et al. "Optical control of mammalian endogenous transcription and epigenetic states," Nature, 500.7463 (2013): 472). Chemical inducibility can be achieved, e.g., by designing a fusion complex wherein FKBP/FRB (FK506 binding protein/FKBP rapamycin binding domain) pairing is used in split CRISPR Enzymes. Rapamycin is required for forming the fusion complex, thereby activating the CRISPR enzymes (see, e.g., Zetsche, Volz, and Zhang, "A split-Cas9 architecture for inducible genome editing and transcription modulation," *Nature Biotech.*, 33.2 (2015): 139-142).

Furthermore, expression of the CRISPR enzymes can be modulated by inducible promoters, e.g., tetracycline or doxycycline controlled transcriptional activation (Tet-On and Tet-Off expression systems), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless, Stephen J. et al. "Direct and specific chemical control of eukaryotic translation with a synthetic RNA-protein interaction," *Nucl. Acids Res.*, 40.9 (2012): e64-e64).

Various embodiments of inducible CRISPR enzymes and inducible CRISPR systems are described, e.g., in U.S. Pat. No. 8,871,445, US20160208243, and WO2016205764, each of which is incorporated herein by reference in its entirety.

Functional Mutations

Various mutations or modifications can be introduced into CRISPR enzymes as described herein to improve specificity and/or robustness. In some embodiments, the amino acid residues that recognize the Protospacer Adjacent Motif (PAM) are identified. The CRISPR enzymes described herein can be modified further to recognize different PAMs, e.g., by substituting the amino acid residues that recognize PAM with other amino acid residues. In some embodiments, the CRISPR enzymes can recognize alternative PAMs, e.g., as described herein.

In some embodiments, the CRISPR-associated proteins include at least one (e.g., 1, 2, 3, 4, 5, 6, 7, 8, 9, or 10) Nuclear Localization Signal (NLS) attached to the N-terminal or C-terminal of the protein. Non-limiting examples of NLSs include an NLS sequence derived from: the NLS of the SV40 virus large T-antigen, having the amino acid sequence PKKKRKV (SEQ ID NO: 300); the NLS from nucleoplasmin (e.g., the nucleoplasmin bipartite NLS with the sequence KRPAATKKAGQAKKKK (SEQ ID NO: 301)); the c-myc NLS having the amino acid sequence PAAKRVKLD (SEQ ID NO: 302) or RQRRNELKRSP (SEQ ID NO: 303); the hRNPA1 M9 NLS having the sequence NQSSNFGPMKGGNFG-GRSSGPYGGGGQYFAKPRNQGGY (SEQ ID NO: 304); the sequence RMRIZFKNKGKDTAELRRRRVEVS-VELRKAKKDEQILKRRNV (SEQ ID NO: 305) of the IBB domain from importin-alpha; the sequences VSRKRPRP (SEQ ID NO: 306) and PPKKARED (SEQ ID NO: 307) of the myoma T protein; the sequence PQPKKKPL (SEQ ID NO: 308) of human p53; the sequence SALIKKKKKMAP (SEQ ID NO: 309) of mouse c-abl IV; the sequences DRLRR (SEQ ID NO: 310) and PKQKKRK (SEQ ID NO: 311) of the influenza virus NS1; the sequence RKLKK-KIKKL (SEQ ID NO: 312) of the Hepatitis virus delta antigen; the sequence REKKKFLKRR (SEQ ID NO: 313) of the mouse Mx1 protein; the sequence KRKGDEVDGVDEVAKKKSKK (SEQ ID NO: 314) of the human poly(ADP-ribose) polymerase; and the sequence RKCLQAGMNLEARKTKK (SEQ ID NO: 315) of the human glucocorticoid receptor. In some embodiments, the CRISPR-associated protein includes at least one (e.g., 1, 2, 3, 4, 5, 6, 7, 8, 9, or 10) Nuclear Export Signal (NES) attached the N-terminal or C-terminal of the protein. In a preferred embodiment, a C-terminal and/or N-terminal NLS or NES is attached for optimal expression and nuclear targeting in eukaryotic cells, e.g., human cells.

In some embodiments, the CRISPR enzymes described herein are mutated at one or more amino acid residues to alter one or more functional activities. For example, in some embodiments, the CRISPR enzyme is mutated at one or more amino acid residues to alter its helicase activity. In some embodiments, the CRISPR enzyme is mutated at one or more amino acid residues to alter its nuclease activity (e.g., endonuclease activity or exonuclease activity). In some embodiments, the CRISPR enzyme is mutated at one or more amino acid residues to alter its ability to functionally associate with a RNA guide. In some embodiments, the CRISPR enzyme is mutated at one or more amino acid residues to alter its ability to functionally associate with a target nucleic acid.

In some embodiments, the CRISPR enzymes described herein are capable of cleaving a target nucleic acid molecule. In some embodiments, the CRISPR enzyme cleaves both strands of the target nucleic acid molecule. However, in some embodiments, the CRISPR enzyme is mutated at one or more amino acid residues to alter its cleaving activity. For example, in some embodiments, the CRISPR enzyme may comprise one or more mutations which render the enzyme incapable of cleaving a target nucleic acid. In other embodiments, the CRISPR enzyme may comprise one or more mutations such that the enzyme is capable of cleaving a single strand of the target nucleic acid (i.e., nickase activity). In some embodiments, the CRISPR enzyme is capable of cleaving the strand of the target nucleic acid that is complementary to the strand that the RNA guide hybridizes to. In some embodiments, the CRISPR enzyme is capable of cleaving the strand of the target nucleic acid that the RNA guide hybridizes to.

In some embodiments, a CRISPR enzyme described herein may be engineered to comprise a deletion in one or more amino acid residues to reduce the size of the enzyme while retaining one or more desired functional activities (e.g., nuclease activity and the ability to interact functionally with a RNA guide). The truncated CRISPR enzyme may be advantageously used in combination with delivery systems having load limitations.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blosum 62 scoring matrix with a gap penalty of 12, a gap extend penalty of 4, and a frameshift gap penalty of 5.

Beyond the biochemical and diagnostic applications described herein, programmable Type V-I CRISPR-Cas systems described herein have important applications in eukaryotic cells such as therapeutic modification of the genome, with examples of modifications including, but not limited to; genotype correction, gene knockout, genetic sequence insertion/deletion (by homology directed repair or otherwise), single nucleotide modification, or gene regulation. These gene modification modalities can use the nuclease activity of Cas12i, double nicking, or programmable DNA binding of catalytically inactive Cas12i fused to additional effector domains.

In some embodiments, the CRISPR-associated proteins and accessory proteins described herein can be fused to one or more peptide tags, including a His-tag, GST-tag, FLAG-tag, or myc-tag. In some embodiments, the CRISPR-associated proteins or accessory proteins described herein can be fused to a detectable moiety such as a fluorescent protein (e.g., green fluorescent protein or yellow fluorescent protein). And in some embodiments, CRISPR-associated proteins or accessory proteins of this disclosure are fused to a peptide or non-peptide moiety that allows these proteins to enter or localize to a tissue, a cell, or a region of a cell. For instance, a CRISPR-associated protein or accessory protein of this disclosure (such as Cas12i) may comprise a nuclear localization sequence (NLS) such as an SV40 (simian virus 40) NLS, c-Myc NLS, or other suitable monopartite NLS. The NLS may be fused to an N-terminal and/or a C-terminal of the CRISPR-associated protein or accessory protein, and may be fused singly (i.e., a single NLS) or concatenated (e.g., a chain of 2, 3, 4, etc. NLS).

In those embodiments where a tag is fused to a CRISPR-associated protein, such tag may facilitate affinity-based or charge-based purification of the CRISPR-associated protein, e.g., by liquid chromatography or bead separation utilizing an immobilized affinity or ion-exchange reagent. As a non-limiting example, a recombinant CRISPR-associated protein of this disclosure (such as Cas12i) comprises a polyhistidine (His) tag, and for purification is loaded onto a chromatography column comprising an immobilized metal ion (e.g. a $Zn^{2+}$, $Ni^{2+}$, $Cu^{2+}$ ion chelated by a chelating ligand immobilized on the resin, which resin may be an individually prepared resin or a commercially available resin or ready to use column such as the HisTrap FF column commercialized by GE Healthcare Life Sciences, Marlborough, Massachusetts). Following the loading step, the column is optionally rinsed, e.g., using one or more suitable buffer solutions, and the His-tagged protein is then eluted using a suitable elution buffer. Alternatively or additionally, if the recombinant CRISPR-associated protein of this disclosure utilizes a FLAG-tag, such protein may be purified using immunoprecipitation methods known in the industry. Other suitable purification methods for tagged CRISPR-associated proteins or accessory proteins of this disclosure will be evident to those of skill in the art.

The proteins described herein (e.g., CRISPR-associated proteins or accessory proteins) can be delivered or used as either nucleic acid molecules or polypeptides. When nucleic acid molecules are used, the nucleic acid molecule encoding the CRISPR-associated proteins can be codon-optimized, as discussed in further detail below. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available at www.kazusa.orjp/codon/and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

In some instances, nucleic acids of this disclosure which encode CRISPR-associated proteins or accessory proteins for expression in eukaryotic (e.g., human, or other mammalian cells) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively or additionally, nucleic acids of this disclosure encoding CRISPR-associated proteins or accessory proteins may include, at a 3' end of a DNA coding sequence, a transcription stop signal such as a polyadenylation (polyA) signal. In some instances, the poly A signal is located in close proximity to, or adjacent to, an intron such as the SV40 intron.

RNA Guides

In some embodiments, the CRISPR systems described herein include at least one Type V-I RNA guide. The architecture of many RNA guides is known in the art (see, e.g., International Publication Nos. WO 2014/093622 and WO 2015/070083, the entire contents of each of which are incorporated herein by reference). In some embodiments, the CRISPR systems described herein include multiple RNA guides (e.g., two, three, four, five, six, seven, eight, or more RNA guides).

In some embodiments, the CRISPR systems described herein include at least one Type V-I RNA guide or a nucleic acid encoding at least one Type V-I RNA guide. In some embodiments, the RNA guide includes a crRNA. Generally, the crRNAs described herein include a direct repeat sequence and a spacer sequence. In certain embodiments, the crRNA includes, consists essentially of, or consists of a direct repeat sequence linked to a guide sequence or spacer sequence. In some embodiments, the crRNA includes a direct repeat sequence, a spacer sequence, and a direct repeat sequence (DR-spacer-DR), which is typical of precursor crRNA (pre-crRNA) configurations in other CRISPR systems. In some embodiments, the crRNA includes a truncated direct repeat sequence and a spacer sequence, which is typical of processed or mature crRNA. In some embodiments, the CRISPR-Cas effector protein forms a complex with the RNA guide, and the spacer sequence directs the complex to a sequence-specific binding with the target nucleic acid that is complementary to the spacer sequence.

Suitably, CRISPR systems described herein comprise at least one Type V-I RNA guide or nucleic acids encoding a Type V-I RNA guide, wherein the RNA guide comprises a direct repeat. Suitably, the Type V-I RNA guide may form a secondary structure such as a stem loop structure, e.g., as described herein.

Figure 3:
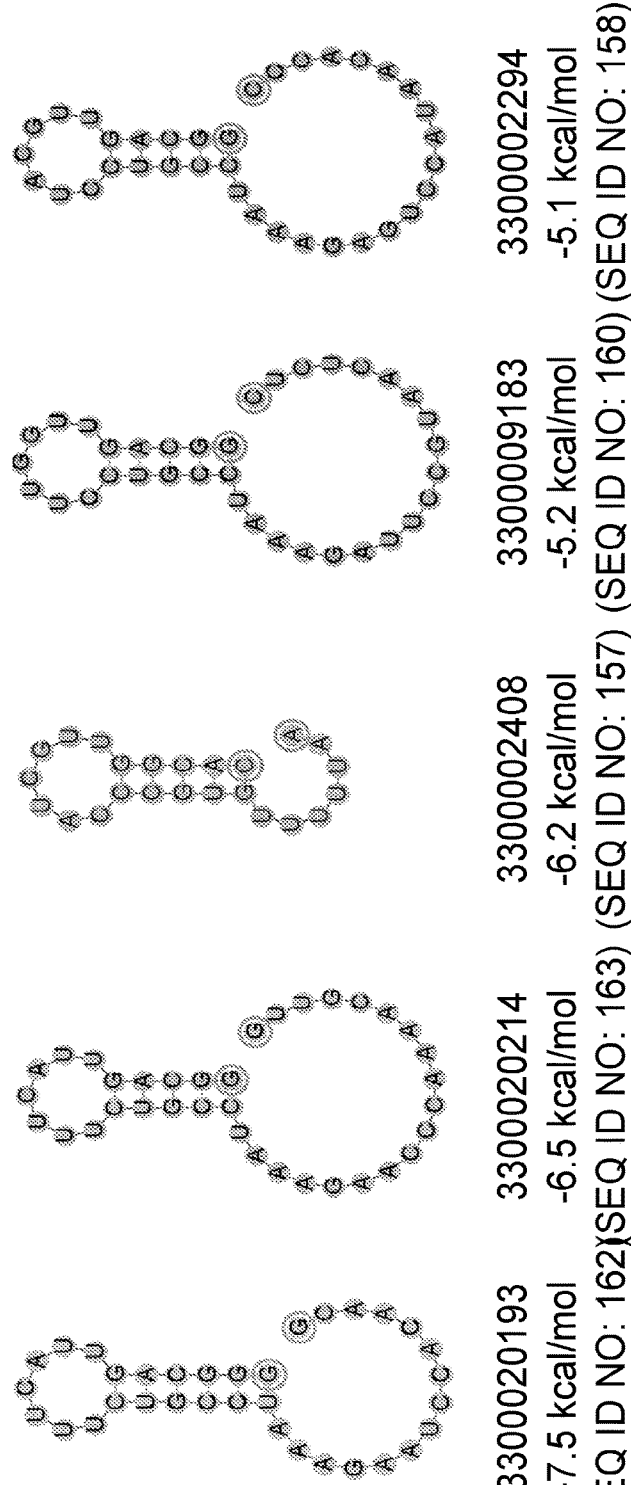
FIG. 3 is a group of schematic diagrams that show predicted secondary structure of the RNA transcript of examples of Type V-I direct repeat sequences.

The direct repeat can include two stretches of nucleotides that may be complementary to one another, separated by intervening nucleotides such that the direct repeat can hybridize to form the double stranded RNA duplex (dsRNA duplex) resulting in a stem-loop structure where the two complementary stretches of nucleotides form a stem and the intervening nucleotides form a loop or hair-pin (FIG. 3). For example, the intervening nucleotides that form the "loop" have a length of from about 6 nucleotides to about 8 nucleotides, or about 7 nucleotides. In different embodiments, the stem can include at least 2, at least 3, at least 4, or 5 base pairs.

Suitably, the direct repeat can include two complementary stretches of nucleotides that are about 5 nucleotides in length separated by about seven intervening nucleotides.

Some exemplary direct repeats of Type V-I systems are illustrated in FIG. 3, suitably when departing from naturally occurring Type V-I direct repeats, the skilled person may mimic the structure of such direct repeats illustrated in FIG. 3.

The direct repeat can include or consist of about 22 to 40 nucleotides, or about 23 to 38 nucleotides or about 23 to 36 nucleotides.

In some embodiments, the CRISPR systems described herein include a plurality of RNA guides (e.g., 2, 3, 4, 5, 10, 15, or more) or a plurality of nucleic acids encoding a plurality of RNA guides.

In some embodiments, the CRISPR system described herein includes an RNA guide or a nucleic acid encoding the RNA guide. In some embodiments, the RNA guide comprises or consists of a direct repeat sequence and a spacer sequence capable of hybridizing (e.g., hybridizes under appropriate conditions) to a target nucleic acid, wherein the direct repeat sequence comprises 5'-CCGU-CNNNNNNNGACGG-3' (SEQ ID NO: 202) proximal to its 3' end and adjacent to the spacer sequence. In some embodiments, the RNA guide comprises or consists of a direct repeat sequence and a spacer sequence capable of hybridizing (e.g., hybridizes under appropriate conditions) to a target nucleic acid, wherein the direct repeat sequence comprises 5'-GUGCCNNNNNNNGGCAC-3' (SEQ ID NO: 203) proximal to its 3' end and adjacent to the spacer sequence. In some embodiments, the RNA guide comprises or consists of a direct repeat sequence and a spacer sequence capable of hybridizing (e.g., hybridizes under appropriate conditions) to a target nucleic acid, wherein the direct repeat sequence comprises 5'-GUGUCN$_{5-6}$UGACAX$_1$-3' (SEQ ID NO: 204) proximal to the 3' end and adjacent to the spacer sequence, wherein N$_{5-6}$ refers to a contiguous sequence of any 5 or 6 nucleobases, and X$_1$ refers to C or T or U.

Examples of RNA guide direct repeat sequences and effector protein pairs are provided in Table 5A. In some embodiments, the direct repeat sequence comprises or consists of a nucleic acid sequence listed in Table 5A (e.g., SEQ ID NOs: 6-10, 19-24). In some embodiments, the direct repeat sequence comprises or consists of a nucleic acid having a nucleic acid sequence listed in Table 5A with a truncation of the initial three 5' nucleotides. In some embodiments, the direct repeat sequence comprises or consists of a nucleic acid having a nucleic acid sequence listed in Table 5A with a truncation of the initial four 5' nucleotides. In some embodiments, the direct repeat sequence comprises or consists of a nucleic acid having a nucleic acid sequence listed in Table 5A with a truncation of the initial five 5' nucleotides. In some embodiments, the direct repeat sequence comprises or consists of a nucleic acid having a nucleic acid sequence listed in Table 5A with a truncation of the initial six 5' nucleotides. In some embodiments, the direct repeat sequence comprises or consists of a nucleic acid having a nucleic acid sequence listed in Table 5A with a truncation of the initial seven 5' nucleotides. In some embodiments, the direct repeat sequence comprises or consists of a nucleic acid having a nucleic acid sequence listed in Table 5A with a truncation of the initial eight 5' nucleotides.

Multiplexing RNA Guides

CLUST.029130 (Type V-I) CRISPR-Cas effectors have been demonstrated to employ more than one RNA guide, thus enabling the ability of these effectors, and systems and complexes that include them, to target multiple different nucleic acid targets. In some embodiments, the CRISPR systems described herein include multiple RNA guides (e.g., two, three, four, five, six, seven, eight, nine, ten, fifteen, twenty, thirty, forty, or more RNA guides). In some embodiments, the CRISPR systems described herein include a single RNA strand or a nucleic acid encoding a single RNA strand, wherein the RNA guides are arranged in tandem. The single RNA strand can include multiple copies of the same RNA guide, multiple copies of distinct RNA guides, or combinations thereof.

In some embodiments, the CLUST.029130 (Type V-I) CRISPR-Cas effector proteins are delivered complexed with multiple RNA guides directed to different target nucleic acids. In some embodiments, the CLUST.029130 (Type V-I) CRISPR-Cas effector proteins can be co-delivered with multiple RNA guides, each specific for a different target nucleic acid. Methods of multiplexing using CRISPR-associated proteins are described, for example, in U.S. Pat. No. 9,790,490, and EP 3009511, the entire contents of each of which are expressly incorporated herein by reference.

RNA Guide Modifications

Spacer Lengths

The spacer length of RNA guides can range from about 15 to 50 nucleotides. In some embodiments, the spacer length of an RNA guide is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 15 to 23 nucleotides, from 16 to 22 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer. In some embodiments, the spacer length of an RNA guide is 31 nucleotides. In some embodiments, the direct repeat length of the RNA guide is at least 21 nucleotides, or is from 21 to 37 nucleotides (e.g., 23, 24, 25, 30, 35, or 36 nucleotides). In some embodiments, the direct repeat length of the RNA guide is 23 nucleotides.

The RNA guide sequences can be modified in a manner that allows for formation of the CRISPR effector complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50%, shorter than respective RNA guides that have nuclease activity. Dead guide sequences of RNA guides can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR enzyme as described herein, and a RNA guide (gRNA) wherein the gRNA comprises a dead guide sequence whereby the gRNA is capable of hybridizing to a target sequence such that the CRISPR system is directed to a genomic locus of interest in a cell without detectable cleavage activity.

A detailed description of dead guides is described, e.g., in WO 2016094872, which is incorporated herein by reference in its entirety.

Inducible Guides

RNA guides can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of RNA guide can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in their entirety.

Chemical Modifications

Chemical modifications can be applied to the RNA guide's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.*, 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2 '-modified oligonucleotide duplexes with improved in vitro potency and stability compared to unmodified small interfering RNA," *J. Med. Chem.*, 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.*, 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized RNA guide molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the RNA guide includes one or more phosphorothioate modifications. In some embodiments, the RNA guide includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965 B2; each which is incorporated by reference in its entirety.

Sequence Modifications

The sequences and the lengths of the RNA guides and crRNAs described herein can be optimized. In some embodiments, the optimized length of RNA guide can be determined by identifying the processed form of the crRNA, or by empirical length studies for RNA guides, of crRNAs.

The RNA guides can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the RNA guide has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.*, 2016 Nov. 16; 44 (20): 9555-9564; and WO 2016205764, which are incorporated herein by reference in their entirety.

Guide: Target Sequence Matching Requirements

In classic CRISPR systems, the degree of complementarity between a guide sequence and its corresponding target sequence can be about 50%, 60%, 75%, 80%, 85%, 90%, 95%, 97.5%, 99%, or 100%. In some embodiments, the degree of complementarity is 100%. The RNA guides can be about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required provided that there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Optimization of CRISPR Systems for Use in Select Organisms

Codon-Optimization

The invention contemplates all possible variations of nucleic acids, such as cDNA, that could be made by selecting combinations based on possible codon choices. These combinations are made in accordance with the standard triplet genetic code as applied to the polynucleotide encoding naturally occurring variant, and all such variations are to be considered as being specifically disclosed. Nucleotide sequences encoding type V-I CRISPR-Cas-associated effector protein variants that have been codon-optimized for expression in bacteria (e.g., *E. coli*) and in human cells are disclosed herein. For example, the codon-optimized sequences for human cells can be generated by substituting codons in the nucleotide sequence that occur at lower frequency in human cells for codons that occur at higher frequency in human cells. The frequency of occurrence for codons can be computationally determined by methods known in the art. An example of a calculation of these codon frequencies for various host cells (e.g., *E. coli*, yeast, insect, *C. elegans, D. melanogaster*, human, mouse, rat, pig, *P. pastoris, A. thalian*, maize, and tobacco) have been published or made available by sources such as the GEN-SCRIPT® Codon Usage Frequence Table Tool (example codon usage tables for *E. coli* and Humans are included below.

TABLE 1

| | | | *E. coli* Codon Usage Table | | | | |
|---|---|---|---|---|---|---|---|
| Triplet | Amino acid | Fraction | Number | Triplet | Amino acid | Fraction | Number |
| TTT | F | 0.58 | 80995 | TCT | S | 0.17 | 38027 |
| TTC | F | 0.42 | 58774 | TCC | S | 0.15 | 33430 |
| TTA | L | 0.14 | 52382 | TCA | S | 0.14 | 32715 |
| TTG | L | 0.13 | 47500 | TCG | S | 0.14 | 31146 |
| TAT | Y | 0.59 | 63937 | TGT | C | 0.46 | 19138 |
| TAC | Y | 0.41 | 44631 | TGC | C | 0.54 | 22188 |
| TAA | * | 0.61 | 7356 | TGA | * | 0.3 | 3623 |
| TAG | * | 0.09 | 989 | TGG | W | 1 | 50991 |
| CTT | L | 0.12 | 43449 | CCT | P | 0.18 | 27340 |
| CTC | L | 0.1 | 37347 | CCC | P | 0.13 | 19666 |
| CTA | L | 0.04 | 15409 | CCA | P | 0.2 | 31534 |
| CTG | L | 0.47 | 177210 | CCG | P | 0.49 | 76644 |
| CAT | H | 0.57 | 45879 | CGT | R | 0.36 | 73197 |
| CAC | H | 0.43 | 34078 | CGC | R | 0.36 | 72212 |
| CAA | Q | 0.34 | 53394 | CGA | R | 0.07 | 13844 |
| CAG | Q | 0.66 | 104171 | CGG | R | 0.11 | 21552 |
| ATT | I | 0.49 | 109072 | ACT | T | 0.19 | 37842 |
| ATC | I | 0.39 | 86796 | ACC | T | 0.4 | 80547 |
| ATA | I | 0.11 | 24984 | ACA | T | 0.17 | 33910 |
| ATG | M | 1 | 96695 | ACG | T | 0.25 | 50269 |
| AAT | N | 0.49 | 75436 | AGT | S | 0.16 | 36097 |
| AAC | N | 0.51 | 78443 | AGC | S | 0.25 | 55551 |
| AAA | K | 0.74 | 129137 | AGA | R | 0.07 | 13152 |
| AAG | K | 0.26 | 45459 | AGG | R | 0.04 | 7607 |
| GTT | V | 0.28 | 72584 | GCT | A | 0.18 | 62479 |
| GTC | V | 0.2 | 52439 | GCC | A | 0.26 | 88721 |
| GTA | V | 0.17 | 42420 | GCA | A | 0.23 | 77547 |
| GTG | V | 0.35 | 89265 | GCG | A | 0.33 | 110308 |
| GAT | D | 0.63 | 119939 | GGT | G | 0.35 | 93325 |
| GAC | D | 0.37 | 70394 | GGC | G | 0.37 | 99390 |
| GAA | E | 0.68 | 143353 | GGA | G | 0.13 | 34799 |
| GAG | E | 0.32 | 68609 | GGG | G | 0.15 | 41277 |

TABLE 2

| | | | Human Codon Usage Table | | | | |
|---|---|---|---|---|---|---|---|
| Triplet | Amino acid | Fraction | Number | Triplet | Amino acid | Fraction | Number |
| TTT | F | 0.45 | 336562 | TCT | S | 0.18 | 291040 |
| TTC | F | 0.55 | 406571 | TCC | S | 0.22 | 346943 |
| TTA | L | 0.07 | 143715 | TCA | S | 0.15 | 233110 |
| TTG | L | 0.13 | 249879 | TCG | S | 0.06 | 89429 |
| TAT | Y | 0.43 | 239268 | TGT | C | 0.45 | 197293 |
| TAC | Y | 0.57 | 310695 | TGC | C | 0.55 | 243685 |
| TAA | * | 0.28 | 14322 | TGA | * | 0.52 | 25383 |
| TAG | * | 0.2 | 10915 | TGG | W | 1 | 255512 |
| CTT | L | 0.13 | 253795 | CCT | P | 0.28 | 343793 |
| CTC | L | 0.2 | 386182 | CCC | P | 0.33 | 397790 |
| CTA | L | 0.07 | 138154 | CCA | P | 0.27 | 331944 |
| CTG | L | 0.41 | 800774 | CCG | P | 0.11 | 139414 |
| CAT | H | 0.41 | 207826 | CGT | R | 0.08 | 93458 |
| CAC | H | 0.59 | 297048 | CGC | R | 0.19 | 217130 |
| CAA | Q | 0.25 | 234785 | CGA | R | 0.11 | 126113 |
| CAG | Q | 0.75 | 688316 | CGG | R | 0.21 | 235938 |
| ATT | I | 0.36 | 313225 | ACT | T | 0.24 | 255582 |
| ATC | I | 0.48 | 426570 | ACC | T | 0.36 | 382050 |
| ATA | I | 0.16 | 140652 | ACA | T | 0.28 | 294223 |
| ATG | M | 1 | 443795 | ACG | T | 0.12 | 123533 |
| AAT | N | 0.46 | 331714 | AGT | S | 0.15 | 237404 |
| AAC | N | 0.54 | 387148 | AGC | S | 0.24 | 385113 |
| AAA | K | 0.42 | 476554 | AGA | R | 0.2 | 228151 |
| AAG | K | 0.58 | 654280 | AGG | R | 0.2 | 227281 |
| GTT | V | 0.18 | 216818 | GCT | A | 0.26 | 370873 |
| GTC | V | 0.24 | 290874 | GCC | A | 0.4 | 567930 |
| GTA | V | 0.11 | 139156 | GCA | A | 0.23 | 317338 |
| GTG | V | 0.47 | 575438 | GCG | A | 0.11 | 150708 |
| GAT | D | 0.46 | 443369 | GGT | G | 0.16 | 215544 |

TABLE 2-continued

Human Codon Usage Table

| Triplet | Amino acid | Fraction | Number | Triplet | Amino acid | Fraction | Number |
|---------|------------|----------|--------|---------|------------|----------|--------|
| GAC | D | 0.54 | 517579 | GGC | G | 0.34 | 453917 |
| GAA | E | 0.42 | 577846 | GGA | G | 0.25 | 325243 |
| GAG | E | 0.58 | 810842 | GGG | G | 0.25 | 326879 |

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders. Without wishing to be bound by any particular theory, CRISPR systems including a Cas12i protein may exhibit increased activity or may be preferentially active when targeting in certain environments, such as DNA plasmids, supercoiled DNA, or transcriptionally-active genomic loci.

Genome Editing Systems Generally

The term "genome editing system" refers to an engineered CRISPR system of the present disclosure having RNA-guided DNA editing activity. Genome editing systems of the present disclosure include at least two components of the CRISPR systems described above: an RNA guide and a cognate CRISPR effector protein. In certain embodiments of this disclosure the effector is a Cas12i protein and the RNA guide is a cognate Type V-I RNA guide. As described above, these two components form a complex that is capable of associating with a specific nucleic acid sequence and editing the DNA in or around that nucleic acid sequence, for instance by making one or more of a single strand break (an SSB or nick), a double strand break (a DSB), a nucleobase modification, a DNA methylation or demethylation, a chromatin modification, etc.

In certain embodiments, a genome editing system is transiently active (e.g., incorporating an inducible CRISPR effector as discussed above), while in other embodiments the system is constitutively (e.g., encoded by nucleic acids in which expression of CRISPR system components is controlled by one or more strong promoters).

Genome editing systems of the present disclosure, when introduced into cells, may alter (a) endogenous genomic DNA (gDNA) including, without limitation, DNA encoding e.g., a gene target of interest, an exonic sequence of a gene, an intronic sequence of a gene, a regulatory element of a gene or group of genes, etc.; (b) endogenous extra-genomic DNA such as mitochondrial DNA (mtDNA); and/or (c) exogenous DNA such as a non-integrated viral genome, a plasmid, an artificial chromosome, etc. Throughout this disclosure, these DNA substrates are referred to as "target DNA."

In instances where a genome editing operates by generating SSBs or DSBs, alterations caused by the system may take the form of short DNA insertions or deletions, which are collectively referred to as "indels." These indels may be formed within or proximate to a predicted cleavage site that is typically proximate to the PAM sequence and/or within a region of complementarity to the spacer sequence, though in some cases indels may occur outside of such predicted cleavage site. Without wishing to be bound by any theory, it is believed that indels are often the result of the repair of an SSB or DSB by "error-prone" DNA damage repair pathways, such as non-homologous end joining (NHEJ).

In some cases, a genome editing is used to generate two DSBs within 50, 60, 70, 80, 90, 100, 200, 300, 400, 500, 600, 700, 800, 900, 1000, 1250, 1500, 1750, or 2000 base pairs of one another, which results in one or more outcomes, including the formation of an indels at one or both sites of cleavage, as well as deletion or inversion of a DNA sequence disposed between the DSBs.

Alternatively, genome editing systems of this disclosure may alter target DNA via integration of new sequences. These new sequences may be distinct from the existing sequence of the target DNA (as a non-limiting example, integrated by NHEJ by ligation of blunt-ends) or the may correspond to a DNA template having one or more regions that are homologous to a region of the targeted DNA. Integration of templated homologous sequences is also referred to as "homology-directed repair" or "HDR." Template DNA for HDR may be endogenous to the cell, including without limitation in the form of a homologous sequence located on another copy of the same chromosome as the target DNA, a homologous sequence from the same gene cluster as the target DNA, etc. Alternatively, or additionally, the template DNA may be provided exogenously, including without limitation as a free linear or circular DNA, as a DNA bound (covalently or non-covalently) to one or more genome editing system components, or as part of a vector genome.

In some instances, editing comprises a temporary or permanent silencing of a gene by CRISPR-mediated interference, as described by Matthew H. Larson et al. "CRISPR interference (CRISPRi) for sequence-specific control of gene expression," *Nature Protocols* 8, 2180-2196 (2013), which is incorporated by reference in its entirety and for all purposes.

Genome editing systems may include other components, including without limitation one or more heterologous functional domains which mediate site specific nucleobase modification, DNA methylation or demethylation, or chromatin modification. In some cases, the heterologous functional domain covalently bound to a CRISPR-associated protein such as a Cas12i, for instance by means of a direct peptide bond or an intervening peptide linker. Fusions of this type are described in greater detail below. In some embodiments, the heterologous functional domain is covalently bound to the crRNA, for instance by means of a chemical cross-link. And in some embodiments, one or more functional groups may be non-covalently associated with a CRISPR associated protein and/or a crRNA. This is done, variously, by means of an aptamer appended to the crRNA and/or the heterologous functional group, a peptide motif fused to the CRISPR-associated protein and a binding domain configured to bind such motif fused to the heterologous functional domain, or vice versa.

Genome editing system designs and genome editing outcomes are described in greater detail elsewhere in this specification.

DNA RNA Detection

In one aspect, the CRISPR-Cas system described herein can be used in DNA/RNA detection by DNA sensing. Single effector RNA-guided DNases can be reprogrammed with RNA guides to provide a platform for specific single-stranded DNA (ssDNA) sensing. Upon recognition of its DNA target, an activated CRISPR Type V-I effector protein engages in "collateral" cleavage of nearby ssDNA with no sequence similarity to the target sequence. This RNA-programmed collateral cleavage activity allows the CRISPR systems to detect the presence of a specific DNA by non-specific degradation of labeled ssDNA.

The collateral ssDNase activity can be combined with a reporter in DNA detection applications such as a method called the DNA Endonuclease-Targeted CRISPR trans reporter (DETECTR) method, which when combined with amplification achieves attomolar sensitivity for DNA detection (see, e.g., Chen et al., Science, 360 (6387): 436-439, 2018), which is incorporated herein by reference in its entirety. One application of using the enzymes described herein is to degrade non-target ssDNA in an in vitro environment. A "reporter" ssDNA molecule linking a fluorophore and a quencher can also be added to the in vitro system, along with an unknown sample of DNA (either single-stranded or double-stranded). Upon recognizing the target sequence in the unknown piece of DNA, the surveillance complex containing a Type V-I effector cleaves the reporter ssDNA resulting in a fluorescent readout.

In other embodiments, the SHERLOCK method (Specific High Sensitivity Enzymatic Reporter UnLOCKing) also provides an in vitro nucleic acid detection platform with attomolar (or single-molecule) sensitivity based on nucleic acid amplification and collateral cleavage of a reporter ssDNA, allowing for real-time detection of the target. Methods of using CRISPR in SHERLOCK are described in detail, e.g., in Gootenberg, et al. "Nucleic acid detection with CRISPR-Cas13a/C2c2," Science, 356 (6336): 438-442 (2017), which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," Science, 2015 Apr. 24; 348 (6233):aaa6090, which is incorporated herein by reference in its entirety.

In some embodiments, the CRISPR systems described herein can be used to detect a target DNA in a sample (e.g., a clinical sample, a cell, or a cell lysate). The collateral DNase activity of the CLUST.029130 (Type V-I) CRISPR-Cas effector proteins described herein is activated when the effector proteins bind to a target nucleic acid. Upon binding to the target DNA of interest, the effector protein cleaves a labeled detector ssDNA to generate or change a signal (e.g., an increased signal or a decreased signal) thereby allowing for the qualitative and quantitative detection of the target DNA in the sample. The specific detection and quantification of DNA in the sample allows for a multitude of applications including diagnostics.

In some embodiments, the methods include a) contacting a sample with: (i) an RNA guide (e.g., crRNA) and/or a nucleic acid encoding the RNA guide, wherein the RNA guide consists of a direct repeat sequence and a spacer sequence capable of hybridizing to the target RNA; (ii) a CLUST.029130 (Type V-I) CRISPR-Cas effector protein and/or a nucleic acid encoding the effector protein; and (iii) a labeled detector ssDNA; wherein the effector protein associates with the RNA guide to form a surveillance complex; wherein the surveillance complex hybridizes to the target DNA; and wherein upon binding of the surveillance complex to the target DNA, the effector protein exhibits collateral DNase activity and cleaves the labeled detector ssDNA; and b) measuring a detectable signal produced by cleavage of the labeled detector ssDNA, wherein said measuring provides for detection of the target DNA in the sample.

In some embodiments, the methods further include comparing the detectable signal with a reference signal and determining the amount of target DNA in the sample. In some embodiments, the measuring is performed using gold nanoparticle detection, fluorescence polarization, colloid phase transition/dispersion, electrochemical detection, and semiconductor based-sensing. In some embodiments, the labeled detector ssDNA includes a fluorescence-emitting dye pair, a fluorescence resonance energy transfer (FRET) pair, or a quencher/fluorophore pair. In some embodiments, upon cleavage of the labeled detector ssDNA by the effector protein, an amount of detectable signal produced by the labeled detector ssDNA is decreased or increased. In some embodiments, the labeled detector ssDNA produces a first detectable signal prior to cleavage by the effector protein and a second detectable signal after cleavage by the effector protein.

In some embodiments, a detectable signal is produced when the labeled detector ssDNA is cleaved by the effector protein. In some embodiments, the labeled detector ssDNA includes a modified nucleobase, a modified sugar moiety, a modified nucleic acid linkage, or a combination thereof.

In some embodiments, the methods include the multi-channel detection of multiple independent target DNAs in a sample (e.g., two, three, four, five, six, seven, eight, nine, ten, fifteen, twenty, thirty, forty, or more target RNAs) by using multiple CLUST.029130 (Type V-I) CRISPR-Cas systems, each including a distinct orthologous effector protein and corresponding RNA guides, allowing for the differentiation of multiple target DNAs in the sample. In some embodiments, the methods include the multi-channel detection of multiple independent target DNAs in a sample, with the use of multiple instances of CLUST.029130 (Type V-I) CRISPR-Cas systems, each containing an orthologous effector protein with differentiable collateral ssDNase substrates. Methods of detecting a DNA in a sample using CRISPR-associated proteins are described, for example, in U.S. Patent Publication No. 2017/0362644, the entire contents of which are incorporated herein by reference.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and DNAs in the vicinity of a protein or DNA of interest in vitro. After UV irradiation, the photoactivatable groups react with proteins and other molecules that are in close proximity to the tagged molecules, thereby labelling them. Labelled interacting molecules can subsequently be recovered and identified. The DNA targeting effector proteins can for instance be used to target probes to selected DNA sequences. These applications can also be applied in animal models for in vivo imaging of diseases or difficult-to culture cell types. The methods of tracking and labeling of nucleic acids are described, e.g., in U.S. Pat. No. 8,795,965; WO 2016205764; and WO 2017070605; each of which is incorporated herein by reference in its entirety.

Genome Editing Using Paired CRISPR Nickases

The CRISPR systems described herein can be used in tandem such that two Cas12i nicking enzymes, or one Cas12i enzyme and one other CRISPR Cas enzyme with nicking activity, targeted by a pair of RNA guides to opposite strands of a target locus, can generate a double-strand break with overhangs. This method may reduce the likelihood of off-target modifications, because a double-strand break is expected to occur only at loci where both enzymes generate a nick, thereby increasing genome editing specificity. This method is referred to as a 'double nicking' or 'paired nickase' strategy and is described, e.g., in Ran et al., "Double nicking by RNA-guided CRISPR Cas9 for enhanced genome editing specificity," *Cell,* 2013 Sep. 12; 154 (6): 1380-1389, and in Mali et al., "CAS9 transcriptional activators for target specificity screening and paired nickases for cooperative genome engineering," *Nature Biotechnology,* 2013 Aug. 1; 31:833-838, which are both incorporated herein by reference in their entireties.

The first applications of paired nickases demonstrated the utility of this strategy in mammalian cell lines. Applications of paired nickases have been described in the model plant *Arabidopsis* (e.g., in Fauser et al., "Both CRISPR/Cas-based nucleases and nickases can be used efficiently for genome engineering in *Arabidopsis thaliana,"* *The Plant Journal* 79 (2): 348-59 (2014), and Shiml et al., "The CRISPR/Cas system can be used as nuclease for in planta gene targeting and as paired nickases for directed mutagenesis in *Arabidopsis* resulting in heritable progeny," *The Plant Journal* 80 (6): 1139-50 (2014); in crops such as in rice (e.g., in Mikami et al., "Precision Targeted Mutagenesis via Cas9 Paired Nickases in Rice," *Plant and Cell Physiology* 57 (5): 1058-68 (2016) and in wheat (e.g., in Čermák et al., "A Multipurpose Toolkit to Enable Advanced Genome Engineering in Plants," *Plant Cell* 29:1196-1217 (2017); in bacteria (e.g., in Standage-Beier et al., "Targeted Large-Scale Deletion of Bacterial Genomes Using CRISPR-Nickases," *ACS Synthetic Biology* 4 (11): 1217-25 (2015); and in primary human cells for therapeutic purposes (e.g., in Dabrowska et al., "Precise Excision of the CAG Tract from the Huntingtin Gene by Cas9 Nickases," *Frontiers in Neuroscience* 12:75 (2018), and in Kocher et al., "Cut and Paste: Efficient Homology-Directed Repair of a Dominant Negative KRT14 Mutation via CRISPR/Cas9 Nickases," *Molecular Therapy* 25 (11): 2585-2598 (2017)), all of which are incorporated herein by reference in their entireties.

The CRISPR systems described herein can also be used as paired nickases to detect splice junctions as described e.g., in Santo & Paik, "A splice junction-targeted CRISPR approach (spJCRISPR) reveals human FOXO3B to be a protein-coding gene," *Gene* 673:95-101 (2018).

The CRISPR systems described herein can also be used as paired nickases to insert DNA molecules into target loci as described in e.g., Wang et al, "Therapeutic Genome Editing for Myotonic Dystrophy Type 1 Using CRISPR/Cas9," *Molecular Therapy* 26 (11): 2617-2630 (2018). The CRISPR systems described herein can also be used as single nickases to insert genes as described in e.g., Gao et al, "Single Cas9 nickase induced generation of NRAMP1 knockin cattle with reduced off-target effects," *Genome Biology* 18 (1): 13 (2017).

Enhancing Base Editing Using CRISPR Nickases

The CRISPR systems described herein can be used to augment the efficiency of CRISPR base editing. In base editing, a protein domain with DNA nucleotide modifying activity (e.g., cytidine deamination) is fused to a programmable CRISPR Cas enzyme that has been deactivated by mutation so as to no longer possess double-strand DNA cleavage activity. In some embodiments, using a nickase as the programmable Cas protein has been shown to improve the efficiency of base editing as described e.g., in Komor et al., "Programmable editing of a target base in genomic DNA without double-stranded DNA cleavage," *Nature* 533:420-424 (2016), and Nishida et al., "Targeted nucleotide editing using hybrid prokaryotic and vertebrate adaptive immune systems," *Science* 353 (6305): aaf8729 (2016), both of which are incorporated herein by reference in their entirety. A nickase that nicks the non-edited strand of the target locus is hypothesized to stimulate endogenous DNA repair pathways—such as mismatch repair or long-patch base excision repair, which preferentially resolves a mismatch generated by base editing to a desired allele—or to provide better accessibility of the catalytic editing domain to the target DNA.

Targeted Mutagenesis and DNA Labeling with Nickases and DNA Polymerases

The CRISPR systems described herein can be used in conjunction with proteins that act on nicked DNA. One such class of proteins is nick-translating DNA polymerases, such as *E. coli* DNA polymerase I or Taq DNA polymerase.

In some embodiments, the CRISPR system (e.g., a CRISPR nickase) can be fused to an error-prone DNA polymerase I. This fusion protein can be targeted with an RNA guide to generate a nick at a target DNA site. The DNA polymerase then initiates DNA synthesis at the nick, displacing downstream nucleotides, and, because an error-prone polymerase is used, resulting in mutagenesis of the target locus. Polymerase variants with varying processivity, fidelity, and misincorporation biases may be used to influence characteristics of the mutants that are generated. This method, called EvolvR, is described in detail, e.g., in Halperin et al., "CRISPR-guided DNA polymerases enable diversification of all nucleotides in a tunable window," *Nature* 560, 248-252 (2018), which is incorporated herein by reference in its entirety.

In some embodiments, a CRISPR nickase can be used in a nick translation DNA labeling protocol. Nick translation, first described by Rigby et al in 1977, involves incubating DNA with a DNA nicking enzyme, such as DNase I, which creates one or more nicks in the DNA molecule. Next, a nick-translating DNA polymerase, such as DNA polymerase I, is used to incorporate labeled nucleic acid residues at the nicked sites. Methods of harnessing the programmability of CRISPR nickases to covalently tag telomeric repeats with fluorescent dyes, using a variant of a classical nick translation labeling protocol, are described in detail e.g., in McCaffery et al., "High-throughput single-molecule telomere characterization," *Genome Research* 27:1904-1915 (2017), which is incorporated herein by reference in its entirety. This method enables haplotype-resolved analysis of telomere lengths at the single-molecule level.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965;

WO 2016205764; and WO 2017070605; each of which is incorporated herein by reference in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR enzyme transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," *BMC Genomics,* 15.1 (2014): 1002, which is incorporated herein by reference in its entirety.

Engineered Microorganisms

Microorganisms (e.g., *E. coli*, yeast, and microalgae) are widely used for synthetic biology. The development of synthetic biology has a wide utility, including various clinical applications. For example, the programmable CRISPR systems described herein can be used to split proteins of toxic domains for targeted cell death, e.g., using cancer-linked RNA as target transcript. Further, pathways involving protein-protein interactions can be influenced in synthetic biological systems with e.g. fusion complexes with the appropriate effectors such as kinases or enzymes.

In some embodiments, RNA guide sequences that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of *Saccharomyces cerevisiae,*" *Yeast,* 2017 Sep. 8. doi: 10.1002/yea.3278; and Hlavova et al., "Improving microalgae for biotechnology—from genetics to synthetic biology," *Biotechnol. Adv.,* 2015 Nov. 1; 33:1194-203, both of which are incorporated herein by reference in their entirety.

In some embodiments, the CRISPR systems described herein can be used to engineer microorganisms that have defective repair pathways, such as the mesophilic cellulolytic bacterium *Clostridium cellylolyticum*, a model organism for bioenergy research. In some embodiments, a CRISPR nickase can be used to introduce single nicks at a target locus, which may result in insertion of an exogenously provided DNA template by homologous recombination. A detailed method regarding how to use a CRISPR nickase to edit repair-defective microbes is described e.g., in Xu et al., "Efficient Genome Editing in *Clostridium cellulolyticum* via CRISPR-Cas9 Nickase," *Appl Environ Microbiology* 81:4423-4431 (2015), which is incorporated herein in its entirety.

In some embodiments, the CRISPR systems provided herein can be used to induce death or dormancy of a cell (e.g., a microorganism such as an engineered microorganism). These methods can be used to induce dormancy or death of a multitude of cell types including prokaryotic and eukaryotic cells, including, but not limited to, mammalian cells (e.g., cancer cells, or tissue culture cells), protozoans, fungal cells, cells infected with a virus, cells infected with an intracellular bacteria, cells infected with an intracellular protozoan, cells infected with a prion, bacteria (e.g., pathogenic and non-pathogenic bacteria), protozoans, and unicellular and multicellular parasites. For instance, in the field of synthetic biology it is highly desirable to have mechanisms of controlling engineered microorganisms (e.g., bacteria) to prevent their propagation or dissemination. The systems described herein can be used as "kill-switches" to regulate and/or prevent the propagation or dissemination of an engineered microorganism. Further, there is a need in the art for alternatives to current antibiotic treatments.

The systems described herein can also be used in applications where it is desirable to kill or control a specific microbial population (e.g., a bacterial population). For example, the systems described herein may include an RNA guide (e.g., a crRNA) that targets a nucleic acid (e.g., a DNA) that is genus-, species-, or strain-specific, and can be delivered to the cell. Upon complexing and binding to the target nucleic acid, the nuclease activity of the CLUST.029130 (Type V-I) CRISPR-Cas effector proteins disrupts essential functions within the microorganisms, ultimately resulting in dormancy or death. In some embodiments, the methods comprise contacting the cell with a system described herein including a CLUST.029130 (Type V-I) CRISPR-Cas effector proteins or a nucleic acid encoding the effector protein, and a RNA guide (e.g., a crRNA) or a nucleic acid encoding the RNA guide, wherein the spacer sequence is complementary to at least 15 nucleotides (e.g., 16, 17, 18, 19, 20, 21, 22, 23, 24, 25, 26, 27, 28, 29, 30, 35, 40, 45, 50 or more nucleotides) of a target nucleic acid.

Without wishing to be bound by any particular theory, the nuclease activity of the CLUST.029130 (Type V-I) CRISPR-Cas effector proteins can induce programmed cell death, cell toxicity, apoptosis, necrosis, necroptosis, cell death, cell cycle arrest, cell anergy, a reduction of cell growth, or a reduction in cell proliferation. For example, in bacteria, the cleavage of DNA by the CLUST.029130 (Type V-I) CRISPR-Cas effector proteins can be bacteriostatic or bactericidal.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants. Plants that can be edited using CRISPR systems of this disclosure (e.g., Cas12i systems) can be monocots or dicots and include, without limitation safflower, maize, cannabis, rice, sugarcane, canola, sorghum, tobacco, rye, barley, wheat, millet, oats, peanut, potato, switchgrass, turfgrass, soybean, alfalfa, sunflower, cotton, and *Arabidopsis*. The present disclosure also encompasses a plant having a trait made according to a method of the disclosure and/or utilizing a CRISPR system of the disclosure.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.*, 11 (3): 222-8 (2011), and WO 2016205764 A1; both of which are incorporated herein by reference in their entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae*," *Nat. Biotechnol.*, 2016 January; 34 (1): 78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of RNA guide (gRNA)-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.*, 2017 March; 14 (3): 297-301, which is incorporated herein by reference in its entirety.

Saturation Mutagenesis ("Bashing")

The CRISPR systems described herein can be used for in situ saturating mutagenesis. In some embodiments, a pooled RNA guide library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature*, 2015 Nov. 12; 527 (7577): 192-7, which is incorporated herein by reference in its entirety.

Therapeutic Applications

The CRISPR systems described herein that have activity in a mammalian cellular context (e.g., Cas12i2) can have a diverse range of therapeutic applications. Moreover, each nuclease ortholog may have unique properties (e.g., size, PAM, etc.) that render it advantaged for certain targeting, treatment, or delivery modalities, so the ortholog selection is important in allocating the nuclease that provides maximum therapeutic benefit.

There are numerous factors that influence the suitability of gene editing as a therapeutic for a particular disease. With nuclease-based gene therapies, the primary approaches to therapeutic editing have been gene disruption and gene correction. In the former, gene disruption generally occurs with an event (such as a nuclease-induced, targeted double stranded break) that activates the endogenous non homologous end joining DNA repair mechanism of the target cell, yielding indels that often result in a loss of function mutation that is intended to benefit the patient. The latter, gene correction utilizes the nuclease activity to induce alternative DNA repair pathways (such as homology directed repair, or HDR) with the help of a template DNA (whether endogenous or exogenous, single stranded or double stranded). The templated DNA can either be an endogenous correction of a disease-causing mutation, or otherwise the insertion of a therapeutic transgene into an alternate locus (commonly safe harbor loci such as AAVS1). Methods of designing exogenous donor template nucleic acids are described, for example, in PCT Publication No. WO 2016094874 A1, the entire contents of which are expressly incorporated herein by reference. A requisite of therapies that use either of these editing modalities is an understanding of the genetic modulators of a certain disease; the diseases do not necessarily have to be monogenic, but insight into how mutations can effect the disease progress or outcome are important to providing guidance as to the potential efficacy of a gene therapy.

Without wishing to be limited, the CRISPR systems described herein can be utilized to treat the following diseases, wherein the specific gene targets are identified, in addition to the relevant references to aid in the adaption of the Type V-I CRISPR systems to specific disease areas; Cystic fibrosis by targeting CFTR (WO2015157070A2), Duchenne Muscular Dystrophy and Becker Muscular Dystrophy by targeting Dystrophin (DMD) (WO2016161380A1), Alpha-1-antitrypsin deficiency by targeting Alpha-1-antitrypsin (A1AT) (WO2017165862A1), lysosomal storage disorders such as Pompe Disease aka Glycogen storage disease type II by targeting acid alpha-glucosidase (GAA), myotonic dystrophy by targeting DMPK, Huntington disease by targeting HTT, Fragile X by targeting FMRI, Friedreich's ataxia by targeting Frataxin, amyotrophic lateral sclerosis (ALS) and frontotemporal dementia (FTD) by targeting C9orf72, hereditary chronic kidney disease by targeting ApoL1, cardiovascular disease and hyperlipidemia by targeting PCSK9, APOC3, ANGPTL3, LPA (*Nature* 555, S23-S25 (2018)), and congenital blindness such as Leber Congenital Amaurosis Type 10 (LCA10) by targeting CEP290 (Maeder et al., *Nat Med.* 2019 February; 25 (2): 229-233). The majority of the aforementioned diseases are best treated with an in vivo gene editing approach, in which the cell types and tissues involved in the disease need to be edited in situ with a sufficient dose and efficiency to yield a therapeutic benefit. Some challenges of in vivo delivery are described in the "Delivery of CRISPR Systems" section below, though in general the smaller gene size of the Type V-I CRISPR effectors enables more versatile packaging into viral vectors with a payload restriction, such as adeno-associated viruses.

Ex vivo editing, in which cells are removed from the patient's body and then edited prior to transplantation back into the patient, present a prime therapeutic opportunity for gene editing technologies. The ability to manipulate cells outside the body presents multiple advantages, ranging from the ability to use technologies for high efficiency delivery of protein, DNA, and RNA into cells such as electroporation and nucleofection that are not amenable in an in vivo context, to being able to evaluate toxicity (such as from off-target effects), then further select and expand successfully edited cells to yield a population that provides a therapeutic advantage. These advantages are counterbalanced by the relatively few cell types and populations that can be successfully harvested, processed, and then returned to the body while preserving functionality. Without wishing to be limited, there nevertheless are serious diseases that are amenable to ex vivo genome editing using the systems described herein. For example, sickle cell disease (SCD) as referenced in WO2015148863A2, and beta-thalassemia as referenced in WO2015148860A1, both are examples of diseases in which the understanding of the pathophysiology has enabled a number of different editing modalities in hematopoietic stem cells for disease treatment. Beta thalassemia and SCD can both be treated with the disruption of the BCL11A erythroid enhancer to increase the levels of fetal hemoglobin (as illustrated using Zinc Finger Nucleases by Psatha et al. *Mol Ther Methods Clin Dev.* 2018 Sep. 21). In addition, methods of gene correction can be used to reverse the deleterious mutations in SCD and beta thalassemia. In another instance, the addition of a beta globin expressed from a safe harbor locus provides another alternative therapeutic strategy for ex vivo gene editing.

As a corollary of ex vivo editing of hematopoietic stem cells, immune cells can also be edited. In cancer immunotherapy, one therapeutic mode is to modify immune cells such as T-cells to recognize and fight cancer, as referenced in WO2015161276A2. To increase the efficacy and availability while decreasing cost, the creation of 'off-the-shelf' allogeneic T-cell therapies is attractive, and gene editing has the potential to modify surface antigens to minimize any immunological side effects (Jung et al., *Mol Cell.* 2018 Aug. 31).

In another embodiment, the invention be used to target viruses or other pathogens with a double stranded DNA intermediate stage of their life cycle. Specifically, targeting viruses whose initial infection leaves a latent infection that persists permanently would be of significant therapeutic value. In the following examples, the Type V-I CRISPR systems can be used to directly target the viral genome (such as with HSV-1, HSV-2 or HIV), or used to edit the host cells to reduce or eliminate the receptors enabling infection to make them impervious to the virus (HIV), as referenced for HSV-1 and HSV-2 in WO2015153789A1, WO2015153791A1, and WO2017075475A1, and for HIV in WO2015148670A1 and WO2016183236A1.

In another aspect, the CRISPR systems described herein can be engineered to enable additional functions that utilize enzymatically inactive Cas12i as a chassis on top of which protein domains can be attached to confer activities such as transcriptional activation, repression, base editing, and methylation/demethylation.

Thus, this disclosure provides CRISPR-Cas systems and cells for use in the treatment or prevention of any of the disease disclosed herein.

Delivery of CRISPR Systems

The CRISPR systems described herein, or components thereof, nucleic acid molecules thereof, or nucleic acid molecules encoding or providing components thereof, can be delivered by various delivery systems such as vectors, e.g., plasmids, viral delivery vectors, such as adeno-associated viruses (AAV), lentiviruses, adenoviruses, and other viral vectors, or methods, such as nucleofection or electroporation of ribonucleoprotein complexes consisting of Type V-I effectors and their cognate RNA guide or guides. The proteins and one or more RNA guides can be packaged into one or more vectors, e.g., plasmids or viral vectors. For bacterial applications, the nucleic acids encoding any of the components of the CRISPR systems described herein can be delivered to the bacteria using a phage. Exemplary phages, include, but are not limited to, T4 phage, Mu, λ phage, T5 phage, T7 phage, T3 phage, Φ29, M13, MS2, Qβ, and ΦX174.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adeno-associated viruses (AAV), e.g., AAV2, AAV8, or AAV9, which can be administered in a single dose containing at least $1 \times 10^5$ particles (also referred to as particle units, pu) of adenoviruses or adeno-associated viruses. In some embodiments, the dose is at least about $1 \times 10^6$ particles, at least about $1 \times 10^7$ particles, at least about $1 \times 10^8$ particles, or at least about $1 \times 10^9$ particles of the adeno-associated viruses. The delivery methods and the doses are described, e.g., in WO 2016205764 and U.S. Pat. No. 8,454,972, both of which are incorporated herein by reference in their entirety. Due to the limited genomic payload of recombinant AAV, the smaller size of the Type V-I CRISP-Cas effector proteins described herein enables greater versatility in packaging the effector and RNA guides with the appropriate control sequences (e.g., promoters) required for efficient and cell-type specific expression.

In some embodiments, the delivery is via a recombinant adeno-associated virus (rAAV) vector. For example, in some embodiments, a modified AAV vector may be used for delivery. Modified AAV vectors can be based on one or more of several capsid types, including AAV1, AV2, AAV5, AAV6, AAV8, AAV8.2. AAV9, AAV rhlO, modified AAV vectors (e.g., modified AAV2, modified AAV3, modified AAV6) and pseudotyped AAV (e.g., AAV2/8, AAV2/5 and AAV2/6). Exemplary AAV vectors and techniques that may be used to produce rAAV particles are known in the art (see, e.g., Aponte-Ubillus et al. (2018) Appl. Microbiol. Biotechnol. 102 (3): 1045-54; Zhong et al. (2012) J. Genet. Syndr. Gene Ther. S1: 008; West et al. (1987) Virology 160:38-47 (1987); Tratschin et al. (1985) Mol. Cell. Biol. 5:3251-60); U.S. Pat. Nos. 4,797,368 and 5,173,414; and International Publication Nos. WO 2015/054653 and WO 93/24641, each of which is incorporated by reference).

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR enzymes, operably linked to the promoter; (iii) a selectable marker; (iv) an origin of replication; and (v) a transcription terminator downstream of and operably linked to (ii). The plasmids can also encode the RNA components of a CRISPR-Cas system, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofectin formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in the delivery of RNA.

Further means of introducing one or more components of the new CRISPR systems into cells is by using cell penetrating peptides (CPP). In some embodiments, a cell penetrating peptide is linked to the CRISPR enzymes. In some embodiments, the CRISPR enzymes and/or RNA guides are coupled to one or more CPPs to transport them inside cells effectively (e.g., plant protoplasts). In some embodiments, the CRISPR enzymes and/or RNA guide(s) are encoded by one or more circular or non-circular DNA molecules that are coupled to one or more CPPs for cell delivery.

CPPs are short peptides of fewer than 35 amino acids derived either from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin β3 signal peptide sequence, polyarginine peptide Args sequence, Guanine rich-molecular transporters, and sweet arrow peptide. CPPs and methods of using them are described, e.g., in Hällbrink et al., "Prediction of cell-penetrating peptides," Methods Mol. Biol., 2015; 1324:39-58; Ramakrishna et al., "Gene disruption by cell-penetrating peptide-mediated delivery of Cas9 protein and guide RNA," Genome Res., 2014 June; 24 (6): 1020-7; and WO 2016205764 A1; each of which is incorporated herein by reference in its entirety.

Delivery of the Type V-I CRISPR system as a ribonucleoprotein complex by electroporation or nucleofection, in which purified Cas12i protein is pre-incubated with a RNA guide and electroporated (or nucleofected) into cells of interest, is another method of efficiently introducing the CRISPR system to cells for gene editing. This is particularly useful for ex vivo genome editing and the development of cellular therapies, and such methods are described in Roth et al. "Reprogramming human T cell function and specificity with non-viral genome targeting," Nature, 2018 July; 559 (7714): 405-409.

Various delivery methods for the CRISPR systems described herein are also described, e.g., in U.S. Pat. No. 8,795,965, EP 3009511, WO 2016205764, and WO 2017070605; each of which is incorporated herein by reference in its entirety Kits This disclosure also encompasses kits for carrying out the various methods of the disclosure utilizing the CRISPR systems described herein. One exemplary kit of the present disclosure comprises (a) one or more nucleic acids encoding a CRISPR-associated protein and a cognate crRNA, and/or (b) a ribonucleoprotein complex of a CRISPR-associated protein and a cognate crRNA. In some embodiments, the kit comprises a Cas12i protein and a Cas12i guide RNA. As described above, a complex of the protein and guide RNA has an editing activity such as SSB formation, DSB formation, CRISPR interference, nucleobase modification, DNA methylation or demethylation, chromatin modification, etc.

In certain embodiments, the CRISPR-associated protein is a variant, such as a variant having reduced endonuclease activity.

Kits of this disclosure also optionally include additional reagents, including one or more of a reaction buffer, a wash buffer, one or more control materials (e.g., a substrate or a nucleic acid encoding a CRISPR system component), etc. A kit of the present disclosure also optionally includes instructions for performing a method of this disclosure using materials provided in the kit. The instructions are provided in physical form, e.g., as a printed document physically packaged with another item of the kit, and/or in digital form, e.g., a digitally published document downloadable from a website or provided on computer readable media.

EXAMPLES

The invention is further described in the following examples, which do not limit the scope of the invention described in the claims.

Example 1: Identification of Minimal Components for the CLUST.029130 (Type V-I) CRISPR-Cas System (FIGS. 1-3)

This protein family describes a large single effector associated with CRISPR systems found in uncultured metagenomic sequences collected from freshwater environments (Table 3). CLUST.029130 (Type V-I) effectors, designated Cas12i, include the exemplary proteins detailed in Tables 3 and 4. Exemplary direct repeat sequences for these systems are shown in Table 5.

Genome and metagenome sequences were downloaded from NCBI (Benson et al. (2013) GenBank. Nucleic Acids Res. 41, D36-42; Pruitt et al. (2012) NCBI Reference Sequences (RefSeq): current status, new features and genome annotation policy. Nucleic Acids Res. 40, D130-135), NCBI whole genome sequencing (WGS), and DOE JGI Integrated Microbial Genomes (Markowitz et al. (2012) IMG: the Integrated Microbial Genomes database and comparative analysis system. Nucleic Acids Res. 40, D115-122) and compiled to construct a database of 293,985 putative CRISPR-Cas systems within which we identified novel nuclease systems. This approach to pipeline engineering performs minimal filtering in the intermediate stages to expand the search space for novel CRISPR effector discovery and reduce biases.

Figure 1A:
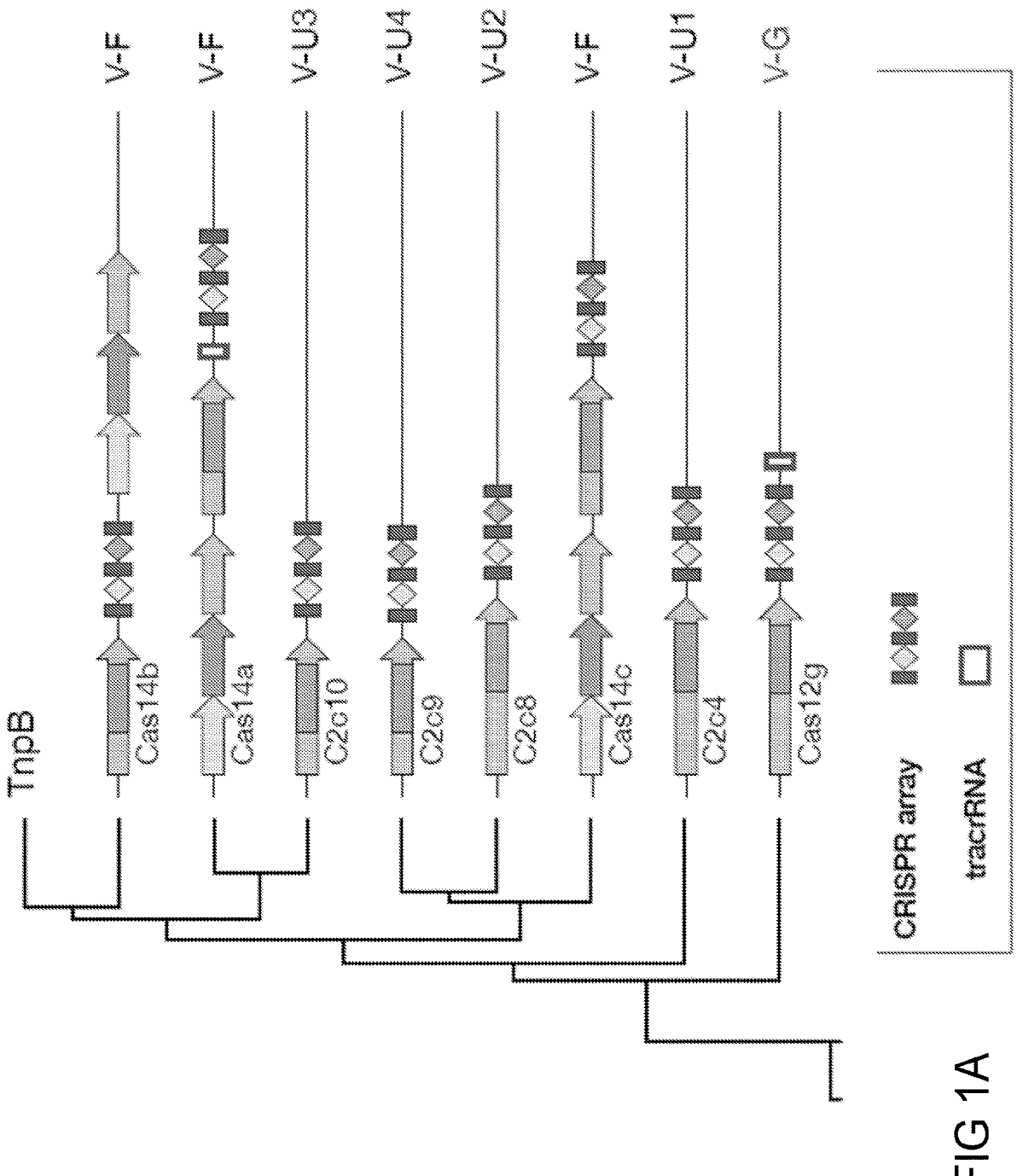
Figure 1B:
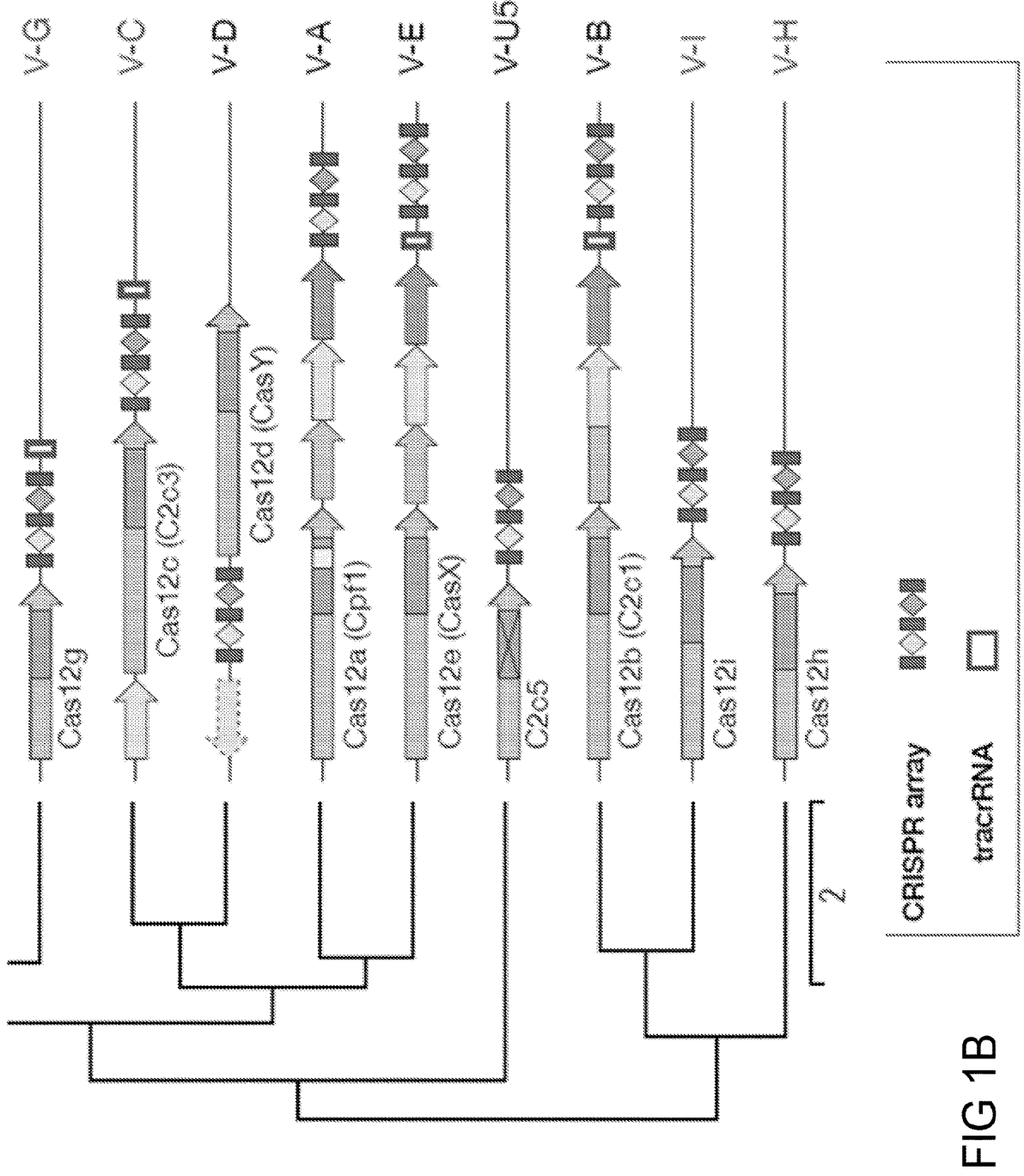

The classification tree depicted in FIGS. 1A-1B was constructed by comparing sequence profiles extracted from multiple alignments of groups of readily alignable Cas12 proteins. Profile-profile comparisons were performed using HHsearch (Söding et al. (2005) Protein homology detection by HMM-HMM comparison. Bioinforma. Oxf. Engl. 21, 951-960); scores between two profiles were normalized by the minimum of the self-scores and converted to a distance matrix on the natural log scale. The UPGMA dendrogram was reconstructed from the distance matrix. The tree at the depth of 2 distance unites (corresponding to the pairwise HHsearch score of $e^{-2D}=0.02$ relative to the self-score) typically reliably recovers profile similarity and can serve as a guide for subtype classification (Shmakov et al., 2017).

Figure 2A:
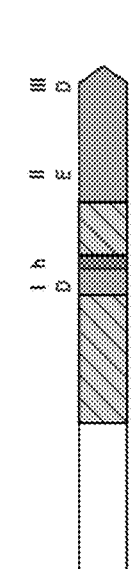
FIG. 2B is a schematic representation of a multiple sequence alignment of Cas12i effector proteins, with the relative locations of the conserved catalytic residues of the RuvC domain denoted by RuvC I/II/III.
Figure 2B:
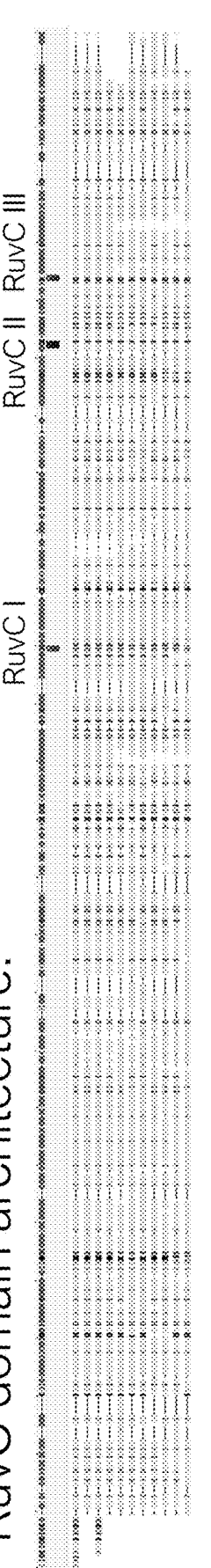

The domain architecture of Cas12i, depicted in FIGS. 2A and 2B indicate that the effector contains the active catalytic residues of the RuvC nuclease domain. Additionally, the predicted secondary structure of the most prevalent direct repeat for Type V-I loci, depicted in FIG. 3, indicates a stem-loop structure that is conserved in the crRNA of many exemplary Type V-I CRISPR-Cas systems.

TABLE 3

Representative CLUST.029130 (Type V-I) Effector Proteins

| species | Cas12i accession | # spacers | cas1 | cas2 | effector size |
|---|---|---|---|---|---|
| SRR1522973 (SRR1522973) | SRR1522973_megahit_k177_1081830_2\|M | 9 | N | N | 1098 |
| SRR1522973 (SRR1522973) | SRR1522973_megahit_k177_427371_1\|M | 20 | N | N | 1088 |
| SRR2179954 (SRR2179954) | SRR2179954_megahit_k177_1417524_4\|M | 7 | N | N | 1074 |
| SRR6475631 (SRR6475631) | SRR6475631_megahit_k177_2773783_7\|M | 22 | N | N | 1031 |
| SRR6837575 (SRR6837575) | SRR6837575_megahit_k177_919599_7\|M | 4 | N | N | 1066 |
| SRR6837577 (SRR6837577) | SRR6837577_megahit_k177_410843_33\|P | 20 | N | N | 1066 |
| 3300020508 (3300020508\|Ga0208225_1000010) | 3300020508\|Ga0208225_1000010_34\|M | 10 | N | N | 1093 |
| aquatic-freshwater (3300002408\|release\|scaffold05697) | 3300002408\|release\|scaffold05697_22\|M | 13 | N | N | 1091 |
| aquatic-freshwater (3300002408\|release\|scaffold05697) | 3300002408\|release\|scaffold05697_22\|P | 13 | N | N | 1046 |
| aquatic-freshwater (3300002408\|release\|scaffold08426) | 3300002408\|release\|scaffold08426_1\|P | 6 | N | N | 1093 |
| aquatic-freshwater (3300028569\|Ga0247843_1000055) | 3300028569\|Ga0247843_1000055_230\|M | 12 | N | N | 1080 |
| aquatic-freshwater (3300028569\|Ga0247843_1000055) | 3300028569\|Ga0247843_1000055_232\|P | 12 | N | N | 1046 |
| aquatic-freshwater (3300028571\|Ga0247844_1000101) | 3300028571\|Ga0247844_1000101_90\|M | 12 | N | N | 1080 |
| aquatic-freshwater (3300028571\|Ga0247844_1000101) | 3300028571\|Ga0247844_1000101_88\|P | 12 | N | N | 1046 |
| aquatic-freshwater-freshwater lake (3300009183\|Ga0114974_10028552) | 3300009183\|Ga0114974_10028552_1\|M | 7 | N | N | 1033 |
| aquatic-freshwater-freshwater lake (3300010885\|Ga0133913_10053227) | 3300010885\|Ga0133913_10053227_5\|M | 26 | N | N | 1046 |
| aquatic-freshwater-freshwater lake (3300020193\|Ga0194131_10013618) | 3300020193\|Ga0194131_10013618_4\|P | 5 | N | N | 1054 |
| aquatic-freshwater-freshwater lake (3300020214\|Ga0194132_10015959) | 3300020214\|Ga0194132_10015959_3\|M | 8 | N | N | 1054 |

TABLE 4

Amino Acid Sequences of Representative CLUST.029130 (Type V-I) Effector Proteins

```
>SRR1522973_megahit_k177_1081830_2|M
[SRR1522973]
MSISNNNILPYNPKLLPDDRKHKMLVDTFNQLDLIRNNLHDMIIALYGALKYDNIKQFASKEKPHISADALCSINW
FRLVKTNERKPAIESNQIISKFIQYSGHTPDKYALSHITGNHEPSHKWIDCREYAINYARIMHLSFSQFQDLATAC
LNCKILILNGTLTSSWAWGANSALFGGSDKENFSVKAKILNSFIENLKDEMNTTKFQVVEKVCQQIGSSDAADLFD
LYRSTVKDGNRGPATGRNPKVMNLFSQDGEISSEQREDFIESFQKVMQEKNSKQIIPHLDKLKYHLVKQSGLYDIY
SWAAAIKNANSTIVASNSSNLNTILNKTEKQQTFEELRKDEKIVACSKILLSVNDTLPEDLHYNPSTSNLGKNLDV
FFDLLNENSVHTIENKEEKNKIVKECVNQYMEECKGLNKPPMPVLLTFISDYAHKHQAQDFLSAAKMNFIDLKIKS
IKVVPTVHGSSPYTWISNLSKKNKDGKMIRTPNSSLIGWIIPPEEIHDQKFAGQNPIIWAVLRVYCNNKWEMHHFP
FSDSRFFTEVYAYKPNLPYLPGGENRSKREGYRHSTNLSNESRQILLDKSKYAKANKSVLRCMENMTHNVVFDPKT
SLNIRIKTDKNNSPVLDDKGRITFVMQINHRILEKYNNTKIEIGDRILAYDQNQSENHTYAILQRTEEGSHAHQFN
GWYVRVLETGKVTSIVQGLSGPIDQLNYDGMPVTSHKENCWQADRSAFVSQFASLKISETETFDEAYQAINAQGAY
TWNLFYLRILRKALRVCHMENINQFREEILAISKNRLSPMSLGSLSQNSLKMIRAFKSIINCYMSRMSFVDELQKK
EGDLELHTIMRLTDNKLNDKRVEKINRASSFLTNKAHSMGCKMIVGESDLPVADSKTSKKQNVDRMDWCARALSHK
VEYACKLMGLAYRGIPAYMSSHQDPLVHLVESKRSVLRPRFVVADKSDVKQHHLDNLRRMLNSKTKVGTAVYYREA
VELMCEELGIHKTDMAKGKVSLSDFVDKFIGEKAIFPQRGGRFYMSTKRLTTGAKLICYSGSDVWLSDADEIAAIN
IGMFVVCDQTGAFKKKKKEKLDDEECDILPFRPM (SEQ ID NO: 14)

>SRR1522973_megahit_k177_427371_1|M
[SRR1522973]
MSSQVVRPYNAKFLPDDRKHKMLTDTINQLDKISSKHFDLLVAFYGSIQHKHVSINDKQEEHITPDSVCAINWFRP
MSKDYAKYQVKIDSMITNFKEYAGHIPDKYAIEYMGSNIDTDRFVWVDCRNFAKDYVRNMDMSFSEFQNLVDALVF
CKILALNESTSTNWAWGAISAIYGGGDKEDSQFKAKVLNTFVKALNDENNKTKFDVINKVCSDLGYNDHLSLIEDF
RSTIDENGNKKSASGSPPAIAKFTEDGEISDNYRRACISSFSKTAKEKQDKKSIPHLDILKTHMIAMCGEYNTYAW
TEAIKNANTDITSRNTRNMTFIKEKIESRNSLKIYDTEENMKAAKILNGINHKLTPDLHYTPAPKHLGKNLKDLFE
MLEEKNILAQNEKEKKAALDECIKQYIDDCKGLNQQPIASLLAHISNYHKEITAENFLDGAKLLVLLQKINRQKAH
PSVFSPKAYTWGSKLEKNRRAANSALLGWIVPPEEKHKDRHAGQHPVMWVTMTLLNNGKWEKHHVPFTNSRFFSEV
YAYQPELPYKEGGYARNSKTATKPSQIMLPAYAESMRHHIATKGNGHKKSEKIVLRALSNIRHNVRFDPSTSFFVR
IMRDKKGNHRLDTKGRITFGLQINHRITVGKTKSEINIGDRLLAFDQNQSENHTFAIMQRVEENTPNSHQFNGWNI
```

TABLE 4-continued

Amino Acid Sequences of Representative CLUST.029130 (Type V-I) Effector Proteins

```
RVLETGKVVSMTKGIESYYDQLSYDGVPYETKKFEDWRNERKAFVKKNKDIVIKEEKTFGQMFAEIKKSSLYKWNL
SYLKILRMAIRAKSGDTVSLFREELISIAKNRFGPLGLGSLSASSLKMLGAFCGVIQSYTKVLNCLDDKDKSNFDS
ELYFYLVSAFEKRVFKRNEKTSRASSFIMAMAYNHGCKMIVCEDDLPTAGAGANKRQNSDRMDWCARSLAQKIKTG
CEAMSIAYRAIPAYMSSHQDPLVHLADGKTSVLCPRFALVSKDDIKQYQLDGMRRMLNSKSKIGTAVYYRAAVELL
CKELGINKTDIAKGKLSVSQFADIVNGEILLPQRGGRVYLATKELTNGAKLVSYNGSDVWLSNADEIAAINIGMFV
VCTQTGVFGKKKKKDEQDGDIEIA (SEQ ID NO: 15)
```

>SRR2179954_megahit_k177_1417524_4|M
[SRR2179954]
```
MASISRPYGTKLRPDARKKEMLDKFFNTLTKGQRVFADLALCIYGSLTLEMAKSLEPESDSELVCAIGWFRLVDKT
IWSKDGIKQENLVKQYEAYSGKEASEVVKTYLNSPSSDKYVWIDCRQKFLRFQRELGTRNLSEDFECMLFEQYIRL
TKGEIEGYAAISNMFGNGEKEDRSKKRMYATRMKDWLEANENITWEQYREALKNQLNAKNLEQVVANYKGNAGGAD
PFFKYSFSKEGMVSKKEHAQQLDKFKTVLKNKARDLNFPNKEKLKQYLEAEIGIPVDANVYSQMFSNGVSEVQPKT
TRNMSFSNEKLDLLTELKDLNKGDGFEYAREVLNGFFDSELHTTEDKFNITSRYLGGDKSNRLSKLYKIWKKEGVD
CEEGIQQFCEAVKDKMGQIPIRNVLKRYLWQFRETVSAEDFEAAAKANHLEEKISRVKAHPIVISNRYWAFGTSALV
GNIMPADKRHQGEYAGQNFKMWLEAELHYDGKKAKHHLPFYNARFFEEVYCYHPSVAEITPFKTKQFGCEIGKDIP
DYVSVALKDNPYKKATKRILRAIYNPVANTTGVDKTTNCSFMIKRENDEYKLVINRKISVDRPKRIEVGRTIMGYD
RNQTASDTYWIGRLVPPGTRGAYRIGEWSVQYIKSGPVLSSTQGVNNSTTDQLVYNGMPSSSERFKAWKKARMAFI
RKLIRQLNDEGLESKGQDYIPENPSSFDVRGETLYVFNSNYLKALVSKHRKAKKPVEGILDEIEAWTSKDKDSCSL
MRLSSLSDASMQGIASLKSLINSYFNKNGCKTIEDKEKFNPVLYAKLVEVEQRRTNKRSEKVGRIAGSLEQLALLN
GVEVVIGEADLGEVEKGKSKKQNSRNMDWCAKQVAQRLEYKLAFHGIGYFGVNPMYTSHQDPFEHRRVADHIVMRA
RFEEVNVENIAEWHVRNFSNYLRADSGTGLYYKQATMDFLKHYGLEEHAEGLENKKIKFYDFRKILEDKNLTSVII
PKRGGRIYMATNPVTSDSTPITYAGKTYNRCNADEVAAANIVISVLAPRSKKNEEQDDIPLITKKAESKSPPKDRK
RSKTSQLPQK (SEQ ID NO: 16)
```

>SRR6475631_megahit_k177_2773783_7|M
[SRR6475631]
```
MVSDSTIRPYTSKLAPNDPKRKMLNDTFNWLDHAYKVFFDVSVALFGGIDYEAAEELIDEKSTFDADLLCAIMWFR
LEEKSNNPGPLQTTEQRTRLFQKYSGHEPSSFAQEYIKGNTDTEKYEWVDCRLKFADLARNIHTTQESLKTDAYTL
FMNKLIPVSKDDEFNAYGFISQLFGTGKKEDRSVKASMLEEISNIIEDKKPNTWEEYQDLIKKTFNVSNYKELKEK
LSAGSSGRDGSLVIDLKEEKTGLLQPNFIKNRIVKFREDADKKRTVFSLPNRMKLREFISSQIGPFEQNSWSAVLN
RSMAAIQSKNSSNILYTNQKQERNNEIQELLKEDILSAASILNDFRRGEFNSSVVSKNHLGSRLNELFEMWQALKM
NDGIEKYTDLCKDNFSRRPVSALLQYIYPYFDKITAKQFLDAASYNTLVETNNRKKIHPTVTGPTVCNWGPKSTIN
GSITPPNQMVKDRPAGSHGMIWVTMTVRDNGRWVKHHLPFHNSRYYEEHYCYREGLPTKNQPRTKQLGTQVGSIIS
APSLAILKSQEEQDRRNDRKSRFKAHKSIIRSQENIKYNVAPDKSTNFDVTRKNGEFFITISSRVTTPKYSHKLNV
GDIIMGLDNNQTAPCTYSIWRIVEKDTEGSFFHNKIWLQLVTDGKITSIVDNNRQVDQLSYAGVEYSNFAEWRKDR
RQFLRSINEDYVKKSDNWLNMNLYQWNAEYSRLLLGVMKDNKDKNIQNTFRAEIEELICGKFGIRLGSLSHHSLQF
LTNCKSLISSYFMLNNKKEEHDQESFDSDFFRLMRSIDDKRIRKRKEKSSRISSSVLQIARENNVKSLCVEGDLPT
ATKKTKPKQNQKSIDWCARAVVKKLNDGCKVLGINLQAIDPRDTSHLDPFVYYGKKSTKVGKEARYVIVEPSNIKE
YMTKKFTDWHRGVSKKSKKGDVQTSTTAPLYQEALKQFADHYKLDFDSLPKMKEYELAKILEDHKQVIIPCRGGRA
YLSTYPITKDSSKINFNGRERWYNQSDVVAAVNIVLRGIRDEN (SEQ ID NO: 17)
```

>SRR6837575_megahit_k177_919599_7|M
[SRR6837575]
```
MPDPIKSYKSPIIIDPNNAHDVEKLDFLRETEVYLSNGTKCFMHVELSLLGGMNETLAKKIVSLETPKKEKKKKSN
KPSHKIELFLAICWFRLVKISKNESSVLPALLGNRFEKYFGAKATPEVMEYFSANYDEATYAWKDMREEFVSLKSK
LKVSEKDLISDIGSMINERYIGLKEGKPWGIISGLFGEGKKVDRSLKVELLKNVLEEIEKNPPKTKDQLAKMILKC
ADCKNGQEIHAKCGKIGRMSSVSNWADEVGSEKEIVLSFVKSKISQDLAKQSNERNWKCVNALKSYILSEIGNCED
QSSWSEMLNNSLSVIQSKTTRNYNFCIEQLEEKKNLNQNHRKFGTMIEDYFSSRFFTGENKFIICNFHVGDKDKVS
ALLASCEGLSEEELEEKIQNFCESQKQESKMPIPALLMYLNSLKDSITVDQMFQGILYNKIRDKIERQKLHPIVPN
NDSFDWGMSSKINGRIISPKEKAKHNAQNNRSLYDSGIWIEISVLKNKEWAKHHYKISNTRFVEEFYYPSSNDENS
LDQVERTGRNGENNPAKNNLSLEQVSNIKNAPKNRRRAIKRQMRVEAAHQQNVLPHVKWDDNYCITISKYGDKEVT
FISKKFKSKKSKEYVVFLGFDQNQTASHTFAAVQICDSKDENVIPYCGLFVKPLECGHITSVQKVKDRSIDQLSYS
GLPWKDFISWSQERKEFVSKWRMVEVKTRNGEKLDDLTVKINKLDENKHGLYAYNSKYFWYLKSIMRKKTKDELFE
IRKELLTVIKTGRLCVLRLSSLNHSSFLMLKNAKSAISCYFNNLLKGVSNDQEKYEADPEMFELRREVEAKRQNKC
MSKKNLISSQIVSKAIELRGNYGSVAIIGEDLSDYVPDKGKKSTQNANLLDWLSRGVANKVKQIANMHDNISFKDV
SPQWTSHQDSFVDRNPNSALRVREGSCDPEEMYEKDFESLIKFLKEDCGHYTNSMNDFLSHYGVSRKDMLEIKESA
FKILMKNILNKTGEKSLLYPKRGGRLYLATHKLGQCTRRTYNGVDFWECDADCVAAFNIALSGIRKYYGIKSEAVS
PV (SEQ ID NO: 18)
```

>SRR6837577_megahit_k177_410843_33|P
[SRR6837577]
SEQ ID NO: 18

>3300020508|Ga0208225_1000010_34|M
[3300020508]
```
MSNKEKNASETRKAYTTKMIPRSHDRMKLLGNFMDYLMDGTPIFFELWNQFGGGIDRDIISGTANKDKISDDLLLA
VNWFKVMPINSKPQGVSPSNLANLFQQYSGSEPDIQAQEYFASNFDTEKHQWKDMRVEYERLLAELQLSRSDMHHD
LKLMYKEKCIGLSLSTAHYITSVMFGTGAKNNRQTKHQFYSKVIQLLEESTQINSVEQLASIILKAGDCDSYRKLR
IRCSRKGATPSILKIVQDYELGTNHDDEVNVPSLIANLKEKLGRFEYECEWKCMEKIKAFLASKVGPYYLGSYSAM
LENALSPIKGMTTKNCKFVLKQIDAKNDIKYENEPFGKIVEGFFDSPYFESDTNVKWVLHPHHIGESNIKTLWEDL
NAIHSKYEEDIASLSEDKKEKRIKVYQGDVCQTINTYCEEVGKEAKTPLVQLLRYLYSRKDDIAVDKIIDGITFLS
KKHKVEKQKINPVIQKYPSFNFGNNSKLLGKIISPKDKLKHNLKCNRNQVDNYIWIEIKVLNTKTMRWEKHHYALS
STRFLEEVYYPATSENPPDALAARFRTKTNGYEGKPALSAEQIEQIRSAPVGLRKVKKRQMRLEAARQQNLLPRYT
WGKDFNINICKRGNNFEVTLATKVKKKKEKNYKVVLGYDANIVRKNTYAAIEAHANGDGVIDYNDLPVKPIESGFV
TVESQVRDKSYDQLSYNGVKLLYCKPHVESRRSFLEKYRNGTMKDNRGNNIQIDFMKDFEAIADDETSLYYFNMKY
CKLLQSSIRNHSSQAKEYREEIFELLRDGKLSVLKLSSLSNLSFVMFKVAKSLIGTYFGHLLKKPKNSKSDVKAPP
ITDEDKQKADPEMFALRLALEEKRLNKVKSKKEVIANKIVAKALELRDKYGPVLIKGENISDTTKKGKKSSTNSFL
```

TABLE 4-continued

Amino Acid Sequences of Representative CLUST.029130 (Type V-I) Effector Proteins

```
MDWLARGVANKVKEMVMMHQGLEFVEVNPNFTSHQDPFVHKNPENTFRARYSRCTPSELTEKNRKEILSFLSDKPS
KRPTNAYYNEGAMAFLATYGLKKNDVLGVSLEKFKQIMANILHQRSEDQLLFPSRGGMFYLATYKLDADATSVNWN
GKQFWVCNADLVAAYNVGLVDIQKDFKKK (SEQ ID NO: 3)
```

>3300002408|release|scaffold05697_22|M
[aquatic-freshwater]
```
MFTLLLSDISQQNFNKFLKNFFFTRNKTVVHCSSEIRHKGYRSNVMVSESTIRPYTSKLAPNDPKLKMLNDTFNWL
DHAYKVFFDVSVALFGAIEHETAQELIGEKSKFDADLLCAIMWFRLEEKSDNPGPLQTVEQRMRLFQKYSGHEPSS
FTQEYIKGNIDSEKYQWVDCRLKFIDLARNINTTQESLKIDAYTLFMNKLIPVSKDDEFNAYGLISQLFGTGKKED
RSIKASMLEEISNIIEDKKPNTWEEYHDLIKKTFNVDNYKELKEKLSAGSSGRDSSLVIDLKEEKTGLLQPNFIKN
RIVKFREDADKKRTVFLLPNRMKLREFIASQIGPFEQNSWSAVLNRSMAAIQSKNSSNILYTNEKEERNNEIQELL
KKDILSAASILGDFRRGEFNRSVVSKNHLGARLNELFEIWQELTMDDGIKKYVDLCKDKFSRRPVKALLQYIYPYF
DKINAKQFLDAASYNTLVETNNRKKIHPTVTGPTVCNWGPKSTINGSITPPNQMVKGRPAGSHGMIWVTMTVIDNG
RWIKHHLPFHNSRYYEEHYCYREGLPTKNKPRTKQLGTQVGSTISAPSLAILKSQEEQDRRNDRKNRFKAHKSIIR
SQENIEYNVAFDKSTNFDVTRKNGEFFITISSRVATPKYSYKLNIGDMIMGLDNNQTAPCTYSIWRVVEKDTEGSF
FHNKIWLQLVTDGKVTSIVDNNRQVDQLSYAGIEYSNFAEWRKDRRQFLRSINEDYVKKSDNWRNMNLYQWNAEYS
RLLLLDVMKENKGKNIQNTFRAEIEELICGKFGIRLGSLFHHSLQFLTNCKSLISSYFMLNNKKEEYDQELFDSDFF
RLMKSIGDKRVRKRKEKSSRISSTVLQIARENNVKSLCVEGYLPTSTKKTKPKQNQKSIDWCARAVVKKLNDGCKV
LGINLQAIDPRDTSHLDPFVYYGKKSTKVGKEARYTIVEPSNIKEYMTNRFDDWHRGVTKKSKKGDVQTSTTVLLY
QEALRQFASHYKLDFDSLPKMKFYELAKILGDHEKVIIPCRGGRAYLSTYPVTKDSSKITFNGRERWYNESDVVAA
VNIVLRGIIDEDEQPDGAKKQALARTK (SEQ ID NO: 2)
```

>3300002408|release|scaffold05697_22|P
[aquatic-freshwater]
```
MVSESTIRPYTSKLAPNDPKLKMLNDTFNWLDHAYKVFFDVSVALFGAIEHETAQELIGEKSKFDADLLCAIMWFR
LEEKSDNPGPLQTVEQRMRLFQKYSGHEPSSFTQEYIKGNIDSEKYQWVDCRLKFIDLARNINTTQESLKIDAYTL
FMNKLIPVSKDDEFNAYGLISQLFGTGKKEDRSIKASMLEEISNIIEDKKPNTWEEYHDLIKKTFNVDNYKELKEK
LSAGSSGRDSSLVIDLKEEKTGLLQPNFIKNRIVKFREDADKKRTVFLLPNRMKLREFIASQIGPFEQNSWSAVLN
RSMAAIQSKNSSNILYTNEKEERNNEIQELLKKDILSAASILGDFRRGEFNRSVVSKNHLGARLNELFEIWQELTM
DDGIKKYVDLCKDKFSRRPVKALLQYIYPYFDKINAKQFLDAASYNTLVETNNRKKIHPTVTGPTVCNWGPKSTIN
GSITPPNQMVKGRPAGSHGMIWVTMTVIDNGRWIKHHLPFHNSRYYEEHYCYREGLPTKNKPRTKQLGTQVGSTIS
APSLAILKSQEEQDRRNDRKNRFKAHKSIIRSQENIEYNVAFDKSTNFDVTRKNGEFFITISSRVATPKYSYKLNI
GDMIMGLDNNQTAPCTYSIWRVVEKDTEGSFFHNKIWLQLVTDGKVTSIVDNNRQVDQLSYAGIEYSNFAEWRKDR
RQFLRSINEDYVKKSDNWRNMNLYQWNAEYSRLLLLDVMKENKGKNIQNTFRAEIEELICGKFGIRLGSLFHHSLQF
LTNCKSLISSYFMLNNKKEEYDQELFDSDFFRLMKSIGDKRVRKRKEKSSRISSTVLQIARENNVKSLCVEGYLPT
STKKTKPKQNQKSIDWCARAVVKKLNDGCKVLGINLQAIDPRDTSHLDPFVYYGKKSTKVGKEARYTIVEPSNIKE
YMTNRFDDWHRGVTKKSKKGDVQTSTTVLLYQEALRQFASHYKLDFDSLPKMKFYELAKILGDHEKVIIPCRGGRA
YLSTYPVTKDSSKITFNGRERWYNESDVVAAVNIVLRGIIDEDEQPDGAKKQALARTK (SEQ ID NO: 1)
```

>3300002408|release|scaffold08426_1|P
aquatic-freshwater
SEQ ID NO: 3

>3300028569|Ga0247843_1000055_230|M
[aquatic-freshwater]
```
MPRNYFLGIFSLQKNKSVVHCSVEIRHKGYRSSVMVSDSTIRPYASKLAPNDPKLKMLNDTFNWLDHAYKVFFDVS
VALFGAIEHETAQELIGEKSKFDADLICAIMWFRLEEKSDNPGPLQTVEQRMRLFQKYSGHEPSSFTQEYIKGNID
SEKYEWVDCRLKFIDLARNINTTQESLKIDAYTLFMNKLIPVSKDDEFNAYGLISQLFGTGKKEDRSIKAAMLEEI
SNILADKKPDTWEEYHDLIKKNFNVDNYKELKEKLSAGSSGRDSSLVIDLKEEKTGLLQPNFIKNRIVKFREDADK
KKTVFLLPNRMKLREFIASQIGPFEQNSWSAVLNRSMAAIQSKNSSNILYTNEKEERNNEIQELLKKDILSAASIL
GDFRRGEFNRSVVSKNHLGARLNELFEIWQDLTMDDGIRKYVDLCKDKFSRRPVKALLQYIYPYFDKITAKQFLDA
ASYNTLVETNNRKKIHPTVTGPTVCNWGPKSTINGSITPPNQMVTMTVIDNGRWIKHHLPFYN
SRYYEEHYCYREGLPTKNQPRTKQLGTQVGSTISATSLAALKSQEEQDRRNDRKNRFKAHKSIIRSQENIEYNVAF
DKSTNFDVTRKNGEFFITISSRVATPKYSYKLNIGDMIMGLDNNQTAPCTYSIWRVVEKDTEGSFFHNKIWLQLVT
DGKITSIVDNNRQVDQLSYAGIEYSNFAEWRKDRRQFLRSINEDYVKKSDNWRNMNLYQWNAEYSRLLLLDVMKENK
GKNIQNTFRAEIEELICGKFGIRLGSLFHHSLQFLTNCKSLISSYFMLNNKKEEYDQELFDSDFFRLMKSIGDKRV
RKRKEKSSRISSTVLQIARENNIKSLCVEGDLPTATKKTKPKQNQKSIDWCARAVVKKLNDGCKVLGINLQAIDPR
DTSHLDPFVYYGKKSTKVGKEARYTIVEPSNIKEYMTNRFDDWHRGVTKKSKKGDVQTSTTVLLYQEALRQFASHY
ELDFDSLPKMKFYDLAKRLGDHEKVIIPCRGGRAYLSTYPVTKDSSKITFNGRERWYNESDVVAAVNIVLRGIRDE
DEQPDDAKKQALARTK (SEQ ID NO: 11)
```

>3300028569|Ga0247843_1000055_232|P
[aquatic-freshwater]
```
MVSDSTIRPYASKLAPNDPKLKMLNDTFNWLDHAYKVFFDVSVALFGAIEHETAQELIGEKSKFDADLICAIMWFR
LEEKSDNPGPLQTVEQRMRLFQKYSGHEPSSFTQEYIKGNIDSEKYEWVDCRLKFIDLARNINTTQESLKIDAYTL
FMNKLIPVSKDDEFNAYGLISQLFGTGKKEDRSIKAAMLEEISNILADKKPDTWEEYHDLIKKNFNVDNYKELKEK
LSAGSSGRDSSLVIDLKEEKTGLLQPNFIKNRIVKFREDADKKKTVFLLPNRMKLREFIASQIGPFEQNSWSAVLN
RSMAAIQSKNSSNILYTNEKEERNNEIQELLKKDILSAASILGDFRRGEFNRSVVSKNHLGARLNELFEIWQDLTM
DDGIRKYVDLCKDKFSRRPVKALLQYIYPYFDKITAKQFLDAASYNTLVETNNRKKIHPTVTGPTVCNWGPKSTIN
GSITPPNQMVKGRPAGSHGMIWVTMTVIDNGRWIKHHLPFYNSRYYEEHYCYREGLPTKNQPRTKQLGTQVGSTIS
ATSLAALKSQEEQDRRNDRKNRFKAHKSIIRSQENIEYNVAFDKSTNFDVTRKNGEFFITISSRVATPKYSYKLNI
GDMIMGLDNNQTAPCTYSIWRVVEKDTEGSFFHNKIWLQLVTDGKITSIVDNNRQVDQLSYAGIEYSNFAEWRKDR
RQFLRSINEDYVKKSDNWRNMNLYQWNAEYSRLLLLDVMKENKGKNIQNTFRAEIEELICGKFGIRLGSLFHHSLQF
LTNCKSLISSYFMLNNKKEEYDQELFDSDFFRLMKSIGDKRVRKRKEKSSRISSTVLQIARENNIKSLCVEGDLPT
ATKKTKPKQNQKSIDWCARAVVKKLNDGCKVLGINLQAIDPRDTSHLDPFVYYGKKSTKVGKEARYTIVEPSNIKE
YMTNRFDDWHRGVTKKSKKGDVQTSTTVLLYQEALRQFASHYELDFDSLPKMKFYDLAKRLGDHEKVIIPCRGGRA
YLSTYPVTKDSSKITFNGRERWYNESDVVAAVNIVLRGIRDEDEQPDDAKKQALARTK (SEQ ID NO: 12)
```

TABLE 4-continued

Amino Acid Sequences of Representative CLUST.029130 (Type V-I) Effector Proteins >3300028571|Ga0247844_1000101_90|M
[aquatic-freshwater]
SEQ ID NO: 11

>3300028571|Ga0247844_1000101_88|P
[aquatic-freshwater]
SEQ ID NO: 12

>3300009183|Ga0114974_10028552_1|M
[aquatic-freshwater-freshwater lake]
MMSDNIILPYNSKLAPDERKQRLLNDTFNWFDMCNEVFFDFVKNLYGGVKHEHLILVNFAEKPKKVSNSKKPKKKD
QEVNIHVEPNQAEWVDNACATFWFRLQAKSTVQLDQSVQTAEERIRRFRDYAGHEPSSFAKSYLNGNYDPEKTEWV
DCRLLYVNFCRNLNVNLDADIRTMVEHNLLPVLPGQDFKTNNVFSNIFGVGNKEDKGQKTNWLNTVSEGLQSKEIW
NWDEYRDLISRSTGCSTAAELRSESIGRPSMLAVDFASEKSGQISQEWLAERVKSFRAAASQKSKIYDMPNRLVLK
EYIASKIGPFKLERWSAAAVSAYKDVRSKNSINLLYSKERLWRCKEIAQILVDNTQVAEAQQILVNYSSGDTNSFT
VENRHMGDLTVLFKIWEKMDMDSGIEQYSEIYRDEYSRDPITELLRYLYNHRHISAKTFRAAARLNSLLLKNDRKK
IHPTISGRTSVSFGHSTIKGCITPPDHIVKNRKENAGSTGMIWVTMQLIDNGRWADHHIPFHNSRYYRDFYAYRAD
LPTISDPRRKSFGHRIGNNISDTRMINHDCKKASKMYLRTIQNMTHNVAFDQQTQFAVRRYADNNFTITIQARVVG
RKYKKEISVGDRVMGVDQNQTTSNTYSVWEVVAEGTENSYPYKGNNYRLVEDGFIRSECSGRDQLSYDGLDFQDFA
QWRRERYAFLSSVGCILNDEIEPQIPVSAEKAKKKKKFSKWRGCSLYSWNLCYAYYLKGLMHENLANNPAGFRQEI
LNFIQGSRGVRLCSLNHTSFRLLSKAKSLIHSFFGLNNIKDPESQRDFDPEIYDIMVNLTQRKTNKRKEKANRITS
SILQIANRLNVSRIVIENDLPNASSKNKASANQRATDWCARNVSEKLEYACKMLGISLWQIDPRDTSHLDPFVVGK
EARFMKIKVSDINEYTISNFKKWHANIATTSTTAPLYHDALKAFSSHYGIDWDNLPEMKFWELKNALKDHKEVFIP
NRGGRCYLSTLPVTSTSEKIVFNGRERWLNASDIVAGVNIVLRSV (SEQ ID NO: 4)

>3300010885|Ga0133913_10053227_5|M
[aquatic-freshwater-freshwater lake]
MVSESTIRPYTSKLAPNDSKLKMLNDTFNWLDHAYKVFFDVSVALFGAIEHETAQELIGEKSKFDADLLCAIMWFR
LEEKSDNPGPLQTVEQRMRLFQKYSGHEPSSFTQEYIKGNIDSEKYQWVDCRLKFIDLARNINTTQESLKIDAYTL
FMNKLIPVSKDDEFNAYGLISQLFGTGKKEDRSIKASMLEEISNILADKNPNTWEYQDLIKKTFNVDNYKELKEK
LSAGSSGRDGSLVIDLKEEKTGLLQPNFIKNRIVKFREDADKKRTVFLLPNRMKLREFIASQIGPFEQNSWSAVLN
RSMAAIQSKNSSNILYTNEKEERNNEIQELLKKDILSAASILGDFRRGEFNRSVVSKNHLGARLNELFEIWQELTM
DDGIKKYVDLCKDKFSRRPVKALLQYIYPYFDKINAKQFLDAASYNTLVETNNRKKIHPTVTGPTVCNWGPKSTIN
GSITPPNQMVKGRPAGSHGMIWVTMTVIDNGRWIKHHLPFHNSRYYEEHYCYREGLPTKNKPRTKQLGTQVGSTIS
APSLAILKSQEEQDRRNDRKNRFKAHKSIIRSQENIEYNVAFDKSTNFDVTRKNGEFFITISSRVATPKYSYKLNI
GDMIMGLDNNQTAPCTYSIWRVVEKDTEGSFFHNKIWLQLVTDGKVTSIVDNNRQVDQLSYAGIEYSNFAEWRKDR
RQFLRSINEDYVKKSDNWRNMNLYQWNAEYSRLLLDVMKENKGKNIQNTFRAEIEELICGKFGIRLGSLFHHSLQF
LTNCKSLISSYFMLNNKKEEYDQELFDSDFFRLMKSIGDKRVRKRKEKSSRISSTVLQIARENNVKSLCVEGYLPT
STKKTKPKQNQKSIDWCARAVVKKLNDGCKVLGIYLQAIDPRDTSHLDPFVYYGKKSTKVGKEARHTIVEPSNIKE
YMTNRFDDWHRGVTKKSKKGDVQTSTTVLLYQEALRQFASHYKLDFDSLPKMKFYELAKILGDHEKVIIPCRGGRA
YLSTYPVTKDSSKITFNGRERWYNESDVVAAVNIVLRGIIDEDEQPDGAKKQATTRRT (SEQ ID NO: 13)

>3300020193|Ga0194131_10013618_4|P
[aquatic-freshwater-freshwater lake]
MSSAIKSYKSVLRPNERKNQLLKSTIQCLEDGSAFFFKMLQGLFGGITPEIVRFSTEQEKQQQDIALWCAVNWFRP
VSQDSLTHTIASDNLVEKFEEYYGGTASDAIKQYFSASIGESYYWNDCRQQYYDLCRELGVEVSDLTHDLEILCRE
KCLAVATESNQNNSIISVLFGTGEKEDRSVKLRITKKILEAISNLKEIPKNVAPIQEIILNVAKATKETFRQVYAG
NLGAPSTLEKFIAKDGQKEFDLKKLQTDLKKVIRGKSKERDWCCQEELRSYVEQNTIQYDLWAWGEMFNKAHTALK
IKSTRNYNFAKQRLEQFKEIQSLNNLLVVKKLNDFFDSEFFSGEETYTICVHHLGGKDLSKLYKAWEDDPADPENA
IVVLCDDLKNNFKKEPIRNILRYIFTIRQECSAQDILAAAKYNQQLDRYKSQKANPSVLGNQGFTWTNAVILPEKA
QRNDRPNSLDLRIWLYLKLRHPDGRWKKHHIPFYDTRFFQEIYAAGNSPVDTCQFRTPRFGYHLPKLTDQTAIRVN
KKHVKAAKTEARIRLAIQQGTLPVSNLKITEISATINSKGQVRIPVKFDVGRQKGTLQIGDRFCGYDQNQTASHAY
SLWEVVKEGQYHKELGCFVRFISSGDIVSITENRGNQFDQLSYEGLAYPQYADWRKKASKFVSLWQITKKNKKKEI
VTVEAKEKFDAICKYQPRLYKFNKEYAYLLRDIVRGKSLVELQQIRQEIFRFIEQDCGVTRLGSLSLSTLETVKAV
KGIIYSYFSTALNASKNNPISDEQRKEFDPELFALLEKLELIRTRKKKQKVERIANSLIQTCLENNIKFIRGEGDL
STTNNATKKKANSRSMDWLARGVFNKIRQLAPMHNITLFGCGSLYTSHQDPLVHRNPDKAMKCRWAAIPVKDIGDW
VLRKLSQNLRAKNIGTGEYYHQGVKEFLSHYELQDLEEELLKWRSDRKSNIPCWVLQNRLAEKLGNKEAVVYIPVR
GGRIYFATHKVATGAVSIVFDQKQVWVCNADHVAAANIALTVKGIGEQSSDEENPDGSRIKLQLTS (SEQ ID
NO: 5)

>3300020214|Ga0194132_10015959_3|M
[aquatic-freshwater-freshwater lake]
SEQ ID NO: 5

TABLE 5A

Representative CLUST.029130 (Type V-I) Effector Proteins and DirectRepeats

| CLUST.201934 Effector Protein Accession | Direct Repeat Nucleotide Sequence |
|---|---|
| SRR1522973_megahit_k177_1081830_2\|M (SEQ ID NO: 11) | CTAGCAATGACCTAATAGTGTGTCCTTAGTTGACAT (SEQ ID NO: 19) |
| SRR1522973_megahit_k177_427371_1\|M (SEQ ID NO: 12) | CTAGCAATGACCTAATAGTGTGTCCTTAGTTGACAT (SEQ ID NO: 19) |
| SRR2179954_megahit_k177_1417524_4\|M (SEQ ID NO: 13) | TCTCAACGATAGTCAGACATGTGTCCTCAGTGACAC (SEQ ID NO: 20) |
| SRR6475631_megahit_k177_2773783_7\|M (SEQ ID NO: 14) | CCTACAATACCTAAGAAATCCGTCCTAAGTTGACGG (SEQ ID NO: 21) |
| SRR6837575_megahit_k177_919599_7\|M (SEQ ID NO: 15) | GTAGCAATCAGTACATATTGTGCCTTTCATTGGCACA (SEQ ID NO: 22) |
| SRR6837577_megahit_k177_410843_33\|P (SEQ ID NO: 15) | GTAGCAATCAGTACATATTGTGCCTTTCATTGGCAC (SEQ ID NO: 23) |
| 3300020508\|Ga0208225_1000010_34\|M (SEQ ID NO: 3) | GTTGGAATGACTAATTTTTGTGCCCACCGTTGGCAC (SEQ ID NO: 24) |
| 3300002408\|release\|scaffold05697_22\|M (SEQ ID NO: 2) | CCCACAATACCTGAGAAATCCGTCCTACGTTGACGG (SEQ ID NO: 6) |
| 3300002408\|release\|scaffold05697_22\|P (SEQ ID NO: 1) | CCCACAATACCTGAGAAATCCGTCCTACGTTGACGG (SEQ ID NO: 6) |
| 3300002408\|release\|scaffold08426_1\|P (SEQ ID NO: 3) | AATTTTTGTGCCCATCGTTGGCAC (SEQ ID NO: 7) |
| 3300028569\|Ga0247843_1000055_230\|M (SEQ ID NO: 16) | CCCACAATACCTGAGAAATCCGTCCTACGTTGACGG (SEQ ID NO: 6) |
| 3300028569\|Ga0247843_1000055_232\|P (SEQ ID NO: 17) | CCCACAATACCTGAGAAATCCGTCCTACGTTGACGG (SEQ ID NO: 6) |
| 3300028571\|Ga0247844_1000101_90\|M (SEQ ID NO: 16) | CCCACAATACCTGAGAAATCCGTCCTACGTTGACGG (SEQ ID NO: 6) |
| 3300028571\|Ga0247844_1000101_88\|P (SEQ ID NO: 17) | CCCACAATACCTGAGAAATCCGTCCTACGTTGACGG (SEQ ID NO: 6) |
| 3300009183\|Ga0114974_10028552_1\|M (SEQ ID NO: 4) | CTCTCAATGCCTTAGAAATCCGTCCTTGGTTGACGG (SEQ ID NO: 8) |
| 3300010885\|Ga0133913_10053227_5\|M (SEQ ID NO: 18) | CCCACAATACCTGAGAAATCCGTCCTACGTTGACGG (SEQ ID NO: 6) |
| 3300020193\|Ga0194131_10013618_4\|P (SEQ ID NO: 5) | GCAACACCTAAGAAATCCGTCTTTCATTGACGGG (SEQ ID NO: 9) |
| 3300020214\|Ga0194132_10015959_3\|M (SEQ ID NO: 5) | GTTGCAAAACCCAAGAAATCCGTCTTTCATTGACGG (SEQ ID NO: 10) |

TABLE 5B

Example CLUST.029130 (TypeV-I) pre-crRNA sequences

| Effector Accession | Example pre-crRNA sequence | Spacer Lens 1 | Spacer Lens 2 | Spacer Lens 3 |
|---|---|---|---|---|
| SRR1522973_megahit_ k177_1081830_ 2\|M (SEQ ID NO: 11) | CUAGCAAUGACCUAAUAGUGUGUCCUUAGUUGACAUNNNN NNNNNNNNNNNNNNNNNNNNNNNNNNNNNNNCUAGCAAUGA CCUAAUAGUGUGUCCUUAGUUGACAU (SEQ ID NO: 150) | 34-36 | 33-37 | 20-41 |
| SRR1522973_megahit_ k177_427371_ 1\|M (SEQ ID NO: 12) | CUAGCAAUGACCUAAUAGUGUGUCCUUAGUUGACAUNNNN NNNNNNNNNNNNNNNNNNNNNNNNNNNNNNNCUAGCAAUG ACCUAAUAGUGUGUCCUUAGUUGACAU (SEQ ID NO: 151) | 35-36 | 33-37 | 23-38 |

TABLE 5B-continued

Example CLUST.029130 (TypeV-I) pre-crRNA sequences

| Effector Accession | Example pre-crRNA sequence | Spacer Lens 1 | Spacer Lens 2 | Spacer Lens 3 |
|---|---|---|---|---|
| SRR2179954_megahit_ k177_1417524_ 4\|M (SEQ ID NO: 13) | UCUCAACGAUAGUCAGACAUGUGUCCUCAGUGACACNNNN NNNNNNNNNNNNNNNNNNNNNNNNNNNNNNNNUCUCAACG AUAGUCAGACAUGUGUCCUCAGUGACAC (SEQ ID NO: 152) | 36-45 | 36-51 | 36-59 |
| SRR6475631_megahit_ k177_2773783_ 7\|M (SEQ ID NO: 14) | CCUACAAUACCUAAGAAAUCCGUCCUAAGUUGACGGNNNN NNNNNNNNNNNNNNNNNNNNNNNNNNNNNNNNCCUACAAUA CCUAAGAAAUCCGUCCUAAGUUGACGG (SEQ ID NO: 153) | 35-38 | 27-44 | 21-47 |
| SRR6837575_megahit_ k177_919599_ 7\|M (SEQ ID NO: 15) | GUAGCAAUCAGUACAUAUUGUGCCUUUCAUUGGCACANNN NNNNNNNNNNNNNNNNNNNNNNNNNNNNNNNGUAGCAAUCA GUACAUAUUGUGCCUUUCAUUGGCACA (SEQ ID NO: 154) | 33-34 | 30-35 | 26-36 |
| SRR6837577_megahit_ k177_410843_ 33\|P (SEQ ID NO: 15) | GUAGCAAUCAGUACAUAUUGUGCCUUUCAUUGGCACNNNN NNNNNNNNNNNNNNNNNNNNNNNNNNNNNNNGUAGCAAUCA GUACAUAUUGUGCCUUUCAUUGGCAC (SEQ ID NO: 155) | 34-37 | 27-38 | 20-42 |
| 3300020508\| Ga0208225_1000010_ 34\|M (SEQ ID NO: 3) | GUUGGAAUGACUAAUUUUUGUGCCCACCGUUGGCACNNNN NNNNNNNNNNNNNNNNNNNNNNNNNNNNNNNNNGUUGGAAU GACUAAUUUUUGUGCCCACCGUUGGCAC (SEQ ID NO: 156) | 36-38 | 35-43 | 28-47 |
| 3300002408\|release\| scaffold08426_ 1\|P (SEQ ID NO: 3) | AAUUUUUGUGCCCAUCGUUGGCACNNNNNNNNNNNNNNNNN NNNNNNNNNNNNNNNNNNNNNAAUUUUUGUGCCCAUCGUUG GCAC (SEQ ID NO: 157) | 36-38 | 36-42 | 28-47 |
| 3300028569\|Ga0247843_ 1000055_230\|M (SEQ ID NO: 16) | CCCACAAUACCUGAGAAAUCCGUCCUACGUUGACGGNNNN NNNNNNNNNNNNNNNNNNNNNNNNNNNNNNNNCCCACAAU ACCUGAGAAAUCCGUCCUACGUUGACGG (SEQ ID NO: 158) | 36-37 | 20-38 | 19-41 |
| 3300028569\|Ga0247843_ 1000055_232\|P (SEQ ID NO: 17) | CCCACAAUACCUGAGAAAUCCGUCCUACGUUGACGGNNNN NNNNNNNNNNNNNNNNNNNNNNNNNNNNNNNNCCCACAAU ACCUGAGAAAUCCGUCCUACGUUGACGG (SEQ ID NO: 159) | 36-37 | 20-38 | 19-41 |
| 3300009183\|Ga0114974_ 10028552_1\|M (SEQ ID NO: 4) | CUCUCAAUGCCUUAGAAAUCCGUCCUUGGUUGACGGNNNN NNNNNNNNNNNNNNNNNNNNNNNNNNNNNNNNCUCUCAAU GCCUUAGAAAUCCGUCCUUGGUUGACGG (SEQ ID NO: 160) | 36-37 | 36-40 | 36-46 |
| 3300010885\|Ga0133913_ 10053227_5\|M (SEQ ID NO: 18) | CCCACAAUACCUGAGAAAUCCGUCCUACGUUGACGGNNNN NNNNNNNNNNNNNNNNNNNNNNNNNNNNNNNNCCCACAAUAC CUGAGAAAUCCGUCCUACGUUGACGG (SEQ ID NO: 161) | 34-37 | 26-38 | 19-39 NO: |
| 3300020193\|Ga0194131_ 10013618_4\|P (SEQ ID NO: 5) | GCAACACCUAAGAAAUCCGUCUUUCAUUGACGGGNNNNNN NNNNNNNNNNNNNNNNNNGCAACACCUAAGAAAUCCGUCU UUCAUUGACGGG (SEQ ID NO: 162) | 24-25 | 21-26 | 20-33 |
| 3300020214_Ga0194132_ 10015959_3\|M (SEQ ID NO: 5) | GUUGCAAAACCCAAGAAAUCCGUCUUUCAUUGACGGNNNN NNNNNNNNNNNNNNNNNNNNNNNNNNNNNNGUUGCAAAACCCA AGAAAUCCGUCUUUCAUUGACGG (SEQ ID NO: 163) | 31-33 | 29-35 | 20-47 |

Example 2: In Vivo Bacterial Validation of Engineered CLUST.029130 (Type V-I) CRISPR-Cas Systems (FIGS. 4A-10B)

Having identified the minimal components of Type V-I CRISPR-Cas systems, we selected two systems for functional validation, one comprising the effector designated Cas12i1 (SEQ ID NO: 3), and the other comprising the effector designated Cas12i2 (SEQ ID NO: 5).
Methods
Gene Synthesis and Oligo Library Cloning
The *E. coli* codon-optimized protein sequences for CRISPR effectors, accessory proteins were cloned into pET-28a(+) (EMD MILLIPORE™) to create the Effector Plasmid. Noncoding sequences flanking Cas genes (including 150 nt of terminal CDS coding sequence) or the CRISPR array were synthesized (GENSCRIPT™) into pACYC184 (NEW ENGLAND BIOLABS™) to create the Non-coding Plasmid (FIG. 4A). Effector mutants (e.g., D513A or A513D) plasmids were cloned by site directed mutagenesis using the indicated primers in the sequence table: sequence changes were first introduced into PCR fragments, which were then re-assembled into a plasmid using NEBuilder HiFi DNA Assembly Master Mix or NEB™ Gibson Assembly Master Mix (NEW ENGLAND BIOLABS™) following the manufacturer's instructions.

For the pooled spacer library, we first computationally designed an oligonucleotide library synthesis (OLS) pool (AGILENT™) to express a minimal CRISPR array of "repeat-spacer-repeat" sequences. The "repeat" elements were derived from the consensus direct repeat sequence found in the CRISPR array associated with the effector, and "spacer" represents ~8,900 sequences targeting the pACYC184 plasmid and *E. coli* essential genes, or negative control non-targeting sequences. The spacer length was determined by the mode of the spacer lengths found in the endogenous CRISPR array. Flanking the minimal CRISPR array were unique PCR priming sites that enabled amplification of a specific library from a larger pool of oligo synthesis.

We next cloned the minimal CRISPR array library into the Effector Plasmid to create an Effector Plasmid library. We appended flanking restriction sites, a unique molecular identifier, and a J23119 promoter for array expression onto the oligo library using PCR (NEBNEXT™ High-Fidelity 2×PCR Master Mix), and then used NEB™ Golden Gate Assembly Master Mix (NEW ENGLAND BIOLABS™) to assemble the full plasmid library of effectors with their targeting arrays. This represented the "input library" for the screen.

In Vivo *E. coli* Screen

We performed the in vivo screen using electrocompetent E. CLONI™ EXPRESS BL21 (DE3) *E. coli* cells (LUCIGEN™), unless otherwise indicated. Competent cells were co-transformed with the Effector Plasmid and/or Non-coding (FIG. 4B). The cells were electroporated with the "input library" according to the manufacturer's protocols using a GENE PULSER™ Xcell® (BIO-RAD™) with a 1.0 mm cuvette. The cells were plated onto bioassay plates containing both Chloramphenicol (Fisher) and Kanamycin (ALFA AESAR™), and grown for 11 hours, after which we estimated the approximate colony count to ensure sufficient library representation and harvested the cells.

Plasmid DNA fractions were extracted from the harvested cells to create the 'output library' using a QIAPREP® Spin Miniprep Kit (QIAGEN™), while total RNA=17 nt was harvested by lysing the harvested cells in DIRECT-ZOL® (ZYMO RESEARCH™), followed by extraction using the DIRECT-ZOL™ RNA miniprep kit (ZYMO RESEARCH™).

The next generation sequencing library for the DNA depletion signal was prepared by performing a PCR on both the input and output libraries, using custom primers flanking the CRISPR array cassette of the Effector Plasmid library and containing barcodes and handles compatible with ILLUMINA™ sequencing chemistry. This library was then normalized, pooled, and loaded onto a NEXTSEQ™ 550 (ILLUMINA™) to evaluate the activity of the effectors.

Bacterial Screen Sequencing Analysis

Next generation sequencing data for screen input and output libraries were demultiplexed using ILLUMINA™ bcl2fastq. Reads in resulting fastq files for each sample contained the CRISPR array elements for the screening plasmid library. The direct repeat sequence of the CRISPR array was used to determine the array orientation, and the spacer sequence was mapped to the source (pACYC184 or *E. coli* essential genes) or negative control sequence (GFP) to determine the corresponding target. For each sample, the total number of reads for each unique array element ($r_a$) in a given plasmid library was counted and normalized as follows: $(r_a+1)$/total reads for all library array elements. The depletion score was calculated by dividing normalized output reads for a given array element by normalized input reads.

To identify specific parameters resulting in enzymatic activity and bacterial cell death, we used next generation sequencing (NGS) to quantify and compare the representation of individual CRISPR arrays (i.e., repeat-spacer-repeat) in the PCR product of the input and output plasmid libraries. We defined the fold depletion for each CRISPR array as the normalized input read count divided by the normalized output read count (with 1 added to avoid division by zero). An array was considered to be "strongly depleted" if the fold depletion was greater than 3. When calculating the array fold depletion across biological replicates, we took the maximum fold depletion value for a given CRISPR array across all experiments (i.e. a strongly depleted array must be strongly depleted in all biological replicates). We generated a matrix including array fold depletion and the following features for each spacer target: target strand, transcript targeting, ORI targeting, target sequence motifs, flanking sequence motifs, and target secondary structure. We investigated the degree to which different features in this matrix explained target depletion for Type V-I systems, thereby yielding a broad survey of functional parameters within a single screen.

Results

FIGS. 5A-D depict the location of strongly depleted targets for Cas12i1 and Cas12i2 targeting pACYC184 and *E. coli* E. CLONI® essential genes. Notably, the location of strongly depleted targets appears dispersed throughout the potential target space.

We found that dsDNA interference activities of the Type V-I effectors, Cas12i1 (1094aa), and Cas12i2 (1054aa), are abolished by mutation of the conserved aspartate in the RuvC I motif (FIGS. 6A, and 6B). The RuvC-dependent dsDNA interference activity of Cas12i shows no requirement for non-coding sequences flanking the CRISPR array or cas genes (FIGS. 7A and 7B), indicating that the minimal V-I interference module includes only the effector and crRNA (FIGS. 8A and 8B).

Analysis of the target-flanking sequences corresponding to strongly depleted arrays from in vivo screens show that dsDNA interference by Cas12i is PAM-dependent. Specifically, we found that Cas12i1 and Cas12i2 both showed a 5' TTN PAM preference (FIGS. 9A-B and 10A-B). These results suggest that the compact Cas 12i effectors are capable of autonomous PAM-dependent dsDNA interference.

Example 3: Biochemical Mechanistic Characterization of Engineered CLUST.029130 (Type V-I) CRISPR-Cas Systems (FIGS. 11A-13, 15-17B)

Cas12i Processes Pre-crRNAs In Vivo

To investigate crRNA biogenesis for Type V-I CRISPR-Cas systems, we purified and sequenced small RNAs from *E. coli* expressing Cas12i and the minimal CRISPR array library from the bacterial screen. FIGS. 11A and 11B show the pile-up of RNA-sequencing reads, showing a strong consensus form of the Cas12i1 and Cas12i2 mature crRNA, respectively, as well as a distribution of spacer lengths. The most common spacer length observed was 21, with length variation between 16 nt and 22 nt.

For the Type V-I CRISPR-Cas system containing Cas12i1, the mature crRNA can take the form 5'-AUUUUU-GUGCCCAUCGUUGGCAC[spacer]-3' (SEQ ID NO: 100).

For the Type V-I CRISPR-Cas system containing Cas12i2, the mature crRNA can take the form 5'-AGAAAUCCGUCUUUCAUUGACGG[spacer]-3' (SEQ ID NO: 101).

Sequencing the small RNA from the in vivo bacterial screen was performed by extracting total RNA from harvested bacteria using the DIRECT-ZOL™ RNA MiniPrep Plus with TRI Reagent (ZYMO RESEARCH™). Ribosomal RNA was removed using a Ribo-Zero rRNA Removal Kit for Bacteria, followed by cleanup using a RNA Clean and Concentrator-5 kit. The resultant ribosomal RNA depleted-total RNA was treated with T4 PNK for 3 hours without ATP to enrich for 3'-P ends, after which ATP was added and the reaction incubated for another hour to enrich for 5'-OH ends. The samples were then column purified, incubated with RNA 5' polyphosphatase (LUCIGEN™) and column purified again prior to preparation for next-generation sequencing using the NEBNEXT™ Multiplex Small RNA Library Prep Set for ILLUMINA™ (NEW ENGLAND BIOLABS™). The library was paired-end sequenced on a NEXTSEQ™ 550 (ILLUMINA™), and the resulting paired end alignments were analyzed using Geneious™ 11.0.2 (Biomatters).

Cas12i Effector Purification

Effector vectors were transformed into E. coli NiCo21 (DE3) (NEW ENGLAND BIOLABS™) and expressed under a T7 promoter. Transformed cells were initially grown overnight in 3 mL Luria Broth (SIGMA™)+50 µg/mL kanamycin, followed by inoculation of 1 L of Terrific Broth media (SIGMA™)+50 µg/mL kanamycin with 1 mL of overnight culture. Cells were grown at 37° C. until an OD600 of 1-1.5, then protein expression was induced with 0.2 mM IPTG. Cultures were then grown at 20° C. for an additional 14-18 hours. Cultures were harvested and pelleted via centrifugation, then resuspended in 80 mL of lysis buffer (50 mM HEPES pH 7.6, 0.5M NaCl, 10 mM imidazole, 14 mM 2-mercaptoethanol, and 5% glycerol)+ protease inhibitors (SIGMA™). Cells were lysed via cell disruptor (Constant System Limited), then centrifuged twice at 28,000×g for 20 minutes at 4° C. to clarify the lysate. The lysate was loaded onto a 5 mL HisTrap FF column (GE Life Sciences), then purified via FPLC (AKTA PURE™, GE Life Sciences) over an imidazole gradient from 10 mM to 250 mM. Cas12i1 was purified in low salt buffer (50 mM HEPES-KOH PH 7.8, 500 mM KCl, 10 mM MgCl2, 14 mM 2-mercaptoethanol, and 5% glycerol). After purification, fractions were run on SDS-PAGE gels and fractions containing protein of the appropriate size were pooled and concentrated using 10 kD AMICON™ Ultra-15 Centrifugal Units. Protein concentration was determined by Qubit protein assay (THERMO FISHER™).

Cas12i Processes Pre-crRNAs In Vitro

To determine whether Cas12i1 is capable of autonomous crRNA biogenesis, we incubated the effector protein purified from E. coli with a pre-crRNA expressed from a minimal CRISPR array (repeat-spacer-repeat-spacer-repeat). We observed that purified Cas12i1 processes the pre-crRNA into fragments matching the mature crRNAs identified from the in vivo small RNAseq, suggesting Cas12i1 is capable of autonomous pre-crRNA processing (FIG. 12).

Pre-crRNA processing assays for Cas12i1 were performed at 37° C. for 30 minutes in cleavage buffer at a final pre-cr-RNA concentration of 100 nM. The reaction was performed in optimized cleavage buffer (50 mM Tris-HCl pH 8.0, 50 mM NaCl, 1 mM DTT, 10 mM MgCl$_2$, 50 µg/ml BSA) for Cas12i. Reactions were quenched with the addition of 1 ug/uL of proteinase K (AMBION™) and incubated at 37° C. for 15 minutes. 50 mM EDTA was added to the reactions before mixing with equal volume of 2×TBE-Urea sample buffer (INVITROGEN™) and denaturing at 65° C. for 3 minutes. Samples were analyzed on 15% TBE-Urea gels (INVITROGEN™). Gels were stained for 5 minutes with SYBR Gold nucleic acid stain (INVITROGEN™) and imaged on Gel Doc EZ (BIO-RAD™). Gels containing labeled pre-crRNA were first imaged on Odyssey CLx scanner (LI-COR™ Biosciences) prior to SYBR staining.

Cas12i1 DNA Manipulation Using Strongly Depleted Arrays

To explore the mechanism of the interference activity of Cas12i1, we selected strongly depleted CRISPR array sequences from the in vivo negative selection screen and generated pre-crRNAs with the DR-spacer-DR-spacer-DR arrangement. The pre-crRNAs were designed to target Cas12i1 to 128 nt ssDNA and dsDNA substrates containing target sequences complementary to the second spacer of the pre-crRNA. We observed that Cas12i1 binary complex consisting of the effector protein and pre-crRNA cleaved 100 nM of target ssDNA to saturation at a 62.5 nM complex concentration (FIG. 13). Additional degradation of cleaved ssDNA to short fragments or single nucleotides was observed at increasing concentrations of the complex, suggestive of collateral ssDNA cleavage activated by binding of the binary complex to an ssDNA target (FIG. 13).

To explore the dsDNA interference activity of Cas12i, we targeted the Cas12i1 binary complex to target dsDNA substrates containing a 5' end label on the non-spacer-complementary strand. To assess both dsDNA cleavage and nicking activity comprehensively, the resulting dsDNA cleavage reactions were split into three fractions for different analyses. The first two fractions were quenched and analyzed by denaturing or nondenaturing gel electrophoresis conditions, respectively. The third fraction was treated with 0.1U of S1 nuclease to convert any dsDNA nicks to double-stranded breaks, quenched, and analyzed by nondenaturing gel electrophoresis.

We observed dose-dependent cleavage under denaturing conditions, suggestive of either target nicking or dsDNA cleavage (FIG. 15). Under non-denaturing conditions with no S1 nuclease treatment, we observed a dose-dependent increase in a primary product that migrated with slightly lower electrophoretic mobility than the input dsDNA, suggestive of a nicked dsDNA product (FIG. 16). When these products were incubated with S1 nuclease, the upward shifted band was converted to a smaller dsDNA product indicative of the S1-mediated conversion of nicked dsDNA to double-stranded breaks (FIG. 16). We also observed minor dsDNA cleavage products at high concentrations and incubation times, indicating that Cas12i1 is a dsDNA nuclease that cleaves the spacer complementary ("SC") and non-spacer complementary ("NSC") strands of target dsDNA with substantially different efficiencies (FIG. 17A).

The observation of nicking activity accompanying 5' labeling of the spacer complementary strand of dsDNA substrates suggests that Cas12i1 preferentially nicks the DNA strand opposing the crRNA-target DNA hybrid. To validate this bias in DNA strand cleavage by Cas12i1, we generated dsDNA substrates that were IR800 dye-labeled at either the 5' end of the spacer complementary or at the 5' end of the non-spacer complementary strand. At lower concentrations of the effector complex, we observed only cleavage of the NSC strand of the DNA duplex, whereas at higher concentrations of the effector complex, cleavage of both the NSC and the SC strand was observed (FIG. 17A-B). Comparing the SYBR stain labeling all nucleic acid products versus the strand-specific labeling using IR800 dye reveals a difference in the rate of stranded product formation versus the overall accumulation of cleavage products. These results suggest an ordered series of events leading to dsDNA interference, whereby the Cas12i1 binary complex first nicks the NSC strand and then cleaves the SC strand with a lower efficiency, resulting in dsDNA cleavage. Taken together, these findings indicate that Cas12i is an effector capable of autonomous pre-crRNA processing, ssDNA target and collateral cleavage, and dsDNA cleavage. This spectrum of catalytic activities closely parallels those of Cas12a and Cas12b except for the notable bias towards non-spacer complementary strand cleavage, resulting in preferential dsDNA nicking.

crRNA and Substrate RNA Preparation

Single stranded DNA oligo templates for crRNA and substrate RNA were ordered from IDT. Substrate RNA and pre-crRNA templates were PCR amplified to generate a double stranded in vitro transcription (IVT) template DNA using NEBNEXT Hifi 2× master mix (NEW ENGLAND BIOLABS™). Double stranded DNA templates for mature cr-RNA was generated by annealing T7 primer with templates followed by extension using DNA Polymerase I, Large (Klenow) Fragment (NEW ENGLAND BIO-LABS™). Annealing was performed by incubating for 5 min at 95° C. followed by a −5° C./min ramp down to 4° C. In vitro transcription was performed by incubating the dsDNA templates with T7 RNA polymerase at 37° C. for 3 hours using HISCRIBE™ T7 Quick High Yield RNA kit (NEW ENGLAND BIOLABS™). After incubation, IVT samples were treated with TURBO DNASE® (THERMO SCIENTIFIC™) and then purified using RNA Clean & Concentrator kit (ZYMO RESEARCH™). Mature cr-RNA generated from IVT was treated with Calf Intestinal Alkaline Phosphatase (THERMO FISHER™) or RNA 5'-polyphosphatase (LUCIGEN™) for 2 hours at 37° C. to generate 5'-hydroxyl or 5'-monophosphate, respectively, followed by clean up with RNA Clean & Concentrator kit (ZYMO RESEARCH™). Concentrations were measured via Nanodrop 2000 (THERMO FISHER™).

Pre-crRNA sequences used in biochemical characterization Cas12i are included in Table 6. Oligonucleotide templates and primers for preparation of crRNAs are included in Table 9.

Preparation of IR-800 Labeled Substrate RNA and DNA

RNA substrates from IVT were treated with Calf Intestinal Alkaline Phosphatase (THERMO FISHER™) for 30 minutes at 37° C. to convert the 5'-triphosphate to 5' terminal hydroxyl group and purified using RNA Clean & Concentrator kit (ZYMO RESEARCH™). A thiol end group was added to the 5' terminal hydroxyl group of the DNA and RNA substrates via 5' ENDTAG™ Labeling Kit (Vector Labs), then substrates were labeled with IRDye 800CW Maleimide (LI-COR™ Biosciences). Substrates were purified using DNA Clean & Concentrator kit or RNA Clean & Concentrator kit (ZYMO RESEARCH™). Labeled dsDNA substrates were generated by labeling the non-target (non-spacer complementary) ssDNA strand, annealing with a primer, then extending with DNA Polymerase I, Large (Klenow) Fragment (NEW ENGLAND BIOLABS™) for 15 minutes at 25° C. These substrates were purified with DNA Clean & Concentrator kit (ZYMO RESEARCH™). Concentrations were measured via Nanodrop 2000 (THERMO FISHER™).

RNA and DNA substrate sequences used in the biochemical characterization of Cas12i are included in Tables 7 and 8.

Target Cleavage Assays with Cas12i ssDNA: Cas12i target cleavage assays with ssDNA were performed in optimized cleavage buffer (50 mM Tris-HCl pH 8.0, 50 mM NaCl, 1 mM DTT, 10 mM MgCl2, 50 µg/ml BSA). Binary complex was formed by incubating a 1:2 molar ratio of Cas12i: pre-crRNA for 10 minutes at 37° C., followed by transfer to ice. All further complex dilutions were done on ice keeping the protein: RNA ratio fixed. The complex was added to 100 nM IR800 labeled substrates and incubated at 37° C. for 30 minutes. Reactions were treated with RNAse cocktail and proteinase K and analyzed as above.

dsDNA: dsDNA target cleavage assays were set up in the optimized cleavage buffer at 37° C. for 1 hour. Binary complex was formed as described above and added to 100 nM dsDNA substrate. Reactions were first treated with RNAse cocktail with incubation at 37° C. for 15 minutes. Next, they were treated with proteinase K with incubation at 37° C. for 15 minutes. To detect dsDNA cleavage products the reactions were analyzed with 15% TBE-Urea gel as described before. To detect nicking activity of Cas12i, reactions were SPRI purified after proteinase K treatment and split into three fractions. One fraction was analyzed on a 15% TBE-Urea gel as described above. Another fraction was mixed with 5× hi-density TBE sample buffer and analyzed on a non-denaturing 4-20% TBE gel to detect nicked dsDNA products. The last fraction was incubated with 0.01U/uL of S1 Nuclease (THERMO SCIENTIFIC™) at 50° C. for 1 hour to convert nicks into double stranded breaks followed by mixing with 5× hi-density TBE sample buffer and analyzed on a non-denaturing 4-20% TBE gel. All gels were imaged on Odyssey CLx scanner followed by a 5 minute SYBR stain and image on Gel Doc imager.

To identify the nicked strand, dsDNA was prepared by labeling either the target strand (complementary to crRNA) or the non-target strand (non-spacer complementary, same sequence as the crRNA). The cleavage reaction was performed as described. The labeled strands were then annealed with the corresponding primers and extended with DNA Polymerase I, Large (Klenow) Fragment (NEW ENGLAND BIOLABS™) for 15 minutes at 25° C. The dsDNA substrates were then purified using SPRI purification.

TABLE 6

| Pre-crRNAs used for CLUST.029130 (TypeV-I) invitro | | | | | | |
|---|---|---|---|---|---|---|
| Name | Sequence | DR | Spacer1 | Spacer2 | Target | FIG. |
| Cas12i1 pre- crRNA 1 | gggAAUUUUUGUGCCC AUCGUUGGCACCCUA AUGCGGAAGUAGUGG GUAACCCGGAAUUUU UGUGCCCAUCGUUGG CACUCCGCAAGAAUU | AAUUUUU GUGCCCAU CGUUGGC AC (SEQ ID NO: 401) | CCUAA UGCGG AAGUA GUGGG UAACC CGG | UCCGC AAGAA UUGAU UGGCU CCAAU UCU | Cas12i1 Target 1 | FIG. 12 |

TABLE 6-continued

| | Pre-crRNAs used for CLUST.029130 (TypeV-I) invitro | | | | | | |
|---|---|---|---|---|---|---|---|
| Name | Sequence | DR | Spacer1 | Spacer2 | Target | FIG. | |
| | GAUUGGCUCCAAUUC UAAUUUUUGUGCCCA UCGUUGGCAC (SEQ ID NO: 400) | | (SEQ ID NO: 402) | (SEQ ID NO: 403) | | | |
| Cas12i1 pre-crRNA 2 | gggAAUUUUUGUGCCC AUCGUUGGCACAGGC AUCAUCAGCAUUAAC CACGCAAACAAUUUU UGUGCCCAUCGUUGG CACGCGUGCUGGAUU GCUUCGAUGGUCUGC GAAUUUUUGUGCCCA UCGUUGGCAC (SEQ ID NO: 404) | AAUUUUU GUGCCCAU CGUUGGC AC (SEQ ID NO: 405) | AGGCA UCAUC AGCAU UAACC ACGCA AAC (SEQ ID NO: 406) | GCGUG CUGGA UUGCU UCGAU GGUCU GCG (SEQ ID NO: 407) | Cas12i1 Target 2 | FIGS. 13-17B | |

TABLE 7

| Substrates used for CLUST.029130 (Type V-I) in vitro biochemistry | | | |
|---|---|---|---|
| Name | Sequence | Nucleic acid | FIG |
| Cas12i1 ssDNA1, dsDNA1 | CATGTGGACCACATTAGGCTGCAAAACTGCGCA TTTACGAAAACGCGAAAGTTTGCGTGGTTAATG CTGATGATGCCTTAACAATGCCGATTCGCGGTG CGGATGAACGTAATTTCTCGAGGCGTATT (SEQ ID NO: 408) | DNA | FIG. 12 |
| Cas12i1 ssDNA2, dsDNA2 | CATGTGGACCACATTAGGCTTGGTTGTTGCTGC CGACGACGGTGTGATGCCGCAGACCATCGAAGC AATCCAGCACGCGAAAGCGGCGCAGGTACCGG TGGTGGTTGCGTAATTTCTCGAGGCGTATT (SEQ ID NO: 409) | DNA | FIGs. 13-17B |

TABLE 8

| Collateral nucleic acids used for CLUST.029130 (Type V-I) in vitro Biochemistry | | | |
|---|---|---|---|
| Name | Sequence | Nucleic acid | FIG |
| Cas12i1 ssDNA6_RC | AATACGCCTCGAGAAATTACAAAGTGATGCAGGCGTTTCCAGGTG CTTTCCCTAATGCGGAAGTAGTGGGTAACCCGGTGCGTACCGATG TGTTGGCGCTGCCGTTGCAGCCTAATGTGGTCCACATG (SEQ ID NO: 410) | DNA | FIG. 14 |

TABLE 9

| IDT Template oligos and primers for crRNAs used for CLUST.029130 (Type V-I) in vitro biochemistry | | | |
|---|---|---|---|
| Name | Template Sequence | T7 fwd primer | Rev primer |
| Cas12i1 pre-crRNA 1 | GTGCCAACGATGGGCACAAAAATTAGAA TTGGAGCCAATCAATTCTTGCGGAGTGC CAACGATGGGCACAAAAATTAGAATTGG AGCCAATCAATTCTTGCGGAGTGCCAAC GATGGGCACAAAAATTccctatagtgagtcgtattac tcgagggatccTTATTACATTT (SEQ ID NO: 411) | TAATACGA CTCACTAT AG (SEQ ID NO: 412) | GTGCCAACGAT GGGCACAAAAA TTAGAATTGGA GCCAATCAATTC TTGCGGA (SEQ ID NO: 413) |

TABLE 9-continued

IDT Template oligos and primers for crRNAs used for CLUST.029130
(Type V-I) in vitro biochemistry

| Name | Template Sequence | T7 fwd primer | Rev primer |
|------|-------------------|---------------|------------|
| Cas12i1 pre- crRNA 2 | GTGCCAACGATGGGCACAAAAATTCGCA GACCATCGAAGCAATCCAGCACGCGTGC CAACGATGGGCACAAAAATTGTTTGCGT GGTTAATGCTGATGATGCCTGTGCCAAC GATGGGCACAAAAATTccctatagtgagtcgtattac tcgagggatccTTATTACATTT (SEQ ID NO: 414) | TAATACGA CTCACTAT AG (SEQ ID NO: 415) | GTGCCAACGAT GGGCACAAAAA TTCGCAGACCAT CGAAGCAATCC AGCACGC (SEQ ID NO: 416) |

15

Example 4: In Vitro Pooled Screening for Rapid
Evaluation of CRISPR-Cas Systems (FIGS. 20-25)

As described herein, in vitro pooled screening serves as an
efficient and high throughput method to perform biochemi-
cal evaluation. As an overview, we begin by in vitro recon-
stitution of the CRISPR-Cas system (FIG. 20). In one
embodiment, the effector protein is produced using an in
vitro transcription and translation reagent that uses dsDNA
template containing a T7-RNA polymerase promoter driving
the expression of the effector protein(s), and produces pro-
teins for the reaction. In another embodiment, the minimal
CRISPR arrays and the tracrRNAs include T7 promoter
sequences appended onto either the top strand or bottom
strand transcription directions using PCR in order to inter-
rogate all possible RNA orientations. As shown in FIG. 20,
the Apo form contains the effector only, the Binary form
contains the effector protein and T7 transcript minimal
CRISPR array, and the Binary+tracrRNA form adds any T7
transcribed tracrRNA elements to the complex for incuba-
tion.

In one embodiment, the endonucleolytic activity of the
CRISPR-Cas systems is the primary biochemical activity
assayed. FIG. 21 shows one form of the ssDNA and dsDNA
substrates, in which a target sequence is flanked on both
sides by 6 degenerate bases to create a pool of possible PAM
sequences that may gate ssDNA and dsDNA cleavage activ-
ity. Apart from the PAM sequence, the substrates include 5'
and 3' fiducial marks designed to facilitate downstream next
generation sequencing library preparation protocols that
selectively enrich for the substrate ssDNA or dsDNA, as
well as provide unique sequences that facilitate mapping of
the cleavage products. In one embodiment, the dsDNA
substrate is generated by second strand synthesis in the
5'-to-3' direction using a short DNA primer and DNA
polymerase I. Similar reactions can be performed using
pools of different targets in the minimal CRISPR array, as
well as libraries of different ssDNA and dsDNA sequences.

The CRISPR-Cas cleavage reaction is performed by mix-
ing and incubating the preformed Apo/Binary/Binary-
tracrRNA complexes with either targeting or non-targeting
substrates. While other methods such as gel electrophoresis
are possible, a useful embodiment for maximum sensitivity
and base-pair resolution capture of the cleavage is next
generation sequencing of the ssDNA or dsDNA substrate
after incubation with the effector complex. FIG. 22 is a
schematic that describes the library preparation for enrich-
ment of the ssDNA substrates. By annealing a primer to
well-defined sequences within the fiducial marks, the second
strand synthesis and end repair occurs to produce fragments
of dsDNA that represent both cut and uncut ssDNA. Afterwards, the newly-formed dsDNA molecules are a substrate
for adaptor ligation, after which a selective PCR is per-
formed using one primer (I5/P5) complementary to the
ligation adaptor and another (I7/P7) that is complementary
to the 3' fiducial of the original ssDNA substrate. This
ultimately produces a sequencing library that contains both
the full length, as well as cleaved and degraded ssDNA
products, as demonstrated in FIG. 24A. The dsDNA readout
NGS library prep begins without requiring the primer
annealing and second strand synthesis, so the end repair and
subsequent adaptor ligation can be directly performed. FIG.
23 describes the general overview of the library preparation
that, similar to the ssDNA prep, labels both the cleaved/
degraded as well as uncleaved fragments. Of note, either end
of the dsDNA cleavage fragment can be enriched based on
the PCR primer choice. In one embodiment, illustrated in
FIG. 24A, dsDNA manipulation next generation sequencing
libraries for readout can be prepared with a first primer
complementary to a handle ligated to the 5' end of the full
length or cleaved substrate (and containing I5/P5 sequences)
and a second primer complementary to the 3' fiducial
sequence of the substrate (and containing I7/P7 sequences).
In one embodiment, illustrated in FIG. 24B, DNA manipu-
lation next generation sequencing libraries for readout can
be prepared with a first primer complementary to the 5'
fiducial sequence of the substrate (and containing I5/P5
sequences) and a second primer complementary to a handle
ligated to the 3' end of the full length or cleaved substrate
(and containing I7/P7 sequences). Target length and sub-
strate length can be extracted from resulting NGS reads from
RNA/ssDNA/dsDNA manipulation experiments as depicted
in FIGS. 25A-B, respectively. Target length and substrate
lengths extracted can be used to investigate the presence of
RNA/ssDNA/dsDNA nicking or cleavage.

Example 5: Characterization of dsDNA Cleavage
Activity for the Type V-I1 CRISPR-Cas System
(FIGS. 26-32)

Having computationally identified the minimal compo-
nents of Type V-I CRISPR-Cas systems, we investigated
double stranded DNA (dsDNA) cleavage activity from the
Type V-I1 system containing effector Cas12i1.

IVTT-expressed Cas12i1 in complex with a top-strand
expressed crRNA targeting dsDNA resulted in a population
of truncated target lengths not present in the apo (effector-
only) controls as shown in FIG. 26A-B. Libraries prepared
using a 5' ligation adapter and selecting for the 3' fiducial (as
depicted in FIG. 24A) showed a cleavage product not
present in the Apo control at the +24 position within the
target sequence. This result indicates either nicking of the non-target dsDNA strand or both strands of the dsDNA between the +24 and +25 nucleotides relative to the PAM. Target length analysis shows a peak at +24 indicating truncation of the target between nucleotides +24 and +25 (FIG. 27A). This population of truncated target sequences coincides with substrate lengths indicating cleavage of the non-target dsDNA strand between nucleotides +24 and +25 of the target sequence (FIG. 28A).

Libraries prepared using a 3' ligation adapter and selecting for the 5' fiducial (as depicted in FIG. 24B) showed a cleavage product not present in the Apo control at the −9 position. (+19 given a 28 nt target) within the target sequence. This result indicates either nicking of the target dsDNA strand or both strands of the dsDNA between the +19 and +20 nucleotides relative to the PAM. Target length analysis shows a peak at −9 nucleotides from the PAM (28 nt full length target) indicating truncation of the target between nucleotides +19 and +20 (FIG. 27B). This population of truncated target sequences coincides with substrate lengths indicating cleavage of the target dsDNA strand between nucleotides +19 and +20 of the target sequence (FIG. 28B).

Sequence motif analysis for substrates showing non-target strand cleavage between the +24/+25 nucleotides relative to the PAM revealed a 5' TTN PAM motif to the left of the target sequence for Cas12i1 (FIG. 29). No PAM sequence requirement was observed on the right side of the Cas12i1 target. Taken together, in vitro screening of Cas12i1 indicates predominant nicking between the +24/+25 nucleotides of the non-target strand relative to a TTN PAM with a significant fraction of these products converted to double strand breaks with a 5 nt 3' overhang by cleavage of the target strand between the +19/+20 nucleotides relative to the PAM (FIG. 30). Targeting of Cas12i1 in complex with a top-strand expressed non-target crRNA resulted in no manipulation of dsDNA relative, indicating that Cas12i1 cleavage specificity is conferred by the crRNA spacer (FIG. 31A-B). Cas12i1 showed no cleavage activity in the presence of a bottom strand-expressed crRNA targeting the dsDNA substrate indicating that the top-strand oriented crRNA is required for formation of the active Cas 12i1 complex (FIG. 32A-B).

Example 6: Characterization of dsDNA Cleavage Activity for the Type V-I2 CRISPR-Cas System (FIGS. 33-39)

Having computationally identified the minimal components of Type V-I CRISPR-Cas systems, we investigated double stranded DNA (dsDNA) cleavage activity from the Type V-I2 system containing effector Cas12i2.

IVTT-expressed Cas12i2 in complex with a top-strand expressed crRNA targeting dsDNA resulted in a population of truncated target lengths not present in the apo (effector-only) controls as shown in FIG. 33A-B. Libraries prepared using a 5' ligation adapter and selecting for the 3' fiducial (as depicted in FIG. 24A) showed a cleavage product not present in the Apo control at the +24 position within the target sequence. This result indicates either nicking of the non-target dsDNA strand or both strands of the dsDNA between the +24 and +25 nucleotides relative to the PAM. Target length analysis shows a peak at +24 indicating truncation of the target between nucleotides +24 and +25 (FIG. 34A). This population of truncated target sequences coincides with substrate lengths indicating cleavage of the non-target dsDNA strand between nucleotides +24 and +25 of the target sequence (FIG. 35A).

Libraries prepared using a 3' ligation adapter and selecting for the 5' fiducial (as depicted in FIG. 33B) showed a cleavage product not present in the Apo control at the −7 position (+24 given 31 nt target) within the target sequence. This result indicates either nicking of the target dsDNA strand or both strands of the dsDNA between the +24 and +25 nucleotides relative to the PAM. Target length analysis shows a peak at −7 nucleotides from the PAM (28 nt full length target) indicating truncation of the target between nucleotides +24 and +25 (FIG. 34B). This population of truncated target sequences coincides with substrate lengths indicating cleavage of the target dsDNA strand between nucleotides +24 and +25 of the target sequence (FIG. 35B).

Sequence motif analysis for substrates showing non-target strand cleavage between the +24/+25 nucleotides relative to the PAM revealed a 5' TTN PAM motif to the left of the target sequence for Cas12i2 (FIG. 36). No PAM sequence requirement was observed on the right side of the Cas 1212 target. Taken together, in vitro screening of Cas12i2 indicates predominant nicking between the +24/+25 nucleotides of the non-target strand relative to a TTN PAM with a significant fraction of these products converted to double strand breaks with a blunt cut by cleavage of the target strand between the +24/+25 nucleotides relative to the PAM (FIG. 37). Targeting of Cas12i2 in complex with a top-strand expressed non-target crRNA resulted in no manipulation of dsDNA relative, indicating that Cas12i2 cleavage specificity is conferred by the crRNA spacer (FIG. 38A-B). Cas12i2 showed no cleavage activity in the presence of a bottom strand-expressed crRNA targeting the dsDNA substrate indicating that the top-strand oriented crRNA is required for formation of the active Cas12i2 complex (FIG. 39A-B).

Example 7: CLUST.029130 (Type V-I) CRISPR Cas Systems can be Used for Gene Silencing In Vitro An in vitro gene-silencing assay (FIGS. 18A and 18B) was developed to mimic in vivo gene silencing activity for rapid validation of the activity of a novel CRISPR-Cas system. This assay can simultaneously evaluate in an unbiased manner different activity mechanisms and functional parameters outside the natural cellular environment.

First, a reconstituted IVTT (in vitro transcription and translation) system was supplemented with *E. coli* RNA polymerase core enzyme to allow gene expression (protein synthesis) to occur from not only T7 promoter but also any *E. coli* promoter, as long as the corresponding *E. coli* sigma factor is present.

Second, to facilitate rapid and high throughput experimentation, linear DNA templates generated from PCR reactions were directly used. These linear DNA templates included those encoding the Type V-I effector, a RNA guide, and *E. coli* sigma factor 28. Incubation of these DNA templates with the reconstituted IVTT reagent results in co-expression of the Type V-I effector and a RNA guide, and the formation of the RNP (ribonucleoprotein complex). *E. coli* sigma factor 28 was also expressed for subsequent expression of GFP and RFP as described below.

Third, as the target substrate, a linear or plasmid DNA encoding GFP expressed from the sigma factor 28 promoter was included in the above incubation reaction such that the newly synthesized RNP has the immediate access to the target substrate. As an internal control, a non-target linear DNA encoding RFP expressed from the sigma factor 28 promoter was also included. The RNA polymerase core enzyme alone does not recognize the sigma factor 28 promoter until sufficient sigma factor 28 protein is synthesized. This delay in the GFP and RFP expression allows the newly synthesized RNP to interfere with the GFP target substrate, which could result in a decrease in the GFP expression and a depletion of the GFP fluorescence. The RFP expression, on the other hand, was not negatively affected, which serves as the internal control for protein synthesis and fluorescence measurement.

Certain important advantages of the in vitro gene-silencing assay described herein include:

(1) Modularity—The reconstituted IVTT is a synthetic system consisting of individually purified components, which allows the assay to be custom designed for a variety of controls and activities. Each component of the CRISPR-Cas system is encoded in a separate linear DNA template, allowing rapid assays of a combination of different effectors, effector variants, and RNA guides;

(2) Complexity—The assay contains all essential components for RNA transcription and protein synthesis, allowing diverse mechanisms of interference to be tested in a single one-pot reaction, such as DNA and RNA cleavage, and transcription-dependent interference. The kinetic fluorescence readouts of the assay provide significantly more data points than endpoint activity assays;

(3) Sensitivity—The assay couples effector and RNA guide synthesis with substrate interference, allowing newly synthesized RNPs (ribonucleoprotein complexes of effector protein and RNA guide) to immediately interact with the substrate in the same reaction. There are no separate purification steps, thus potentially allowing small amounts of RNPs to be sufficient to generate signal. Furthermore, the interference of the GFP expression is amplified due to the coupled transcription and translation of GFP that can generate >100 GFP protein per DNA template.

(4) Efficiency—The assay is designed to be highly compatible to high throughput platforms. Due to its modularity, all components of the assay can be added in 96-, 384- and 1536-well formats by commonly available liquid handling instruments, and fluorescence can be measured by commonly available plate fluorometers.

(5) Relevance—The assay tests the ability of a CRISPR-Cas effector protein to interfere with the gene expression during transcription and translation in an in vitro engineered system outside of its natural cellular environment. It may be possible that a highly active CRISPR-Cas effector measured by this gene-silencing assay is also highly efficient for gene editing in mammalian cells.

This assay has been used to measure the gene-silencing effect of a Cas12i effector complex as illustrated here when targeting GFP encoded in plasmid DNA. Multiple Type V-I RNA guides are designed—one with a spacer sequence complementary to the template strand of the GFP sequence, and another with a spacer sequence complementary to the coding strand of the GFP sequence. The degree of gene-silencing by the Cas12i1 effector protein was then compared with that of the mutants Cas12i1 D647A, Cas12i1 E894A, and Cas12i1 D948A.

FIG. 19A depicts the fold-depletion of each of the four tested Cas12i effectors when complexed with an RNA guide complementary to the template strand. In this case, the non-target strand, preferentially being nicked, is the coding strand. While Cas12i1 shows approximately 2-fold depletion of GFP expression after 400 minutes, each of the three mutant forms shows smaller degrees of depletion.

FIG. 19B depicts the fold-depletion of each of the four tested Cas12i1 effectors when complexed with an RNA guide complementary to the coding strand. In this case, the non-target strand, preferentially being nicked, is the template strand. The ability for RNA polymerase to produce a functional RNA transcript appears to be significantly impaired by Cas12i1 in this configuration, with greater than 4-fold depletion in the case of Cas12i. The gene-silencing ability of the three mutant forms appears significantly diminished.

Taken together, the data shown in FIG. 19A and FIG. 19B indicate that the assay is effective in detecting the gene silencing activity of Cas12i1 when using RNA guides targeting both the coding and template strands. The significant higher depletion when targeting the coding strand than targeting the template strand suggests Cas12i1 interferes with the GFP expression by preferentially nicking the non-target strand. All three Cas12i1 mutants substitute the postulated catalytic residues (aspartic acid (D) and glutamic acid (E)) with alanine (A). The diminishing silencing activities of these Cas12i1 mutants further support that DNA stand cleavage, rather than just binding, underlies the mechanism of the gene silencing by Cas12i1

Example 8: CLUST.029130 (Type V-I) CRISPR-Cas Systems can be Used with a Fluorescent Reporter for the Specific Detection of Nucleic Acid Species The nuclease activities of Cas12i proteins (i.e., non-specific collateral DNase activities activated by a target ssDNA substrate complementary to the crRNA spacer) make these effectors promising candidates for use in the detection of nucleic acid species. Some of these methods have been previously described (see, e.g., East-Seletsky et al. "Two distinct RNase activities of CRISPR-C2c2 enable guide-RNA processing and RNA detection," *Nature.* 2016 Oct. 13; 538 (7624): 270-273), Gootenberg et al. (2017), Chen et al. 2018, and Gootenberg et al. (2018) "Multiplexed and portable nucleic acid detection platform with Cas13, Cas12a, and Csm6 " *Science* 15 Feb. 2018: eaaq0179), describing the general principle of RNA detection using Cas13a (East-Seletsky et al. (2016)), supplemented by amplification to increase the detection sensitivity and optimization of additional Cas13a enzymes (Gootenberg et al. (2017)), and most recently, the inclusion of additional RNA targets, orthologous and paralogous enzymes, and Csm6 activator to enable multiplexed detection of nucleic acids along with an increase in detection sensitivity (Gootenberg et al. (2018)). The addition of Cas12i to this toolkit provides an additional channel of orthogonal activity for nucleic acid detection.

The in vitro biochemical activity of Cas12i1 suggests that it may have promise in applications for sensitive nucleic acid detection, given that a dye-labeled, collateral DNA was efficiently cleaved at low target ssDNA concentrations and background nuclease activity was limited with a non-targeting substrate (FIG. 14). Adapting Cas12i1 towards sensitive nucleic acid detection application requires several steps, including, but not limited to, optimizing the substrate for sensitive readout of the collateral activity and identifying per-base mismatch tolerance between the spacer and the target substrate.

Identification of the optimal substrate for nucleic acid detection can be informed by performing next generation sequencing (NGS) on the cleavage products of Cas12i collateral activity on both DNA substrates. The enzyme concentration may have to be titrated or incubation time adjusted in order to yield cleavage fragments that are still of a sufficient size to be prepared into a next generation sequencing library. The NGS data reveal the enzyme cleavage sites and the adjacent base preferences. It has been demonstrated that the individual effectors within the Cas13a and b families have different dinucleotide base preferences for RNA cleavage, yielding markedly different cleavage magnitudes and signal to noise ratios (Gootenberg et al. (2018)). The collateral NGS data thus enable better insight into the preferences for Cas12i. A separate experimental approach to identifying the dinucleotide preference of Cas12i collateral cleavage is to create a collateral DNA substrate with degenerate N's in consecutive positions so as to have a broader sequence space than a defined sequence. The library prep and analysis of the NGS data would proceed similarly to identify base preferences for cleavage. To verify the preference, collateral substrates containing synthesized short DNAs with a fluorophore/quencher pair on the 5' and 3' ends can be introduced into a cleavage reaction to assess the signal to noise ratio. Further optimization can be done on the length of the collateral DNA substrate to determine whether Cas12i1 has a length preference.

Having identified the preferred substrate, another important parameter to determine is the mismatch tolerance of the Cas12i system, as it has implications for guide design that affects the ability of the enzyme to distinguish single base pair mismatches. The mismatch tolerance can be determined by designing a panel of targets bearing different positions and types of mismatches (for example, insertion/deletions, single base pair mismatches, adjacent double mismatches, separated double mismatches, triple mismatches, and more). Mismatch tolerance can be measured by assessing the amount of cleavage of collateral DNA for targets containing varying amounts of mismatches. As an example, the collateral DNA substrate could be a short ssDNA probe containing a fluorophore and quencher on opposite sides. For reactions containing the Cas12i effector, an RNA guide, and a target substrate containing different numbers of mismatches, insertions and deletions in the target sequence, successful activation of the Cas12i system by targeting of altered target DNA sequence will result in collateral cleavage of the fluorescent probe. Hence resulting fluorescent measurements denoting cleaved collateral substrate can be background subtracted using negative control samples and normalized to the signal from perfectly matching targets to estimate the impact of target alterations on the efficiency of collateral cleavage by Cas12i. Resulting maps of mismatch, insertion, and deletion tolerance by the Cas12i enzyme over the target length relative to the PAM can be used to design optimal RNA guides to distinguish between different DNA sequences or genotypes for specific detection or distinction between different Nucleic Acid Species. Using the fluorometric cleavage readout and the preferred collateral substrate, the fluorescence activity would be compared against the fully matched sequence to determine the position and types of mismatch to which the enzyme is most sensitive.

The optimization process can be furthermore applied to other Cas12i orthologs to yield other systems that may have different properties. For example, orthogonal dinucleotide preferences of collateral cleavage would be helpful in generating separate channels of detection.

Example 9. CLUST.029130 (Type V-I) CRISPR Cas Systems can be Used for Paired Nicking to Enable Highly Specific dsDNA Manipulation The CLUST.029130 effector Cas 12i is capable of manipulating dsDNA via nicking of the non-target strand (FIGS. 15, 16, 17A-B). Catalytically inactivated Cas12i can also be fused with a FokI nuclease domain to create a fusion protein capable of binding and nicking dsDNA. Some of these methods have been previously described. Ran et al. (2013) "Double Nicking by RNA-Guided CRISPR Cas9 for Enhanced Genome Editing Specificity" Science 29 Aug. 2013 describes the general principle and optimization of double nicking using Cas9; Guilinger et al. (2014) "Fusion of catalytically inactive Cas9 to FokI nuclease improves the specificity of genome modification" Science 25 Apr. 2014 described the principle of double nicking using a FokI-dCas9 fusion.

The use of paired Cas12i nickases enables highly specific dsDNA manipulation as follows. A first Cas12i complex with a crRNA targeting one strand of a dsDNA target region and second Cas12i-crRNA complex targeting the opposing strand of the dsDNA are introduced together to enable a dsDNA cleavage reaction. By targeting the Cas12i complexes to different dsDNA strands, the first and second Cas12i complexes cleave opposing dsDNA strands resulting in a double strand break.

To optimize the efficiency of dsDNA double strand break formation by double nicking, pairs of crRNA spacer sequences are chosen with different lengths separating their expected nuclease cleavage sites. Cleavage of the top and bottom strand of dsDNA by Cas12i paired nickases with different target displacements produces different length sequence overhangs, resulting in different efficiencies of double strand break formation. Paired nickase targets can be selected with specific orientations to generate either 3' or 5' overhangs, or a blunt (overhang length of 0) double strand breaks.

For nicking applications with the Cas12i1 and Cas12i2-WT enzymes containing 5' TTN PAMs, orientation of the paired nickase targets with PAMs 'out' (PAMs at the outside of the paired targets) results in a 5' overhang, whereas pairing of nickase targets with PAMs at the inside of the target pair results in a 3' overhang. In some instances 3' and 5' overhangs range from 1-200 nt. In some instances, 3' and 5' overhangs are between 20 and 100 nt.

Autonomous pre-crRNA processing facilitates Cas12i delivery for double nicking applications (FIG. 12), as two separate genomic loci can be targeted from a single crRNA transcript. Therein, Cas12i and a CRISPR array containing two spacer sequences targeting the Cas12i to nick opposing strands of dsDNA can be expressed from a single viral vector or plasmid. Cas12i and the CRISPR array can also be delivered on separate plasmids or viral vectors. The Cas12i protein then processes the CRISPR array into two cognate crRNAs that result in the formation of paired nicking complexes. Viral vectors can include phage or adeno-associated virus for delivery to bacteria or mammalian cells, respectively.

Apart from viral or plasmid delivery methods, paired nicking complexes can be delivered directly using nanoparticle or other direct protein delivery methods, such that complexes containing both paired crRNA elements are co-delivered. Furthermore, protein can be delivered to cells by viral vector or directly, followed by the direct delivery of a CRISPR array containing two paired spacers for double nicking. In some instances, for direct RNA delivery the RNA may be conjugated to at least one sugar moiety, such as N-acetyl galactosamine (GalNAc) (particularly, triantennary GalNAc).

Example 10: Adaptation of CLUST.029130 (Type V-I) CRISPR Cas System Effectors for Eukaryotic and Mammalian Activity To develop CLUST.029130 (Type V-I) CRISPR Cas systems for eukaryotic applications, the constructs encoding the protein effectors were first codon-optimized for expression in mammalian cells, and specific localization tags were optionally appended to either or both the N-terminus or C-terminus of the effector protein. These localization tags can include sequences such as nuclear localization signal (NLS) sequences, which localize the effector to the nucleus for modification of genomic DNA. These sequences are described above in the "Functional Mutations" section. Some examples of non-naturally occurring, engineered nucleotide sequences to encode mammalian codon-optimized Cas12i effectors with a localization tag are provided in TABLE 10. Other accessory proteins, such as fluorescent proteins, may be further appended. It has been demonstrated that the addition of robust, "superfolding" proteins such as superfolding green fluorescent protein (GFP) can increase the activity of CRISPR enzymes in mammalian cells when appended to the effector (Abudayyeh et al. (2017) *Nature* 550 (7675): 280-4, and Cox et al. (2017) *Science* 358 (6366): 1019-27).

The codon-optimized sequence coding for the Cas12i and appended accessory proteins and localization signals was then cloned into a eukaryotic expression vector with the appropriate 5' Kozak eukaryotic translation initiation sequence, eukaryotic promoters, and polyadenylation signals. In mammalian expression vectors, these promoters can include, e.g., general promoters such as CMV, EF1a, EFS, CAG, SV40, and cell-type specific RNA polymerase II promoters such as Syn and CamKIIa for neuronal expression, and thyroxine binding globulin (TBG) for hepatocyte expression to name a few. Similarly, useful polyadenylation signals include, but are not limited to, SV40, hGH, and BGH. Additional transcript stabilization or transcript nuclear export elements such as WPRE can be used for increasing the expression of such constructs. For expression of the pre-crRNA or mature crRNA, RNA polymerase III promoters such as H1 or U6 can be used.

Depending on the application and mode of packaging, the eukaryotic expression vector can be a lentiviral plasmid backbone, adeno-associated viral (AAV) plasmid backbone, or similar plasmid backbone capable of use in recombinant viral vector production. Notably, the small size of CLUST.029130 (Type V-I) CRISPR Cas effector proteins, e.g., Cas12i proteins, make them ideally suited for packaging along with its crRNA and appropriate control sequences into a single adeno-associated virus particle; the packaging size limit of 4.7 kb for AAV may preclude the use of larger effectors, particularly if large cell-type specific promoters are used for expression control.

After adapting the sequences, delivery vectors, and methods for eukaryotic and mammalian use, different Cas12i constructs as described herein were characterized for performance. An initial characterization was performed by lipofection of DNA constructs expressing the minimal components of the Cas12i system with the adaptations for eukaryotic use as described above. In one embodiment, the Cas12i effector is mammalian codon optimized and a nucleoplasmin nuclear localization sequence (npNLS) is appended to the C-terminus of the protein. The expression of the effector is driven by the elongation factor alpha short (EFS) promoter, and terminated using a bGH poly(A) signal (TABLE 10). A double-stranded, linear PCR product containing a U6 promoter was used to express the cognate RNA guides for the Cas12i system, as adapted from (Ran et al. "Genome engineering using the CRISPR-Cas9 system," *Nat Protoc.* 2013 November; 8 (11): 2281-2308). This approach is well suited to testing a larger number of sgRNAs over plasmid cloning and sequence verification. (FIG. 40) The effector plasmid and U6-guide PCR fragment were co-transfected into 293T cells at an approximately 1:2 molar ratio of plasmid to PCR product with 400 ng of effector plasmid and 30 ng of U6-guide PCR product for a 24 well plate format. The resulting gene editing event was evaluated using next generation sequencing of a targeted PCR amplicon surrounding the target site (Hsu et al., "DNA targeting specificity of RNA-guided Cas9 nucleases," *Nat Biotechnol.* 2013 September; 31 (9): 827-32).

Initial evaluation of Cas 1212 yielded indel activity of 13% at the VEGFA locus at a target site with a TTC PAM. We tested different RNA guide designs as described in FIG. 41, with the strongest indel efficiency achieved using pre-crRNA, and with indel rates decreasing with shorter spacer lengths. Examining the indels created by Cas12i2 reveals that the predominant location of the indels are centered around +20 relative to the PAM sequence.

Multiplexing of Type V-I effectors is accomplished using the pre-crRNA processing capability of the effectors, where multiple targets with different sequences can be programmed on a single RNA guide. As such, multiple genes or DNA targets can be manipulated simultaneously for therapeutic applications. One embodiment of a RNA guide design is a pre-crRNA expressed from a CRISPR array consisting of target sequences interleaved by unprocessed DR sequences, repeated to enable targeting of one, two, or more loci simultaneously by the intrinsic pre-crRNA processing of the effector.

In addition to testing various construct configurations and accessory sequences on individual targets, pooled library-based approaches are used to determine 1) any targeting dependency of specific Cas12i proteins in mammalian cells as well as 2) the effect of mismatch locations and combinations along the length of the targeting crRNA. Briefly, the pooled library includes a plasmid that expresses a target DNA containing different flanking sequences as well as mismatches to the guide or guides used in the screening experiment, such that the successful target recognition and cleavage results in depletion of the sequence from the library. Furthermore, targeted indel sequencing or unbiased genome-wide cleavage assays can be used to evaluate the specificity of the CLUST.029130 (Type V-I) CRISPR-Cas system (Hsu et al. (2013), Tsai et al. "GUIDE-seq enables genome-wide profiling of off-target cleavage by CRISPR-Cas nucleases." *Nat Biotechnol.* 2015 February; 33 (2): 187-197, Kim et al. "Digenome-seq: genome-wide profiling of CRISPR-Cas9 off-target effects in human cells," *Nat Methods.* 2015 March; 12 (3): 237-43, Tsai et al., "CIRCLE-seq: a highly sensitive in vitro screen for genome-wide CRISPR-Cas9 nuclease off-targets," *Nat Methods.* 2017 June; 14 (6): 607-614).

Mutations are additionally created to extend the functional range of Cas 12i proteins. In some embodiment, catalytically-inactive Cas12i proteins can be made in which the conserved residues of the RuvC domain are mutated to alanine (such as the D647A mutation for Cas12i1 and D599A mutation for Cas12i2). Catalytically inactive Cas12i versions (referred to as dCas12i) retains its programmable DNA binding activity, though it will no longer be able to cleave target or collateral ssDNA or dsDNA. Direct uses of dCas12i include immunoprecipitation and transcriptional repression. Further functionality is provided by appending other domains onto the dCas12i protein Activities of these domains include, but are not limited to, DNA base modification (ex: ecTAD and its evolved forms, APOBEC), DNA methylation (m6A methyltransferases and demethylases), localization factors (KDEL retention sequence, mitochondrial targeting signal), transcription modification factors (ex: KRAB, VP64). Additionally, domains can be appended to provide additional control, such as light-gated control (cryptochromes) and chemically inducible components (FKBP-FRB chemically inducible dimerization).

Optimizing the activity of such fusion proteins requires a systematic way of comparing linkers that connect the dCas12i with the appended domain. These linkers may include, but are not limited to, flexible glycine-serine (GS) linkers in various combinations and lengths, rigid linkers such as the alpha-helix forming EAAAK sequence, XTEN linker (Schellenberger V, et al. *Nat. Biotechnol.* 2009; 27:1186-1190), as well as different combinations thereof (see TABLE 11). The various designs are then assayed in parallel over the same crRNA target complex and functional readout to determine which one yields the desired properties.

For adapting Cas12i for use in targeted DNA base modification (see, e.g., Gaudelli et al. (2017) "Programmable base editing of A•T to G•C in genomic DNA without DNA cleavage" Science 25 Oct. 2017), we begin with the Cas12i ortholog and NLS combination that yielded the highest endogenous mammalian DNA cleavage activity and mutate the conserved residues of the RuvC domain to create a catalytically inactive enzyme (dCas12i). Next, a linker is used to create the fusion protein between dCas12i-NLS and the base editing domain. Initially, this domain will consist of the ecTadA (wt)/ecTadA*(7.10) heterodimer (hereafter referred to as the dCas12i-TadA heterodimer) engineered previously for hyperactivity and modification of dsDNA A•T dinucleotides to G•C (TABLE 11). Given the likely structural differences between the smaller Cas12i versus the previously characterized Cas9 effectors, alternate linker designs and lengths may yield the optimal design of the base editing fusion protein.

To evaluate the activity of the dCas12i-derived base editors, the HEK 293T cells are transiently transfected with the dCas12i-TadA heterodimer construct, a plasmid expressing the crRNA, and optionally, a reporter plasmid if targeting the reporter and not an endogenous locus. The cells are harvested 48 hours after transient transfection, the DNA is extracted and prepared for next generation sequencing. Analysis of the base composition of loci of samples containing the targeting vs. negative control non-targeting crR-NAs provide information about the editing efficiency, and analysis of broader changes to the transcriptome will yield information about the off-target activity.

One particular advantage of developing a DNA base editing system using Cas12i is that the small size, smaller than the existing Cas9 and Cas12a effectors, enables more ready packaging in AAV of dCas12i-TadA heterodimer along with its crRNA and control elements without the need for protein truncations. This all-in-one AAV vector enables greater efficacy of in vivo base editing in tissues, which is particularly relevant as a path towards therapeutic applications of Cas12i.

In addition to editing using Cas12i and an RNA guide, additional template DNA sequences can be co-delivered either in a vector, such as an AAV viral vector, or as linear single stranded or double stranded DNA fragments. For insertion of template DNA by homology directed repair (HDR), template sequences are designed containing a payload sequence to be inserted into the locus of interest as well as flanking sequences that are homologous to endogenous sequences flanking the desired insertion site. In some instances, for insertion of short DNA payloads less than (for example: less than 1 kb in length), flanking homologous sequences can be short (for example: ranging from 15 to 200 nt in length). In other instances, for the insertion of long DNA payloads (for example: 1 kb or greater in length), long homologous flanking sequences are required to facilitate efficient HDR (for example: greater than 200 nt in length). Cleavage of target genomic loci for HDR between sequences homologous to template DNA flanking regions can significantly increase the frequency of HDR. Cas12i cleavage events facilitating HDR include, but are not limited to dsDNA cleavage, double nicking, and single strand nicking activity.

DsDNA fragments may contain overhang sequences complementary to the overhangs resulting from double nicking using Cas12i. Pairing of the insert and double-nicking overhangs and subsequent ligation by endogenous DNA repair machinery result in the seamless insertion of the template DNA at the site of double-nicking.

TABLE 10

Sequences enabling mammalian expression of Cas12i effectors with included N-terminal mH6 tag and C-terminal nucleoplasmin NLS sequence (bolded)

>EF1alpha short (EFS) promoter
GGGCAGAGCGCACATCGCCCACAGTCCCCGAGAAGTTGGGGGGAGGGGTC
GGCAATTGATCCGGTGCCTAGAGAAGGTGGCGCGGGGTAAACTGGGAAAG
TGATGTCGTGTACTGGCTCCGCCTTTTTCCCGAGGGTGGGGGAGAACCGT
ATATAAGTGCAGTAGTCGCCGTGAACGTTCTTTTTCGCAACGGGTTTGCC
GCCAGAACACAG (SEQ ID NO: 500)

>Cas12i1_mammalian_effector
atgAAAATCGAAGAAGGTAAAGGTCACCATCACCATCACCACATGTCTAA
CAAGGAGAAGAATGCCAGCGAGACCCGGAAGGCCTACACCACAAAGATGA
TCCCCAGGAGCCACGACCGCATGAAGCTGCTGGGCAACTTTATGGACTAT
CTGATGGATGGCACCCCTATCTTCTTTGAGCTGTGGAATCAGTTCGGCGG
CGGCATCGACAGAGATATCATCAGCGGCACAGCCAACAAGGATAAGATCT
CCGACGATCTGCTGCTGGCCGTGAACTGGTTTAAAGTGATGCCAATCAAT
TCTAAGCCCCAGGGCGTGTCCCCTTCTAACCTGGCCAATCTGTTCCAGCA
GTACAGCGGATCCGAGCCTGACATCCAGGCACAGGAGTATTTCGCCTCCA
ACTTTGACACCGAGAAGCACCAGTGGAAGGATATGCGGGTGGAGTACGAG
AGACTGCTGGCCGAGCTGCAGCTGTCTAGGAGCGACATGCATCACGATCT
GAAGCTGATGTACAAGGAGAAGTGCATCGGCCTGTCCCTGTCTACCGCCC
ACTATATCACAAGCGTGATGTTTGGCACCGGCGCCAAGAACAATCGCCAG
ACAAAGCACCAGTTCTATTCCAAAGTGATCCAGCTGCTGGAGGAGAGCAC
CCAGATCAATTCCGTGGAGCAGCTGGCCTCCATCATCCTGAAGGCCGGCG
ACTGCGATTCTTACAGGAAGCTGAGGATCAGGTGTTCCCGCAAGGGAGCA
ACCCCATCTATCCTGAAGATCGTGCAGGACTATGAGCTGGGCACAAACCA
CGACGATGAAGTGAATGTGCCCTCCCTGATCGCCAACCTGAAGGAGAAGC
TGGGCAGGTTTGAGTACGAGTGCGAGTGGAAGTGTATGGAGAAGATCAAG
GCCTTCCTGGCCTCTAAAGTGGGCCCTTACTATCTGGGCAGCTATTCCGC
CATGCTGGGAAATGCCCTGAGCCCAATCAAGGGCATGACCACAAAGAACT
GTAAGTTCGTGCTGAAGCAGATCGACGCCAAGAACGATATCAAGTACGAG
AATGAGCCCTTTGGCAAGATCGTGGAGGGCTTCTTTGACTCTCCTTATTT
CGAGAGCGATACCAATGTGAAGTGGGTGCTGCACCCTCACCACATCGGCG
AGTCTAACATCAAGACACTGTGGGAGGACCTGAATGCCATCCACAGCAAG
TACGAGGAGGACATCGCCTCTCTGAGCGAGGATAAGAAGGAGAAGCGGAT
CAAGGTGTACCAGGGCGATGTGTGCCAGACCATCAACACATATTGTGAGG
AAGTGGGCAAGGAGGCCAAGACCCCACTGGTGCAGCTGCTGAGGTACCTG
TATTCCCGCAAGGACGATATCGCCGTGGACAAGATCATCGATGGCATCAC
ATTCCTGTCTAAGAAGCACAAGGTGGAGAAGCAGAAGATCAACCCAGTGA
TCCAGAAGTACCCCAGCTTCAATTTTGGCAACAATTCCAAGCTGCTGGGC
AAGATCATCAGCCCAAAGGACAAGCTGAAGCACAACCTGAAGTGCAACAG
AAATCAGGTGGATAATTACATCTGGATCGAGATCAAGGTGCTGAACACCA
AGACAATGCGGTGGGAGAAGCACCACTATGCCCTGAGCTCCACCAGATTT
CTGGAGGAGGTGTACTATCCCGCCACATCCGAGAATCCACCTGACGCACT
GGCAGCACGGTTCAGAACCAAGACAAACGGCTACGAGGGCAAGCCAGCCC
TGTCTGCCGAGCAGATCGAGCAGATCAGGAGCGCCACCAGTGGGACTGAGA
AAGGTGAAGAAGCGGCAGATGAGACTGGAGGCAGCAAGGCAGCAGAATCT TABLE 10-continued Sequences enabling mammalian expression of Cas12i
effectors with included N-terminal mH6 tag and C-
terminal nucleoplasmin NLS sequence (bolded)

```
GCTGCCACGCTATACCTGGGGCAAGGATTTTAACATCAATATCTGTAAGA
GGGGCAACAATTTCGAGGTGACCCTGGCCACAAAGGTGAAGAAGAAGAAG
GAGAAGAACTACAAGGTGGTGCTGGGCTATGACGCCAACATCGTGCGCAA
GAATACCTACGCAGCAATCGAGGCACACGCAAACGGCGATGGCGTGATCG
ACTATAATGATCTGCCTGTGAAGCCAATCGAGTCTGGCTTTGTGACAGTG
GAGAGCCAGGTGAGGGACAAGTCCTACGATCAGCTGTCTTATAACGGCGT
GAAGCTGCTGTACTGCAAGCCTCACGTGGAGAGCCGGAGATCCTTCCTGG
AGAAGTATCGGAACGGCACCATGAAGGACAATAGAGGCAACAATATCCAG
ATCGACTTCATGAAGGATTTTGAGGCCATCGCCGACGATGAGACAAGCCT
GTACTACTTCAACATGAAGTACTGTAAGCTGCTGCAGTCTAGCATCCGCA
ACCACTCCTCTCAGGCCAAGGAGTATAGGGAGGAGATCTTCGAGCTGCTG
CGCGATGGCAAGCTGTCCGTGCTGAAGCTGAGCTCCCTGTCTAATCTGAG
CTTCGTGATGTTTAAGGTGGCCAAGTCTCTGATCGGCCACCTACTTTGGCC
ACCTGCTGAAGAAGCCTAAGAACTCCAAGTCTGACGTGAAGGCCCCACCC
ATCACAGACGAGGATAAGCAGAAGGCCGATCCAGAGATGTTCGCACTGCG
GCTGGCACTGGAGGAGAAGAGACTGAATAAGGTGAAGAGCAAGAAGGAAG
TGATCGCCAACAAGATCGTGGCCAAGGCACTGGAGCTGAGAGCAAGTAC
GGACCAGTGCTGATCAAGGGCGAGAATATCAGCGATACCACAAAGAAGGG
CAAGAAGCTTAGCACCAATTCCTTCCTGATGGACTGGCTGGCCAGAGGCG
TGGCCAACAAGGTGAAGGAGATGGTCATGATGCACCAGGGCCTGGAGTTC
GTGGAGGTGAACCCCAATTTTACCTCCCACCAGGATCCTTTGTGCACAA
GAACCCAGAGAATACCTTCCGGGCAAGGTACAGCAGGTGCACCCCTTCCG
AGCTGACAGAGAAGAACCGCAAGGAGATCCTGTCCTTCCTGTCTGACAAG
CCCAGCAAGCGGCCTACTAACGCCTACTATAATGAGGGCGCCATGGCCTT
TCTGGCCCACATATGGCCTGAAGAAGAATGACGTGCTGGGCGTGTCCCTGG
AGAAGTTCAAGCAGATCATGGCCAACATCCTGCACCAGCGGTCCGAGGAT
CAGCTGCTGTTTCCCTCTAGAGGCGGCATGTTCTACCTGGCCACCTATAA
GCTGGACGCCGATGCCACAAGCGTGAACTGGAATGGCAAGCAGTTTTGGG
TGTGTAACGCCGACCTGGTGGCCGCCTACAATGTGGGCCTGGTGGACATC
CAGAAGGATTTCAAGAACGAAGAAAAGCCGGCGGCCACGAAAAAGGCCGG
CCAGGCAAAAAAGAAAAAGTAATAA (SEQ ID NO: 501)
```

>Cas12i2_mammalian_effector
```
atgAAAATCGAAGAAGGTAAAGGTCACCATCACCATCACCACATGAGCTC
CGCCATCAAGTCCTACAAGTCTGTGCTGCGGCCAAACGAGAGAAAGAATC
AGCTGCTGAAGAGCACCATCCAGTGCCTGGAGGACGGCTCCGCCTTCTTT
TTCAAGATGCTGCAGGGCCTGTTTGGCGGCATCACCCCCGAGATCGTGAG
ATTCAGCACAGAGCAGGAGAAGCAGCAGCAGGATATCGCCCTGTGGTGTG
CCGTGAATTGGTTCAGGCCTGTGAGCCAGGACTCCCTGACCCACACAATC
GCCTCCGATAACCTGGTGGAGAAGTTTGAGGAGTACTATGGCGGCACAGC
CAGCGACGCCATCAAGCAGTACTTCAGCGCCTCCATCGGCGAGTCCTACT
ATTGGAATGACTGCCGCCAGCAGTACTATGATCTGTGTCGGGAGCTGGGC
GTGGAGGTGTCTGACCTGACCCACGATCTGGAGATCCTGTGCCGGGAGAA
GTGTCTGGCCGTGGCCACAGAGAGCAACCAGAACAATTCTATCATCAGCG
TGCTGTTTGGCACCGGCGAGAAGGAGGATAGGTCTGTGAAGCTGCGCATC
ACAAAGAAGATCCTGGAGGCCATCAGCAACCTGAAGGAGATCCCAAAGAA
TGTGGCCCCCATCCAGGAGATCATCCTGAATGTGGCCAAGGCCACCAAGG
AGACATTCAGACAGGTGTACGCAGGAAACCTGGGAGCACCATCCACCCTG
GAGAAGTTTATCGCCAAGGACGGCCAGAAGGAGTTCGATCTGAAGAAGCT
GCAGCAGACCTGAAGAAAGTGATCCGGGGCAAGTCTAAGGAGAGAGATT
GGTGCTGTCAGGAGGAGCTGAGGAGCTACGTGGAGCAGAATACCATCCAG
TATGACCTGTGGGCCTGGGCGAGATGTTCAACAAGGCCCACACCGCCCT
GAAGATCAAGTCCACAAGAAACTACAATTTTGCCAAGCAGAGGCTGGAGC
AGTTCAAGGAGATCCAGTCTCTGAACAATCTGCTGGTGGTGAAGAAGCTG
AACGACTTTTTCGATAGCGAGTTTTTCTCCGGCGAGGAGACCTACACAAT
CTGCGTGCACCACCTGGGCGGCAAGGACCTGTCCAAGCTGTATAAGGCCT
GGGAGGACGATCCCGCCGATCCTGAGAATGCCATCGTGGTGCTGTGCGAC
GATCTGAAGAACAATTTTAAGAAGGAGCCTATCAGGAACATCCTGCGCTA
CATCTTCACCATCCGCCAGGAGTGTAGCGCACAGGACATCCTGGCAGCAG
CAAAGTACAATCAGCAGCTGGATCGGTATAAGAGCCAGAAGGCCAACCCA
TCCGTGCTGGGCAATCAGGGCTTTACCTGGACAAACGCCGTGATCCTGCC
AGAGAAGGCCCAGCGGAACGACAGACCCAATTCTCTGGATCTGCGCATCT
GGCTGTACCTGAAGCTGCGGCACCCTGACGGCAGATGGGAGCAACCAC
ATCCCATTCTACGATACCCGGTTTTTCCAGGAGATCTATGCCGCCGGCAA
TAGCCCTGTGGACACCTGTCAGTTTAGGCACACCCCGCTTCGGCTATCACC
TGCCTAAGCTGACCGATCAGACAGCCATCCGCGTGAACAAGAAGCACGTG
AAGGCAGCAAAGACCGAGGCACGGATCAGACTGGCCATCCAGCAGGGCAC
ACTGCCAGTGTCCAATCTGAAGATCAACGAGATCTCCGCCAATCAACT
CTAAGGGCCAGGTGCGCATCCCCGTGAAGTTTGACGTGGGAAGGCAGAAG
GGAACCCTGCAGATCGGCGACCGGTTCTGCGGCTACGATCAGAACCGAC
AGCCTCTCCACGCCTATAGCCTGTGGAGGTGGTGAAGAGGAGGGCCAGTACC
ACAAGGAGCTGGGCTGTTTGTGCGCTTCATCTCTAGCGGCGACATCGTG
TCCATCACCGAGAACGGGGCAATCAGTTTGATCAGCTGTCTTATGAGGG
CCTGGCCTACCCCCAGTATGCCGACTGGAAAGAAGGCCTCCAAGTTCG
TGTCTCTGTGGCAGATCACCAAGAAGAACAAGAAGAAGGAGATCGTGACA
GTGGAGGCCAAGGAGAAGTTTGACGCCATCTGCAAGTACCAGCCTAGGCT
```

TABLE 10-continued

Sequences enabling mammalian expression of Cas12i
effectors with included N-terminal mH6 tag and C-
terminal nucleoplasmin NLS sequence (bolded)

```
GTATAAGTTCAACAAGGAGTACGCCTATCTGCTGCGGGATATCGTGAGAG
GCAAGAGCCTGGTGGAGCTGCAGCAGATCAGGCAGGAGATCTTTCGCTTC
ATCGAGCAGGACTGTGGAGTGACCCGCCTGGGATCTCTGAGCCTGTCCAC
CCTGGAGACAGTGAAGGCCGTGAAGGGCATCATCTACTCCTATTTTTCTA
CAGCCCTGAATGCCTCTAAGAACAATCCCATCAGCGACGAGCAGCGGAAG
GAGTTTGATCCTGAGCTGTTCGCCCTGCTGGAGAAGCTGGAGCTGATCAG
GACTCGGAAGAAGAAGCAGAAGGTGGAGAGAATCGCCAATAGCCTGATCC
AGACATGCCTGGAGAACAATATCAAGTTCATCAGGGGCGAGGGCGACCTG
TCCACCACAAACAATGCCACCAAGAAGAAGGCCAACTCTAGGAGCATGGA
TTGGCTGGCCAGAGGCGTGTTTAATAAGATCCGGCAGCTGGCCCCAATGC
ACAACATCACCCTGTTCGGCTGCGGCAGCCTGTACACATCCCACCAGGAC
CCTCTGGTGCACAGAAACCCAGATAAGGCCATGAAGTGTAGATGGGCAGC
AATCCCAGTGAAGGACATCGGCGATTGGGTGCTGAGAAAGCTGTCCCAGA
ACCTGAGGGCCAAGAATATCGGCACCGGCGAGTACTATCACCAGGGCGTG
AAGGAGTTCCTGTCTCACTATGAGCTGCAGGACCTGGAGGAGGAGCTGCT
GAAGTGGCGGTCTGATAGAAAGAGCAACATCCCTTGCTGGGTGCTGCAGA
ATAGACTGGCCGAGAAGCTGGGCAACAAGGAGGCCGTGGTGTACATCCCA
GTGAGGGGCGGCCGCATCTTATTTTGCAACCCACAAGGTGGCAACAGGAGC
CGTGAGCATCGTGTTCGACCAGAAGCAAGTGTGGGTGTGTAATGCAGATC
ACGTGGCAGCAGCAAACATCGCACTGACCGTGAAGGGCATCGGCGAGCAG
TCCTCTGACGAGGAGAACCCCGATGGCTCCAGGATCAAGCTGCAGCTGAC
ATCTAAAAAGGCCGGCGGCCACGAAAAAGGCCGGCCAGGCAAAAAAGAAAA
AGTAATAA (SEQ ID NO: 502)
```

>bGH polyA Tail
```
CGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGG
GTGGGGTGGGGCAGGACAGCAAGGGGGAGGATTGGGAAGACAATAGCAGG
CATGCTGGGGATGCGGTGGGCTCTATGG (SEQ ID NO: 503)
```

TABLE 11

Amino Acid Sequences of Motifs and Functional
Domains in Engineered Variants of CLUST.029130
(TypeV-I) CRISPR-Cas Effector Proteins

>LINKER_1
GS (SEQ ID NO: 600)

>LINKER_2
GSGGGGS (SEQ ID NO: 601)

>LINKER_3
GGGGSGGGGSGGGGS (SEQ ID NO: 602)

>LINKER_4
GGSGGSGGGGSGGSGGS (SEQ ID NO: 603)

>LINKER 5 (Gaudelli et al., 2017)
SGGSSGGSSGSGETPGTSESATPESSGGSSGGS (SEQ ID NO: 604)

>ecTadA(wt) (Gaudelli et al., 2017) [N-term
fusion to ecTadA*(7.10)]
MSEVEFSHEYWMRHALTLAKRAWDEREVPVGAVLVHNNRVIGEGWNRPI
GRHDPTAHAEIMALRQGGLVMQNYRLIDATLYVTLEPCVMCAGAMIHSR
IGRVVFGARDAKTGAAGSLMDVLHHPGMNHRVEITEGILADECAALLSD
FFRMRRQEIKAQKKAQSSTD (SEQ ID NO: 605)

>ecTadA*(7.10) (Gaudelli et al., 2017) [N-term
fusion to CRISPR nuclease]
MSEVEFSHEYWMRHALTLAKRAWDEREVPVGAVLVHNNRVIGEGWNRPI
GRHDPTAHAEIMALRQGGLVMQNYRLIDATLYVTLEPCVMCAGAMIHSR
IGRVVFGARDAKTGAAGSLMDVLHHPGMNHRVEITEGILADECAALLSD
FFRMRRQEIKAQKKAQSSTD (SEQ ID NO: 606)

TABLE 11-continued

Amino Acid Sequences of Motifs and Functional
Domains in Engineered Variants of CLUST.029130
(TypeV-I) CRISPR-Cas Effector Proteins

[Cytidine deaminase, AID, APOBEC1: N-term fusion
(or optionally C-term)]
>AID-APOBEC1 (Dickerson et al., 2003, Komor et
al., 2017)
MDSLLMNRRKFLYQFKNVRWAKGRRETYLCYVVKRRDSATSFSLDFGYL
RNKNGCHVELLFLRYISDWDLDPGRCYRVTWFTSWSPCYDCARHVADFL
RGNPNLSLRIFTARLYFCEDRKAEPEGLRRLHRAGVQIAIMTFKDYFYC
WNTFVENHERTFKAWEGLHENSVRLSRQLRRILLPLYEVDDLRDAFRTL
GL (SEQ ID NO: 607)

>Lamprey_AID-APOBEC1 (Rogozin et al., 2007,
Komor et al., 2017)
MTDAEYVRIHEKLDIYTFKKQFFNNKKSVSHRCYVLFELKRRGERRACF
WGYAVNKPQSGTERGIHAEIFSIRKVEEYLRDNPGQFTINWYSSWSPCA
DCAEKILEWYNQELRGNGHTLKIWACKLYYEKNARNQIGLWNLRDNGVG
LNVMVSEHYQCCRKIFIQSSHNQLNENRWLEKTLKRAEKRRSELSIMIQ
VKILHTTKSPAV (SEQ ID NO: 608)

>APOBEC1_BE1 (Komor et al., 2016)
MSSETGPVAVDPTLRRRIEPHEFEVFFDPRELRKETCLLYEINWGGRHS
IWRHTSQNTNKHVEVNFIEKFTTERYFCPNTRCSITWFLSWSPCGECSR
AITEFLSRYPHVTLFIYIARLYHHADPRNRQGLRDLISSGVTIQINTEQ
ESGYCWRNFVNYSPSNEAHWPRYPHLWVRLYVLELYCIILGLPPCLNIL
RRKQPQLTFFTIALQSCHYQRLPPHILWATGLK (SEQ ID NO: 609)

These results suggest that members of the compact Type V-I CRISPR family can be engineered for activity in eukaryotic cells, and specifically, for genome editing in mammalian cells. A mammalian functional Type V-I effector enables the development of additional technologies based on further engineering on top of a DNA binding chassis.

Example 11. Type V-I CRISPR-Cas Systems can be Used to Provide Genotype-Gated Control of Genome Replication, Viral Propagation, Plasmid Propagation, Cell Death, or Cell Dormancy Hybridization of the Type V-I CRISPR-Cas effector protein and crRNA with a specific ssDNA or dsDNA target results in nicking or cleavage of the substrate. The dependence of such activity on the presence of a specific DNA target in a cell is valuable since it enables targeting of specific genomic material or cell populations based on specific underlying genotypes. Numerous applications exist in both eukaryotic, prokaryotic, and viral/plasmid settings for such control of genome replication, cell death, or cell dormancy.

For prokaryotic, viral, and plasmid applications, a Type V-I CRISPR-Cas system (e.g., including a Type V-I effector and a RNA guide) can be delivered (e.g., in vitro or in vivo) in order to stop genome replication and/or induce cell death or dormancy of specific prokaryote populations (e.g., bacterial populations) in a genotype-specific way. For instance, the Type V-I CRISPR-Cas system can include one or more RNA guides that specifically target a particular virus, plasmid, or prokaryotic genus, species, or strain. As shown in FIG. 5A-D cleavage, nicking, or interference with the *E. coli* genome or plasmid DNA conferring antibiotic resistance in *E. coli* by a Type V-I system results in specific depletion of the *E. coli* containing these sequences. Specific targeting of viruses, plasmids, or prokaryotes has many therapeutic benefits as it may be used to induce death or dormancy of undesirable bacteria (e.g., pathogenic bacteria such as *Clostridium difficile*). In addition, the Type V-I systems provided herein may be used to target prokaryotic cells having specific genotypes. Within the microbial diversity that colonizes humans, only a small number of bacterial strains can induce pathogenesis. Further, even within pathogenic strains such as *Clostridium difficile*, not all members of the bacterial population exist continuously in active, disease-causing states. Thus, targeting the Type V-I system based on the genotype of a virus, plasmid, or prokaryotic cell allows for specific control of which genomes or cell populations are targeted without disrupting the entire microbiome.

Additionally, bacterial strains can be readily engineered with genetic circuits or environmentally-controlled expression elements to generate genetic kill switches that limit the growth, colonization, and/or shedding of the engineered bacterial strains. For example, the expression of a TypeV-I effector and specific crRNA, can be controlled using promoters derived from the regulatory regions of genes encoding proteins expressed in response to external stimuli, such as cold sensitive proteins (PcspA), heat shock proteins (Hsp), chemically inducible systems (Tet, Lac, AraC). The controlled expression of one or more elements of the Type V-I system allows for the full functional system to be expressed only upon exposure to an environmental stimulus, which results in genotype-specific DNA interference activity of the system and thereby induces cell death or dormancy. Kill switches including Cas12i effectors as those described herein may be advantageous over traditional kill switch designs such as toxin/antitoxin systems (e.g., CcdB/CcdA Type II toxin/antitoxin systems), since they are not dependent on relative protein expression ratios which may be affected by leaky expression from a promoter (e.g., an environmental-stimulus dependent promoter), and thus allow for more precise control of the kill-switch.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Regularly Interspaced Short Palindromic Repeat (CRISPR)-associated (Cas) system comprising:

(a) an RNA guide or a nucleic acid encoding the RNA guide, wherein the RNA guide comprises a direct repeat sequence and a spacer sequence; and (b) a CRISPR-Cas effector protein or a nucleic acid encoding the CRISPR-Cas effector protein, wherein the CRISPR-Cas effector protein comprises an amino acid sequence with at least 95% identity to SEQ ID NO: 14 or SEQ ID NO: 16, and the CRISPR-Cas effector protein further comprises at least one nuclear localiza-tion signal (NLS), at least one nuclear export signal (NES), or at least one NLS and at least one NES, wherein the CRISPR-Cas effector protein binds to the RNA guide, and wherein the spacer sequence is capable of hybridizing to a target nucleic acid in a eukaryotic cell.

2. The system of claim 1, wherein the system does not include a tracrRNA.

3. The system of claim 1, wherein the CRISPR-Cas effector protein comprises one or more of:

(a) a RuvC domain comprising the amino acid sequence $X_1SHX_4DX_6X_7$ (SEQ ID NO: 200), wherein $X_1$ is S or T, $X_4$ is Q or L, $X_6$ is P or S, and $X_7$ is For L, (b) a RuvC domain comprising the amino acid sequence X₁XDXNX₆X₇XXXX₁₁ (SEQ ID NO: 201), wherein X₁ is A, G, or S, X is any amino acid, X₆ is Q or I, X₇ is T, S, or V, and X₁₁ is T or A; and (c) a RuvC domain comprising the amino acid sequence X₁X₂X₃E (SEQ ID NO: 210), wherein X₁ is C, F, I, L, M, P, V, W, or Y, X₂ is C, F, I, L, M, P, R, V, W, or Y, and X₃ is C, F, G, I, L, M, P, V, W, or Y.

4. The system of claim 1, wherein:

(a) the CRISPR-Cas effector protein comprises an amino acid sequence with least 95% identity to SEQ ID NO: 14, and the direct repeat sequence comprises an RNA molecule comprising a nucleotide sequence with at least 95% sequence identity to SEQ ID NO: 21; or (b) the CRISPR-Cas effector protein comprises an amino acid sequence with least 95% identity to SEQ ID NO: 16, and the direct repeat sequence comprises an RNA molecule comprising a nucleotide sequence with at least 95% sequence identity to SEQ ID NO: 6.

5. The system of claim 1, wherein:

(a) the CRISPR-Cas effector protein comprises an amino acid sequence with at least 95% identity to SEQ ID NO: 14, and the direct repeat sequence comprises an RNA molecule comprising a nucleotide sequence set forth in SEQ ID NO: 21; or (b) the CRISPR-Cas effector protein comprises an amino acid sequence with at least 95% identity to SEQ ID NO: 16, and the direct repeat sequence comprises an RNA molecule comprising a nucleotide sequence set forth in SEQ ID NO: 6.

6. The system of claim 1, wherein the CRISPR-Cas effector protein comprises the amino acid sequence set forth in SEQ ID NO: 14 or SEQ ID NO: 16.

7. The system of claim 1, wherein the spacer sequence comprises between 15 and 47 nucleotides in length.

8. The system of claim 7, wherein the spacer sequence comprises between 24 and 38 nucleotides in length.

9. The system of claim 1, wherein the target nucleic acid comprises a sequence complementary to a nucleotide sequence in the spacer sequence.

10. The system of claim 1, wherein the CRISPR-Cas effector protein recognizes a protospacer adjacent motif (PAM) sequence, wherein the PAM sequence comprises a nucleotide sequence set forth as 5'-TTN-3', wherein N is any nucleotide.

11. The system of claim 1, wherein the CRISPR-Cas effector protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

12. The system of claim 1, wherein the nucleic acid encoding the CRISPR-Cas effector protein is codon-optimized for expression in a cell.

13. The system of claim 1, wherein the nucleic acid encoding the CRISPR-Cas effector protein is operably linked to a promoter.

14. The system of claim 1, wherein the nucleic acid encoding the CRISPR-Cas effector protein is in a vector.

15. The system of claim 1, wherein the system is present in a delivery system comprising a nanoparticle, a liposome, an exosome, a microvesicle, or a gene-gun.

16. The system of claim 1, wherein the CRISPR-Cas effector protein comprises an amino acid sequence with at least 95% identity to SEQ ID NO: 14.

17. The system of claim 1, wherein the CRISPR-Cas effector protein comprises an amino acid sequence with at least 95% identity to SEQ ID NO: 16.

18. The system of claim 1, wherein the CRISPR-Cas effector protein comprises an amino acid sequence with at least 98% identity to SEQ ID NO: 14.

19. The system of claim 1, wherein the CRISPR-Cas effector protein comprises an amino acid sequence with at least 98% identity to SEQ ID NO: 16.

20. The system of claim 1, wherein the CRISPR-Cas effector protein comprises an amino acid sequence with at least 99% identity to SEQ ID NO: 14.

21. The system of claim 1, wherein the CRISPR-Cas effector protein comprises an amino acid sequence with at least 99% identity to SEQ ID NO: 16.

22. An isolated cell comprising the system of claim 1.

23. The isolated cell of claim 22, wherein the isolated cell is a mammalian cell or a plant cell.

24. The isolated cell of claim 22, wherein the isolated cell is a human cell.

25. A method of binding the system of claim 1 to the target nucleic acid in a cell comprising:

(a) providing the system; and (b) delivering the system to the cell, wherein the cell comprises the target nucleic acid, wherein the CRISPR-Cas effector protein binds to the RNA guide, and wherein the spacer sequence binds to the target nucleic acid.

26. The method of claim 25, wherein binding the system to the target nucleic acid results in cleavage of the target nucleic acid.

27. The method of claim 26, wherein cleavage of the target nucleic acid results in formation of an insertion or a deletion in the target nucleic acid.

28. An engineered, non-naturally occurring Clustered Regularly Interspaced Short Palindromic Repeat (CRISPR)-associated (Cas) system comprising:

(a) an RNA guide or a nucleic acid encoding the RNA guide, wherein the RNA guide comprises a direct repeat sequence and a spacer sequence, and wherein the direct repeat sequence comprises an RNA molecule comprising a nucleotide sequence set forth in SEQ ID NO: 21; and (b) a CRISPR-Cas effector protein or a nucleic acid encoding the CRISPR-Cas effector protein, wherein the CRISPR-Cas effector protein comprises an amino acid sequence with at least 95% identity to SEQ ID NO: 14, wherein the CRISPR-Cas effector protein binds to the RNA guide, and wherein the spacer sequence is capable of hybridizing to a target nucleic acid in a eukaryotic cell.

29. An engineered, non-naturally occurring Clustered Regularly Interspaced Short Palindromic Repeat (CRISPR)-associated (Cas) system comprising:

(a) an RNA guide or a nucleic acid encoding the RNA guide, wherein the RNA guide comprises a direct repeat sequence and a spacer sequence, and wherein the direct repeat sequence comprises an RNA molecule comprising a nucleotide sequence set forth in SEQ ID NO: 6; and (b) a CRISPR-Cas effector protein or a nucleic acid encoding the CRISPR-Cas effector protein, wherein the CRISPR-Cas effector protein comprises an amino acid sequence with at least 95% identity to SEQ ID NO: 16, wherein the CRISPR-Cas effector protein binds to the RNA guide, and wherein the spacer sequence is capable of hybridizing to a target nucleic acid in a eukaryotic cell.

* * * * *